(12) United States Patent
York et al.

(10) Patent No.: US 9,920,009 B2
(45) Date of Patent: Mar. 20, 2018

(54) UV ABSORBING COMPOUNDS, COMPOSITIONS COMPRISING SAME AND USES THEREOF

(71) Applicant: CORAL SUNSCREEN PTY LTD, Aitkenvale, Queensland (AU)

(72) Inventors: Mark York, Clayton (AU); John Ryan, Clayton (AU); Gregory Paul Savage, Clayton (AU); Adam Gerhard Meyer, Clayton (AU); Karen Jarvis, Clayton (AU)

(73) Assignee: CORAL SUNSCREEN PTY LTD, Aitkenvale, Queensland (AU)

( * ) Notice: Subject to any disclaimer, the term of this patent is extended or adjusted under 35 U.S.C. 154(b) by 0 days.

(21) Appl. No.: 14/905,217

(22) PCT Filed: Jul. 15, 2014

(86) PCT No.: PCT/AU2014/000721
§ 371 (c)(1),
(2) Date: Jan. 14, 2016

(87) PCT Pub. No.: WO2015/006803
PCT Pub. Date: Jan. 22, 2015

(65) Prior Publication Data
US 2016/0244409 A1    Aug. 25, 2016

(30) Foreign Application Priority Data

Jul. 15, 2013  (AU) ................................. 2013902607
May 27, 2014  (AU) ................................. 2014902000

(51) Int. Cl.
*A61K 8/49*        (2006.01)
*C08K 5/3432*      (2006.01)
*A61Q 17/04*       (2006.01)
*C07D 211/70*      (2006.01)
*C07D 211/72*      (2006.01)
*C07D 211/78*      (2006.01)
*C07F 7/21*        (2006.01)
*C09D 5/32*        (2006.01)
*C07D 223/04*      (2006.01)
*C07D 401/04*      (2006.01)
*C07D 401/06*      (2006.01)
*C07D 207/20*      (2006.01)
*C07D 211/88*      (2006.01)
*C08K 5/3412*      (2006.01)
*C08K 5/3445*      (2006.01)
*C08K 5/544*       (2006.01)
*A61K 8/58*        (2006.01)
*C07D 403/04*      (2006.01)
*C07D 405/06*      (2006.01)
*C08K 5/3415*      (2006.01)
*C09D 7/12*        (2006.01)
*C08K 5/41*        (2006.01)
*C08K 5/435*       (2006.01)

(52) U.S. Cl.
CPC .......... *C07D 211/70* (2013.01); *A61K 8/4926* (2013.01); *A61K 8/4946* (2013.01); *A61K 8/585* (2013.01); *A61Q 17/04* (2013.01); *C07D 207/20* (2013.01); *C07D 211/72* (2013.01); *C07D 211/78* (2013.01); *C07D 211/88* (2013.01); *C07D 223/04* (2013.01); *C07D 401/04* (2013.01); *C07D 401/06* (2013.01); *C07D 403/04* (2013.01); *C07D 405/06* (2013.01); *C07F 7/21* (2013.01); *C08K 5/3412* (2013.01); *C08K 5/3415* (2013.01); *C08K 5/3432* (2013.01); *C08K 5/3445* (2013.01); *C08K 5/5442* (2013.01); *C09D 5/32* (2013.01); *C09D 7/1233* (2013.01); *C08K 5/41* (2013.01); *C08K 5/435* (2013.01)

(58) Field of Classification Search
CPC .. C07D 211/72; C07D 223/04; C09D 7/1233; C08K 5/3445; A61K 8/4926
See application file for complete search history.

(56) References Cited

U.S. PATENT DOCUMENTS

| | | | | |
|---|---|---|---|---|
| 4,081,450 A | * | 3/1978 | Zimmerman | C07D 207/20 546/185 |
| 5,637,718 A | * | 6/1997 | Bird | A61K 8/4926 546/16 |
| 7,476,679 B2 | * | 1/2009 | Carroll | C07D 217/16 514/307 |

FOREIGN PATENT DOCUMENTS

| | | |
|---|---|---|
| WO | 1998/002251 | 4/1999 |
| WO | 1990/009995 | 9/1999 |
| WO | 2014/082124 | 6/2014 |

OTHER PUBLICATIONS

Gamini Gunawardena, title: Alkenyl group; downloaded from http://www.ochempal.org/index.php/alphabetical/a-b/alkenyl-group/ Apr. 17, 2017.*

Authors: W.C. Dunlap, et al.; title: Uric acid photo-oxidation assay: in vitro comparison of sunscreening agents, International Journal of Cosmetic Science, vol. 20, Issue 1, pp. 1-18, First published Feb. 1998.*

(Continued)

*Primary Examiner* — Yanzhi Zhang
(74) *Attorney, Agent, or Firm* — Robert C. Netter, Jr.; Dann, Dorfman, Herrell & Skillman

(57) ABSTRACT

There is provided a range of novel compounds which have been demonstrated to have useful UV absorbing properties. These compounds will find use in a range of applications such as active components in sunscreen formulations, paints, plastics, fabrics, glass and UV protective coatings.

27 Claims, No Drawings

(56) References Cited

OTHER PUBLICATIONS

Hesse, K. et al, "Uber zweistufige Redoxsysteme, XXX: Spektroskopische und elecktrochemische Eigenschaften N-subslituierter 1,4-Dihydro-4,4-dimethylpyridine", Licbigs Annalen der Chemic, 1982, pp. 2079-2086, In foreign language.

Ohno, A. et al, "Reduction by a Model of NAD(P)H . 35. Spectroscopic Detection of Charge-transfer Intermediate", Bulletin of the Chemical Society of Japan, 19& I, vol. 54, pp. 3489-3491.

Kosower, E.M. et al, "The Synthesis and Properties of Some Simple 1,4-Dihydropyridines", Journal of Organic Chemistry, 1962, vol. 27(11), pp. 3746-3771.

CAS RN 1349997-46-1; STN entry date: Dec. 7, 2011 1,3-dihydro-3,3-dimethyl-1-[2-methyl-4'-[(2,5,6,7-tetrahydro-1'-methylspiro[3H-furo[2,3-f]indolc-3,4 '-piperidin)-5-yl) carbonyl] (1,1'-biphenyl]-4-yl]-2H-pyrrol•2-one.

CAS RN 1222816-87-6; STN entry date: May 13, 2010 1,4-dihydro-1,4,4-trimethyl-N-propyl-3-pyridinecarboxamide.

CAS RN 1222802-59-6; STN entry date: May 13, 2010 1,4-dihydro-4,4-dimethyl-1-(phenylmethyl)-N-propyl-3-pyridinecarboxamide.

CAS RN 109434-61-9; STN entry date: Jul. 25, 1987 1,2,3,4-tetrahydro-1,1,4,4-tetramethyl-pyridinium.

CAS RN 86310-33-0; STN entry date: Nov. 16, 1984 1-[2-(2,4-dichlorophenoxy)ethyl]-1,3-dihydro-3,3,5-trimethyl-2H-pyrrol-2-one.

CAS RN 86240-04-2; STN entry date: Nov. 16, 1984 1-(2-(ethenyloxy)ethyl)-1,3-dihydro-3,3,5-trimethyl-2H-pyrrol-2-one.

CAS RN 86219-66-1; STN entry date: Nov. 16, 1984 2-(3,3,5-trimothyl-2-oxo-2,3-dihydro-IH-pyrrol-1-yl)ethyl methacrylate.

CAS RN 86219-57-0; STN entry date: Nov. 16, 1984 1-cyclohexyl-1,3-dihydro-3,3,5-trimethyl-2H-pyrrol-2-one.

CAS RN 86177-91-5; STN entry date: Nov. 16, 1984 2,3-dihydro-3,3,5-trimethyl-1H-pyrrole-1-ethanol.

Jacobson, A.E. et al, "The Stevens Rearrangement of I-p-Methoxybenzyl-1,2,5,6-tetrahydropyridinium Salts", Journal of Organic Chemistry, 1967, vol. 32, pp. 1894-1896.

Jacobson, A.E., "An Unusual Stevens Rearrangement of a Tetrahydropyridinium Salt", Journal of Organic Chemistry, 1966, vol. 31, pp. 1569-1573.

Takasu, N. et al, "Iron-Catalyzed Oxidative C(3)-H Functionalization of Amines", Organic Letters, 2013, vol. 15, pp. 1918, pp. 1918-1921.

Lan et al., "The first enantioselective synthesis of cytotoxic marine natural product palau' imide and assignment of its C-20 stereochemistry", Chemical Communications, 2010, vol. 46, pp. 5319-5321.

Bosch, J. et al, "Benzomorphan Related Compounds. IV (I ). The Stevens Rearrangement of a Trimethoxybenzyl-1,2,5,6-tetrahydropyridinium Salt", Journal of Heterocyclic Chemistry, 1975, vol. 12, pp. 1117-1121.

Enz, W., "26. Reduktionen von Estem mit Phenol und Natrium", Helvetica Chimica Acta, 1961, vol. 44, pp. 206-212, In foreign language.

\* cited by examiner

UV ABSORBING COMPOUNDS, COMPOSITIONS COMPRISING SAME AND USES THEREOF

This application is a § 371 application of PCT/AU2014/000721, filed Jul. 15, 2014, which in turn claims priority to Australian Patent Application 2013902607, filed Jul. 15, 2013, and Australian Patent Application 2014902000, filed May 27, 2014. The entire disclosure of each of the foregoing applications is incorporated by reference herein.

FIELD OF THE INVENTION

The invention relates to the field of ultraviolet light absorbing compounds. More particularly, this invention relates to ultraviolet light absorbing compounds, their synthesis and compositions comprising said compounds.

BACKGROUND TO THE INVENTION

Any reference to background art herein is not to be construed as an admission that such art constitutes common general knowledge in Australia or elsewhere.

Ultraviolet light (UV) absorbing or screening compounds have found use in a range of applications where protection from the sun's harmful UV rays is desirable. This includes their use in glass and lense coating, paints and materials including fabrics as well as, perhaps most notably, in sun screen formulations to protect the skin of the user from damage caused by UV radiation.

UV radiation can be subdivided into three bands; UVA at 315-400 nm; UVB at 280-315 nm; and UVC at 100-280 nm. UVC is almost completely absorbed by stratospheric ozone and so it is UVA and UVB that present the main risk to people and materials subjected to prolonged exposure.

Amongst the most active natural UV absorbing compounds are the mycosporine-like amino acids (MAA's) examples of which are known with a peak absorption either in the UVA or UVB range and absorption coefficients comparable to those of synthetic sunscreens. There has therefore been considerable focus on the isolation and characterisation of naturally occurring MAA's as well as strong interest in the generation of active derivatives and analogues thereof.

U.S. Pat. No. 5,637,718 (the 718 patent) describes a range of MAA analogues as UV absorbing compounds based on a cyclic enaminoketone core. While a number of these compounds showed useful absorption in the UVB range none of them showed a useful broad range of absorption extending into the UVA region. Indeed, all but two of the compounds synthesised demonstrated maximum absorption within a narrow band of 305-308 nm. This is largely as a result of the limited variance of substitutions around the cyclic enaminoketone core. All but one of the compounds in the 718 patent are substituted on the ring nitrogen with only a simple alkyl chain or, in a single example, a cycloalkyl ring. Further, at the 6-position of the enaminoketone ring no substitutions were made at all. Only a single substitution with a methyl group was proposed at the 2-position of the enaminoketone ring and, again, it does not appear as if this compound was, in fact, synthesised. While some range of substitution was provided for at the 3-position, all compounds had a carbonyl group attached directly to the ring at this position and all but three of the proposed substitutions were with straight chain alkyls.

The simplest compounds disclosed in the 718 patent tend to have an absorbance maximum ($\lambda_{max}$) of 307 nm which can be attributed solely to the enaminoketone chromophore. This has not been modified to any real extent by the pattern and nature of substitutions presented in the 718 patent and so the value of the proposed compounds as even somewhat broad spectrum UV absorbing agents is minimal.

It would therefore be desirable to provide for UV absorbing compounds with a greater range of variance in the absorbance maximum to provide a compound or suitable combination of compounds which may afford greater UV protection when formulated for use in a sunscreen composition, a coating composition, or the like.

SUMMARY OF INVENTION

The present inventors have postulated that substitution of a cyclic enaminoketone core with a range of groups which are likely to either affect the electron density of the enaminoketone or which will provide additional UV absorbance characteristics themselves will result in extending the absorbance maximum into the UVA range or at least provide a useful variance in absorbance.

According to a first aspect of the present invention, there is provided a compound of formula I, or a salt thereof:

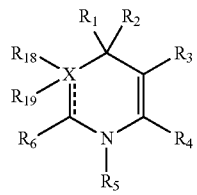

formula I wherein, the dashed line may represent a bond and X, if present, is one or two carbon atoms forming part of the ring structure;

$R_1$ and $R_2$ are independently selected from the group consisting of hydrogen, $C_1$ to $C_{10}$ alkyl, $C_1$ to $C_{10}$ alkenyl and $C_1$ to $C_{10}$ alkoxy, each of which groups may be substituted or unsubstituted;

$R_3$ is selected from the group consisting of hydrogen, hydroxyl, sulfonyl, substituted or unsubstituted $C_1$ to $C_6$ alkyl, substituted or unsubstituted $C_1$ to $C_6$ alkenyl, substituted or unsubstituted $C_1$ to $C_6$ alkoxy and

wherein W is sulphur or oxygen and $R_7$ is selected from the group consisting of $C_1$ to $C_{20}$ alkyl, $C_2$ to $C_{20}$ alkenyl, $C_2$ to $C_{20}$ alkynyl, aryl, heteroaryl, aroyl, $C_2$ to $C_{20}$ alkanone, $C_5$ to $C_7$ cycloalkyl, $C_4$ to $C_7$ cycloalkanone, $C_5$ to $C_7$ cycloalkenyl, $C_2$ to $C_{20}$ alkanoyl, $C_2$ to $C_{20}$ alkanoyloxy, $C_2$ to $C_{20}$ alkoxycarbonyl, $C_2$ to $C_{20}$ carbamoyl, $C_2$ to $C_{20}$ carboxyl, haloalkyl, N-alkyl, N-aryl, N-heterocyclyl and heterocyclic all of which groups may be substituted or unsubstituted;

$R_4$ is selected from the group consisting of hydrogen, $C_1$ to $C_{12}$ alkyl, $C_2$ to $C_{12}$ alkenyl, aryl, heteroaryl, $C_5$ to $C_7$ cycloalkyl, $C_5$ to $C_7$ cycloalkenyl, $C_1$ to $C_{12}$ alkanoyl, $C_1$ to $C_{12}$ alkanoyloxy, $C_1$ to $C_{12}$ carboalkoxy and $C_1$ to $C_{12}$ alkanone all of which groups may be substituted or unsubstituted;

$R_5$ is selected from the group consisting of $C_1$ to $C_{12}$ alkyl, $C_2$ to $C_{12}$ alkenyl, $C_2$ to $C_{12}$ alkynyl, aryl, heteroaryl, $C_5$ to $C_9$ cycloalkyl, $C_5$ to $C_7$ cycloalkenyl, $C_2$ to $C_9$ alkanoyl, $C_1$ to $C_{12}$ alkanoyloxy and carbamoyl all of which groups may be substituted or unsubstituted;

$R_6$ is selected from the group consisting of hydrogen, oxo, substituted or unsubstituted $C_1$ to $C_6$ alkyl, substituted or unsubstituted $C_2$ to $C_6$ alkenyl and substituted or unsubstituted $C_2$ to $C_6$ alkanoyl;

$R_{18}$ and $R_{19}$ are independently selected from the group consisting of hydrogen, $C_1$ to $C_6$ alkyl, $C_1$ to $C_6$ alkenyl and $C_1$ to $C_6$ alkoxy, each of which groups may be substituted or unsubstituted, with the proviso that when $R_5$ is alkyl or cycloalkyl and the dashed line is not a bond and $R_4$ is hydrogen then $R_7$ is not an unsubstituted alkyl chain, an ester or an ether; and when $R_5$ is unsubstituted benzyl then $R_7$ is not hexyl.

In one embodiment, the compound of the first aspect is a non-naturally occurring compound.

In one embodiment, the compound of the first aspect is not a compound selected from the group consisting of:

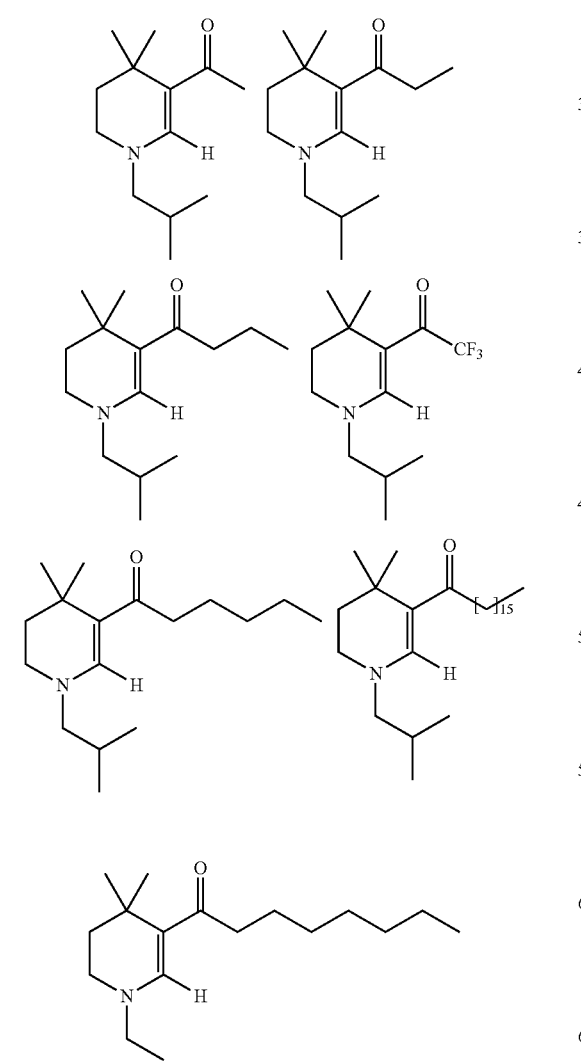

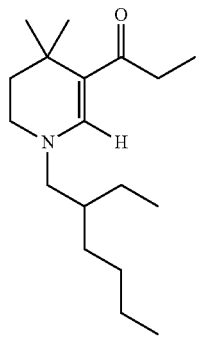

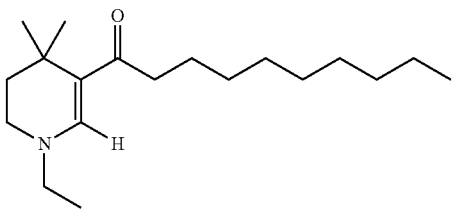

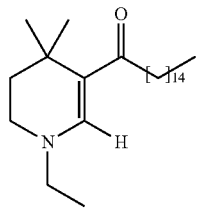

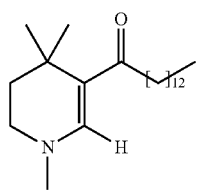

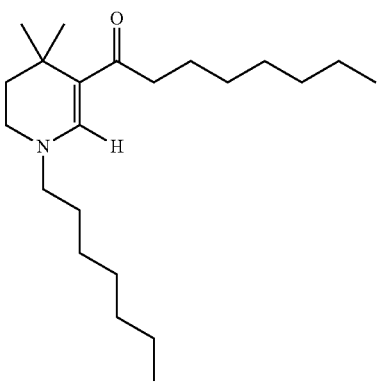

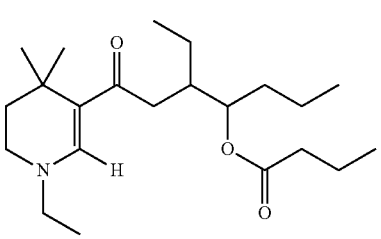

-continued
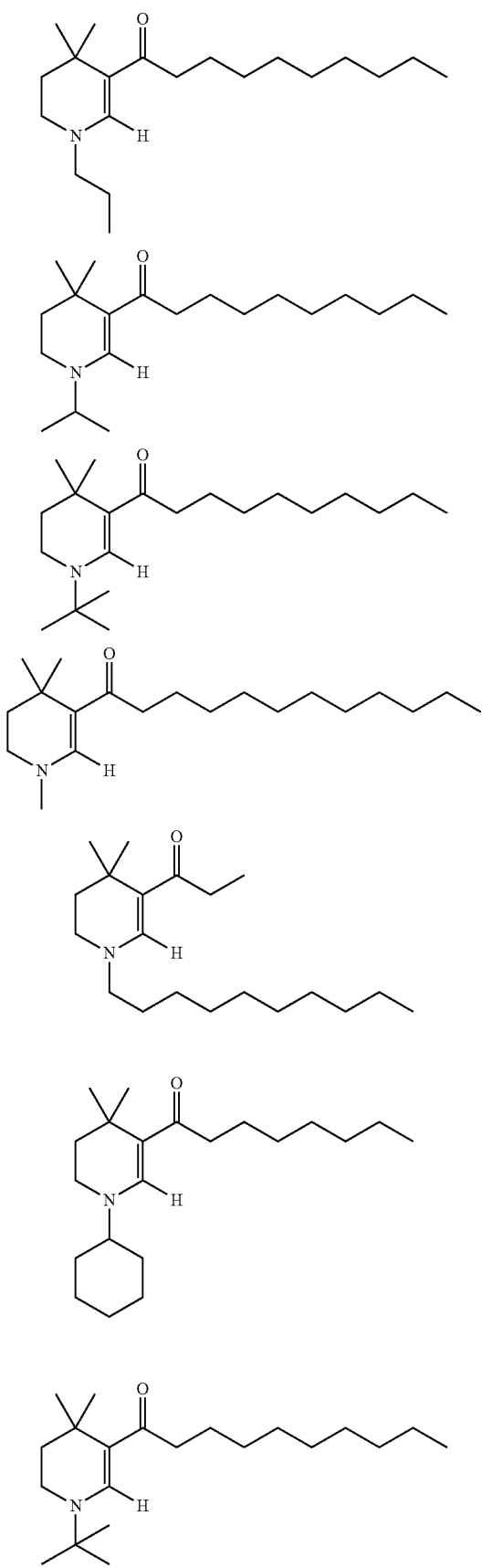
-continued
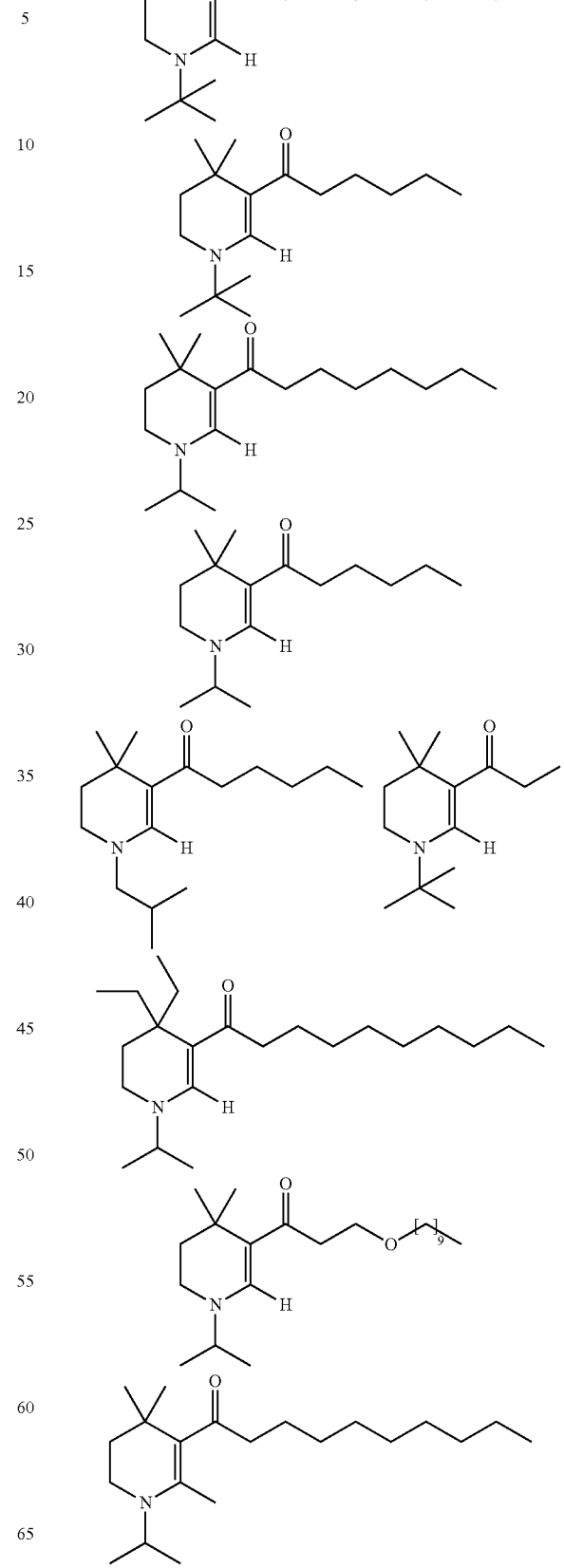

-continued

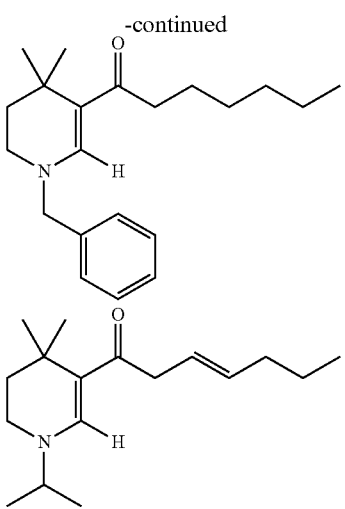

According to a second aspect of the present invention there is provided a composition comprising a compound of formula I, or a salt thereof, and a suitable carrier.

A third aspect of the present invention resides in the use of a compound of formula I, or a salt thereof, as a UV absorbing compound.

A fourth aspect of the present invention resides in a method of protecting a surface or tissue from UV rays including the step of applying a compound of the first aspect to the surface or tissue.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

DETAILED DESCRIPTION

The present invention is predicated, at least in part, on the provision of a number of substituted cyclic enamine UV absorbing compounds. The present compounds provide a wide variation in substitution pattern allowing access to a range of absorption capabilities which may prove useful as part of a UV absorbing or UV protective composition such as paint formulations, glass, protective films or sunscreen compositions.

According to an embodiment of the present invention, there is provided a compound of formula I, or a salt thereof:

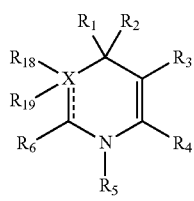

formula I wherein, the dashed line may represent a bond and X, if present, is one or two carbon atoms forming part of the ring structure;

$R_1$ and $R_2$ are independently selected from the group consisting of hydrogen, $C_1$ to $C_{10}$ alkyl, $C_1$ to $C_{10}$ alkenyl and $C_1$ to $C_{10}$ alkoxy, each of which groups may be substituted or unsubstituted;

$R_3$ is selected from the group consisting of hydrogen, hydroxyl, sulfonyl, substituted or unsubstituted $C_1$ to $C_6$ alkyl, substituted or unsubstituted $C_1$ to $C_6$ alkenyl, substituted or unsubstituted $C_1$ to $C_6$ alkoxy and

wherein W is sulphur or oxygen and $R_7$ is selected from the group consisting of $C_1$ to $C_{20}$ alkyl, $C_2$ to $C_{20}$ alkenyl, $C_2$ to $C_{20}$ alkynyl, aryl, heteroaryl, aroyl, $C_2$ to $C_{20}$ alkanone, $C_5$ to $C_7$ cycloalkyl, $C_4$ to $C_7$ cycloalkanone, $C_5$ to $C_7$ cycloalkenyl, $C_2$ to $C_{20}$ alkanoyl, $C_2$ to $C_{20}$ alkanoyloxy, $C_2$ to $C_{20}$ alkoxycarbonyl, $C_2$ to $C_{20}$ carbamoyl, $C_2$ to $C_{20}$ carboxyl, haloalkyl, N-alkyl, N-aryl, N-heterocyclyl, N—SO$_2$—R$_{20}$ and heterocyclic all of which groups may be substituted or unsubstituted and wherein $R_{20}$ is selected from the group consisting of $C_1$ to $C_6$ alkyl and phenyl each of which may be substituted or unsubstituted;

$R_4$ is selected from the group consisting of hydrogen, $C_1$ to $C_{12}$ alkyl, $C_2$ to $C_{12}$ alkenyl, aryl, heteroaryl, $C_5$ to $C_7$ cycloalkyl, $C_5$ to $C_7$ cycloalkenyl, $C_1$ to $C_{12}$ alkanoyl, $C_1$ to $C_{12}$ alkanoyloxy, $C_1$ to $C_{12}$ carboalkoxy and $C_1$ to $C_{12}$ alkanone all of which groups may be substituted or unsubstituted;

$R_5$ is selected from the group consisting of $C_1$ to $C_{12}$ alkyl, $C_2$ to $C_{12}$ alkenyl, $C_2$ to $C_{12}$ alkynyl, aryl, heteroaryl, $C_5$ to $C_9$ cycloalkyl, $C_5$ to $C_7$ cycloalkenyl, $C_2$ to $C_9$ alkanoyl, $C_2$ to $C_9$ alkanoyloxy and carbamoyl all of which groups may be substituted or unsubstituted;

$R_6$ is selected from the group consisting of hydrogen, oxo, substituted or unsubstituted $C_1$ to $C_6$ alkyl, substituted or unsubstituted $C_2$ to $C_6$ alkenyl and substituted or unsubstituted $C_2$ to $C_6$ alkanoyl; and $R_{18}$ and $R_{19}$ are independently selected from the group consisting of hydrogen, $C_1$ to $C_6$ alkyl, $C_1$ to $C_6$ alkenyl and $C_1$ to $C_6$ alkoxy, each of which groups may be substituted or unsubstituted, with the proviso that when $R_5$ is alkyl or cycloalkyl and the dashed line is not a bond and $R_4$ is hydrogen then $R_7$ is not an unsubstituted alkyl chain, an ester or an ether; and when $R_5$ is unsubstituted benzyl then $R_7$ is not hexyl.

In certain embodiments, X is one carbon atom;

$R_1$ and $R_2$ are independently selected from the group consisting of $C_1$ to $C_6$ alkyl, $C_1$ to $C_6$ alkenyl and $C_1$ to $C_6$ alkoxy, each of which groups may be substituted or unsubstituted;

$R_3$ is selected from the group consisting of hydrogen, sulfonyl, substituted or unsubstituted $C_1$ to $C_6$ alkyl, substituted or unsubstituted $C_1$ to $C_6$ alkenyl, substituted or unsubstituted $C_1$ to $C_6$ alkoxy, and

wherein W is sulphur or oxygen and $R_7$ is selected from the group consisting of $C_1$ to $C_6$ alkyl, trihaloalkyl, $C_2$ to $C_6$ alkenyl, $C_2$ to $C_6$ alkynyl, aryl, aroyl, $C_2$ to $C_{12}$ alkanone, $C_2$ to $C_9$ alkanoyl, $C_2$ to $C_9$ alkanoyloxy, $C_2$ to $C_9$ alkoxycarbonyl, $C_2$ to $C_6$ carboxyl, $C_1$ to $C_6$ haloalkyl, $C_4$ to $C_7$ cycloalkanone, N—$C_1$ to $C_6$ alkyl, N— $C_5$ to $C_7$ aryl, N— $C_5$ to $C_7$ heterocycyl, N—$SO_2$—$R_{20}$ and $C_5$ or $C_6$ heterocyclic all of which groups may be substituted or unsubstituted and wherein $R_{20}$ is selected from the group consisting of $C_1$ to $C_6$ alkyl and phenyl each of which may be substituted or unsubstituted;

$R_4$ is selected from the group consisting of hydrogen, $C_1$ to $C_6$ alkyl, $C_2$ to $C_6$ alkenyl, phenyl, heteroaryl, $C_6$ cycloalkyl, $C_1$ to $C_{12}$ alkanoyl, $C_1$ to $C_9$ alkanoyloxy, $C_1$ to $C_9$ carboalkoxy and $C_1$ to $C_6$ alkanone all of which groups may be substituted or unsubstituted;

$R_5$ is selected from the group consisting of $C_1$ to $C_6$ alkyl, $C_2$ to $C_6$ alkenyl, phenyl, naphthyl, $C_6$ cycloalkyl, $C_2$ to $C_6$ alkanoyl and $C_2$ to $C_6$ alkanoyloxy all of which groups may be substituted or unsubstituted;

$R_6$ is selected from the group consisting of hydrogen, oxo and substituted or unsubstituted $C_1$ to $C_6$ alkyl; and $R_{18}$ and $R_{19}$ are independently selected from the group consisting of hydrogen and $C_1$ to $C_6$ alkyl, each of which groups may be substituted or unsubstituted with the proviso that when $R_5$ is alkyl or cycloalkyl and the dashed line is not a bond and $R_4$ is hydrogen then $R_7$ is not an unsubstituted alkyl chain, an ester or an ether.

In certain embodiments, X is one carbon atom;

$R_1$ and $R_2$ are independently selected from $C_1$ to $C_4$ alkyl substituted or unsubstituted;

$R_3$ is selected from the group consisting of hydrogen, arylsulfonyl and

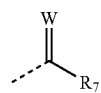

wherein W is sulphur or oxygen and $R_7$ is selected from the group consisting of $C_1$ to $C_4$ alkyl, trifluoro substituted $C_1$ to $C_4$ alkyl, $C_2$ to $C_6$ alkenyl, phenyl, phenylheterocyclic, alkylbenzoyl, phenyl substituted alkanone, $C_2$ to $C_9$ alkanoyloxy, $C_2$ to $C_9$ alkoxycarbonyl, $C_2$ to $C_4$ carboxyl, $C_5$ or $C_6$ heterocyclic, N— $C_1$ to $C_6$ alkyl, N— $C_6$ aryl, N—$SO_2$—$R_{20}$, POSS substituted alkanoyloxy and POSS substituted carboalkoxy all of which groups may be substituted or unsubstituted and wherein $R_{20}$ is selected from the group consisting of $C_1$ to $C_6$ alkyl and phenyl each of which may be substituted or unsubstituted;

$R_4$ is selected from the group consisting of hydrogen, $C_1$ to $C_6$ alkyl, $C_2$ to $C_6$ alkenyl, phenyl, $C_6$ cycloalkyl, $C_1$ to $C_{12}$ alkanoyl and $C_1$ to $C_{12}$ alkanoyloxy all of which groups may be substituted or unsubstituted;

$R_5$ is selected from the group consisting of $C_1$ to $C_6$ alkyl, phenyl, naphtyl and $C_6$ cycloalkyl all of which groups may be substituted or unsubstituted;

$R_6$ is hydrogen or oxo; and $R_{18}$ and $R_{19}$ are hydrogen, with the proviso that when $R_5$ is alkyl or cycloalkyl and the dashed line is not a bond and $R_4$ is hydrogen then $R_7$ is not an unsubstituted alkyl chain, an ester or an ether.

In combination with any of the above described embodiments, X is one carbon, $R_1$ and $R_2$ are methyl, ethyl or propyl;

$R_3$ is selected from the group consisting of hydrogen, benzenesulfonyl and

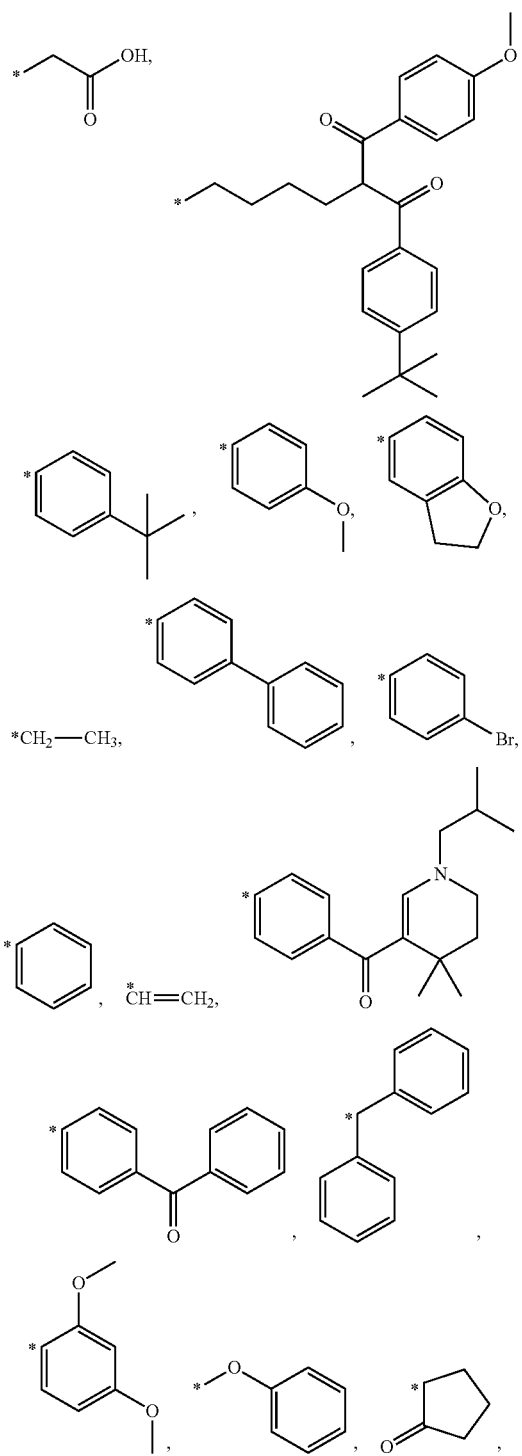

wherein W is sulphur or oxygen and $R_7$ is selected from the group consisting of

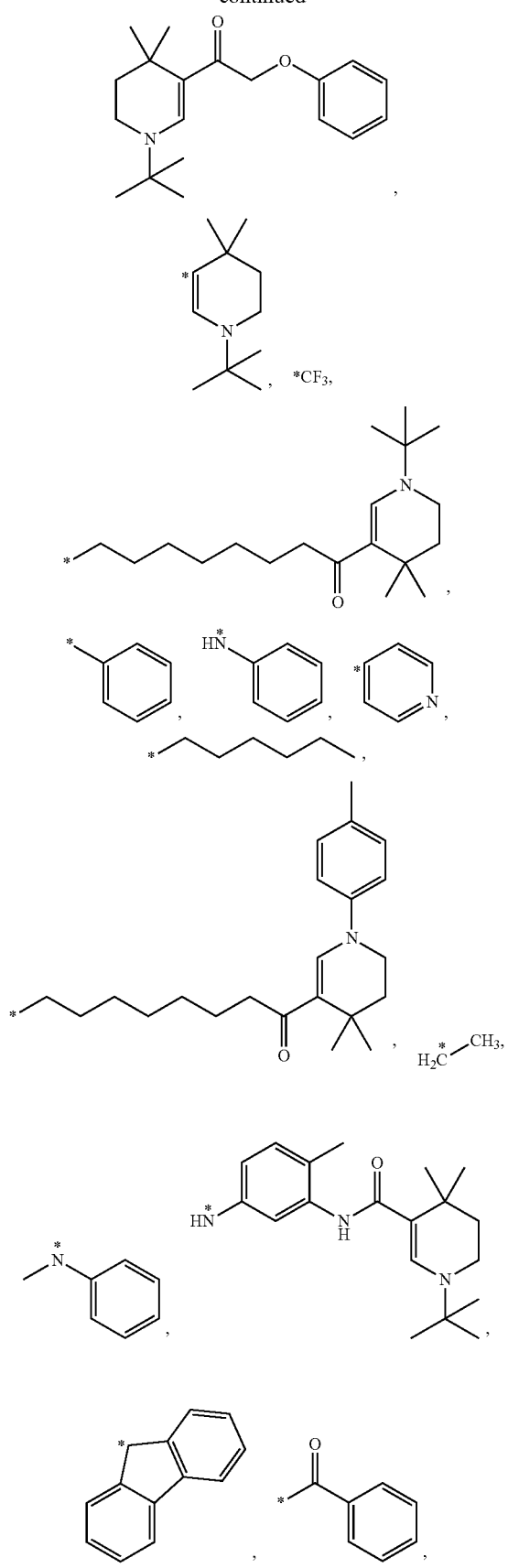
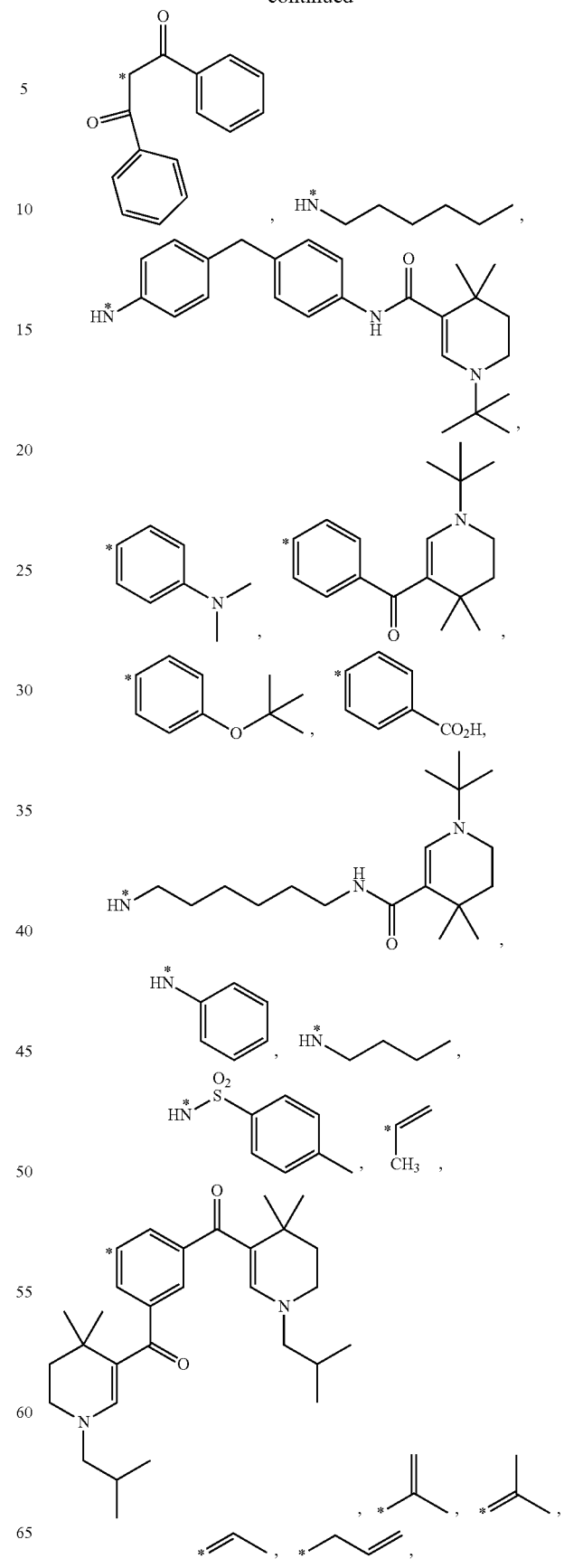

-continued

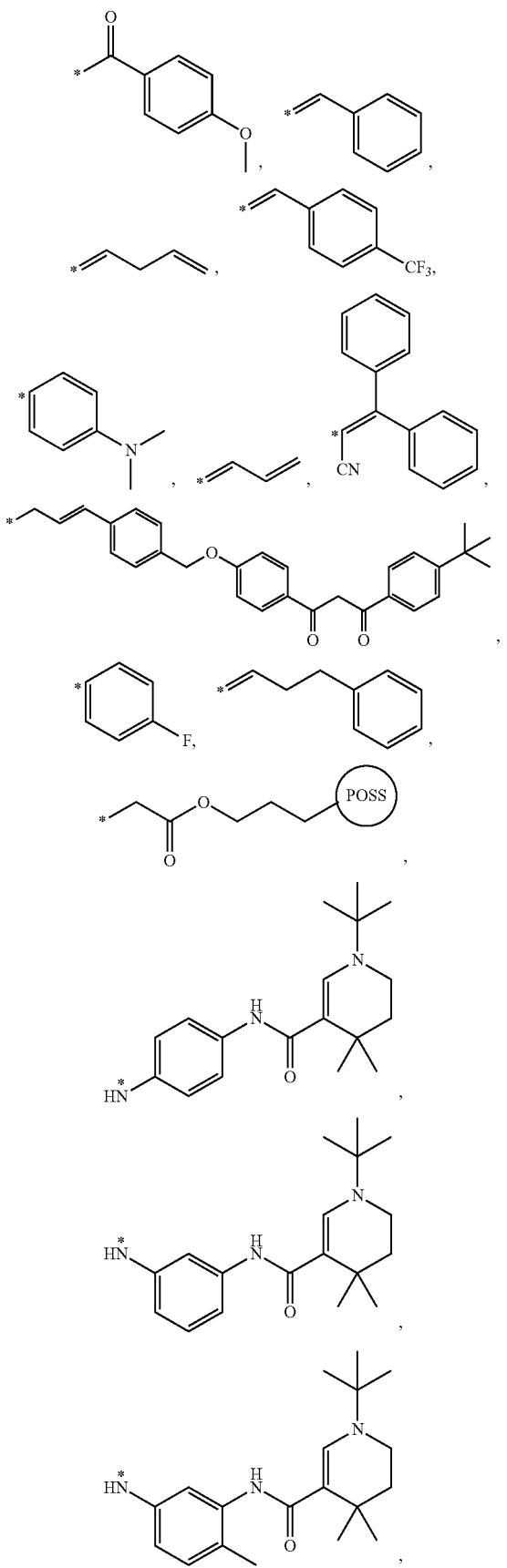

-continued

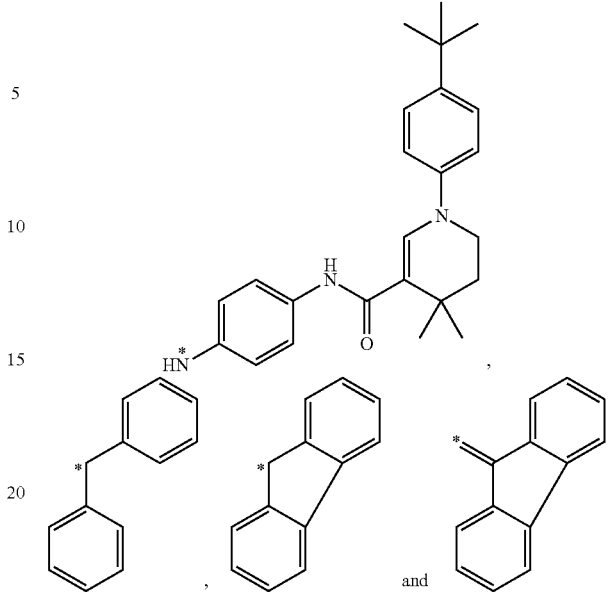

wherein * represents the carbon atom which is attached to the carbonyl carbon;

$R_4$ is selected from the group consisting of hydrogen, phenyl, butan-2-one and but-1-ene-2-yl propionate;

$R_5$ is selected from the group consisting of ethyl, propyl, isopropyl, n-butyl, sec-butyl, isobutyl, tert-butyl, phenyl and phenyl substituted with $C_1$ to $C_3$ alkoxy;

$R_6$ is hydrogen or oxo; and $R_{15}$ and $R_{19}$ are hydrogen, with the proviso that when $R_5$ is alkyl and the dashed line is not a bond and $R_4$ is hydrogen then $R_7$ is not an unsubstituted alkyl chain, an ester or an ether.

POSS is an acronym for a polyhedral oligomeric silsesquioxane being a cage-like structure of silicon and oxygen atoms. It can be used to increase the lipophilicity of a molecule.

Referring now to terminology used generically herein, the term "alkyl" means a straight-chain or branched alkyl substituent containing from, for example, 1 to about 12 carbon atoms, preferably 1 to about 9 carbon atoms, more preferably 1 to about 6 carbon atoms, even more preferably from 1 to about 4 carbon atoms, still yet more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like. The number of carbons referred to relates to the carbon backbone and carbon branching but does not include carbon atoms belonging to any substituents, for example the carbon atoms of an alkoxy substituent branching off the main carbon chain.

The term "alkenyl," as used herein, means a linear alkenyl substituent containing at least one carbon-carbon double bond and from, for example, 2 to 6 carbon atoms (branched alkenyls are 3 to 6 carbons atoms), preferably from 2 to 5 carbon atoms (branched alkenyls are preferably from 3 to 5 carbon atoms), more preferably from 3 to 4 carbon atoms. Examples of such substituents include vinyl, propenyl, isopropenyl, n-butenyl, sec-butenyl, isobutenyl, tert-butenyl, pentenyl, isopentenyl, hexenyl, and the like.

The term "alkynyl," as used herein, means a linear alkynyl substituent containing at least one carbon-carbon triple bond and from, for example, 2 to 6 carbon atoms (branched alkynyls are 3 to 6 carbons atoms), preferably from 2 to 5 carbon atoms (branched alkynyls are preferably from 3 to 5 carbon atoms), more preferably from 3 to 4 carbon atoms. Examples of such substituents include ethynyl, propynyl, isopropynyl, n-butynyl, sec-butynyl, isobutynyl, tert-butynyl, pentynyl, isopentynyl, hexynyl, and the like.

The term "cycloalkyl" refers to optionally substituted saturated mono-cyclic, bicyclic or tricyclic carbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclopentenyl, cyclohexyl, cyclohexenyl, cyclohexadienyl and the like.

The term "aryl" refers to an unsubstituted or substituted aromatic carbocyclic substituent, as commonly understood in the art. It is understood that the term aryl applies to cyclic substituents that are planar and comprise 4n+2 π electrons, according to Hückel's Rule.

The term "heteroaryl" refers to an aryl group containing from one or more (particularly one to four) non-carbon atom(s) (particularly N, O or S) or a combination thereof, which heteroaryl group is optionally substituted at one or more carbon or nitrogen atom(s). Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. "Substituted heteroaryl" means a heteroaryl having one or more non-interfering groups as substituents.

"Heterocyclic" or "heterocycle" refers to a non-aromatic ring having 5 to 7 atoms in the ring and of those atoms 1 to 4 are heteroatoms, said ring being isolated or fused to a second ring wherein said heteroatoms are independently selected from O, N and S. Heterocyclic includes partially and fully saturated heterocyclic groups. Heterocyclic systems may be attached to another moiety via any number of carbon atoms or heteroatoms of the radical and may be both saturated and unsaturated. Non-limiting examples of heterocyclic include pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

"Alkanoyl" means alkanoyl groups of a straight or branched configuration and of the specified number of carbon atoms. By way of non-limiting example, alkanoyl may be selected from acetyl, propionoyl, butyryl, isobutyryl, pentanoyl and hexanoyl.

Whenever a range of the number of atoms in a structure is indicated (e.g., a $C_1$-$C_{20}$, $C_1$-$C_{12}$, $C_1$-$C_{10}$, $C_1$-$C_9$, $C_1$-$C_6$, $C_1$-$C_4$, or $C_2$-$C_{20}$, $C_2$-$C_{12}$, $C_2$-$C_{10}$, $C_2$-$C_9$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-20 carbon atoms (e.g., $C_1$-$C_{20}$), 1-12 carbon atoms (e.g., $C_1$-$C_{12}$), 1-10 carbon atoms (e.g., $C_1$-$C_{10}$), 1-9 carbon atoms (e.g., $C_1$-$C_9$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkanoyl, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In one embodiment, the compound of formula I is selected from the group consisting of:

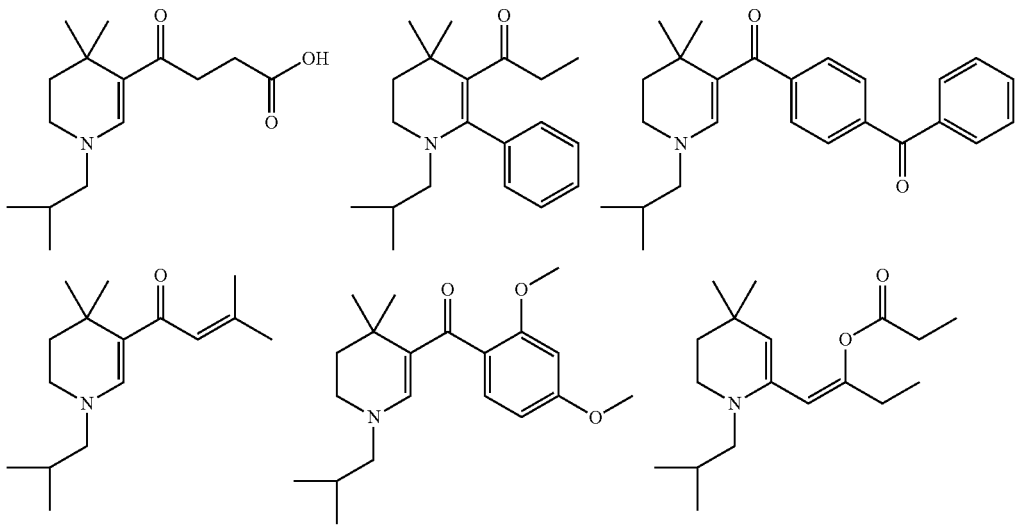

-continued
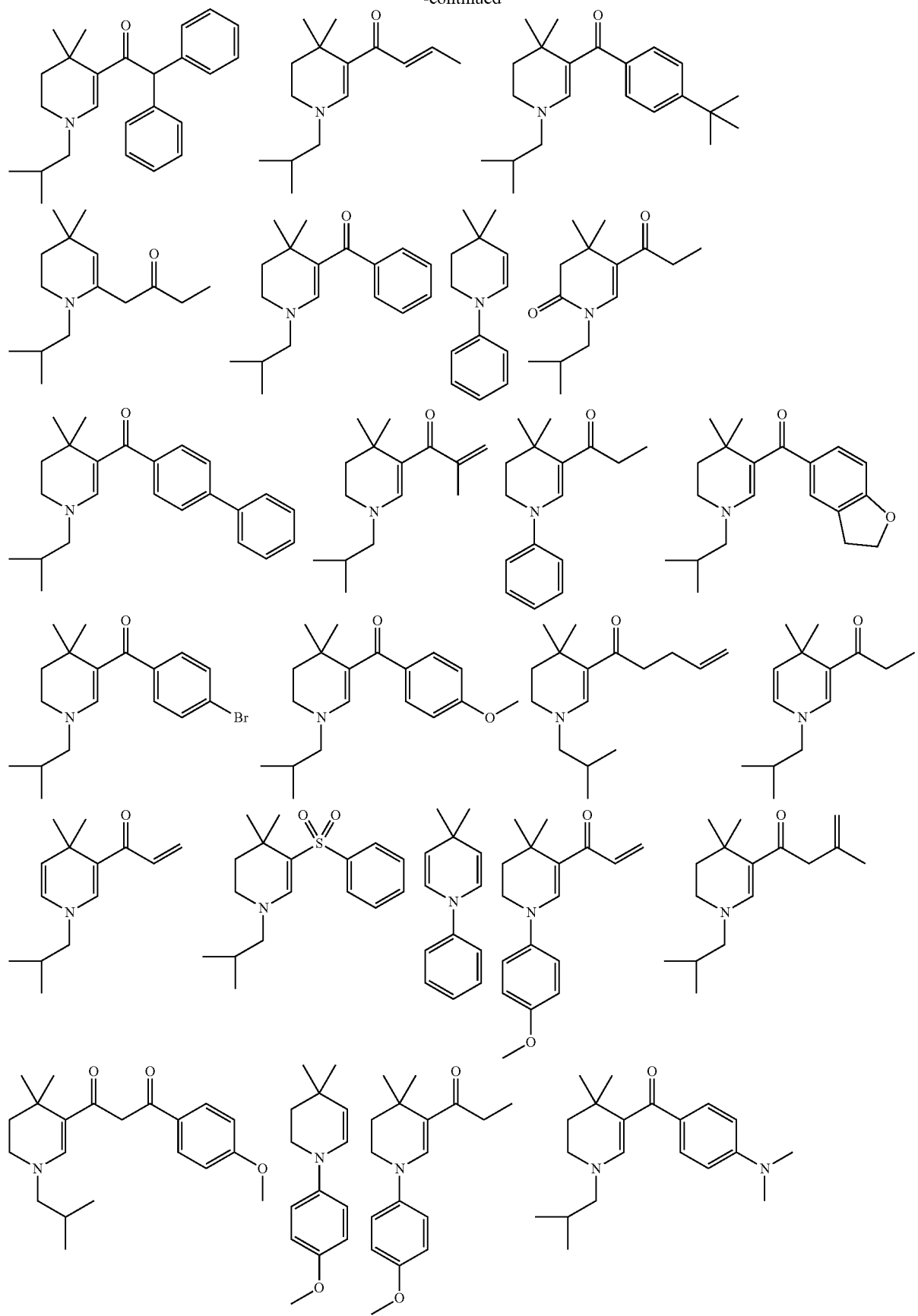

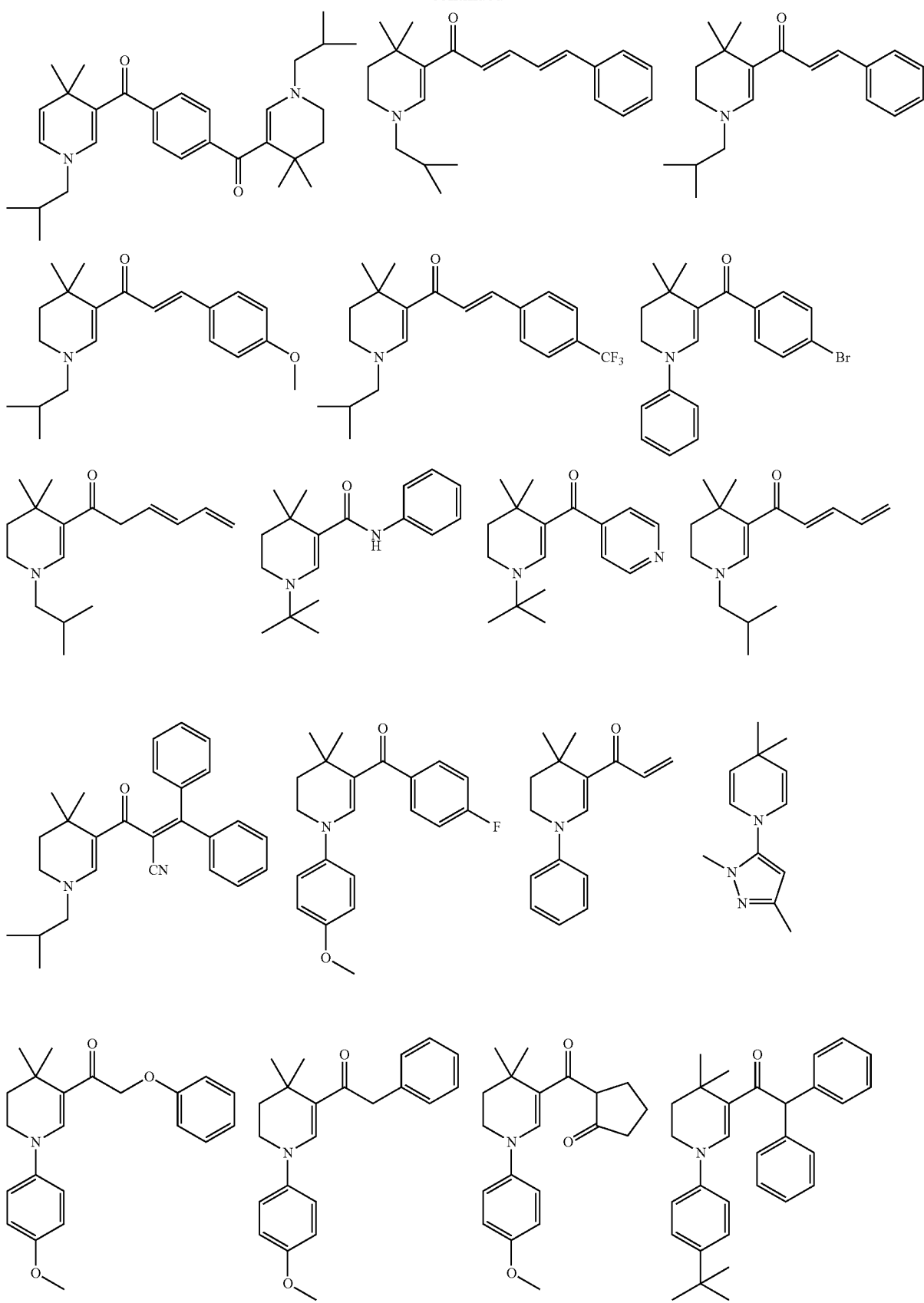

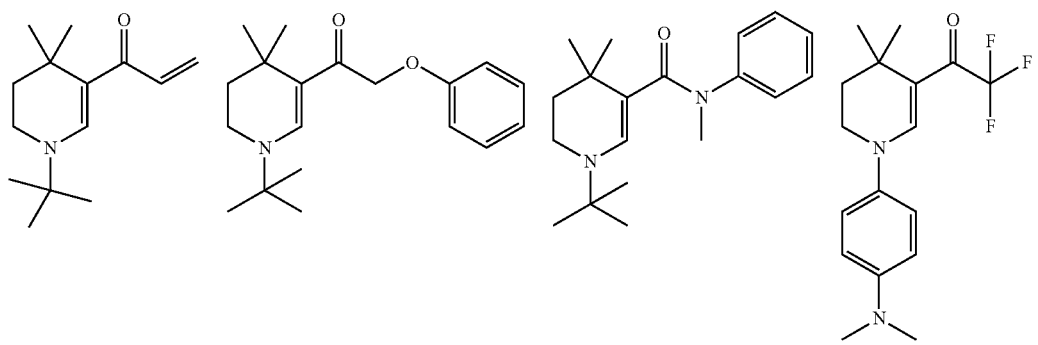
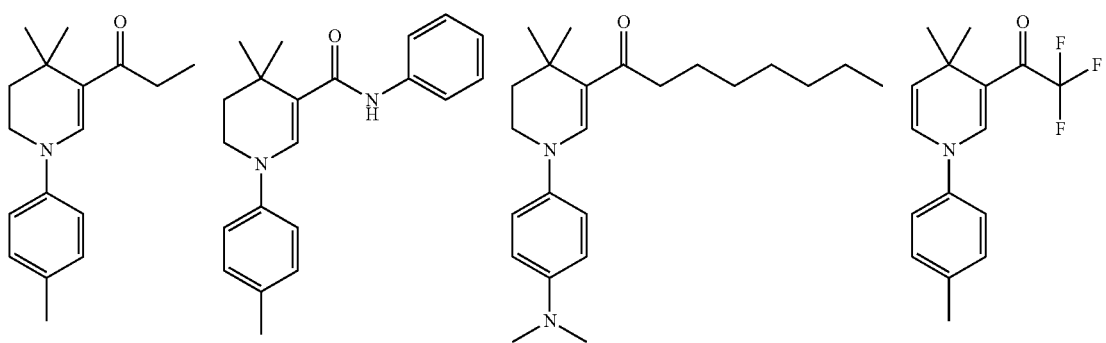
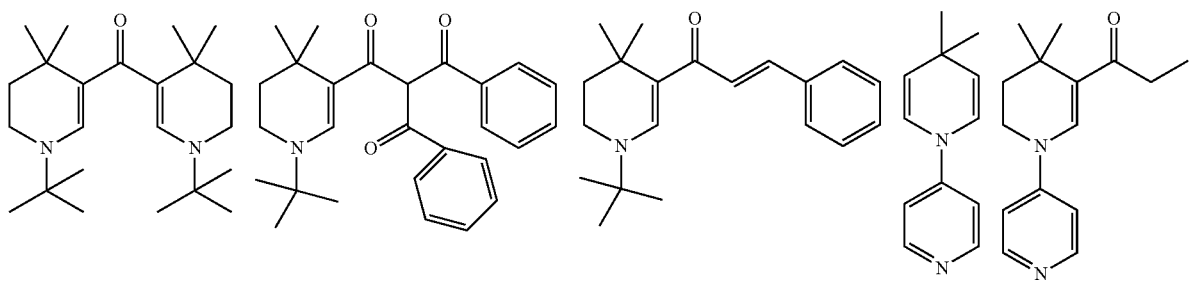
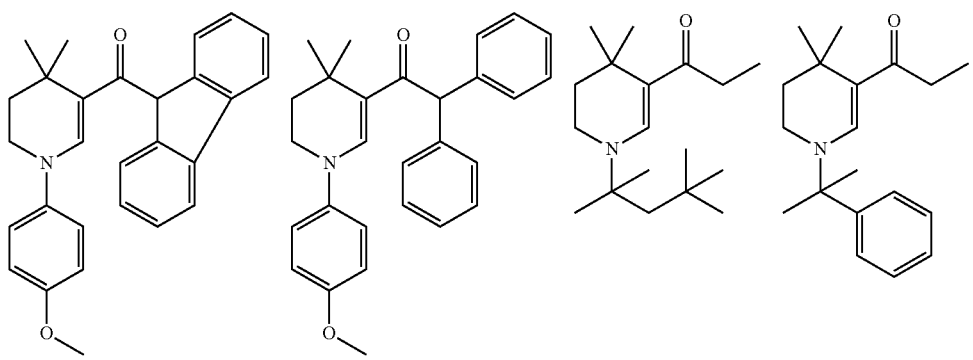

-continued
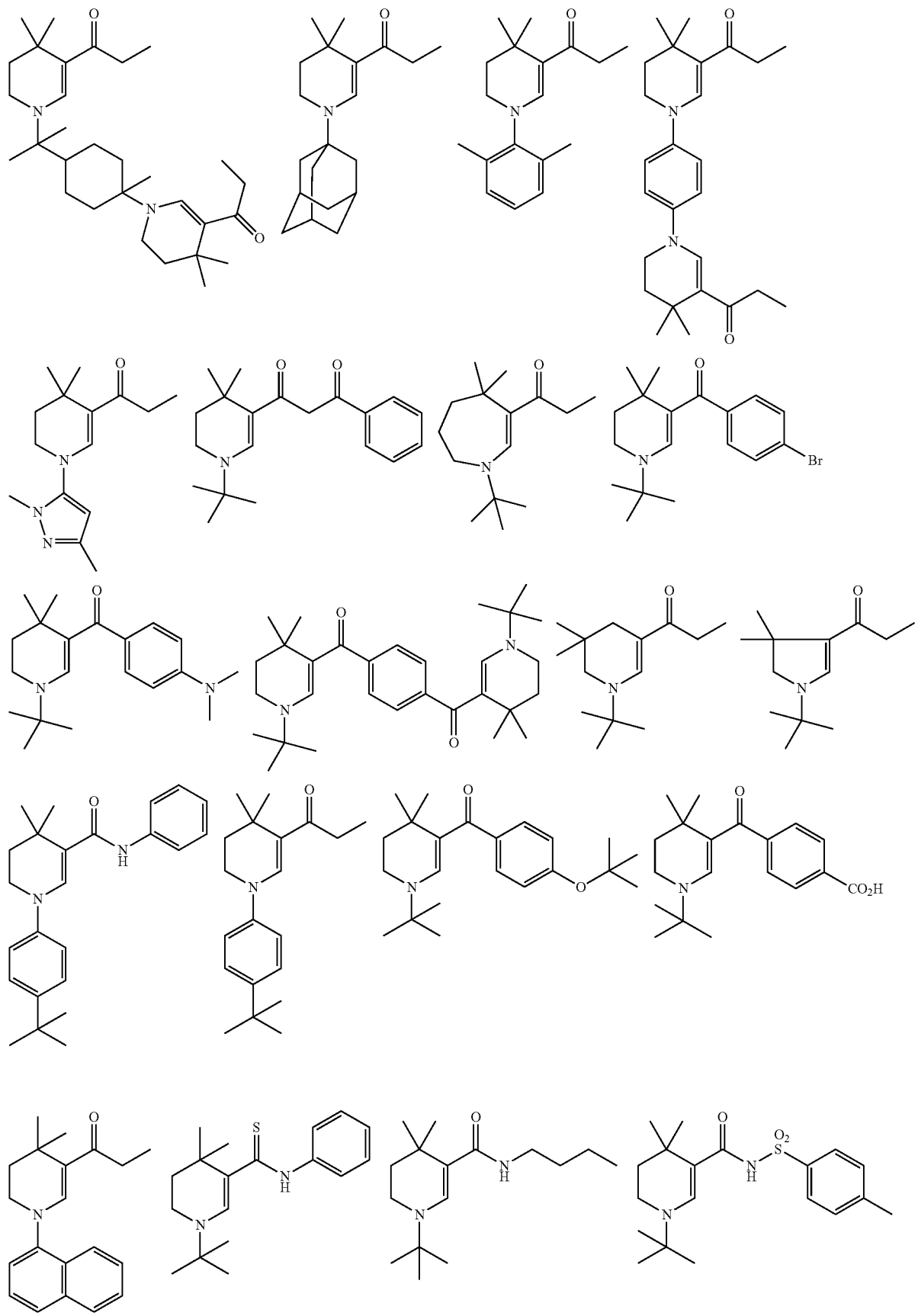

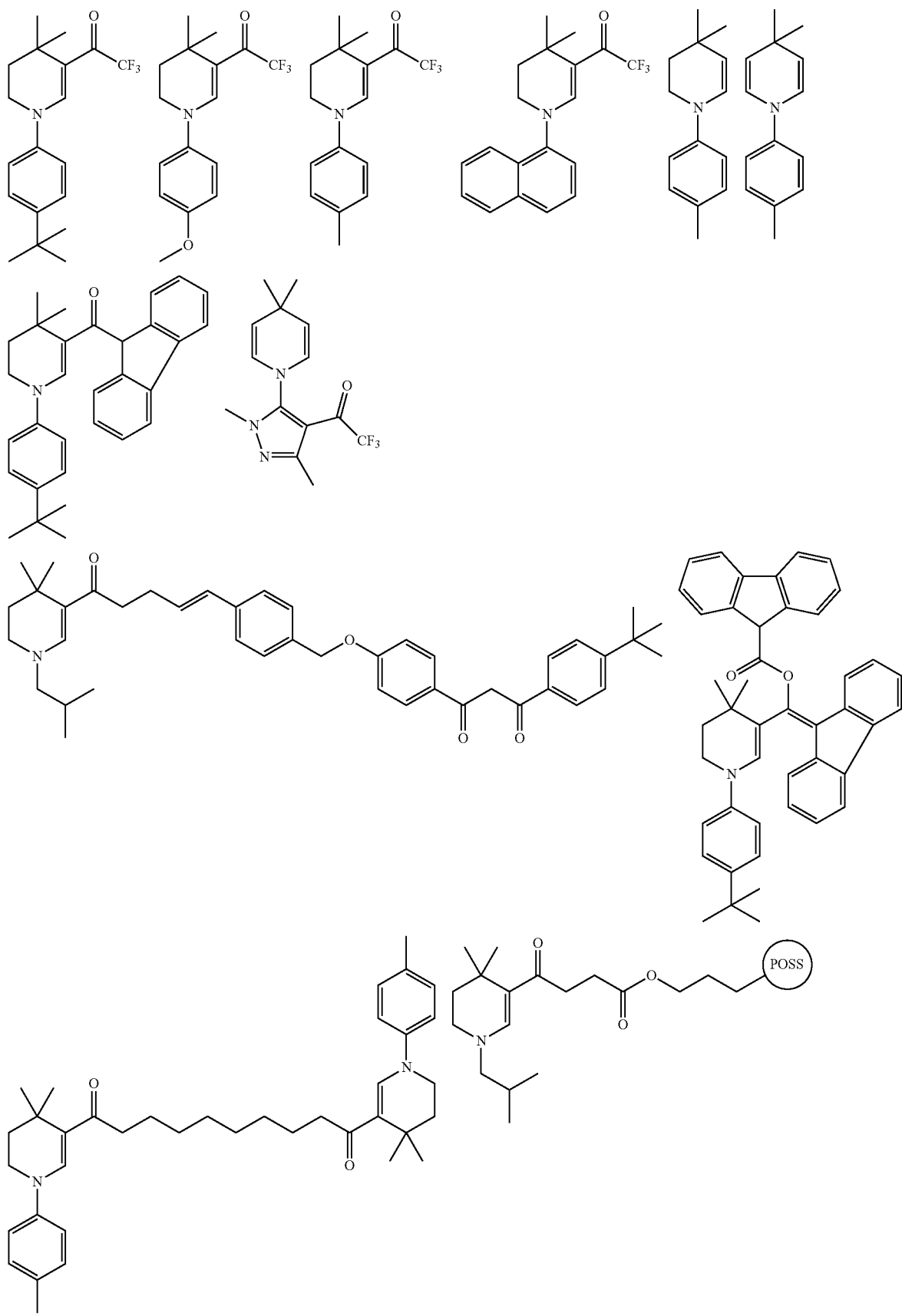

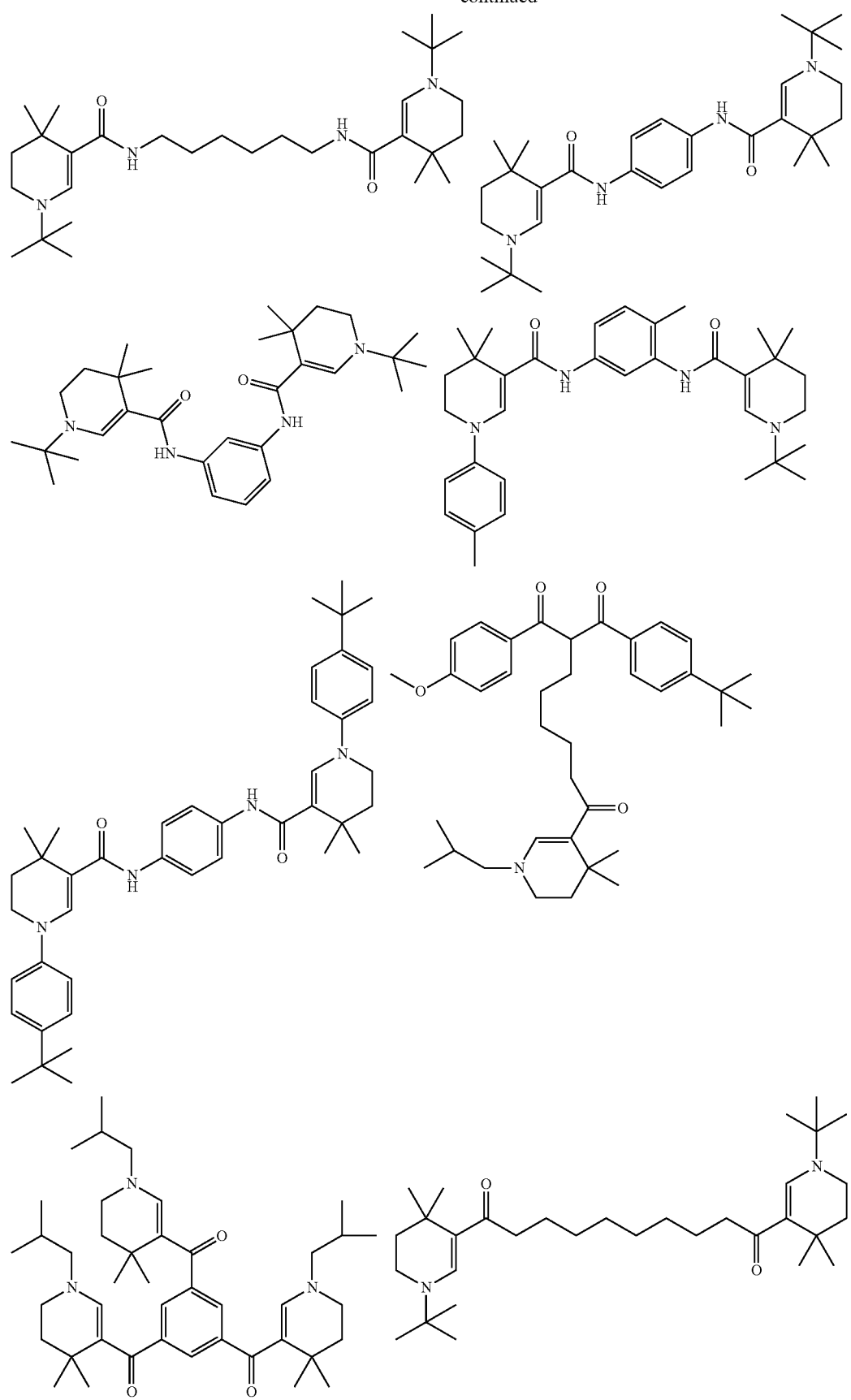
and

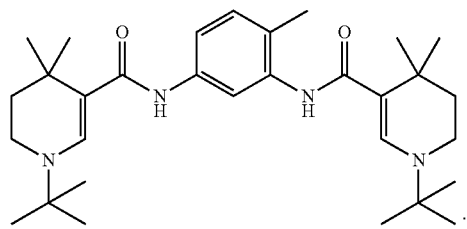

In one embodiment of the compound of formula I, the dashed line is not a bond and X is one carbon;

$R_1$ and $R_2$ are independently selected from the group consisting of methyl, ethyl, propyl and butyl;

$R_4$, $R_6$, $R_{18}$ and $R_{19}$ are hydrogen;

$R_3$ is selected from the group consisting of hydrogen, benzenesulfonyl and

wherein W is sulphur or oxygen, preferably oxygen, and $R_7$ is selected from the group consisting of

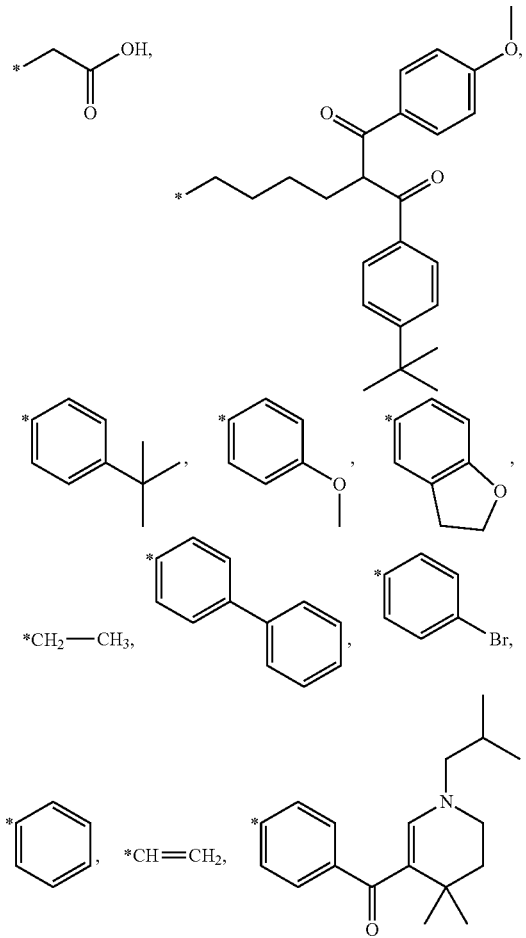

-continued

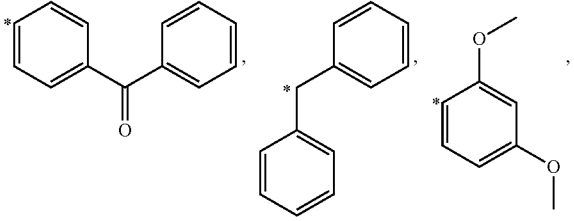

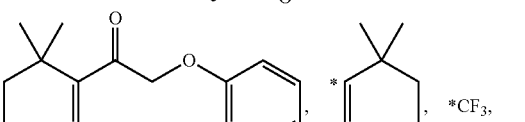

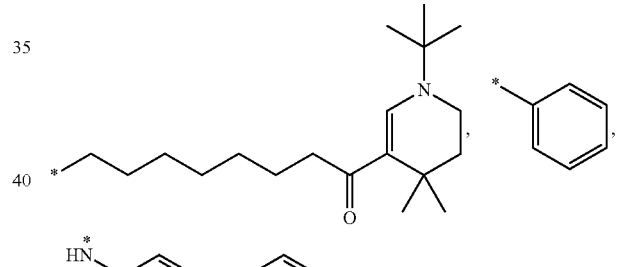

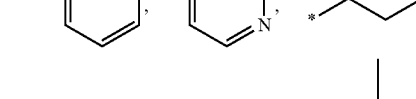

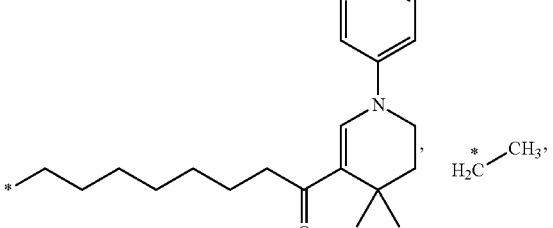

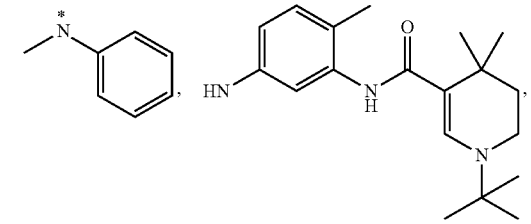

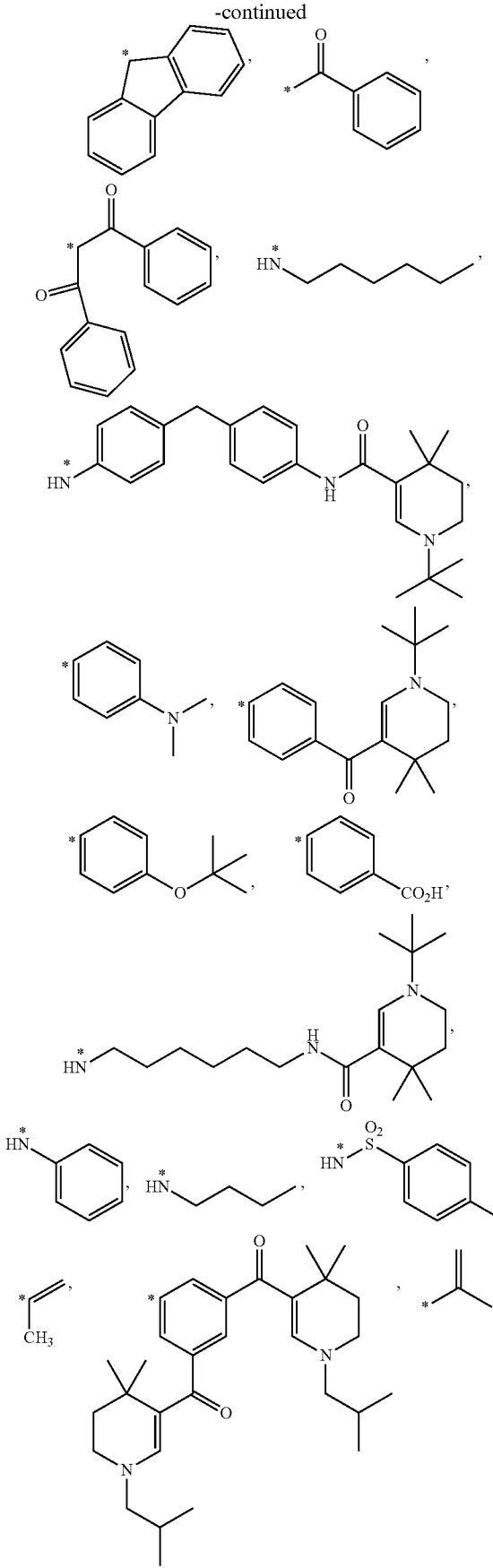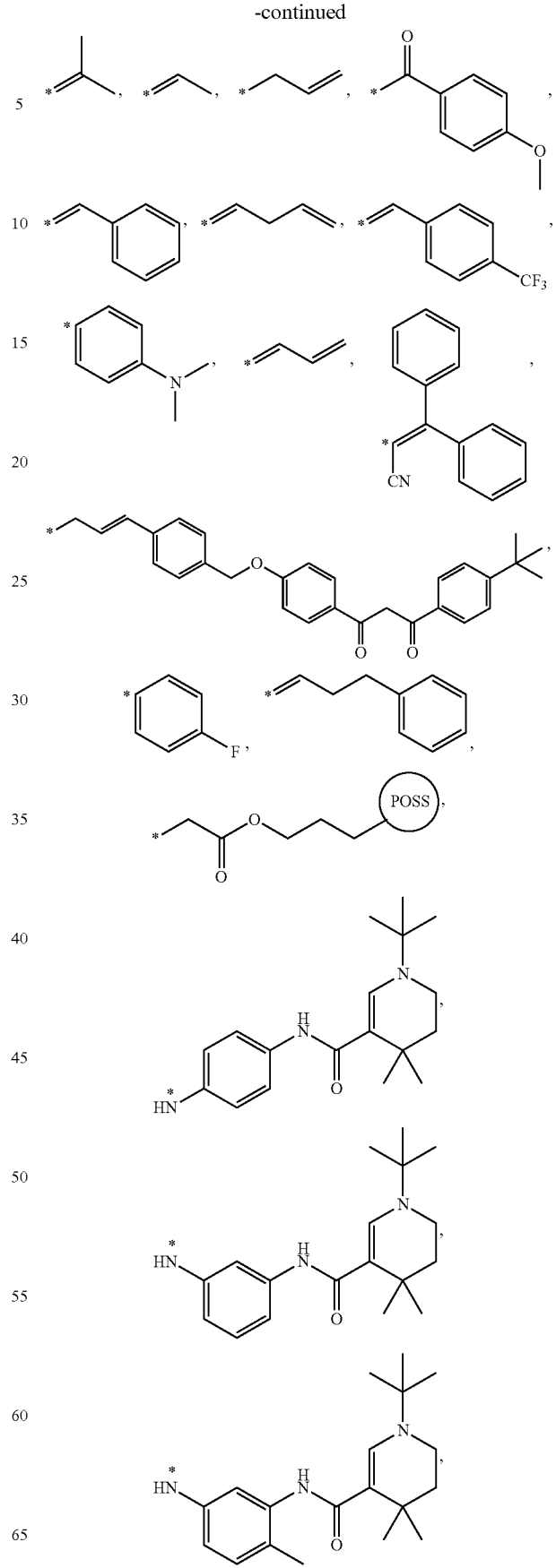

-continued

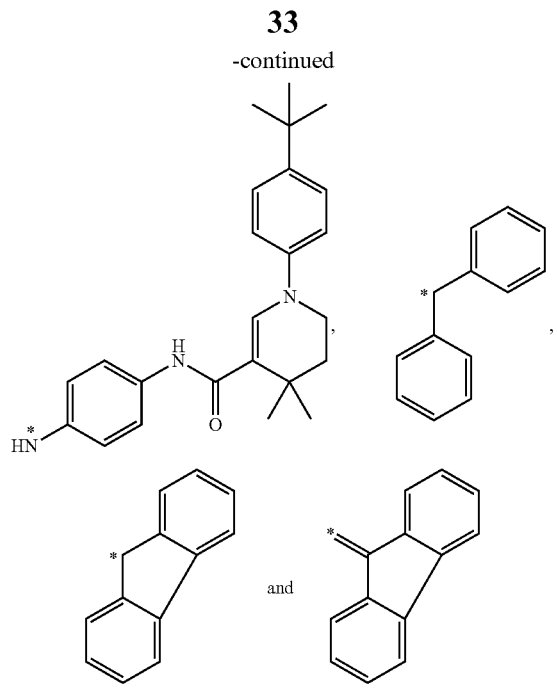

wherein * represents the carbon atom which is attached to the carbonyl carbon; and R₅ is selected from the group consisting of

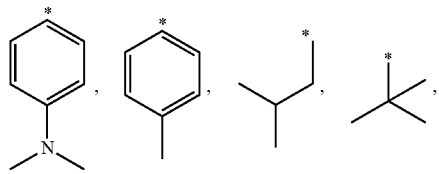

-continued

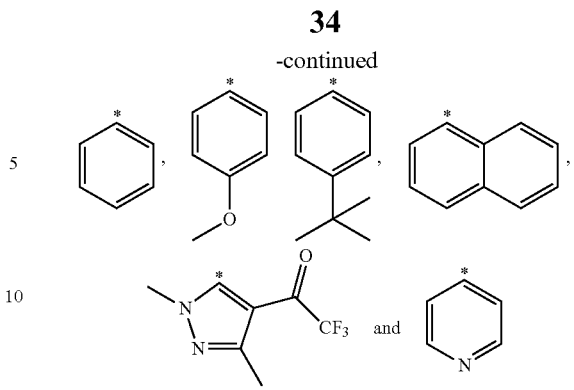

with the proviso that when $R_5$ is alkyl then $R_7$ is not an unsubstituted alkyl chain, an ester or an ether.

In some embodiments, compounds with one or more chiral centers, or exhibiting some form of isomerism, are provided. The compounds disclosed herein as UV absorbing agents may contain chiral centers, which may be either of the (R) or (S) configuration, or which may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds and prodrugs of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Compound Synthesis and Strategy

A general approach to deliver cyclic enaminoketones in large scale quantities has been developed by the applicant and is shown in Scheme 1 below:

Scheme 1: Synthetic route to 1, 3, 4-substituted cyclic enaminoketones.

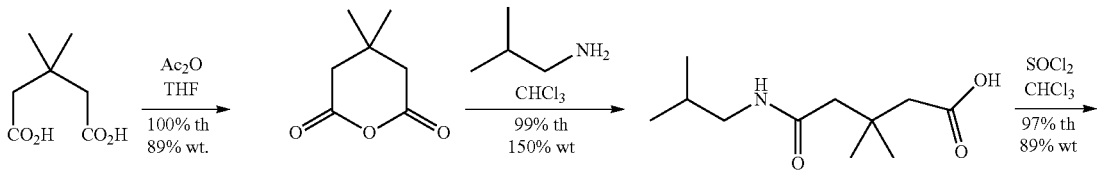

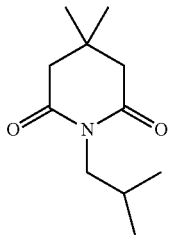

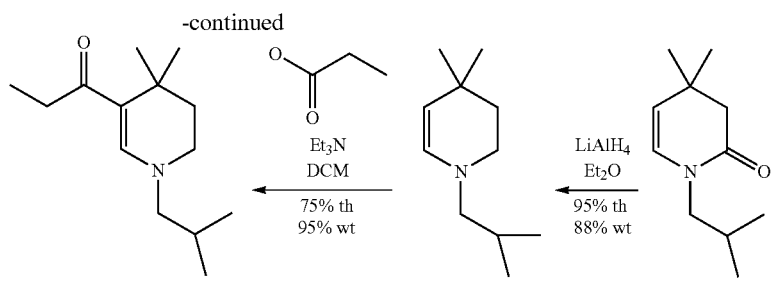

This approach allowed access to a wide range of cyclic enaminoketones with varying substituents. Modifications of the scheme and use of the intermediates to access a variety of products provides for a means to tailor the final product in terms of lipophilicity and absorbance maximum. By way of example, a wide range of amines could be employed at the second step to give a range of alkyl, alkenyl, aryl etc. groups on the ring opened compound. This means that the N-linked isobutyl group in Scheme 1 could be replaced with, for example tert-butyl, aryl, substituted ary and the like in a convenient manner.

Diketone Coupling

The absorbance maximum of an enaminoketone was proposed to be modified by coupling to an aromatic diketone which could potentially extend the absorbance into the UVA range. This was achieved by formation of an alkyl halide enaminoketone (4) which was then reacted, with the 1,3-aromatic diketone shown in scheme 2, in the presence of t-butylammonium fluoride (TBAF).

Scheme 2: Synthesis of covalently linked compound 5.

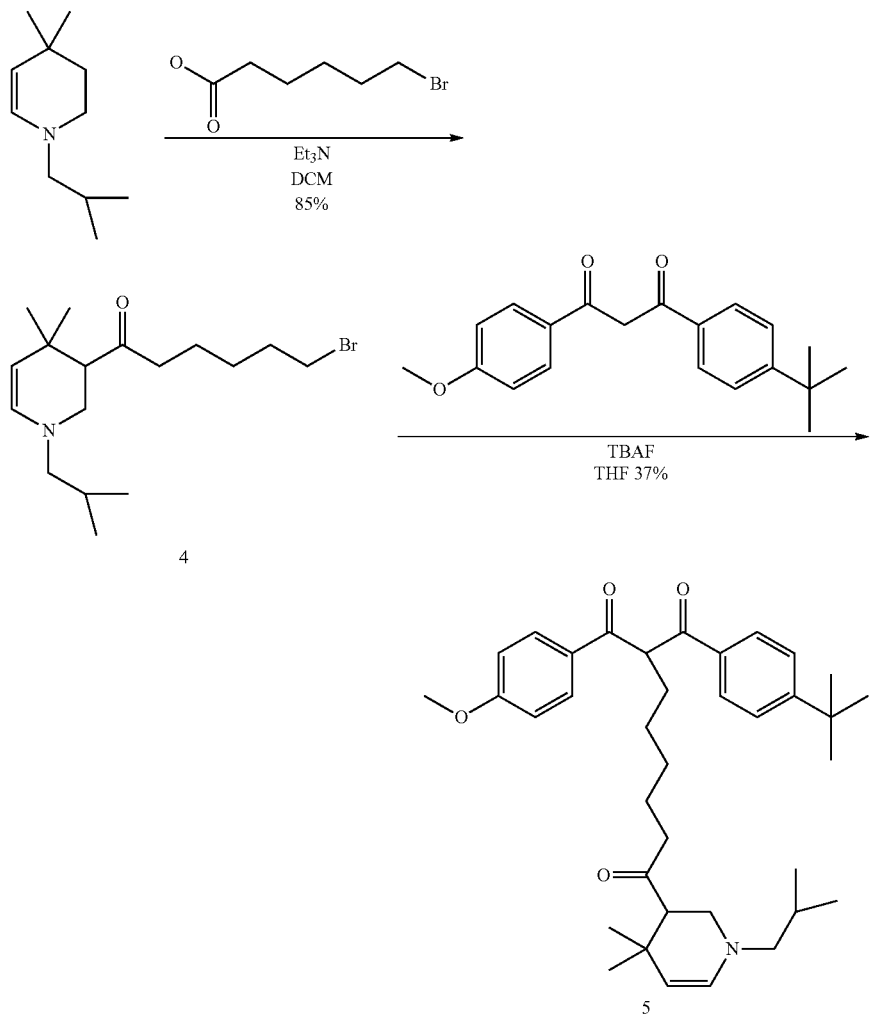

Examination of the UV absorbing properties of 5 showed a single significant maximum in the UV range at 306 nm due to the enaminoketone chromophore. The alkylation of the central carbon of a 1,3-diketone may minimize the formation of the enol tautomers which are believed to be required for UVA absorbance.

To provide alternative compounds a strategy was used involving coupling of a complete 1,3-diketone moiety to a suitably functionalised enaminoketone (Scheme 3). In this way, alkenyl enaminoketone derivative 8 and arylbromide functionalised 1,3-diketone 9 were synthesised and coupled under palladium catalysis to give covalently linked compound 10. Compound 10 was isolated as a mixture of double bond isomers (confirmed by $^1$H NMR and LC-MS which demonstrated multiple closely running peaks with the same mass).

Scheme 3: Strategy for synthesis of O-linked covalently linked compound 10.

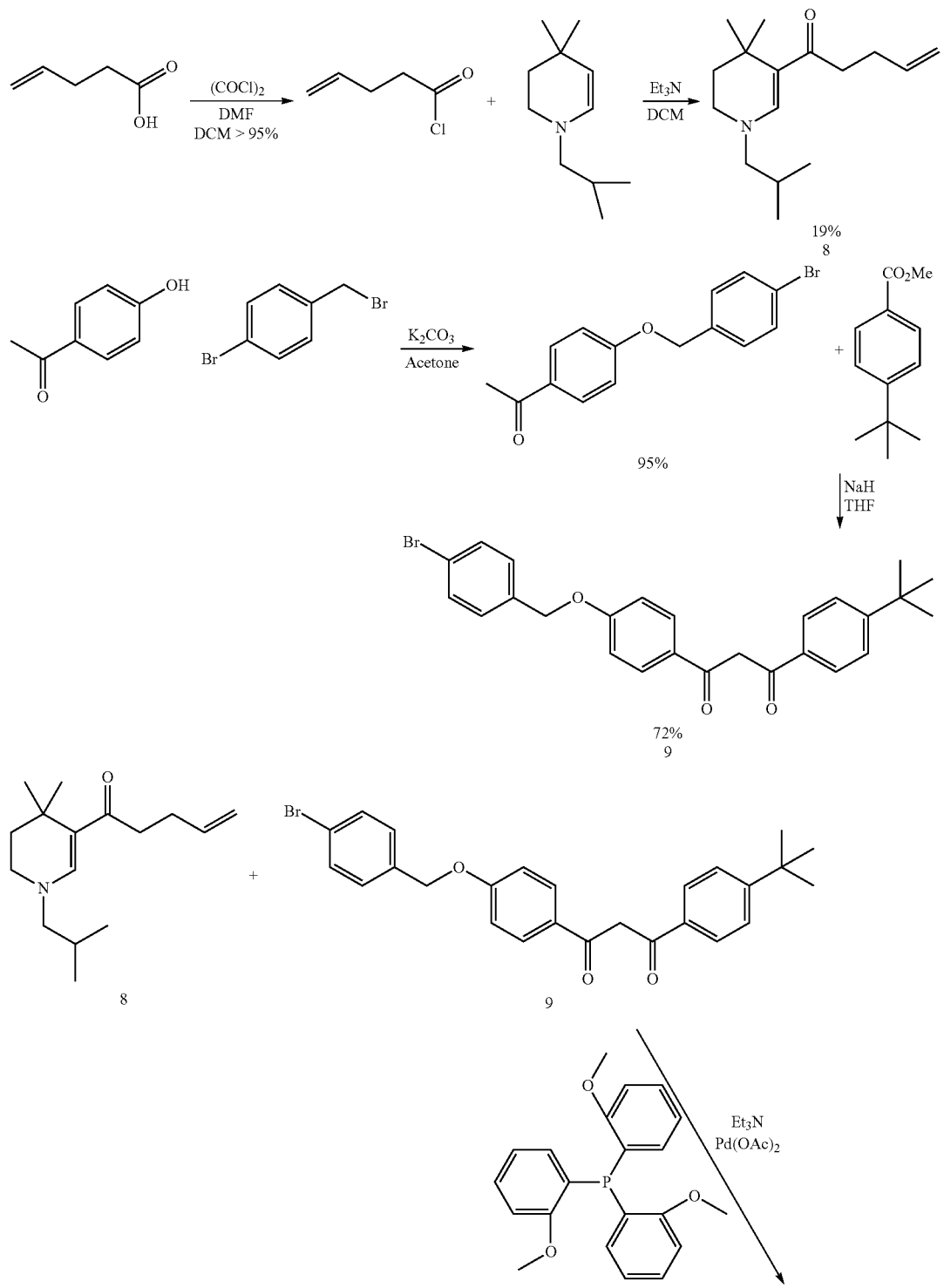

-continued

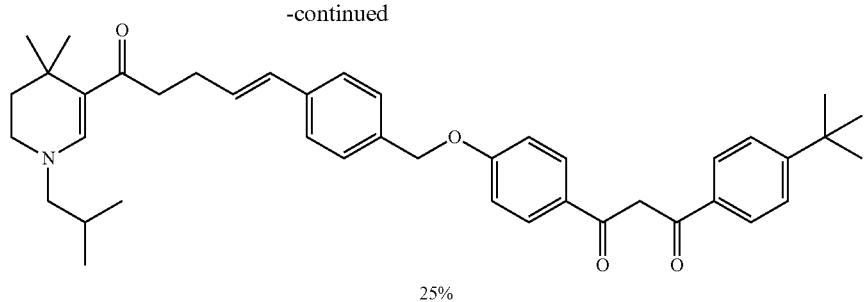

25%

Compound 10 was found to possess advantageous UV absorption characteristics with a double maxima in the UV range—one relating to the enaminoketone chromophore at 314 nm and a second at 357 nm as a result of the benzophenone chromophore (Table 1). This proves that the enaminoketone core can be modified via coupling to extend to broad spectrum coverage. A further advantage of compound 10 is in the higher c Log P value. The UV absorption of intermediate 8 is also presented in Table 1.

TABLE 1

UV absorption properties of covalently coupled compounds.

| Structure | Mw | cLog P | $\lambda_{max}$ (nm) | $\lambda_{crit}$ (nm) | $\varepsilon$ M$^{-1}$ cm$^{-1}$ | E (1%, 1 cm) |
|---|---|---|---|---|---|---|
| 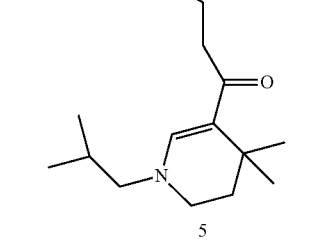 5 | 574 | 8.1 | 306 | ND | ND | ND |
| 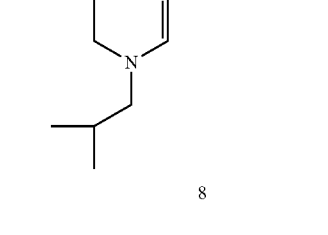 8 | 249 | 3.4 | 308 | ND | 35000 | 1417 |
| 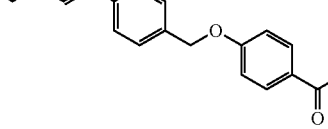 10 | 634 | 9 | 314<br>357 | 375 | 23250<br>24050 | 366<br>379 |

Variation at the Enaminoketone Carbonyl

Compounds 11 and 12 were synthesised which combined either the left or right hand sides of the 1,3-diketone used in the previous covalent coupling experiments with the cyclic enaminoketone core (Scheme 4). Yields were somewhat lower than those generally seen when acylating the cyclic enamine with an alkyl acyl chloride due, at least in part, to the lower electrophilicity of the benzoyl acid chlorides. Furthermore, as the benzyl acid chlorides lack an α proton they are unable to form more reactive ketene intermediates. Compound 13 which incorporates both the familiar cyclic enamine and the 1,3-diketone moiety was produced via a similar pathway although it was necessary to synthesise the acyl chloride from the corresponding commercially available ester (Scheme 4).

Scheme 4: Strategy for the synthesis of compounds varying at the ketone.

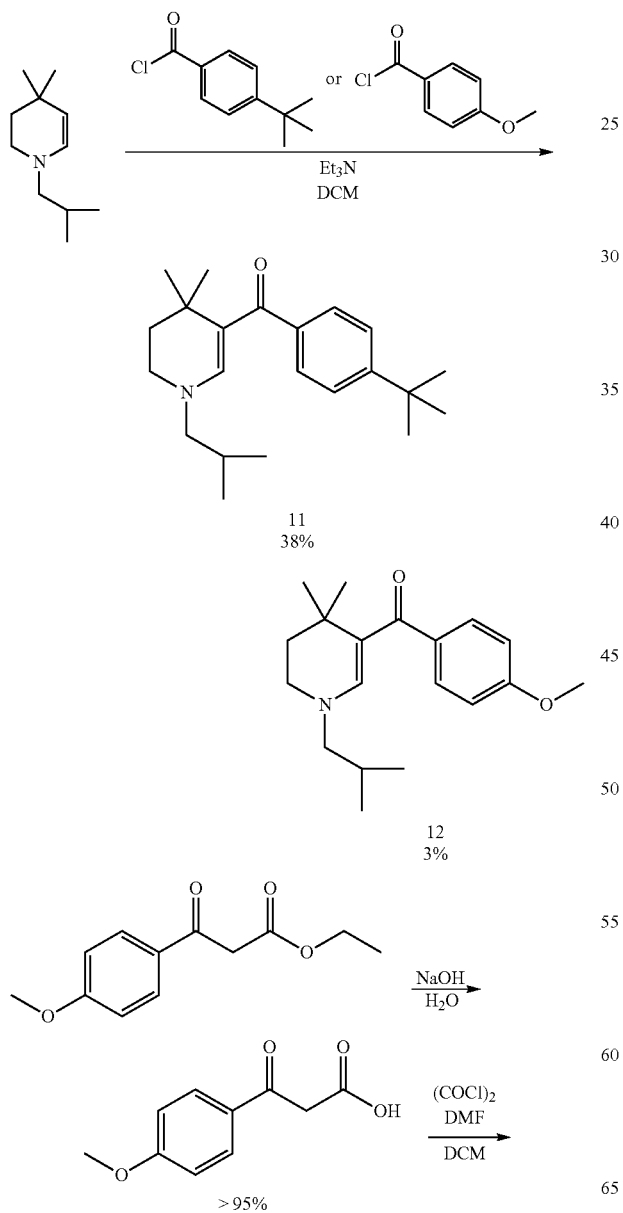

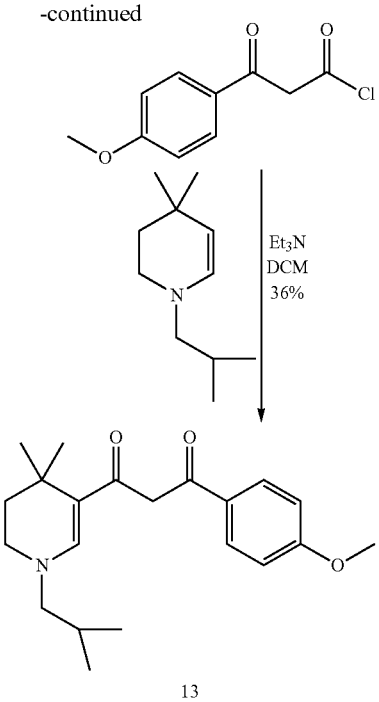

The UV absorbance of these compounds can be seen in Table 2. Introduction of the t-butyl phenyl (11) or methoxy (12) substituted benzoyl groups of the 1,3-diketone used previously resulted in an advantageous shift in absorption of the enaminoketone compound towards the UVA region of approximately 11 nm. Compound 13 exhibited double absorption maxima with $\lambda_{max}$ values of 293 and 396 and a critical wavelength of 389 nm. This provides for absorption over a range unavailable to the simple enaminoketones of the 718 patent. The position of the absorption maxima of this compound could also be optimised by modification of the substituents.

In compounds where it was desirable to have an amido linkage at the $R_3$ position, such as those nonlimiting examples shown below:

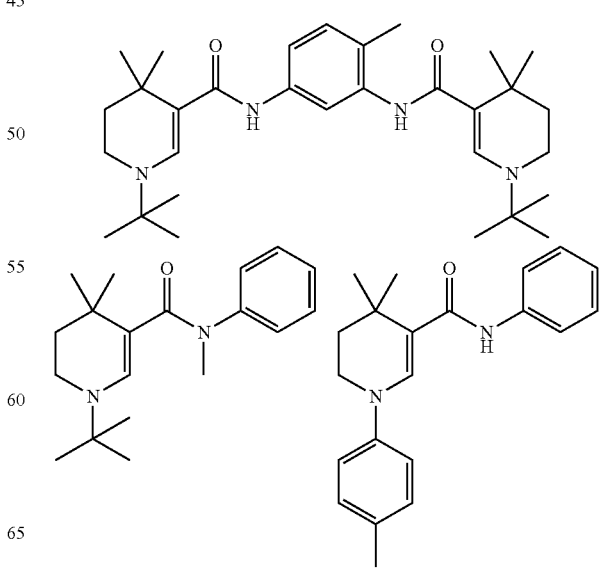

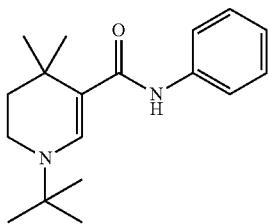

then the group can be formed via reaction with an isocyanate reactant as opposed to the acid chloride approach already described. The starting isocyanates are cheap and readily available and it has been found that the compounds above are highly absorbing colourless solids and therefore potentially useful as UV absorbing agents in formulations such as sunscreen formulations. Therefore, in one embodiment, the $R_3$ moiety is introduced by reaction of an isocyanate with the appropriate core.

TABLE 2

UV absorption properties of compounds 11-13.

| Structure | Mw | cLog P | $\lambda_{max}$ (nm) | $\lambda_{crit}$ (nm) | $\epsilon$ $M^{-1}$ $cm^{-1}$ | E (1%, 1 cm) |
|---|---|---|---|---|---|---|
| 11 | 327 | 5.7 | 317 | ND | 19000 | 581 |
| 12 | 301 | 3.9 | 319 | ND | ND | ND |
| 13 | 343 | 3.5 | 293 396 | 389 | 14250 11150 | 415 324 |

Further, representative reactions between isocyanates and a representative N-substituted enamine are shown below in Scheme 5.

Scheme 5: Representative isocyanate reactions.

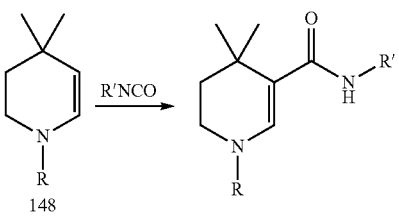

148

A number of specific isocyanate reactions are shown below in Scheme 6.

Scheme 6: Isocyanate reactions on an N-t-butyl enamine scaffold.

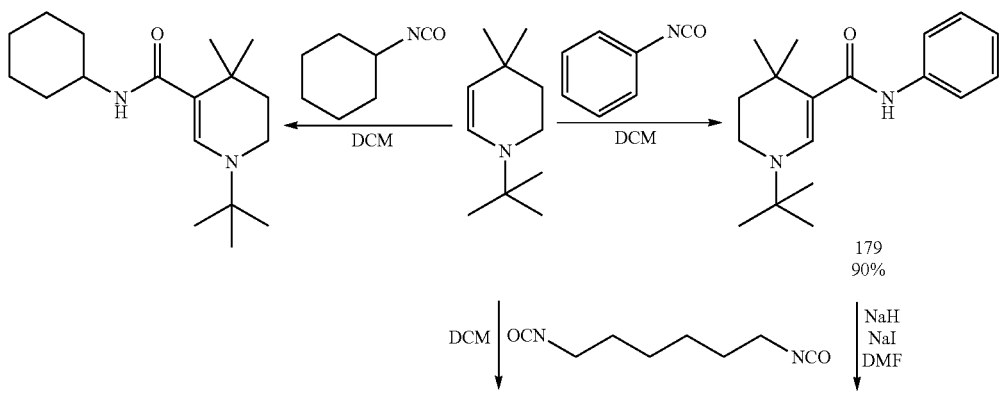

179
90%

-continued

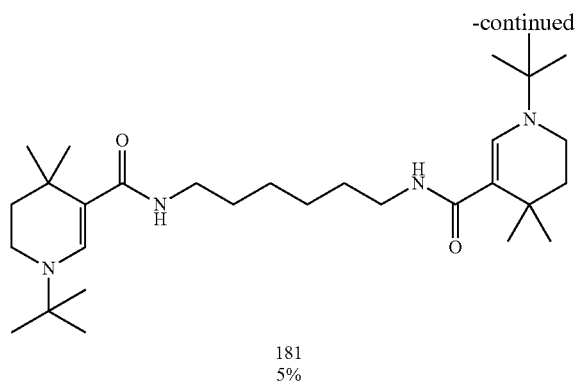

181
5%

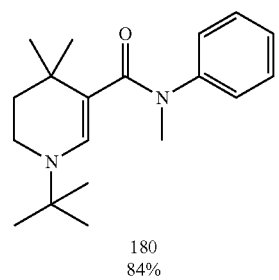

180
84%

A number of reactions were also carried out on this template using isothiocyanates as shown in Scheme 7.

Scheme 7: Isothiocyanate reactions on an N-t-butyl enamine scaffold.

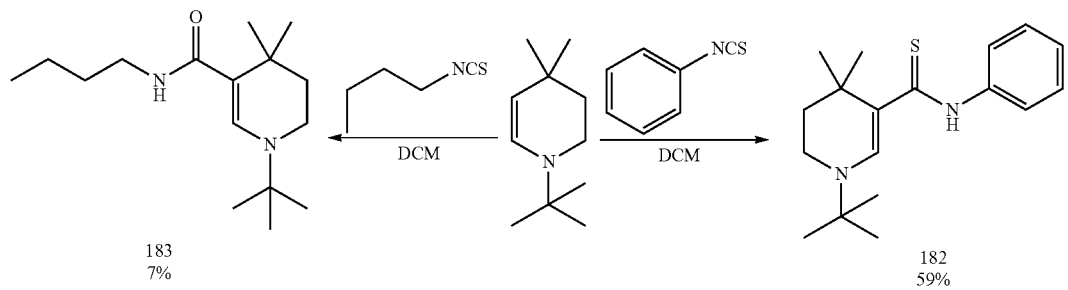

183
7%

182
59%

The compounds prepared and their physical and UV absorption properties can be seen in Table 3. The compound obtained on reaction with phenyl isocyanate 179 was an efficient UV absorber with an ε value of almost 35000. N-methylation gave a slight increase in $\lambda_{max}$ to 312 nm. A number of higher molecular weight compounds were synthesised from commercially available aryl diisocyanates. These generally had similar $\lambda_{max}$ values to compound 179 but much higher ε values due to the presence of a second chromophore. The compound derived from reaction with 1,4-phenylene diisocyanate, 187, had a $\lambda_{max}$ which was shifted upwards to 322 nm. This could be due to the effect of doubling effect of a para-nitrogen substituent on the parent chromophore 179 or the possibility of electron transfer through the whole of the 1,4-disubstituted phenyl system allowing "linking" of the two separate chromophores.

TABLE 3

Compounds synthesized by reaction with isocyanates or isothiocyanates.

| Structure | Mw | ClogP | $\lambda_{max}$ (nm) | $\lambda_{crit}$ (nm) | ε | E (1%, 1 cm) |
|---|---|---|---|---|---|---|
| 179 | 286 | 4.76 | 308 | 326 | 34834 | 1217 |

TABLE 3-continued
Compounds synthesized by reaction with isocyanates or isothiocyanates.
| Structure | Mw | ClogP | $\lambda_{max}$ (nm) | $\lambda_{crit}$ (nm) | ε | E (1%, 1 cm) |
|---|---|---|---|---|---|---|
| 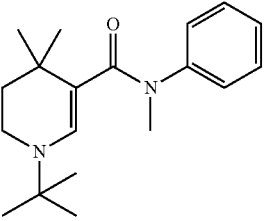 180 | 300 | 5.28 | 312 | 337 | 15174 | 506 |
| 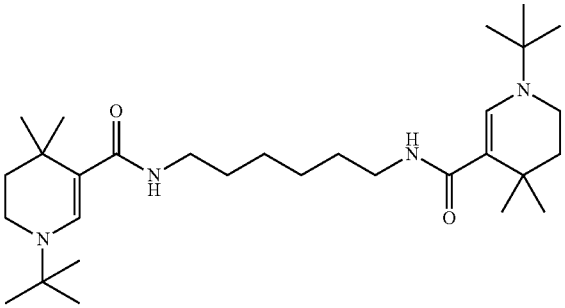 181 | 502 | 7.07 | 289 | 314 | 31072 | 619 |
| 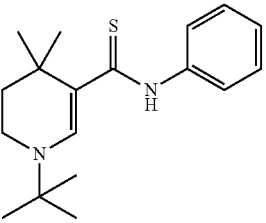 182 | 302 | 5.33 | 363 | 387 | 20881 | 691 |
| 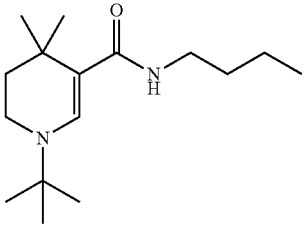 183 | 282 | 4.77 | 288 | 312 | 22531 | 799 |
| 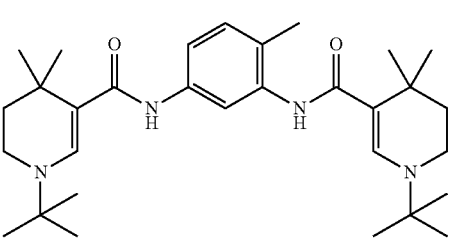 184 | 509 | 6.61 | 308 | 329 | 59763 | 1174 |

TABLE 3-continued

Compounds synthesized by reaction with isocyanates or isothiocyanates.

| Structure | Mw | ClogP | $\lambda_{max}$ (nm) | $\lambda_{crit}$ (nm) | ε | E (1%, 1 cm) |
|---|---|---|---|---|---|---|
| 185 | 584 | 9.13 | 310 | 328 | 64589 | 1105 |
| 186 | 364 | 4.21 | 304 | 319 | 34588 | 950 |
| 187 | 494 | 7.06 | 322 | 346 | 71962 | 1456 |
| 188 | 494 | 7.06 | 313 | 328 | 55779 | 1129 |

Similar reactions using isocyanates could also be carried out on N-aryl enamine scaffolds although longer reaction times and/or heating was typically required to achieve product. Table 4 shows the N-aryl products of select isocyanate reactions along with their UV absorbing properties.

TABLE 4

Compounds prepared by the reaction of N-aryl enamines with isocyanates.

| Structure | Mw | ClogP | $\lambda_{max}$ (nm) | $\lambda_{crit}$ (nm) | ε | E (1%, 1 cm) |
|---|---|---|---|---|---|---|
| 190 | 542 | 7.68 | 314 | 340 | 51743 | 954 |
| 191 | 646 | Can't calc | 331 | 354 | 68095 | 1054 |
| 192 | 320 | 5.52 | 323 | 342 | 33948 | 1060 |

TABLE 4-continued

Compounds prepared by the reaction of N-aryl enamines with isocyanates.

| Structure | Mw | ClogP | $\lambda_{max}$ (nm) | $\lambda_{crit}$ (nm) | ε | E (1%, 1 cm) |
|---|---|---|---|---|---|---|
| 193 | 362 | 6.85 | 324 | 342 | 35759 | 987 |

As observed with the acid chloride-based systems, below, the compounds derived from N-aryl enamines have higher $\lambda_{max}$ values than the corresponding N-t-butyl enamine-based compounds whilst maintaining high ε values.

Acylation reactions using acid chlorides were carried out on t-butyl analogues as shown in Scheme 8, below.

Scheme 8: Acylation reactions of N-t-butyl enamine compound with acid chlorides.

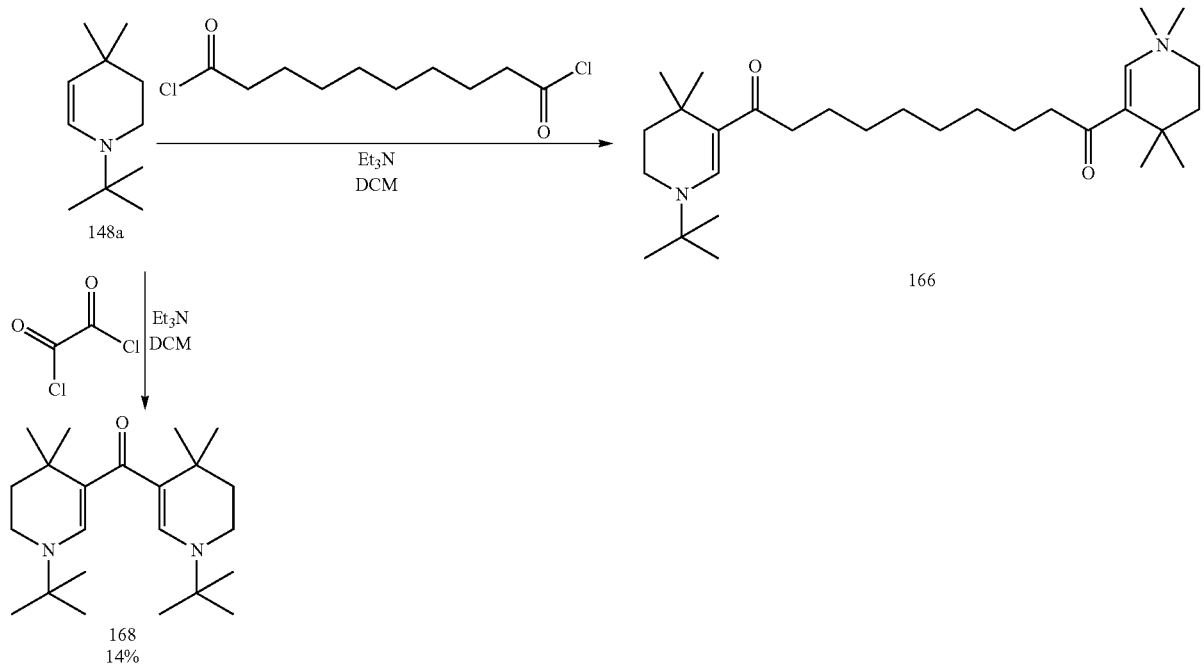

It will be appreciated, again, that a variety of isocyanates, isothiocyanates and acid chlorides can potentially be used to achieve variation at the $R_3$ position.

The compounds prepared and their physical and UV absorption properties can be seen in Table 5.

TABLE 5
Novel UV absorbers prepared by acylation of N-t-Bu enamine
| Structure | Mw | ClogP | $\lambda_{max}$ (nm) | $\lambda_{crit}$ (nm) | ε | E (1%, 1 cm) |
|---|---|---|---|---|---|---|
| 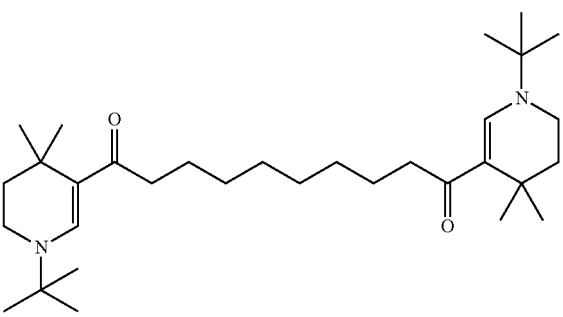 166 | 500 | 9.01 | 307 | 322 | 54797 | 1095 |
| 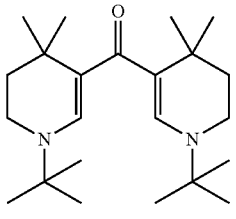 167 | 360 | 7.16 | 305 (330 shoulder) | 351 | 16425 | 456 |
| 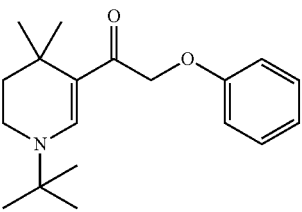 168 | 301 | 4.99 | 313 | 329 | 26154 | 869 |
| 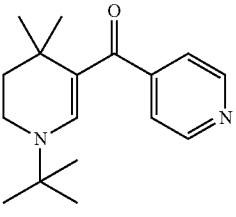 169 | 272 | 4.27 | 316 | 354 | 23556 | 866 |
| 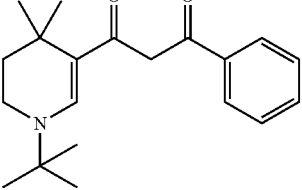 170 | 313 | 4.66 | 309 396 | 385 | 19993 8961 | 638 286 |

As can be seen bis(enaminone) compound 166 was a strongly absorbing high molecular compound with an ε in excess of 54000 due to the presence of 2 chromophores. Compound 170 was observed as an approximately 60:40 mixture of the ketone and enol forms. The enol form was thought to be responsible for the absorption maximum at 396 nm, resulting in a highly coloured compound.

Thus, in one embodiment, the compound of formula I may be a compound of formula IIa or IIb:

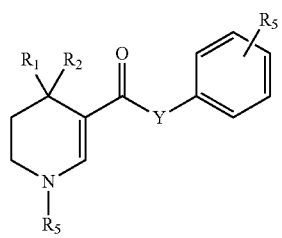

formula IIa

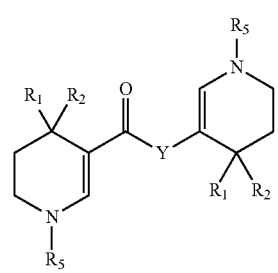

formula IIb

Wherein $R_1$, $R_2$ and $R_6$ are as previously described. Y, when present may be nitrogen, N-alkyl $C_1$ to $C_{18}$ alkyl optionally substituted with oxo, hydroxyl, alkoxy and halo and may be oxygen linked to the ring. $R_8$, when present, may be selected from the group consisting of $C_1$ to $C_6$ alkyl, substituted or unsubstituted, aryl, alkoxy, halo and amino.

Synthesis of Benzoyl Modified Compounds

To further extend the upward shift in UV absorption maximum observed with compounds 11 and 12, it was postulated that benzoyl analogues of the general structure 14 would be of interest (Scheme 9). These were generally prepared by the enamine acylation process shown in Scheme 1. When the desired acid chloride was not commercially available it was prepared from the carboxylic acid as set out in the experimental. Attempts were also made to perform the activation of benzoic acids with the use of 1-ethyl-3-(3-dimethylaminopropyl)carbodiimide) (EDCI), however, no product could be isolated, indicating a level of unpredictability with this reaction.

Scheme 9: Process used for the synthesis of C3-benzoyl substituted compounds.

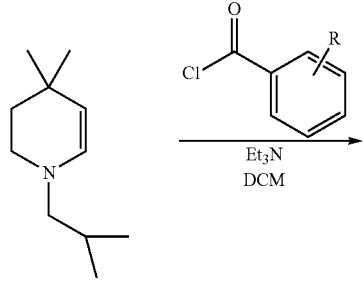

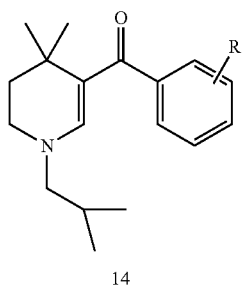

14

In the case of N,N-dimethylamino analogue 15, the corresponding electron rich benzoyl chloride presented a challenge in that it was insufficiently electrophilic to undergo reaction with the enamine under standard conditions. To overcome this problem, the related 4-bromo analogue, 16 was synthesised and a palladium catalysed amination reaction performed to give the desired compound (Scheme 10). The reaction shown in Scheme 11 was also performed using an analogue with the N-isobutyl group replaced by a N-tert-butyl group. This reaction is also outlined in Scheme 10.

Scheme 10: Process used for the synthesis of C3-(4'-N,N-dimethlaminobenzoyl) analogues.

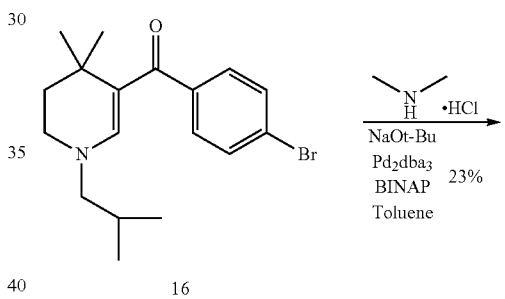

16

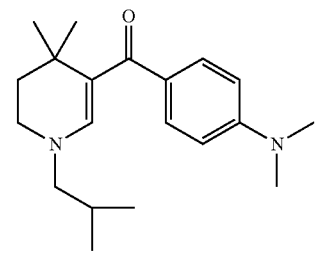

15

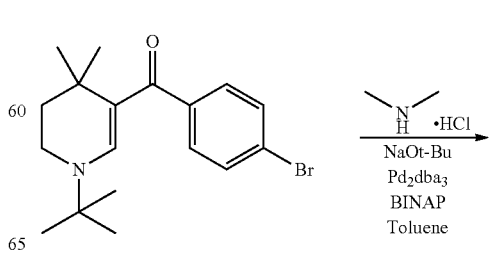

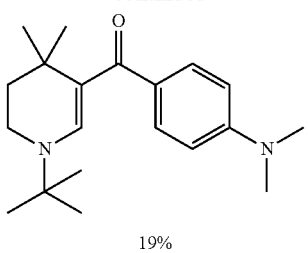

19%

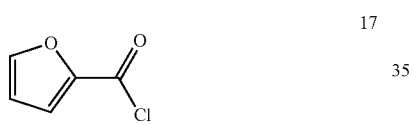

40%

Acylation of the cyclic enamine with 2-furoyl chloride 17 failed to deliver any product. The choice of acyl chloride must therefore be considered in terms of its electrophilicity and an appropriate synthetic approach selected on this basis.

17

Reaction of an N-tert-butyl enamine with terephthaloyl chloride is shown in Scheme 11, below. It was found that both the expected bis(enaminone) product and that derived from single acylation and hydrolysis were obtained in sufficient amounts to be isolated and tested.

Scheme 11: Process used for the synthesis of bis(enaminone) compounds with monoacylated/hydrolysis product also obtained.

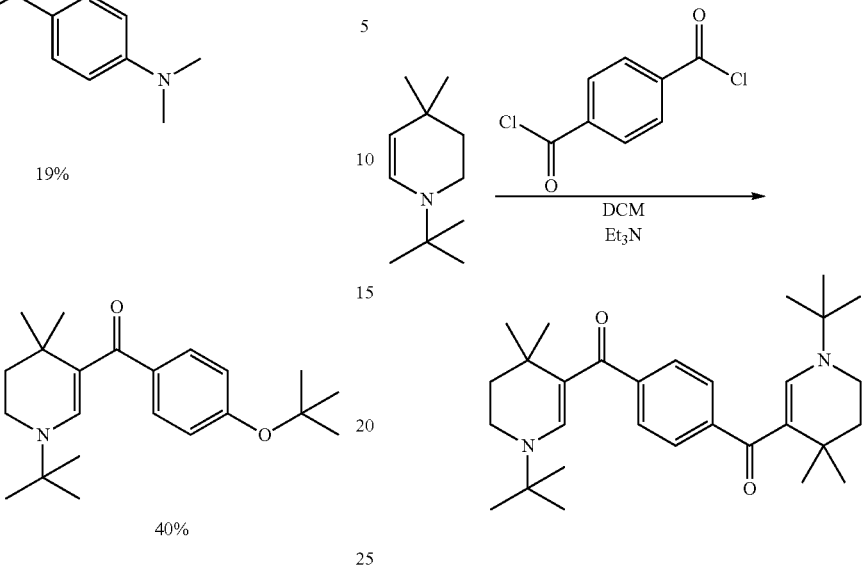

The compounds prepared and their UV absorption properties can be seen in Table 6A and 6B indicating those compounds having an N-isobutyl and N-tert-butyl group, respectively.

TABLE 6A

UV absorption properties of N-isobutyl-C3-benzoyl compounds.

| Structure | Mw | cLog P | $\lambda_{max}$ (nm) | $\lambda_{crit}$ (nm) | $\varepsilon\ M^{-1}\ cm^{-1}$ | E (1%, 1 cm) |
|---|---|---|---|---|---|---|
| 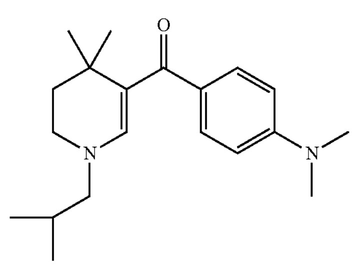 | 315 | 4.3 | 336 | 362 | 17000 | 544 |

TABLE 6A-continued

UV absorption properties of N-isobutyl-C3-benzoyl compounds.

| Structure | Mw | cLog P | $\lambda_{max}$ (nm) | $\lambda_{crit}$ (nm) | $\varepsilon$ M$^{-1}$ cm$^{-1}$ | E (1%, 1 cm) |
|---|---|---|---|---|---|---|
| 16 | 350 | 4.9 | 318 | ND | 22500 | 642 |
| 18 | 313 | 3.9 | 320 | ND | 22000 | 831 |
| 19 | 347 | 5.7 | 320 | ND | 18000 | 509 |
| 20 | 271 | 4.0 | 316 | ND | 19000 | 701 |
| 21 | 364 | 6.0 | 320 | ND | 20000 | 547 |

TABLE 6A-continued

UV absorption properties of N-isobutyl-C3-benzoyl compounds.

| Structure | Mw | cLog P | $\lambda_{max}$ (nm) | $\lambda_{crit}$ (nm) | $\varepsilon$ $M^{-1}$ $cm^{-1}$ | E (1%, 1 cm) |
|---|---|---|---|---|---|---|
| 22 | 658 | ND[a] | 316 | ND | 33000 | 502 |
| 23 | 375 | 5.2 | 295 | ND | 7500 | 200 |
| 24 | 331 | 3.77 | 313 | ND | 9500 | 286 |

[a]cLogP algorithm used could not calculate a value for compound.

TABLE 6B

UV absorption properties of N-tert-butyl-compounds.

| Structure | Mw | ClogP | $\lambda_{max}$ (nm) | $\lambda_{crit}$ (nm) | $\varepsilon$ | E (1%, 1 cm) |
|---|---|---|---|---|---|---|
| 154 | 221 | 4.29 | 328 | 360 | 24907 | 1127 |

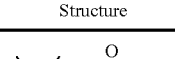

TABLE 6B-continued

UV absorption properties of N-tert-butyl-compounds.

| Structure | Mw | ClogP | $\lambda_{max}$ (nm) | $\lambda_{crit}$ (nm) | ε | E (1%, 1 cm) |
|---|---|---|---|---|---|---|
| 155 | 297 | 5.24 | 360 | 385 | 23198 | 781 |
| 156 | 350 | 6.32 | 317 | 347 | 27506 | 785 |
| 157 | 315 | 5.55 | 333 | 361 | 24966 | 793 |
| 158 | 343 | 6.53 | 317 | 344 | 32556 | 949 |
| 159 | 464 | 8.59 | 317 | 355 | 33982 | 732 |

TABLE 6B-continued

UV absorption properties of N-tert-butyl-compounds.

| Structure | Mw | ClogP | $\lambda_{max}$ (nm) | $\lambda_{crit}$ (nm) | ε | E (1%, 1 cm) |
|---|---|---|---|---|---|---|
| 160 | 315 | 5.39 | 317 | 353 | 17300 | 549 |

As can be seen, the majority of the compounds prepared resulted in an advantageous increase in the $\lambda_{max}$ of the molecules from the value of 307 nm seen for the 'base' enamine compounds. The exception to this being diketone 23, which resulted in marked decreases in both $\lambda_{max}$ (295 nm) and molar extinction coefficient (7500 $M^{-1}$ $cm^{-1}$), which still provides for a useful shift lower in the UVB range. The largest shift in the position of the absorbance maxima was seen for N,N-dimethylamino compound 15 with a $\lambda_{max}$ of 336 nm and a critical wavelength of 362 nm, which provides for an excellent extended scope of coverage.

The formation of bis(enaminone) 21 and tris(enaminone) 22 resulted in compounds with higher molecular weights and c Log P values. Benzoyl compound 20, which could be viewed as a model for bis- and tris-(enaminone) derivatives, has an ε of 19000 $M^{-1}$ $cm^{-1}$ which increases to only 20000 $M^{-1}$ $cm^{-1}$ on addition of a second cyclic enaminone core (21) and 33000 $M^{-1}$ $cm^{-1}$ on addition of a third cyclic enaminone core (22).

As can be seen, in all cases the $\lambda_{max}$ and $\lambda_{crit}$ values are very similar for both N-t-butyl and N-isobutyl compounds. Interestingly, the strength of the absorption in the t-butyl analogues is significantly stronger than that seen for the related isobutyl analogue, resulting in higher values for the molar extinction coefficient (ε) and efficiency (E). Without wishing to be bound by any particular theory, this may be a result of the slightly greater electron donating ability of the t-butyl group. It is notable that the t-butyl analogues largely gave solids and so may be preferable due to the ease of working with a solid versus oils and the like which were often obtained with the isobutyl analogue.

Therefore, in one embodiment, the compound of formula I may be a compound of formula III:

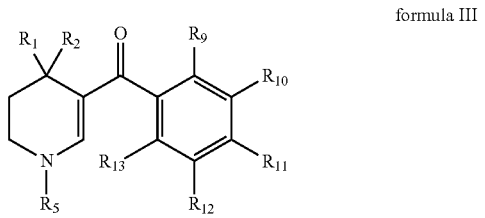

formula III

Wherein, $R_1$, $R_2$ and $R_5$ are as previously described. $R_9$, $R_{10}$, $R_{11}$, $R_{12}$ and $R_{13}$ may be independently selected from the group consisting of hydrogen, $C_1$ to $C_6$ alkyl substituted or unsubstituted, aryl, aroyl such as benzoyl, halo, amino and a further substituted cyclic enamine linked to the benzene ring of formula III by a carbonyl moiety. $R_{10}$ and $R_{11}$ may be joined to form a cyclic aryl or heterocycle.

Synthesis of Unsaturated Compounds

As the benzoyl compounds of the general formula 14 gave interesting variations and, particularly, useful increases in absorption maxima into the UVA range, investigations were carried out using unsaturation adjacent to the carbonyl group of the chromophore. These were generally prepared by enamine acylation with the corresponding acid chloride (Scheme 12) to give compounds of the general structure 25.

Scheme 12: Process used for the synthesis of unsaturated compounds.

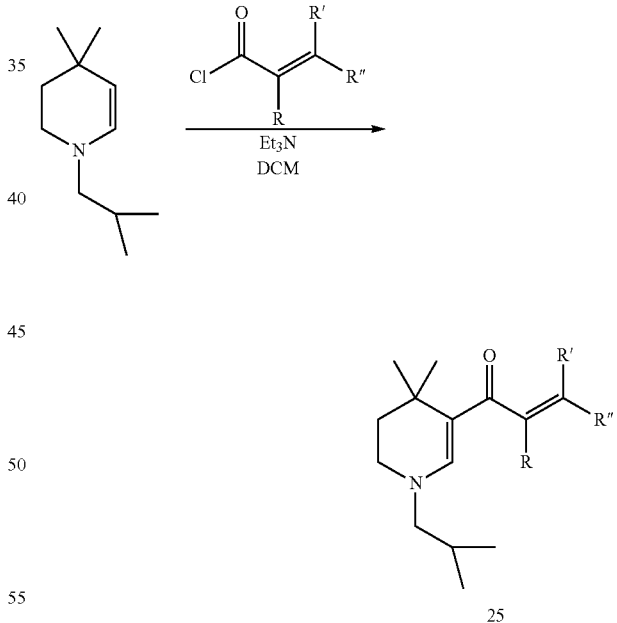

In a number of cases where rearrangement was possible, a second olefin unit was found to have moved out of conjugation on work-up and purification of the acylation reactions. Thus 3,3-dimethylacryloyl chloride gave a mixture of expected product 26 and double-bond migrated product 27. In the case of Sorboyl chloride the doubly migrated product 28 was isolated. When but-2-enoyl chloride was used, the product isolated was that derived from double bond migration 29 (Scheme 13).

Scheme 13: Double-bond migration of conjugated diene containing compounds.

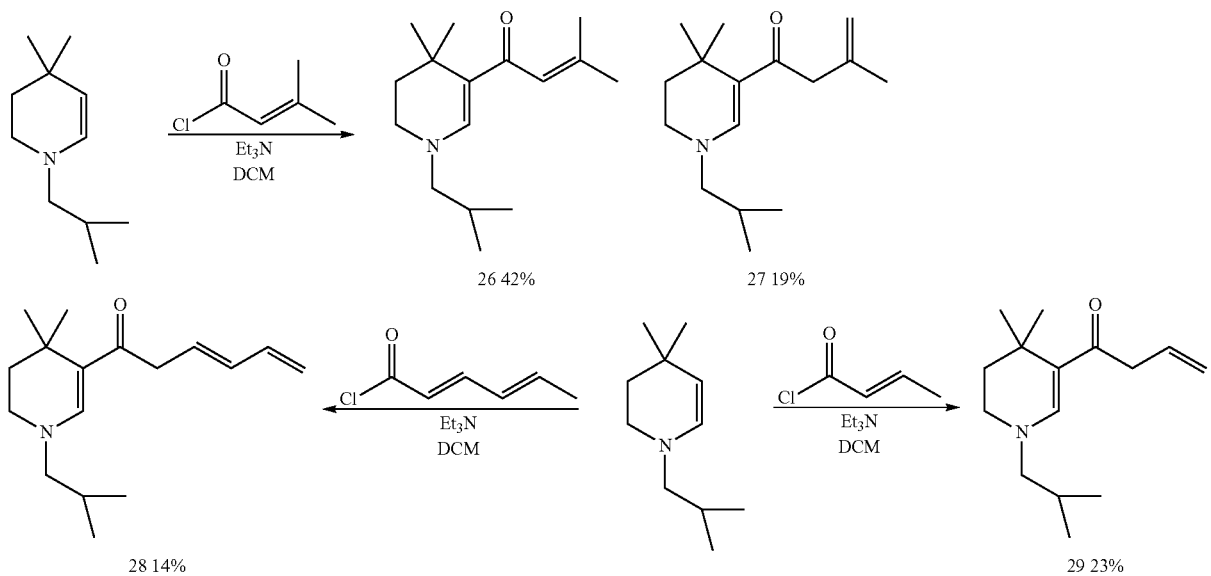

Under the standard acylation conditions a number of acid chlorides failed to give the desired products (FIG. 1). As the product of acylation with cinnamoyl chloride 30 was of interest, alternative strategies for the provision of cinnamoyl derivatives were investigated.

FIG 1.
Acid chlorides which failed to react to the corresponding products 25.

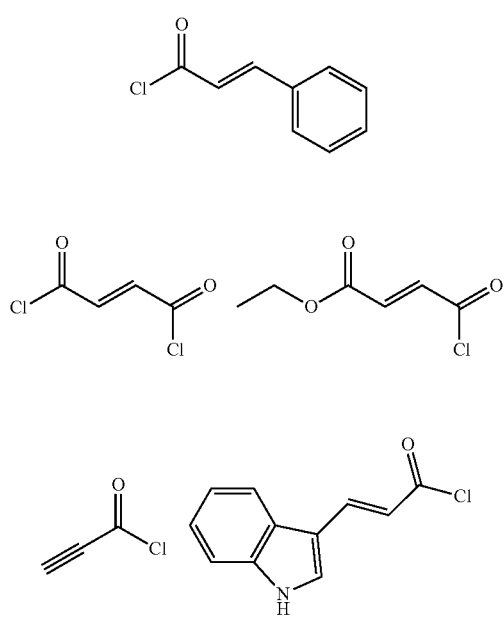

Initial attempts to synthesise cinnamoyl derivative 31 focussed on a ruthenium-catalysed cross-metathesis process between acryloyl derivative 32 and styrene. However, under the conditions attempted no cross metathesis was observed (Scheme 14).

Scheme 14: Attempted cross-metathesis pathway to 31.

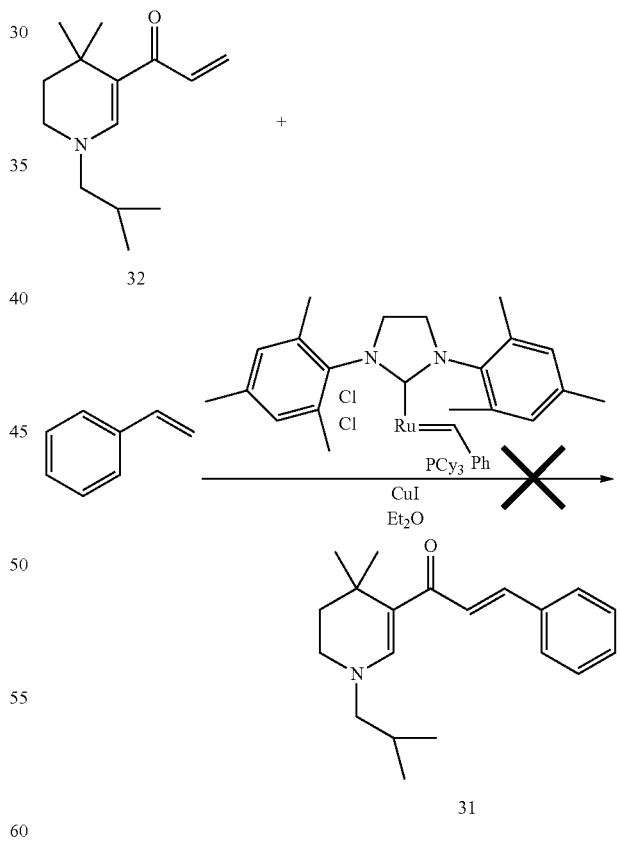

The reaction of compound 32 with aryl halides under palladium catalysis (the Heck reaction) gave the desired cinnamoyl derivatives in cases where the aryl halide was either electron poor or neutral. Electron rich aryl halides required the finding of an alternative catalyst system to generate the required products (Scheme 15). Vinyl halides were also successful coupling partners for this reaction with (2-bromovinyl)benzene giving the desired product 35, albeit as a mixture of cis and trans isomers. However, coupling with 4-iodopyrazole failed to yield any detectable amounts of the corresponding product 36. The unsaturated compounds prepared and their UV absorption properties can be seen in Table 7.
Scheme 15: Palladium-catalysed approaches to cinnamoyl derivatives.
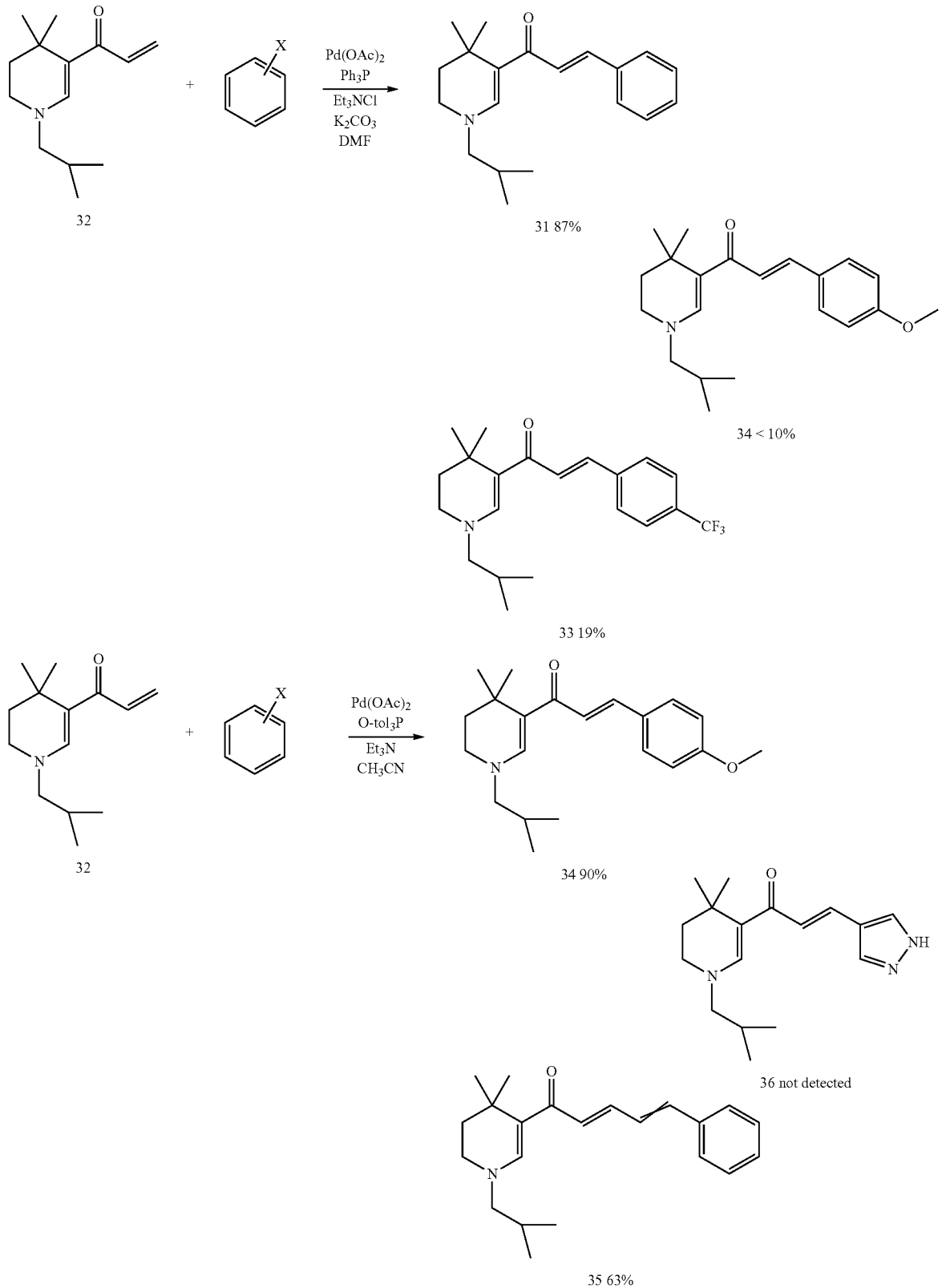

TABLE 7

UV absorption properties of unsaturated compounds.

| Structure | Mw | cLog P | $\lambda_{max}$ (nm) | $\lambda_{crit}$ (nm) | $\varepsilon$ $M^{-1}$ $cm^{-1}$ | E (1%, 1 cm) |
|---|---|---|---|---|---|---|
| 26 | 249 | 3.5 | 314 | ND | 19000 | 757 |
| 27 | 249 | 3.2 | 306 | ND | 14500 | 574 |
| 28 | 261 | 3.8 | 311 | ND | 27500 | 1053 |
| 29 | 235 | 3.3 | 310 | ND | 27000 | 1102 |
| 31 | 297 | 4.5 | 360 | 383 | 16000 | 533 |

TABLE 7-continued

UV absorption properties of unsaturated compounds.

| Structure | Mw | cLog P | $\lambda_{max}$ (nm) | $\lambda_{crit}$ (nm) | $\varepsilon$ M$^{-1}$ cm$^{-1}$ | E (1%, 1 cm) |
|---|---|---|---|---|---|---|
| 32 | 221 | 2.9 | 330 | 363 | 20500 | 915 |
| 33 | 365 | 5.4 | 369 | 388 | 17000 | 463 |
| 34 | 327 | 4.3 | 364 | 386 | 16150 | 493 |
| 35 | 323 | 5.0 | 318 370 | 387 | 14800 13200 | 458 409 |

TABLE 7-continued
UV absorption properties of unsaturated compounds.
| Structure | Mw | cLog P | $\lambda_{max}$ (nm) | $\lambda_{crit}$ (nm) | $\varepsilon$ M$^{-1}$ cm$^{-1}$ | E (1%, 1 cm) |
|---|---|---|---|---|---|---|
| 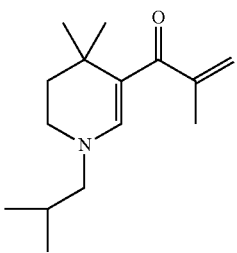<br>36 | 235 | 3.3 | 310 | ND | 18950 | 806 |
| 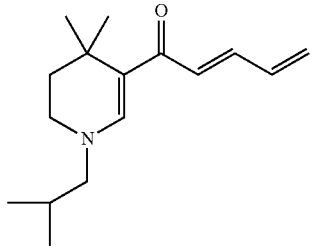<br>38 | 247 | 3.4 | 352 | 381 | 18000 | 730 |
| 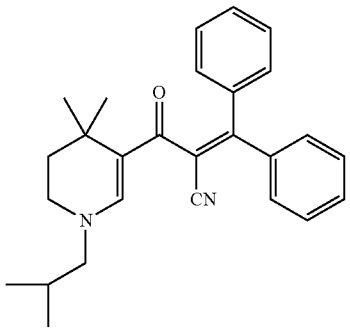<br>39 | 398 | 5.7 | 297<br>317 | 357 | 15750<br>24050 | 366<br>379 |

The majority of the compounds prepared resulted in an advantageous increase in the $\lambda_{max}$ of the molecules from the value of around 307 nm seen for the base compounds. The effect of substitution around the olefin group of these compounds was marked, with unsubstituted acryloyl compound 32 possessing a $\lambda_{max}$ of 331 nm compared to 310 nm when a methyl group was added α or β (36 or 37, respectively) or 2 groups added β (26) to the carbonyl group. The addition of a second conjugatable group in conjugation with the first olefin either as an aromatic ring (31, 33-34) or a further olefin (35, 38) resulted in large upward shifts in $\lambda_{max}$ and concomitant shifts in the value of the critical wavelength above the target value of 370 nm. Compound 39 possesses an interesting double absorption with $\lambda_{max}$ values of 297 and 317 nm.

Therefore, in one embodiment, the compound of formula I is a compound of formula IV:

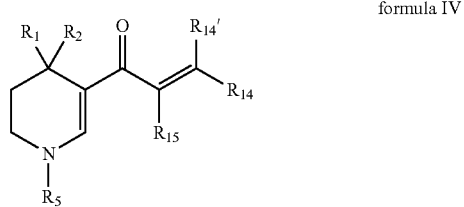

formula IV

Wherein, $R_1$, $R_2$ and $R_5$ are as previously described. $R_{14}$, $R_{14}'$ and $R_{15}$, when present, may be independently selected from the group consisting of amino, cyano, $C_1$ to $C_6$ alkyl substituted or unsubstituted, $C_1$ to $C_6$ alkenyl substituted or unsubstituted and aryl substituted or unsubstituted.

Synthesis of N-Aryl Compounds

It was decided to attempt to increase both stability and the position of absorbance maxima by placing a phenyl ring on the ring nitrogen. The compounds were synthesised using a similar synthetic route to that shown in Scheme 1 (Scheme 16).

Scheme 16: Synthetic route used to deliver N-phenyl derivatives.

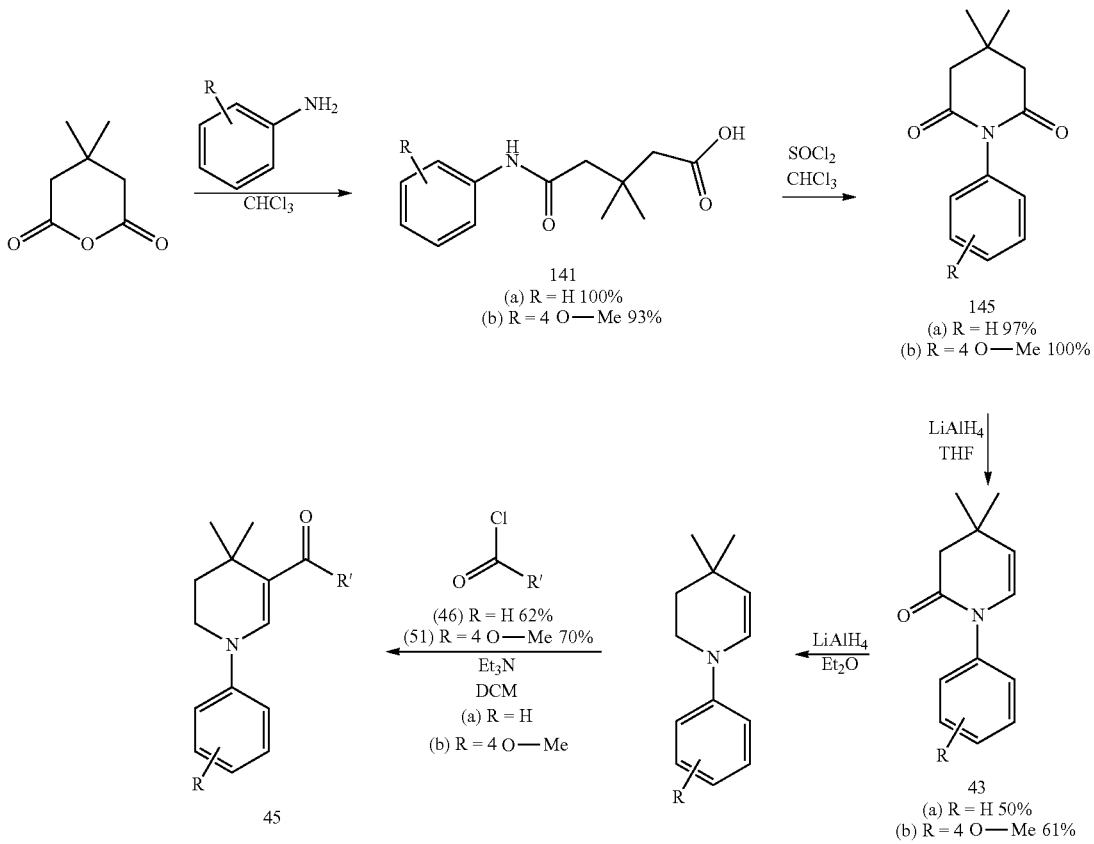

The reaction between 3,3-dimethylglutaric anhydride and an aniline or 4-methoxyaniline to give the corresponding compounds 41a or 41b and the subsequent cyclisation mediated by thionyl chloride to give the corresponding imides 42a or 42b proceeded well in >90% yield for the two anilines used. The subsequent reduction to the corresponding enamides 43a or 43b could be performed adequately but did not give total conversion to the desired product. This may be solved by the use of alternative reducing agents, such as $NaBH_4$. The final reduction to the corresponding enamines 44a or 44b was performed satisfactorily using $LiAlH_4$. Once enamines 44a or 44b were in hand, they were acylated with acid chlorides to give the corresponding desired final products 45a or 45b. In the case of both alkyl and aryl acid chlorides, significant heating was required to perform the acylation process. In the case of the electron rich acid chloride 4-methoxybenzoyl chloride, no product could be isolated. Selected N-phenyl compounds prepared and their UV absorption properties can be seen in Tables 8a and 8b.

TABLE 8a
UV absorption properties of N-phenyl compounds.
| Structure | Mw | cLog P | λ_max (nm) | λ_crit (nm) | ε M⁻¹ cm⁻¹ | E (1%, 1 cm) |
|---|---|---|---|---|---|---|
| 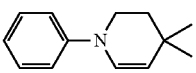 46 | 187 | 4.0 | 278 | ND | 22550 | 1205 |
| 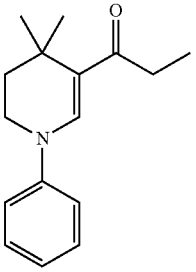 47 | 243 | 3.7 | 321 | 349 | 23000 | 947 |
| 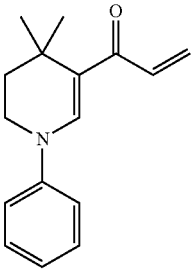 48 | 241 | 3.8 | 346 | 373 | 21000 | 874 |
| 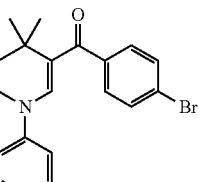 49 | 370 | 5.7 | 338 | 366 | 23300 | 629 |
TABLE 8a-continued
UV absorption properties of N-phenyl compounds.
| Structure | Mw | cLog P | λ_max (nm) | λ_crit (nm) | ε M⁻¹ cm⁻¹ | E (1%, 1 cm) |
|---|---|---|---|---|---|---|
| 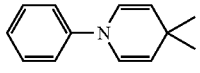 50 | 185 | 3.9 | 285 | ND | 16000 | 866 |
| 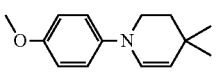 51 | 217 | 3.9 | 275 | ND | ND | ND |
| 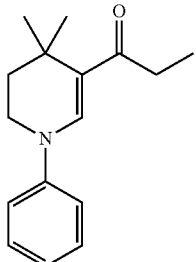 52 | 273 | 3.6 | 328 | 350 | 23500 | 862 |
| 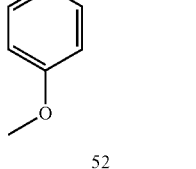 53 | 271 | 3.6 | 350 | 379 | 21500 | 794 |
| 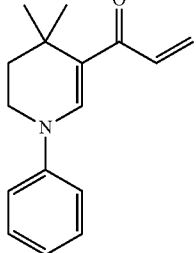 54 | 338 | 4.9 | 341 | 369 | 19350 | 571 |

TABLE 8b
UV absorption properties of N-phenyl compounds.
| Structure | Mw | ClogP | λ$_{max}$ (nm) | λ$_{crit}$ (nm) | ε | E (1%, 1 cm) |
|---|---|---|---|---|---|---|
| 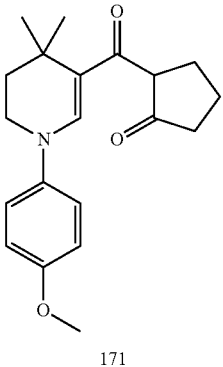 [SMILES: COc1ccc(N2C=C(C(=O)C3CCCC3=O)C(C)(C)CC2)cc1] 171 | 327 | 3.82 | 332 | 358 | 30675 | 938 |
| 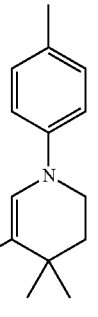 172 | 568 | 10.84 | 328 | 349 | 52737 | 928 |
| 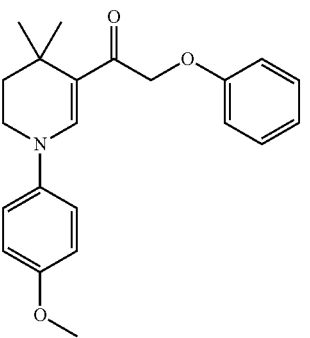 173 | 351 | 5.28 | 339 | 362 | 26633 | 759 |

TABLE 8b-continued

UV absorption properties of N-phenyl compounds.

| Structure | Mw | ClogP | λ$_{max}$ (nm) | λ$_{crit}$ (nm) | ε | E (1%, 1 cm) |
|---|---|---|---|---|---|---|
| 174 | 335 | 5.65 | 334 | 350 | 33786 | 1008 |
| 175 | 357 | 7.02 | 338 | 371 | 28040 | 785 |
| 176 | 257 | 4.71 | 327 | 348 | 34608 | 1347 |
| 177 | 299 | 6.04 | 329 | 348 | 31955 | 1069 |

TABLE 8b-continued

UV absorption properties of N-phenyl compounds.

| Structure | Mw | ClogP | $\lambda_{max}$ (nm) | $\lambda_{crit}$ (nm) | ε | E (1%, 1 cm) |
|---|---|---|---|---|---|---|
| 178 | 293 | 5.38 | 321 | 346 | 23247 | 793 |

Both N-phenyl enamine 46 and N-(4-methoxyphenyl) enamine 51 possess very significant UV absorption values with maxima between 275 and 278 nm. Similarly, dihydropyridine 50, which was an unexpected product from an unsuccessful acylation reaction, shows significant absorption with a maximum at 285 nm.

The presence of a phenyl group as the nitrogen substituent gives compounds with absorbance maxima higher than the corresponding compounds with the N-isobutyl or other simple alkyl substituent. N-phenyl compound 47 and N-(4-methoxyphenyl) compound 52 possess $\lambda_{max}$ values of 321 nm and 328 nm, respectively, compared to 307 nm for the enaminoketone chromophore of the N-isobutyl substituted cyclic enaminone. Acryloyl compounds 48 and 53 both possessed critical wavelengths above the required 370 nm level marking them as potential useful UV absorbing agents.

Compounds possessing a benzoyl substituent showed useful extension of absorbance properties compared to the base enaminone with a critical wavelength of 366 nm for compound 49 and 369 nm for compound 54. As the precise test for critical wavelength was unable to be replicated exactly by the inventors due to the need for specialist equipment and a specific calibration of the spectrophotometer, these values are only approximate to a degree. Correlation with literature values of known absorbers indicates that the values obtained are within a few nm of the values obtained with the standardised test (Avobenzone is reported to have a critical wavelength of 380 nm and was measured at 378 nm by the present inventors). This information suggests that compound 49 and especially compound 54 may give a result of 370 nm or higher in the standardised test for critical wavelength. This represents a highly useful result and so, compounds based around this benzoyl substitution pattern shown, are especially preferred.

Bis(N-aryl-enaminone) compound 172 was a strongly absorbing high molecular weight compound with an ε in excess of 52000 due to the presence of 2 chromophores. As expected, the presence of an N-aryl substituent gives compounds with a higher $\lambda_{max}$ than the corresponding N-alkyl compound. The presence of either a p-methyl (176) or p-t-butyl (177) substituent provides a similar increase in $\lambda_{max}$. The use of the 1-naphthyl group gives a compound (178) that is almost identical to unsubstituted phenyl, in terms of $\lambda_{max}$ and ε values. The p-dimethylamino substituent gives a large increase in $\lambda_{max}$ and a $\lambda_{crit}$ value of 371 nm.

Trifluoroacetic anhydride (TFAA) was tested for trifluoroacetylation of select N-aryl enamines to prove the concept. The reaction proceeded cleanly and in high yield at room temperature in a fraction of the time required for acylation with even reactive acid chlorides. For example enamine 48h gave the desired trifluoroacetylated analogue 194 in 85% yield after reaction at room temperature for 1 hour as shown in Scheme 17 below.

Scheme 17: Trifluoroacetylation of an N-aryl enamine.

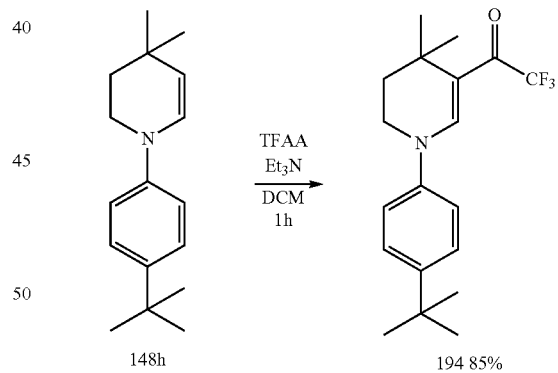

The compounds prepared from reaction with N-aryl enamines and their UV absorption properties can be seen in Table 9. The introduction of the trifluoroacetyl group generally had the effect of producing a 10-16 nm increase in the $\lambda_{max}$ value of the compounds compared to their alkanoyl counterparts. In most cases the strength of the absorption was also improved with significant increases in the molar extinction coefficient.

TABLE 9

C3-trifluoroacetylated N-aryl enamines.

| Structure | Mw | ClogP | λ$_{max}$ (nm) | λ$_{crit}$ (nm) | ε | E (1%, 1 cm) |
|---|---|---|---|---|---|---|
| 194 | 339 | 6.07 | 337 | 361 | 42723 | 1260 |
| 195 | 313 | 4.26 | 339 | 365 | 24235 | 774 |
| 196 | 326 | 4.41 | 354 | 385 | 32744 | 1004 |
| 197 | 297 | 4.74 | 337 | 361 | 43513 | 1465 |
| 198 | 333 | 5.41 | 325 | 348 | 32790 | 985 |

In some cases, N-aryldihydropyridines were sufficiently reactive to react with TFAA. The dihydropyridines enamines are typically less reactive than the corresponding tetrahydropyridine enamines. In the case of dihydropyridine enamine 150, greater than 90% of the desired product 199 was isolated, as is indicated in Scheme 18 below.

Scheme 18: Trifluoroacetylation of an N-aryl bis enamine.

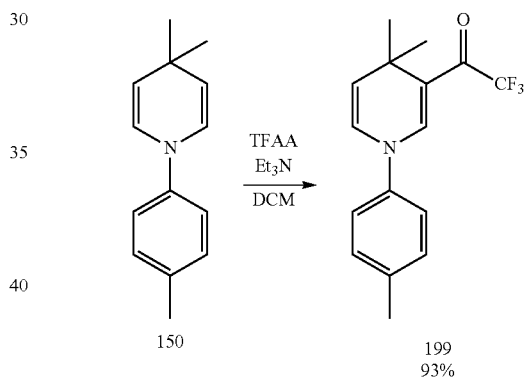

150 → 199 93%

As is indicated in Scheme 19, on treatment with excess TFAA, hydroxyl tetrahydropyridine 151 was converted to dihydropyridine 152. On further reaction, the product 200 was isolated, whereby trifluoroacetylation of the pyrazole ring had occurred.

Scheme 19: Formation of a pyrazole-trifluoroacetylated dihydropyridine.

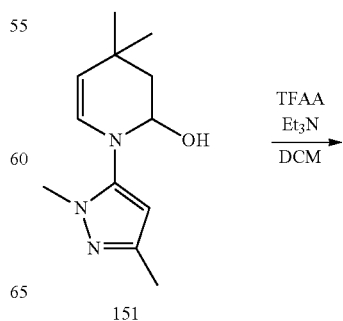

151

-continued

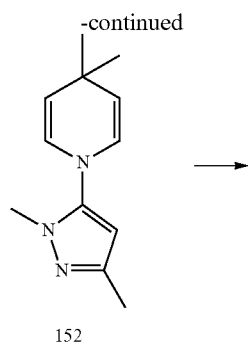
152

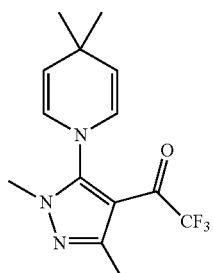
200 39%

The compounds prepared from acylation reactions with dihydropyridines and their UV absorption properties can be seen in Table 10. Also included for completeness are the dihydropyridine enamines and, where isolated, the corresponding tetrahydropyridine enamines.

TABLE 10

Bis and mono enamine compounds synthesized.

| Structure | Mw | ClogP | $\lambda_{max}$ (nm) | $\lambda_{crit}$ (nm) | ε | E (1%, 1 cm) |
|---|---|---|---|---|---|---|
| 148e | 201 | 5.02 | 278 | 321 | 20823 | 1036 |
| 150 | 199 | 4.66 | 283 | 317 | 31871 | 1601 |
| 199 | 295 | 4.36 | 388 | 393 | 14911 | 505 |
| 152 | 203 | 3.09 | 253 | 350 | 11371 | 560 |
| 200 | 299 | 3.55 | 253, 315 weak shoulder | 363 | 10016 | 335 |
| 201 | 186 | 3.22 | 305 | 327 | 18164 | 977 |

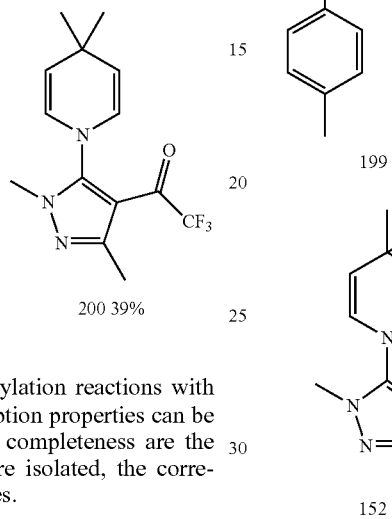

It was decided to test if the reactivity of this TFAA system could be utilised to allow acylation with groups other than trifluoroacetyl. With this in mind two commercially available carboxylic acids, 2,2-diphenylacetic acid or fluorene-9-carboxylic acid were stirred in DCM solution with TFAA to give the corresponding mixed trifluoroacetyl anhydrides 202 or 203 (Scheme 20).

Scheme 20: Synthesis of mixed anhydrids 202 and 203.

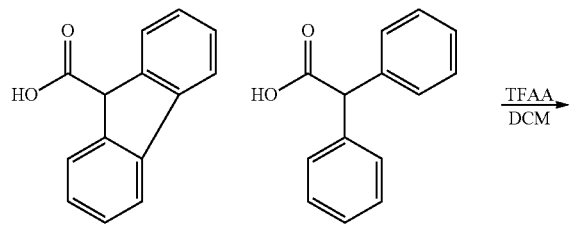

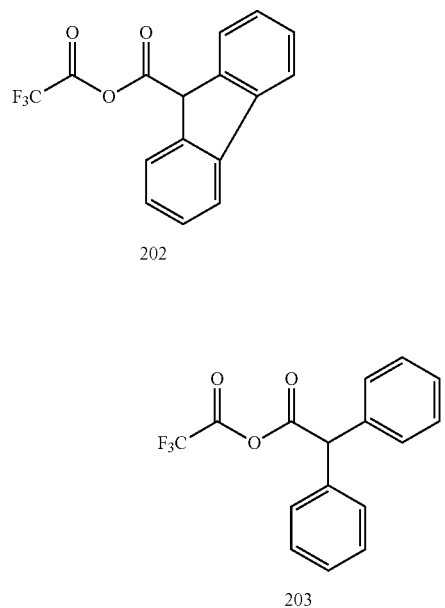

When mixed anhydride 203 was reacted with 48h overnight at room temperature no trace of the starting enamine could be detected and 70% of the corresponding product 204 was isolated. Similarly, mixed anhydride 202 also gave the desired product 205, although in this case the reaction was complicated by the presence of the compound resulting from acylation of the product derived enol 206 (Scheme 21).

Scheme 21: Reactions of mixed anhydrides with an N-aryl enamine.

The compounds synthesised and their corresponding UV properties are shown in Table 11. Compound 204 had a $\lambda_{max}$ of 337 nm but a somewhat weak $\epsilon$ value of approximately 18000. This may arise from the likelihood of achieving overlap of the 2 aromatic rings of the diphenylacetic acid unit. It was felt that such an overlap could be facilitated by the introduction of a conformational restraint such as the link between the two aromatic rings in 9-fluorene carboxylic acid. This proved to be the case with compound 205 which exhibited a similar $\lambda_{max}$ value but greatly increased extinction coefficient.

TABLE 11

Compounds prepared from mixed anhydrides.

| Structure | Mw | ClogP | $\lambda_{max}$ (nm) | $\lambda_{crit}$ (nm) | ε | E (1%, 1 cm) |
|---|---|---|---|---|---|---|
| 204 | 437 | 8.81 | 337 | 356 | 17793 | 407 |
| 205 | 435 | 8.78 | 339 | 358 | 30745 | 707 |

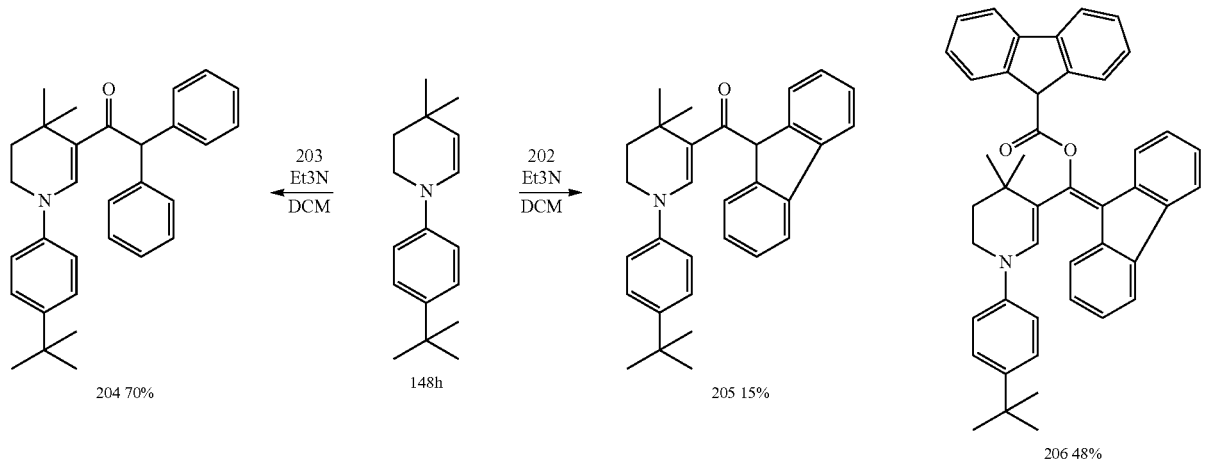

TABLE 11-continued

Compounds prepared from mixed anhydrides.

| Structure | Mw | ClogP | $\lambda_{max}$ (nm) | $\lambda_{crit}$ (nm) | ε | E (1%, 1 cm) |
|---|---|---|---|---|---|---|
| 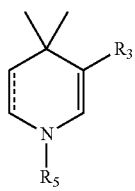 206 | 627 | 12.48 | 407 | 387 | 6635 | 105 |

Therefore, in one embodiment, the compound of formula I may be a compound of formula V:

formula V

Wherein, $R_3$ is as previously described and $R_5$ is aryl substituted or unsubstituted and the dashed line may be a bond. Preferably, the aryl group is substituted with $C_1$ to $C_6$ alkyl, $C_1$ to $C_6$ alkoxy or halo.

Synthesis of Enamines Substituted at the 2-Position

In order to probe the effects of substituents on the 2-position of the tetrahydropyridine ring, the preparation of a number of analogues was contemplated. The performance of an intramolecular process via a suitably functionalised nitrogen substituent could be employed to achieve such compounds (Scheme 22). Such a material may possess enhanced stability relative to the parent molecule.

Scheme 22. Proposed intramolecular process to novel absorbers.

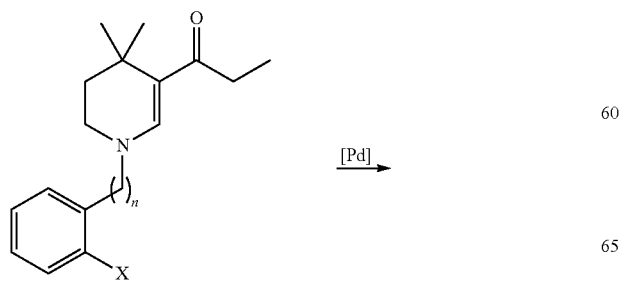

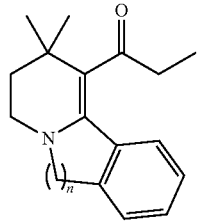

A route to the desired compounds was investigated based on the alkyl addition to imide 55 with an organometallic reagent to give, after elimination of water, intermediate 56. The resulting product of this process could then be carried through the synthesis to give 2-functionalised materials (Scheme 25). The synthesis of intermediates 56 was complicated by the presence of a competing deprotonation of 55 leading to generally poor yields and the need for extended reaction times and the use of excess organometallic reagents. When R was methyl, dehydration to 56a occurred spontaneously during acidic work-up. When R was phenyl, the dehydration to 56b required heating with toluene sulfonic acid to proceed to completion. Subsequent reduction or 56a or 56b with lithium aluminium hydride gave the corresponding enamines 57a or 57b in high yield, which were then acylated with propionyl chloride.

Scheme 23: Synthetic route used to deliver 2-substituted derivatives.

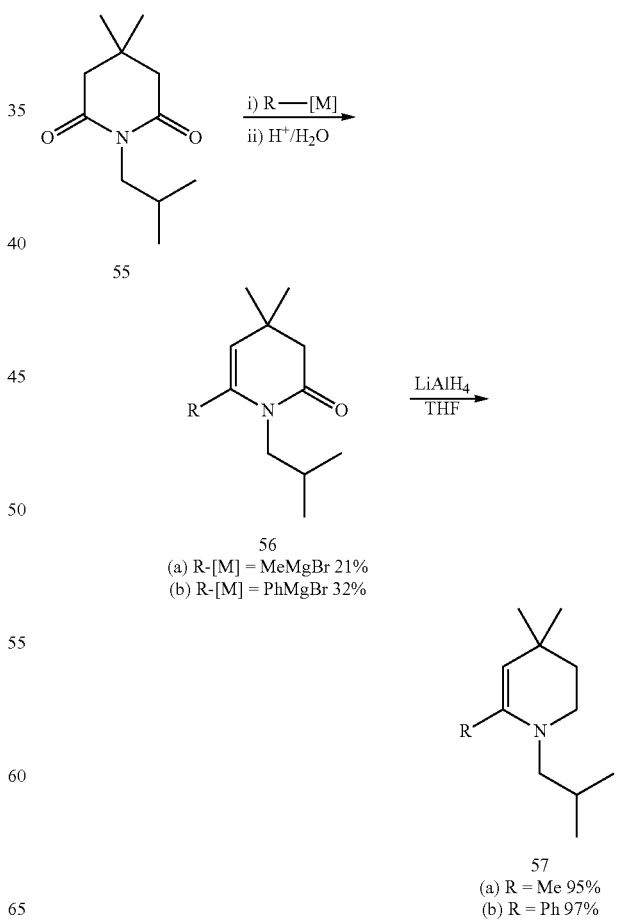

A number of alternative organometallic reagents were employed in the synthesis of 56 such as methyllithium, allylmagnesium chloride, vinylmagesium bromide, and ethylmagnesium bromide. However, in all cases, no significant amount of product could be isolated. Selected 2-substituted compounds prepared, and their UV absorption properties, can be seen in Table 12. The 2-methyl enamine (57a, R=Me) failed to react in the expected manner giving instead the product resulting from acylation at the 2-position (59, 24%) and a mixture of isomers of the product of further acylation (60, 15%).

TABLE 12

UV absorption properties of 2-substituted compounds.

| Structure | Mw | cLogP | $\lambda_{max}$ (nm) | $\lambda_{crit}$ (nm) | $\epsilon$ $M^{-1}$ $cm^{-1}$ | E (1%, 1 cm) |
|---|---|---|---|---|---|---|
| 58 | 299 | 4.6 | 338 | 365 | 8000 | 268 |
| 59 | 237 | 2.5 | 314 | ND | 16000 | 675 |
| 60 | 293 | 3.3 | 323 | 344 | 20000 | 683 |

The presence of a phenyl group in the 2-position gave an absorber with a significant increase in the absorbance maximum with shifts seen from 307 nm for the N-isobutyl substituted cyclic enamine to 338 nm for compound 58. Unexpected products 59 and 60 both gave moderate increases in $\lambda_{max}$ over that of the N-isobutyl substituted cyclic enamine. The results in Table 12 suggest that substitution at the 2-position can provide unexpected benefits in terms of modifying the UV absorbance maximum.

Therefore, in one embodiment, the compound of formula I may be a compound of formula VI:

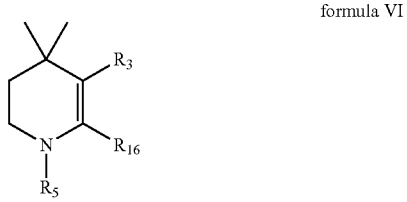

formula VI

Wherein, $R_3$ and $R_5$ are as previously described. $R_{16}$ may be aryl, alkenyl, carboxy or alkanoyl, all of which groups may be substituted or unsubstituted.

Synthesis of Miscellaneous Substituted Enamine Compounds

A number of further compounds are presented in Table 13. As a high level of water solubility is not necessarily desirable in such applications as sunscreen agents, it was decided to make substitutions which would lower the water solubility. The polyhedral oligomeric silsesquioxane (POSS) group is a cage like structure of silicon and oxygen atoms (below). In addition to other properties, the POSS group generally renders any molecules attached to it insoluble in polar solvents and water. Compound 63 is the free base of a POSS containing an analogue of the N-isobutyl substituted cyclic enamine. As can be seen, compound 63 shows useful levels of UV absorption.

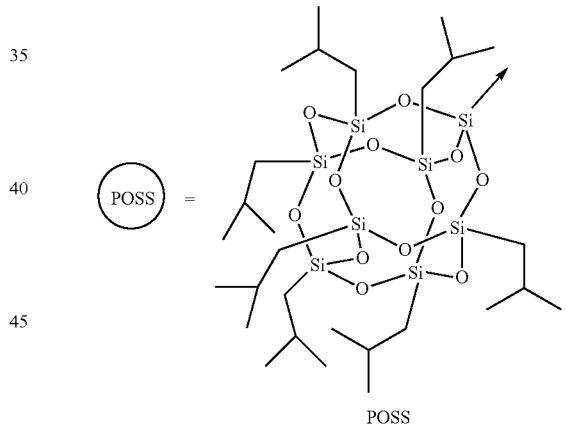

POSS

Compounds 64 and 65 are decomposition products, which were isolated from the forced degradation of the N-isobutyl substituted cyclic enamine under thermal conditions. Whilst lactam 64 possesses only an absorbance with a maximum at 291 nm, the dihydropyridine 65 shows a highly advantageous absorbance with a maximum at 366 nm and a critical wavelength of 386 nm.

Compound 70 was an intermediate generated for the preparation of POSS derivative 63. Compound 71 gives a modest increase in $\lambda_{max}$ whilst maintaining the high molar extinction coefficient of the N-isobutyl substituted cyclic enamine. Compound 71 may be useful in this regard, as it gives significant increases in molecular weight and c Log P. Compound 72 was an attempt to replace the carbonyl group of the absorbers with a sulfonyl moiety. This change resulted in a significant downward change in both the $\lambda_{max}$, further into the UVB range, and $\epsilon$ values.

TABLE 13
UV absorption properties of 2-substituted compounds.
| Structure | Mw | cLogP | $\lambda_{max}$ (nm) | $\lambda_{crit}$ (nm) | $\varepsilon$ $M^{-1}$ $cm^{-1}$ | E (1%, 1 cm) |
|---|---|---|---|---|---|---|
| 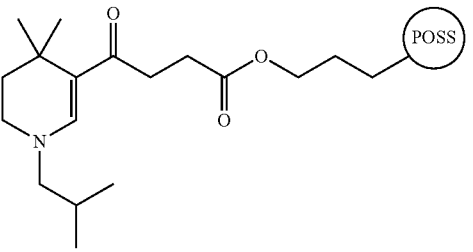 | 1125 | ND[a] | 308 | ND | 21800 | 193 |
| 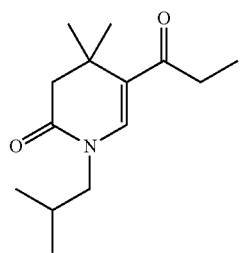 64 | 237 | 2.0 | 291 | ND | ND | ND |
| 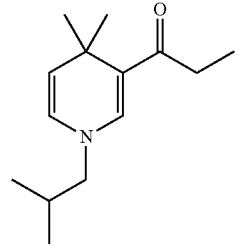 65 | 221 | 3 | 366 | 386 | 8800 | 362 |
| 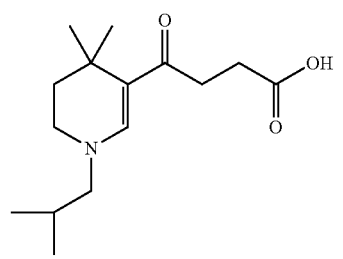 70 | 267 | 1.9 | 308 | ND | ND | ND |
| 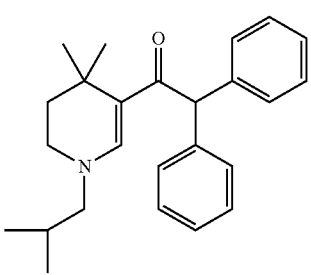 71 | 362 | 5.8 | 314 | ND | 26000 | 716 |

TABLE 13-continued

UV absorption properties of 2-substituted compounds.

| Structure | Mw | cLogP | $\lambda_{max}$ (nm) | $\lambda_{crit}$ (nm) | $\varepsilon$ $M^{-1}$ $cm^{-1}$ | E (1%, 1 cm) |
|---|---|---|---|---|---|---|
| 72 | 307 | 3.3 | 285 | ND | 11000 | 359 |

*a* The algorithm used to determine cLogP could not calculate a value for this molecule.

According to a second preferred embodiment of the present invention, there is provided a composition comprising a compound of formula I, IIa, IIb, III, IV, V or VI and a suitable carrier.

In one embodiment, the composition is a sunscreen composition.

The sunscreen composition may contain dispersing agents, emulsifiers or thickening agents to assist in applying a uniform layer of the active compounds. Suitable dispersing agents for the sunscreen formulations include those useful for dispersing organic UV absorbing agents in a water phase, oil phase, or part of an emulsion, including, for example, chitosan.

Emulsifiers may be used in the sunscreen composition to disperse one or more of the compounds or other components of the sunscreen composition. Suitable emulsifiers include conventional agents such as, for example, ethoxylated alcohols (oleth-2, oleth-20 etc.), glycerol stearate, stearyl alcohol, cetyl alcohol, dimethicone copolyol phosphate, hexadecyl-D-glucoside, octadecyl-D-glucoside, cetearyl alcohol and dicetyl phosphate and ceteth-10-phosphate (Crodafos™ CES), one or more ethoxylated esters of natural derivatives, e.g. polyethoxylated esters of hydrogenated castor oil; or a silicone emulsifier such as silicone polyol; a free or ethoxylated fatty acid soap; an ethoxylated fatty alcohol; a free or ethoxylated sorbitan ester, an ethoxylated fatty acid; or an ethoxylated glyceride.

Emollients may be used in the sunscreen composition including cetyl esters, such as cetyl ethylhexanoate, isostearyl neopentanoate, diisopropyl sebacate, coconut oil and silicones.

Humectants may be used including glycols such as propylene glycol and butylene glycol as well as glycerine.

Rheology modifiers such as various Carbopol® acrylate polymeric compounds, alkyl acrylates as well as neutralisers and preservatives as are standard in the art.

Thickening agents may be used to increase the viscosity of the sunscreen composition. Suitable thickening agents include glyceryl stearate, carbomers, acrylate/acrylonitrile copolymers, xanthan gum and combinations of these. The amount of thickener within the sunscreen composition, on a solids basis without water, may range from about 0.001 to about 5%, preferably from 0.01 to about 1% and optimally from about 0.1 to about 0.5% by weight.

Minor optional adjunct ingredients for the sunscreen composition may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The sunscreen formulations may optionally contain an ingredient which enhances the waterproof properties such as, compounds that form a polymeric film, such as dimethicone copolyol phosphate, diisostearoyl trimethyolpropane siloxysilicate, chitosan, dimethicone, polyethylene, polyvinylpyrrolidone (PVP), polyvinylpyrrolidone/vinylacetate, PVP/Eicosene copolymer and adipic acids/diethylene glycol/glycerine crosspolymer etc. Waterproofing agents may be present at levels of from about 0.01 to about 10% by weight.

There is considerable knowledge in the art in terms of sunscreen formulations and standard texts and journal articles may also provide guidance. One such text which may prove useful is *The Chemistry and Manufacture of Cosmetics*. An appropriate article to refer to may be *Cosmetics & Toiletries*, vol. 116, No. 9, September 2001 and Tanner. P. R., Dermatol. Clin. 2006 January; 24(1):53-62. These articles and textbook are incorporated herein in their entirety by way of reference.

The sunscreen compositions can additionally contain one or more further UV-protective substances, e.g. triazines, 1,3-diketones, such as avobenzone, oxanilides, triazoles or amides containing vinyl groups or cinnamides. Such protective substances are described, for example, in GB-A-2, 286,774 or alternatively are known from Cosmetics & Toiletries (107), 50 et seq. (1992).

The compositions may contain 0.1 to 15, preferably 0.5 to 10% by weight, based on the total weight of the composition, of a compound of the first aspect. The compositions can be prepared by physical mixing of the compounds with the auxiliary by the usual methods, such as, for example, by simply stirring the individual components together. The compositions can be formulated as a water-in-oil or oil-in-water emulsion, as an oil-in-alcohol lotion, as a vesicular dispersion of an ionic or non-ionic amphiphilic lipid, as a gel, solid stick or as an aerosol formulation. As a water-in-oil or oil-in-water emulsion, any compatible auxiliary preferably contains 5 to 50% of an oil phase, 5 to 20% of an emulsifier and 30 to 90% of water. The oil phase can in this case contain any oil suitable for cosmetic formulations, e.g. one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

In one embodiment, the sunscreen composition may comprise more than one compound of formula I, IIa, IIb, III, IV, V or VI or a combination of a compound of formula I, IIa, IIb, III, IV, V or VI and a known UV absorbing sunscreen agent.

In one alternative embodiment, the composition is a coating composition, a plastics composition or a paint composition. UV protective paint or general coating compositions can be useful in external applications such as in automotive paints, masonry and timber paints and UV protective compositions for boats and other marine applications.

The paint composition may contain a diluent or solvent such as water, petroleum distillate, an esters, a glycol ether, a binder or film forming component including include synthetic or natural resins such as alkyds, acrylics, vinyl-acrylics, vinyl acetate/ethylene (VAE), polyurethanes, polyesters, melamine resins, epoxy, or oils, and may comprise a pigment or dye to provide colouration and/or other optional additives such as catalysts, thickeners, stabilizers, emulsifiers, texturizers, adhesion promoters, UV stabilizers, flatteners (de-glossing agents), fungicides, flow control agents, surfactants, and rheology modifiers.

In a further alternative embodiment, the composition may be a glass or plastic film-forming composition. Such compositions may be useful in forming UV protective glass or plastic films useful to prevent UV damage to the enclosed material. They may be useful in forming or coating: automotive glass, architectural glass and plastics, such as PVC, used in similar applications. The compositions may, in one embodiment, result in UV protective ophthalmic lenses including corrective contact lenses and eyeglasses. Such compositions are known in the art but have not comprised the compounds of the present invention to this point.

A third aspect of the present invention resides in the use of a compound of formula I, IIa, IIb, III, IV, V or VI as a UV absorbing compound.

A fourth aspect of the present invention resides in a method of protecting a surface or tissue from UV rays including the step of applying a compound of formula I, IIa, IIb, III, IV, V or VI to the surface or tissue.

Preferably, the use of the third embodiment or the method of the fourth aspect has the compound as a component of a sunscreen composition. The compound of formula I, IIa, IIb, III, IV, V or VI may be present in the sunscreen composition with a range of standard formulation agents including water, various emulsifiers, stabilisers and surfactants.

Alternatively, the use of the third embodiment or the method of the fourth aspect has the compound as a component of a coating composition. The compound of formula I, IIa, IIb, III, IV, V or VI may be present in the coating composition with a range of standard formulation agents including, one or more the agents described above. The coating composition may be a paint, staining, UV protective, tinting or polymeric matrix formulation wherein the compound of formula I, IIa, IIb, III, IV, V or VI provides UV protective or additional UV protective properties to the formulation.

For example, the coating composition may be a paint formulation for the exterior of a building or for exposed timber structures. The coating composition may also be a matrix coating for signage and the like which are exposed to the suns rays for extended periods of time and which display information which it is desirable to protect from fading.

Further, the use of the third embodiment or the method of the fourth aspect may employ the compound of formula I, IIa, IIb, III, IV, V or VI as a component of a UV protective glass and/or UV protective polymeric film. The glass may be prepared in a manner standard in the industry. The polymeric film may be chosen from a range of standard film materials such as polyolefin-based films. The compounds of the present invention may be incorporated by cross-liking during film formation or may be associated with the film forming compounds, such as loosely held within the polymeric matrix.

In one embodiment, the use of the third embodiment or the method of the fourth aspect may have the compound in or on an ophthalmic lenses. This may be in terms of the UV absorbing compounds being cast in a lens formulation where the absorber is added to the bulk lens monomer prior to casting. Alternatively, the UV absorbing compound may be included as part of a coating layer or via imbibition. The lens may be a glass or plastic lens.

Plastic lenses may be tinted by dipping them in a heated soluble dye comprising the UV absorbing compounds. This dye penetrates a uniform distance into the lens surfaces, providing a tint of uniform colour and transmittance and incorporating the UV absorbing compound. Glass lenses may be tinted by the addition of a chemical compound to the molten glass. The UV absorbing compound, if stable under those conditions, may be added in this process.

Some glass lenses are tinted by the application of a coating to one or both lens surfaces. These coatings consist of a thin layer of a coloured glass compound or a metal oxide that is applied using a vacuum deposition process. The UV absorbing compounds of the invention may be incorporated during this standard process.

In embodiments wherein the UV absorbing compound is included in the lens during formation of same it may be co-polymerised with a lens forming monomer. Many lens-forming monomers are known in the art and include both acrylic and silicone-containing monomers, among others. Non-limiting examples of preferred lens-forming monomers are 2-phenylethyl methacrylate; 4-phenylbutyl methacrylate; 5-phenylpentyl methacrylate; 2-benzyloxyethyl methacrylate; and 3-benzyloxypropyl methacrylate; and corresponding acrylates thereof.

The present compounds may also be used in the formation of plastic materials whereby their presence within the plastics matrix, either in the sense of being captured therein or being chemically bonded to the plastics backbone, imparts UV protective properties.

The invention will now be described but it is in no way limited to the following Examples.

EXPERIMENTAL

Example 1—Preparation of 6-bromo-1-(1-isobutyl-4,4-dimethyl-1,2,3,4-tetrahydropyridin-3-yl)hexan-1-one, 4

A solution of 1-isobutyl-4,4-dimethyl-1,2,3,4-tetrahydropyridine (200 mg, 1.2 mmol) and triethylamine (167 µL, 1.2 mmol) in DCM (7 mL) was cooled on an ice bath and treated drop wise with a solution of 6-bromohexanoyl chloride (179 µL, 1.2 mmol) in DCM (4 mL). Once addition was complete the mixture was stirred for a further 1 hour before dilution of the reaction mixture with diethyl ether and shaking with sodium carbonate solution (5% w/w). The organic phase was then separated and dried with sodium sulfate. Evaporation in-vacuo gave the crude material as an yellow oil (350 mg) which was purified by column chromatography over silica gel eluting with 50% ethyl acetate:petroleum ether. Evaporation of the eluents gave the title compound as a yellow oil (340 mg, 85%).

$\delta_H$ (CDCl$_3$, 200 MHz) 7.13 (s, 1H), 3.41 (t, J 6.8, 2H), 3.11 (t, J 6.0, 2H), 2.96 (d, J 7.1, 2H), 2.42 (t, J 7.6, 2H), 2.03-1.81 (m, 3H), 1.70-1.36 (m, 6H), 1.27 (s, 6H), 0.92 (d, J 5.6, 6H). $\delta_C$ (CDCl$_3$, 100 MHz) 195.0, 147.9, 115.2, 64.2, 43.3, 39.3, 36.5, 33.9, 32.8, 30.1, 28.1, 27.4, 25.4, 19.8. HRMS (ES): calc. for C$_{17}$H$_{31}$BrNO [MH$^+$], 344.1595. Found, 344.1586 [MH$^+$].

Example 2—Preparation of 2-(4-(tert-butyl)benzoyl)-8-(1-isobutyl-4,4-dimethyl-1,2,3,4-tetrahydropyridin-3-yl)-1-(4-methoxyphenyl)octane-1,8-dione, 5

A solution of Avobenzone (92 mg, 0.3 mmol) in THF (5 mL) was treated drop wise with a solution of tetra-N-butylammonium fluoride (1 M in THF, 300 µL, 0.3 mmol). Once addition was complete the mixture was stirred for 2 hours before addition of a solution of 6-bromo-1-(1-isobutyl-4,4-dimethyl-1,2,3,4-tetrahydropyridin-3-yl)hexan-1-one 4 (102 mg, 0.3 mmol) in THF (3 mL). The mixture was then stirred at room temperature for 72 hours, diluted with water and the organic phase separated and dried with sodium sulfate. The organic phase was then treated with Celite and evaporated in-vacuo. The residue was then purified by column chromatography over silica gel eluting with 5-30% ethyl acetate petroleum ether. Evaporation of the eluents gave the title compound as a colourless oil (56 mg, 37%).

$\delta_H$ (CDCl$_3$, 200 MHz) 8.02-7.91 (m, 4H), 7.52-7.48 (m, 2H), 7.17 (s, 1H), 6.95 (d, J 9.0, 2H), 5.16 (t, J 6.6, 1H), 3.88 (s, 3H), 3.14-2.96 (m, 4H) 2.56-2.37 (m, 2H), 2.03-1.90 (m, 1H), 1.65-1.19 (m, 23H), 0.93 (d, J 6.6, 6H). HRMS (ES): calc. for C$_{37}$H$_{52}$NO$_4$ [MH$^+$], 574.3891. Found, 574.3892 [MH$^+$]. UV $\lambda_{max}$ 306 nm.

Example 3—General Procedures for Acid Chloride Preparation

Acid chlorides were prepared using one of two alternative methods.
Method 1
A solution of 4-penteneoic acid (250 mg, 2.5 mmol) in DCM (5 mL) was treated with DMF (1 drop) followed by a solution of oxalyl chloride (209 µL, 2.4 mmol) in DCM (2.5 mL). The solution was then stirred at room temperature for 1 hour and used directly with no further purification.
Method 2
A solution of 4-phenylbenzoic acid (502 mg, 2.53 mmol) in thionyl chloride (10 mL) was treated with DMF (1 drop) and heated at reflux for 18 hours. The reaction mixture was then evaporated in-vacuo and the crude material dissolved in DCM and evaporated in-vacuo; this was repeated once more to afford the crude title compound as a tan solid (quant.). Analysis by IR showed the disappearance of the carboxylic acid peak at 3200-2500 cm$^{-1}$. The crude material was used without further purification.

Example 4—Preparation of 1-(1-Isobutyl-4,4-dimethyl-1,4,5,6-tetrahydropyridin-3-yl)pent-4-en-1-one, 8

Prepared according to the procedure above for the preparation of 6-bromo-1-(1-isobutyl-4,4-dimethyl-1,2,3,4-tetrahydropyridin-3-yl) hexan-1-one, 4, as a pale yellow oil in 19% yield.

$\delta_H$ (CDCl$_3$, 400 MHz) 7.08 (s, 1H), 5.87-5.75 (m, 1H), 5.01-4.86 (m, 2H), 3.08-3.03 (m, 2H), 2.90 (d, J 7.5, 2H), 2.48-2.42 (m, 2H), 2.34-2.26 (m, 2H), 1.90 (sept. J 6.7, 1H), 1.57-1.53 (m, 2H), 1.22 (s, 6H), 0.86 (d, J 6.7, 6H). $\delta_C$ (CDCl$_3$, 100 MHz) 194.5, 148.2, 138.8, 115.3, 114.5, 64.4, 43.5, 39.4, 36.3, 30.5, 30.3, 28.2, 27.6, 20.0. HRMS (ES): calc. for C$_{16}$H$_{28}$NO [MH$^+$], 250.2165. Found, 250.2171 [MH$^+$]. UV $\lambda_{max}$ 308 nm, ε 35000 M$^{-1}$ cm$^{-1}$.

Example 5—Preparation of 1-(4-((4-bromobenzyl)oxy)phenyl)-3-(4-(tert-butyl)phenyl)propane-1,3-dione, 9

A mixture of 4-hydroxyacetophenone (5.0 g, 36.7 mmol), 4-bromobenzyl bromide (13.78 g, 55.0 mmol) and potassium carbonate (10.15 g, 73.4 mmol) in acetone (185 mL) was heated at reflux under an atmosphere of nitrogen for 3 hours. The volume of acetone was reduced by rotary evaporation and the residue was partitioned between water and ethyl acetate. The organic phase was separated, washed with water followed by saturated sodium chloride solution and dried with magnesium sulfate. Evaporation in-vacuo gave the crude material as a colourless solid which was purified by column chromatography over silica gel eluting with 0-100% ethyl acetate:heptane. Evaporation of the eluents gave 1-(4-((4-Bromobenzyl)oxy)phenyl)ethanone as a colourless solid (10.75 g, 96%).

$\delta_H$ (CDCl$_3$, 400 MHz) 7.92 (d, J 9.0, 2H), 7.50 (d, J 8.5, 2H), 7.28 (d, J 8.5, 2H), 6.96 (d, J 9.0, 2H), 5.06 (s, 2H), 2.53 (s, 3H). $\delta_C$ (CDCl$_3$, 100 MHz) 196.8, 162.4, 135.4, 132.0, 130.9, 130.8, 129.2, 122.3, 114.7, 69.5, 26.5. HRMS (ES): calc. for C$_{15}$H$_{14}$BrO$_2$ [MH$^+$], 305.0172. Found, 305.0172 [MH+]. Calc. for C$_{15}$H$_{13}$O$_2$BrNa [MNa$^+$] 326.9991. Found 326.9990 [MNa$^+$].

A mixture of sodium hydride (0.75 g, 18.7 mmol, 60% dispersion in oil) suspended in anhydrous THF (50 mL) was treated with methyl tert-butylbenzoate (3.0 g, 15.6 mmol). The reaction mixture was allowed to stir for 30 minutes and was then transferred via a cannula to a solution of 1-(4-((4-bromobenzyl)oxy)phenyl) ethanone (3.97 g, 13.0 mmol) in anhydrous THF (25 mL). Once addition was complete, the mixture was heated at reflux for 18 hours and cooled to ambient temperature. The reaction was then quenched by drop wise addition of saturated sodium bicarbonate. The pH was then adjusted to pH 3 with 1M aqueous HCl. The resultant pale yellow solid was collected by filtration, triturated in 2-propanol, collected by filtration and dried in-vacuo to give the title compound as a pale yellow solid 4.36 g, 76%).

$\delta_H$ (CDCl$_3$, 400 MHz) 7.99-7.92 (m, 2H), 7.92-7.86 (m, 2H), 7.54-7.45 (m, 4H), 7.33-7.27 (m, 2H), 7.04-6.98 (m, 2H), 6.76 (s, 1H), 5.07 (s, 2H), 1.34 (s, 9H). $\delta_C$ (CDCl$_3$, 100 MHz) 185.8, 184.6, 162.1, 156.2, 135.5, 132.9, 132.1, 129.5, 129.3, 129.0, 127.1, 125.8, 122.4, 115.0, 92.4, 69.6, 35.3, 31.4. HRMS (ES): calc. for C$_{26}$H$_{26}$BrO$_3$ [MH$^+$], 465.1060. Found, 465.1061 [MH$^+$]. Calc. for C$_{26}$H$_{25}$O$_3$BrNa [MNa$^+$] 487.0879. Found 487.0882 [MNa$^+$]. UV $\lambda_{max}$ 357 nm, ε 35500 M$^{-1}$ cm$^{-1}$.

Example 6—Preparation of 1-(4-(tert-butyl)phenyl)-3-(4-((4-(5-(1-isobutyl-4,4-dimethyl-1,4,5,6-tetrahydropyridin-3-yl)-5-oxopent-1-en-1-yl)benzyl)oxy)phenyl)propane-1,3-dione, 10

A mixture of 1-(4-((4-bromobenzyl)oxy)phenyl)-3-(4-(tert-butyl)phenyl)propane-1,3-dione, 9 (224 mg, 0.48 mmol) and 1-(1-Isobutyl-4,4-dimethyl-1,4,5,6-tetrahydropyridin-3-yl)pent-4-en-1-one, 8 (100 mg, 0.40 mmol) in acetonitrile (5 mL) was treated with triethylamine (134 µL, 0.96 mmol) and a mixture of palladium(II)acetate (9 mg, 0.04 mmol) and tris(2-methoxyphenyl)phosphine (28 mg, 0.08 mmol) in acetonitrile (1 mL) which had been previously sonicated for 1 minute. The mixture was then heated to reflux for 2 hours followed by heating in a sealed vessel under microwave irradiation at 150° C. for 10 minutes. The reaction mixture was then diluted with ethyl acetate (30 mL), washed with saturated NaCl solution and dried with sodium sulfate. Evaporation in-vacuo gave the crude material as a brown gum (370 mg) which was purified by column chromatography over silica gel eluting with 0-30% ethyl acetate:petroleum ether. Evaporation of the eluents gave the title compound as a cream foam (63 mg, 25%). Analytical data were complicated by the presence of double bond isomers.

$\delta_H$ (CDCl$_3$, 400 MHz) 7.98 (d, J 7.9, 2H), 7.93 (d, J 8.5, 2H), 7.52 (d, J 8.6, 2H), 7.44-7.23 (m, 4H), 7.19-7.03 (m, 3H), 6.97 (s, 1H), 6.63-5.59 (m, 2H), 5.16-5.12 (m, 2H), 3.51-3.20 (m, 2H), 3.14-3.11 (m, 2H), 2.99-2.91 (m, 2H), 2.62-2.53 (m, 2H), 2.03-1.89 (m, 1H), 1.62 (t, J 6.1, 2H), 1.38 (s, 9H), 1.30-1.28 (m, 6H), 0.92-0.89 (m, 6H). HRMS (ES): calc. for C$_{42}$H$_{52}$NO$_4$ [MH$^+$], 634.3891. Found, 634.3884 [MH$^+$]. UV $\lambda_{max}$ 314 nm, $\epsilon$ 23250 M$^{-1}$ cm$^{-1}$ and 357 nm, $\epsilon$ 24050 M$^{-1}$ cm$^{-1}$.

Example 7—Preparation of (4-(tert-butyl)phenyl)(1-isobutyl-4,4-dimethyl-1,4,5,6-tetrahydropyridin-3-yl)methanone, 11

A solution of 1-isobutyl-4,4-dimethyl-1,2,3,4-tetrahydropyridine (200 mg, 1.2 mmol) and triethylamine (167 µL, 1.2 mmol) in DCM (7 mL) was cooled on an ice bath and treated drop wise with a solution of 4-tert-butylbenzoyl chloride (233 µL, 1.2 mmol) in DCM (4 mL). Once addition was complete the mixture was stirred for a further 18 hours before shaking with consecutive portions of water and sodium carbonate solution (5% w/w). The organic phase was then separated and dried with sodium sulfate. Evaporation in-vacuo gave the crude material as a yellow oil (350 mg) which was purified by column chromatography over silica gel eluting with 2.5-10% ethyl acetate:petroleum ether. Evaporation of the eluents gave the title compound as a pale yellow oil (148 mg, 38%).

$\delta_H$ (CDCl$_3$, 200 MHz) 7.41-7.30 (m, 4H), 6.86 (s, 1H), 3.17 (t, J 4.7, 2H), 2.86 (d, J 7.5, 2H), 1.99-1.85 (m, 1H), 1.72 (t, J 7.1, 2H), 1.39 (s, 6H), 1.35 (s, 6H), 0.86 (d, J 6.7, 6H). $\delta_C$ (CDCl$_3$, 100 MHz) 192.9, 152.4, 152.2, 139.4, 128.7, 124.6, 114.5, 63.8, 43.5, 38.9, 34.7, 31.3, 30.2, 27.7, 27.3, 19.7. HRMS (ES): calc. for C$_{22}$H$_{34}$NO [MH$^+$], 328.2635. Found, 328.2634 [MH$^+$]. UV $\lambda_{max}$ 317 nm, $\epsilon$ 19000 M$^{-1}$ cm$^{-1}$.

Example 8—Preparation of (1-isobutyl-4,4-dimethyl-1,4,5,6-tetrahydropyridin-3-yl)(4-methoxyphenyl)methanone, 12

Prepared according to the procedure above for the preparation of (4-(tert-butyl)phenyl)(1-isobutyl-4,4-dimethyl-1,4,5,6-tetrahydropyridin-3-yl)methanone, 11 as a very pale yellow oil (41 mg, 11%).

$\delta_H$ (CDCl$_3$, 200 MHz) 7.51 (d, J 8.8, 2H), 6.90 (d, J 8.8, 2H) 6.83 (s, 1H), 3.87 (s, 3H), 3.20 (t, J 6.0, 2H), 2.87 (d, J 7.5, 2H), 2.04-1.71 (m, 3H), 1.40 (s, 6H), 0.88 (d, J 6.7, 6H). $\delta_C$ (CDCl$_3$, 100 MHz) 192.6, 160.7, 151.8, 134.8, 130.7, 114.5, 113.0, 63.9, 55.3, 43.5, 38.8, 30.2, 27.7, 27.3, 19.7. HRMS (ES): calc. for C$_{19}$H$_{27}$NO$_2$ [MH$^+$], 302.2126. Found, 302.2114 [MH$^+$]. UV $\lambda_{max}$ 319 nm.

Example 9—Preparation of 1-(1-isobutyl-4,4-dimethyl-1,4,5,6-tetrahydropyridin-3-yl)-3-(4-methoxyphenyl)propane-1,3-dione, 13

Prepared according to the procedure above for the preparation of (4-(tert-butyl)phenyl)(1-isobutyl-4,4-dimethyl-1,4, 5,6-tetrahydropyridin-3-yl)methanone, 11 as a yellow oil (292 mg, 36%). Analytical data indicated the presence of an approximately 3:1 mixture of the keto and enol forms.

$\delta_H$ (CDCl$_3$, 200 MHz) 8.15 (d, J 4.4, 1.5H), 7.82 (d, J 8.7, 0.5H), 7.52 (s, 0.75H), 7.32 (s, 0.25H), 6.93 (d, J 9.0, 2H) 6.11 (s, 0.25H), 4.08 (s, 1.5H), 3.88 (s, 3H), 3.22-3.09 (m, 2H), 3.03 (d, J 7.5, 2H), 2.01-1.91 (m, 1H), 1.71-1.55 (m, 2H), 1.37 (s, 1.5H), 1.21 (s, 4.5H), 0.95-0.93 (m, 6H). $\delta_C$ (CDCl$_3$, 100 MHz) 195.0, 188.3, 186.8, 176.2, 163.7, 161.2, 151.4, 146.2, 132.0, 130.1, 129.5, 128.0, 90.8, 64.5, 64.4, 60.5, 55.6, 55.5, 52.6, 43.7, 43.6, 39.6, 39.1, 30.2, 30.1, 28.6, 27.8, 27.6, 21.1, 20.0, 19.9, 14.4. HRMS (ES): calc. for C$_{21}$H$_{30}$NO$_3$ [MH$^+$], 344.2220. Found, 344.2225 [MH$^+$]. UV $\lambda_{max}$ 293 nm, $\epsilon$ 14250 M$^{-1}$ cm$^{-1}$; 396 nm, $\epsilon$ 11150 M$^{-1}$ cm$^{-1}$.

Example 10—Preparation of (4-(dimethylamino)phenyl)(1-isobutyl-4,4-dimethyl-1,4,5,6-tetrahydropyridin-3-methanone, 15

In a Schlenk tube, toluene (2 mL; previously dried over sodium wire) was degassed with a stream of argon. Sodium tert-butoxide (129 mg, 1.34 mmol) was added followed by dimethylamine hydrochloride (50 mg, 0.62 mmol), and the mixture stirred for 5 mins. The remaining materials were added in the following order: (4-bromophenyl)(1-isobutyl-4,4-dimethyl-1,4,5,6-tetrahydropyridin-3-yl)methanone 16 (140 mg, 0.56 mmol), BINAP (21 mg, 0.034 mmol) and tris(dibenzylidene)dipalladium(0) (15 mg, 0.017 mmol). The Schlenk tube was sealed and the reaction stirred at 80° C. for 20 h. The reaction was then cooled, diluted with EtOAc and filtered through Celite, washing thoroughly with extra EtOAc. The filtrate was then washed with water (20 mL), sat. NaHCO$_3$ (20 mL) and brine (20 mL), then dried (MgSO$_4$) and concentrated in-vacuo. The crude material was purified by radial chromatography over silica gel eluting with 33% ethyl acetate:petroleum ether to afford the title compound as a yellow oil (41 mg, 23%).

$\delta_H$ (CDCl$_3$, 400 MHz) 7.49 (m, 2H), 6.82 (s, 1H), 6.64 (m, 2H), 3.15 (m, 2H), 3.00 (s, 6H), 2.83 (d, J 7.6, 2H), 1.90 (m, 1H), 1.70 (m, 2H), 1.35 (s, 6H), 0.85 (d, J 6.7, 6H). $\delta_C$ (CDCl$_3$, 100 MHz) 193.2, 151.7, 150.9, 131.1, 129.9, 114.4, 110.9, 63.9, 43.6, 40.5, 39.1, 30.4, 28.0, 27.5, 20.0. HRMS (ES): calc. for C$_{20}$H$_{31}$N$_2$O [MH$^+$], 315.2431. Found, 315.2431 [MH$^+$]. UV $\lambda_{max}$ 336 nm, $\epsilon$ 17000 M$^{-1}$ cm$^{-1}$.

Example 11—Preparation of (4-bromophenyl)(1-isobutyl-4,4-dimethyl-1,4,5,6-tetrahydropyridin-3-yl)methanone, 16

A solution of 1-isobutyl-4,4-dimethyl-1,2,3,4-tetrahydropyridine (203 mg, 1.2 mmol) and triethylamine (169 µL, 1.2 mmol) in DCM (3 mL) was cooled on an ice bath and treated drop wise with a solution of 4-bromobenzoyl chloride (266 mg, 1.2 mmol) in DCM (4 mL). Once addition was complete the mixture was stirred for a further 18 hours before quenching by pouring into water (10 mL). The organic phase was then separated, combined with two further DCM extracts and the combined organic layers washed with water and dried with magnesium sulfate. Evaporation in-vacuo gave the crude material as a light brown solid (354 mg) which was purified by radial chromatography over silica gel eluting with 10-15% ethyl acetate:petroleum ether. Evaporation of the eluents gave the title compound as a pale yellow solid (166 mg, 39%).

$\delta_H$ (CDCl$_3$, 400 MHz) 7.47 (m, 2H), 7.33 (m, 2H), 6.72 (s, 1H), 3.16 (m, 2H), 2.83 (d, J 7.6, 2H), 1.89 (m, 1H), 1.69 (m, 2H), 1.36 (s, 6H), 0.83 (d, J 6.6, 6H). $\delta_C$ (CDCl$_3$, 100 MHz) 192.0, 152.8, 141.4, 131.1, 130.5, 123.6, 114.8, 64.3, 43.8, 38.9, 30.4, 27.8, 27.5, 19.9. HRMS (APCI): calc. for C$_{18}$H$_{25}$BrNO [MH$^+$], 350.1114. Found 350.1112 [MH$^+$]. UV $\lambda_{max}$ 318 nm, $\epsilon$ 22500 M$^{-1}$ cm$^{-1}$.

Example 12—Preparation of (2,3-dihydrobenzofuran-5-yl)(1-isobutyl-4,4-dimethyl-1,4,5,6-tetrahydropyridin-3-yl)methanone, 18

Prepared according to the procedure above for the preparation of (4-bromophenyl)(1-isobutyl-4,4-dimethyl-1,4,5,6-tetrahydropyridin-3-yl)methanone, 16 as an off-white solid (33 mg, 9%).

$\delta_H$ (CDCl$_3$, 400 MHz) 7.45 (s, 1H), 7.31 (s, 1H), 6.82 (s, 1H), 6.73 (d, J 8.2, 1H), 4.62 (t, J 8.7, 2H), 3.25-3.17 (m, 4H), 2.86 (d, J 7.5, 2H), 1.98-1.89 (m, 1H), 1.69 (m, 2H), 1.38 (s, 6H), 0.87 (d, J 6.7, 6H). $\delta_C$ (CDCl$_3$, 100 MHz) 193.0, 161.5, 151.7, 135.2, 130.0, 126.8, 126.3, 114.7, 108.1, 71.8, 64.0, 43.6, 39.0, 30.4, 29.6, 27.9, 27.5, 19.9. HRMS (APCI): calc. for C$_{20}$H$_{28}$NO$_2$ [MH$^+$], 314.2115. Found, 314.2113 [MH$^+$]. UV $\lambda_{max}$ 320 nm, $\epsilon$ 22000 M$^{-1}$ cm$^{-1}$.

Example 13—Preparation of [1,1'-biphenyl]-4-yl(1-isobutyl-4,4-dimethyl-1,4,5,6-tetrahydropyridin-3-yl)methanone, 19

Prepared according to the procedure above for the preparation of (4-bromophenyl)(1-isobutyl-4,4-dimethyl-1,4,5,6-tetrahydropyridin-3-yl)methanone, 16 as yellow crystalline solid (76 mg, 18%).

$\delta_H$ (CDCl$_3$, 400 MHz) 7.65-7.51 (m, 6H), 7.43 (m, 2H), 7.34 (m, 1H), 6.84 (s, 1H), 3.16 (m, 2H), 2.83 (d, J 7.5, 2H), 1.89 (m, 1H), 1.71 (m, 2H), 1.39 (s, 6H), 0.83 (d, J 6.7, 6H). $\delta_C$ (CDCl$_3$, 100 MHz) 193.0, 152.6, 142.1, 141.4, 140.8, 129.5, 129.0, 127.7, 127.3, 126.6, 114.9, 64.1, 43.7, 39.0, 30.4, 27.9, 27.5, 19.9. HRMS (APCI): calc. for C$_{24}$H$_{30}$NO [MH$^+$], 348.2322. Found, 348.2326 [MH$^+$]. UV $\lambda_{max}$ 320 nm, $\epsilon$ 18000 M$^{-1}$ cm$^{-1}$.

Example 14—Preparation of (1-isobutyl-4,4-dimethyl-1,4,5,6-tetrahydropyridin-3-yl)(phenyl)methanone, 20

Prepared according to the procedure above for the preparation of (4-bromophenyl)(1-isobutyl-4,4-dimethyl-1,4,5,6-tetrahydropyridin-3-yl)methanone, 16 as pale yellow solid (150 mg, 46%).

$\delta_H$ (CDCl$_3$, 400 MHz) 7.47-7.41 (m, 2H), 7.36-7.27 (m, 3H), 6.75 (s, 1H), 3.16 (m, 2H), 2.79 (d, J 7.5, 2H), 1.86 (sept, J 6.7, 1H), 1.70-1.65 (m, 2H), 1.36 (s, 6H), 0.80 (d, J 6.7, 6H). $\delta_C$ (CDCl$_3$, 100 MHz) 193.3, 152.8, 142.4, 129.2, 128.7, 127.8, 114.6, 64.0, 43.6, 38.9, 30.2, 27.7, 27.3, 19.8. HRMS (ES): calc. for C$_{18}$H$_{26}$ON [M$^+$H], 272.2009. Found, 272.2009 [M$^+$H]. UV $\lambda_{max}$ 316 nm $\epsilon$ 19000 M$^{-1}$ cm$^{-1}$.

Example 15—Preparation of 1,4-phenylenebis((1-isobutyl-4,4-dimethyl-1,4,5,6-tetrahydropyridin-3-yl)methanone), 21

Prepared according to the procedure above for the preparation of (4-bromophenyl)(1-isobutyl-4,4-dimethyl-1,4,5,6-tetrahydropyridin-3-yl)methanone, 16 as pale yellow oil (164 mg, 15%).

$\delta_H$ (CDCl$_3$, 400 MHz) 7.37 (s, 4H), 6.75 (s, 2H), 3.15-3.08 (m, 4H), 2.78 (d, J 7.6, 4H), 1.83 (sept. J 6.7, 2H), 1.69-1.62 (m, 4H), 1.34 (s, 12H), 0.78 (d, J 6.7, 12H). $\delta_C$ (CDCl$_3$, 100 MHz) 193.2, 153.4, 143.3, 128.2, 114.8, 64.1, 43.7, 38.9, 30.3, 27.8, 27.5, 19.8. HRMS (ES): calc. for C$_{30}$H$_{43}$N$_2$O$_2$[MH$^+$], 465.3476. Found, 465.3478 [MH$^+$]. UV $\lambda_{max}$ 320 nm, $\epsilon$ 20000 M$^{-1}$ cm$^{-1}$.

Example 16—Preparation of benzene-1,3,5-triyltris((1-isobutyl-4,4-dimethyl-1,4,5,6-tetrahydropyridin-3-yl)methanone), 22

Prepared according to the procedure above for the preparation of (4-bromophenyl)(1-isobutyl-4,4-dimethyl-1,4,5,6-tetrahydropyridin-3-yl)methanone, 16 as a yellow oil (124 mg, 19%).

$\delta_H$ (CDCl$_3$, 400 MHz) 7.52 (s, 3H), 6.74 (s, 3H), 3.10-3.04 (m, 6H), 2.76 (d, J 7.5, 6H), 1.79 (sept. J 6.7, 3H), 1.64-1.57 (m, 6H), 1.28 (s, 18H), 0.72 (d, J 6.7, 18H). $\delta_C$ (CDCl$_3$, 100 MHz) 192.5, 153.0, 141.6, 130.0, 114.5, 64.1, 43.6, 38.7, 30.1, 27.6, 27.3, 19.7. HRMS (ES): calc. for C$_{42}$H$_{64}$N$_3$O$_3$[MH$^+$], 658.4942. Found, 658.4944 [MH$^+$]. UV $\lambda_{max}$ 316 nm, $\epsilon$ 33000 M$^{-1}$ cm$^{-1}$.

Example 17—Preparation of (4-benzoylphenyl)(1-isobutyl-4,4-dimethyl-1,4,5,6-tetrahydropyridin-3-yl)methanone, 23

Prepared according to the procedure above for the preparation of (4-bromophenyl)(1-isobutyl-4,4-dimethyl-1,4,5,6-tetrahydropyridin-3-yl)methanone, 16 as a bright yellow oil which on cooling solidified (385 mg, 43%). Mp 43-44° C.

$\delta_H$ (CDCl$_3$, 400 MHz) 7.84-7.77 (m, 4H), 7.64-7.49 (m, 5H), 6.78 (s, 1H), 3.20 (t, J 5.9, 2H), 2.86 (d, J 7.5, 2H), 1.97-1.86 (m, 1H), 1.74 (t, J 5.9, 2H), 1.42 (s, 6H), 0.85 (d, J 6.7, 6H). $\delta_C$ (CDCl$_3$, 100 MHz) 196.8, 192.1, 153.3, 146.6, 138.1, 137.6, 132.8, 130.3, 129.7, 128.5, 115.0, 64.2, 43.8, 38.9, 30.3, 27.8, 27.5, 19.8. HRMS (ES): calc. for C$_{25}$H$_{30}$NO$_2$ [MH$^+$], 376.2271. Found, 376.2262 [MH$^+$]. UV $\lambda_{max}$ 295 nm, $\epsilon$ 7500 M$^{-1}$ cm$^{-1}$.

Example 18—Preparation of 2,4-dimethoxyphenyl(1-isobutyl-4,4-dimethyl-1,4,5,6-tetrahydropyridin-3-yl)methanone, 24

1-isobutyl-4,4-dimethyl-1,2,3,4-tetrahydropyridine (200 mg, 1.2 mmol) was dissolved in DCM (3 mL) and cooled to 0° C., under an argon atmosphere. Triethylamine (167 µL, 1.0 mmol) was added, and the mixture stirred for 5 min. A solution of 2,4-dimethoxybenzoyl chloride (259 mg, 1.2 mmol) in DCM (4 mL) was then added drop wise and the mixture stirred for 1 h at 0° C. The ice bath was then removed and the reaction allowed stirred for 18 hours. The reaction mixture was then poured into water (10 mL), the layers separated, and the aqueous phase extracted further with DCM (2×10 mL). The combined organic extracts were washed with water (2×10 mL), then dried with magnesium sulfate and concentrated in-vacuo. The crude material was dissolved in methanol/DCM, filtered through a short column of silica, eluting with methanol. The filtrate was concentrated in-vacuo, then subjected to radial chromatography over silica gel twice eluting with 50-75% ethyl acetate:petroleum ether and 50% ethyl acetate:petroleum ether. The material thus obtained was then purified by preparative thin layer chromatography eluting with 50% ethyl acetate:petroleum, ether. The residue was dissolved in DCM (0.5 mL) and 2M HCl in ether (4 drops) added drop wise. Diethyl ether (5 mL) was then added and the solvent decanted leaving a yellow residue in the flask. The residue was washed further with diethyl ether, then dissolved in DCM (1 mL) and treated with triethylamine (3 drops). The solution was then washed with 5% $NaCO_3$ solution, the organic phase separated, dried with magnesium sulfate and evaporated in-vacuo to afford the title compound as a yellow oil (12 mg, 3%).

$\delta_H$ (CDCl$_3$, 400 MHz) 7.16 (br s, 1H), 7.09 (d, J 7.9, 1H), 6.51-6.48 (m, 2H), 3.83 (s, 3H), 3.79 (s, 3H), 3.34 (t, J 5.2, 2H), 3.06 (d, J 7.1, 2H), 1.96 (m, 1H), 1.74 (t, J 5.2, 2H), 1.36 (s, 6H), 0.85 (d, J 6.6, 6H). $\delta_C$ (CDCl$_3$, 100 MHz) 185.9, 163.1, 160.8, 159M, 132.2, 117.1, 115.8, 104.7, 99.3, 65.9, 56.2, 55.7, 45.2, 38.1, 27.2, 27.2, 19.7. HRMS (APCI): calc. for $C_{20}H_{30}O_3N$ [MH$^+$], 332.2220. Found, 332.2226 [MH$^+$], UV $\lambda_{max}$ 313 nm, $\epsilon$9500 M$^{-1}$ cm$^{-1}$.

Example 19—Preparation of 1-(1-isobutyl-4,4-dimethyl-1,4,5,6-tetrahydropyridin-3-yl)-3-methylbut-2-en-1-one, 26 and 1-(1-isobutyl-4,4-dimethyl-1,4,5,6-tetrahydropyridin-3-yl)-3-methylbut-3-en-1-one, 27

A solution of 1-isobutyl-4,4-dimethyl-1,2,3,4-tetrahydropyridine (400 mg, 2.4 mmol) and triethylamine (400 µL, 2.9 mmol) in DCM (10 mL) was cooled on an ice bath and treated drop wise with a solution of 3-methylbut-2-enoyl chloride (373 mg, 2.4 mmol) in DCM (10 mL). Once addition was complete the mixture was stirred for a further 2 hours before quenching by pouring into water (10 mL). The organic phase was then separated, washed with sodium carbonate solution (10% w/w, 20 mL) and dried with magnesium sulfate. Evaporation in-vacuo gave the crude material as a brown oil which was purified by column chromatography over silica gel eluting with 0-10% ethyl acetate:petroleum ether.

Evaporation of the eluents gave: 1-(1-isobutyl-4,4-dimethyl-1,4,5,6-tetrahydropyridin-3-yl)-3-methylbut-2-en-1-one, 26 as a pale yellow oil (250 mg, 42%); $\delta_H$ (CDCl$_3$, 400 MHz) 7.14 (s, 1H), 5.98 (s, 1H), 3.18 (t, J 5.8, 2H), 2.95 (d, J 7.5, 2H), 1.99-1.90 (m, 1H), 1.85 (s, 3H), 1.83 (s, 3H), 1.63 (t, J 5.8, 2H), 1.33 (s, 6H), 0.92 (d, J 6.7, 6H). $\delta_C$ (CDCl$_3$, 100 MHz) 190.5, 150.0, 142.0, 124.8, 116.5, 64.0, 43.5, 39.2, 30.0, 27.9, 27.3, 26.3, 20.2, 19.8. HRMS (APCI): calc. for $C_{16}H_{28}NO$ [MH$^+$], 250.2165. Found, 250.2174 [MH$^+$]. UV $\lambda_{max}$ 314 nm, $\epsilon$ 19000 M$^{-1}$ cm$^{-1}$; and 1-(1-isobutyl-4,4-dimethyl-1,4,5,6-tetrahydropyridin-3-yl)-3-methylbut-3-en-1-one, 27 as a colourless oil (110 mg, 19%).

$\delta_H$ (CDCl$_3$, 400 MHz) 7.23 (s, 1H), 4.84 (s, 1H), 4.77 (s, 1H), 3.19 (s, 2H), 3.12 (t, J 5.9, 2H), 2.95 (d, J 7.9, 2H), 1.98-1.90 (m, 1H), 1.76 (s, 3H), 1.65-1.59 (m, 2H), 1.29 (s, 6H), 0.91 (d, J 6.7, 6H). $\delta_C$ (CDCl$_3$, 100 MHz) 192.8, 149.2, 143.4, 115.2, 112.5, 64.5, 47.9, 43.5, 39.4, 30.2, 28.0, 27.5, 22.5, 20.0. HRMS (APCI): calc. for $C_{16}H_{28}NO$ [MH$^+$], 250.2165. Found, 250.2175 [MH$^+$]. UV $\lambda_{max}$ 306 nm, $\epsilon$ 14500 M$^{-1}$ cm$^{-1}$.

Example 20—Preparation of (E)-1-(1-isobutyl-4,4-dimethyl-1,4,5,6-tetrahydropyridin-3-yl)hexa-3,5-dien-1-one, 28

Prepared according to the procedure above for the preparation of 1-(1-isobutyl-4,4-dimethyl-1,4,5,6-tetrahydropyridin-3-yl)-3-methylbut-2-en-1-one, 26 as a yellow oil (82 mg, 14%).

$\delta_H$ (CDCl$_3$, 400 MHz) 7.10 (s, 1H), 6.35-6.24 (m, 1H), 6.10-6.01 (m, 1H), 5.89-5.80 (m, 1H), 5.09-5.02 (m, 1H), 4.97-4.92 (m, 1H), 3.23-3.20 (m, 2H), 3.10-3.05 (m, 2H), 2.92 (d, J 7.4, 2H), 1.91 (sept, J 6.7, 1H), 1.59-1.54 (m, 21-1), 1.23 (s, 6H), 0.87 (d, J 6.7, 6H). $\delta_C$ (CDCl$_3$, 100 MHz) 192.5, 149.1, 137.3, 132.7, 130.8, 115.5, 114.9, 64.5, 43.6, 41.9, 39.4, 30.3, 28.1, 27.6, 20.0. HRMS (ES): calc. for $C_{17}H_{28}NO$ [MH$^+$], 262.2165. Found, 262.2170 [MH$^+$]. UV $\lambda_{max}$ 311 nm, $\epsilon$ 275000 M$^{-1}$ cm$^{-1}$.

Example 21—Preparation of 1-(1-isobutyl-4,4-dimethyl-1,4,5,6-tetrahydropyridin-3-yl)but-3-en-1-one, 29

Prepared according to the procedure above for the preparation of 1-(1-isobutyl-4,4-dimethyl-1,4,5,6-tetrahydropyridin-3-yl)-3-methylbut-2-en-1-one, 26 as a pale yellow oil (120 mg, 21%).

$\delta_H$ (CDCl$_3$, 400 MHz) 7.16 (s, 1H), 6.07-5.93 (m, 1H), 5.13-5.08 (m, 2H), 3.24 (d, J 6.8, 2H), 3.13 (t, J 5.4, 2H), 2.97 (d, J 7.4, 2H), 2.02-1.93 (m, 1H), 1.62-1.59 (m, 2H), 1.29 (s, 6H), 0.93 (d, J 6.7, 6H). $\delta_C$ (CDCl$_3$, 100 MHz) 192.7, 149.0, 134.8, 116.4, 114.9, 64.5, 43.6, 43.2, 39.3, 30.2, 28.1, 27.6, 20.0. HRMS (ES): calc. for $C_{15}H_{26}NO$ [MH$^+$], 236.2009. Found, 236.2018 [MH$^+$]. UV $\lambda_{max}$ 310 nm, $\epsilon$ 270000 M$^{-1}$ cm$^{-1}$.

Example 22—Preparation of (E)-1-(1-isobutyl-4,4-dimethyl-1,4,5,6-tetrahydropyridin-3-yl)-3-phenyl-prop-2-en-1-one, 31

1-(1-Isobutyl-4,4-dimethyl-1,4,5,6-tetrahydropyridin-3-yl)prop-2-en-1-one (98 mg, 0.44 mmol), iodobenzene (101 mg, 0.50 mmol), triphenylphosphine (24 mg, 0.09 mmol), tetraethylammonium chloride (118 mg, 0.44 mmol), potassium carbonate (124 mg, 0.89 mmol) and palladium (II) acetate (10 mg, 0.04 mmol) in DMF (5 mL) were stirred under a nitrogen atmosphere at 110° C. for 2 hours. The reaction mixture was then cooled to ambient temperature and water (10 mL) was added. The aqueous layer was separated and extracted with diethyl ether (3×10 mL) and the combined organic layers washed with water (10 mL), dried with magnesium sulfate and concentrated in-vacuo to give a yellow oil. The crude material was preabsorbed onto Celite and then chromatographed over Florisil, eluting with 0-100% DCM:heptane followed by 0-7.5% ethyl acetate:heptane to give the title compound as a yellow solid (117 mg, 87%).

$\delta_H$ (CDCl$_3$, 400 MHz) 7.52-7.47 (m, 2H), 7.44 (d, J 15.5, 1H), 7.35-7.26 (m, 3H), 7.29 (s, 1H), 7.08 (d, J 15.5, 1H), 3.17-3.12 (m, 2H), 2.98 (d, J 7.5, 2H), 1.95 (sept, J 6.7, 1H), 1.67-1.62 (m, 2H), 1.33 (s, 6H), 0.89 (d, J 6.7, 6H). $\delta_C$ (CDCl$_3$, 100 MHz) 185.5, 148.9, 138.4, 136.6, 129.0, 128.8, 127.8, 124.5, 117.1, 64.5, 43.8, 39.2, 30.5, 28.0, 27.6, 20.0.

HAMS (ES): calc. for $C_{20}H_{28}NO$ [MH$^+$], 298.2165. Found, 298.2165 [MH$^+$]. UV $\lambda_{max}$ 360 nm, $\epsilon$ 16000 M$^{-1}$ cm$^{-1}$.

Example 23—Preparation of 1-(1-Isobutyl-4,4-Dimethyl-1,4,5,6-tetrahydropyridin-3-yl)prop-2-en-1-one, 32

Prepared according to the procedure above for the preparation of 1-(1-isobutyl-4,4-dimethyl-1,4,5,6-tetrahydropyridin-3-yl)-3-methylbut-2-en-1-one, 26 as a yellow oil (912 mg, 55%).

$\delta_H$ (CDCl$_3$, 400 MHz) 7.22 (s, 1H), 6.71 (dd, J 10.6, 17.0, 1H), 6.00 (dd, J 2.3, 17.0, 1H), 5.44 (dd, J 2.3, 10.6, 1H), 3.5-3.10 (m, 2H), 2.94 (d, J 7.4, 2H), 1.93 (sept, J 6.7, 1H), 1.64-1.59 (m, 2H), 1.29 (s, 6H), 0.88 (d, J 6.7, 6H). $\delta_C$ (CDCl$_3$, 100 MHz) 186.2, 149.7, 134.0, 123.3, 116.1, 64.5, 43.7, 39.1, 30.3, 27.8, 27.6, 20.0. HRMS (ES): calc. for $C_{14}H_{24}NO$ [MH$^+$], 222.1852. Found, 222.1851 [MH$^+$]. UV $\lambda_{max}$ 331 nm, $\epsilon$ 20500 M$^{-1}$ cm$^{-1}$.

Example 24—Preparation of (E)-1-(1-Isobutyl-4,4-dimethyl-1,4,5,6-tetrahydropyridin-3-yl)-3-(4-(trifluoromethyl)phenyl)prop-2-en-1-one, 33

Prepared according to the procedure above for the preparation of (E)-1-(1-Isobutyl-4,4-dimethyl-1,4,5,6-tetrahydropyridin-3-yl)phenylprop-2-en-1-one, 31 as a yellow oil (23 mg, 19%).

$\delta_H$ (CDCl$_3$, 400 MHz) 7.57 (s, 4H), 7.44 (d, J 15.5, 1H), 7.29 (s, 1H), 7.14 (d, J 15.5, 1H), 3.18-3.14 (m, 2H), 3.00 (d, J 7.5, 2H), 1.96 (sept. J 6.7, 1H), 1.68-1.62 (m, 2H), 1.32 (s, 6H), 0.90 (d, J 6.7, 6H). $\delta_C$ (CDCl$_3$, 100 MHz) 184.6, 149.3, 140.1, 136.6, 130.5 (q, J$_{CF}$ 32.4), 130.3, 127.8, 125.8 (q, J$_{CF}$ 3.9), 124.3 (q, J$_{CF}$ 272.3), 117.2, 64.7, 43.8, 39.2, 30.6, 27.9, 27.6, 20.0. HRMS (ES): calc. for $C_{21}H_{27}F_3NO$ [MH$^+$], 366.2039. Found, 366.2042 [MH$^+$]. UV $\lambda_{max}$ 369 nm, $\epsilon$ 17000 M$^{-1}$ cm$^{-1}$.

Example 25—Preparation of (E)-1-(1-isobutyl-4,4-dimethyl-1,4,5,6-tetrahydropyridin-3-yl)-3-(4-methoxyphenyl)prop-2-en-1-one, 34

A mixture of 1-(1-Isobutyl-4,4-dimethyl-1,4,5,6-tetrahydropyridin-3-yl)prop-2-en-1-one (120 mg, 0.54 mmol) and 1-bromo-4-methoxybenzene (136 μL, 1.08 mmol) in acetonitrile (5 mL) was treated with triethylamine (181 μL, 1.30 mmol) and a mixture of palladium(II)acetate (12 mg, 0.05 mmol) and tris(2-methoxyphenyl)phosphine (38 mg, 0.11 mmol) in acetonitrile (1 mL) which had been previously sonicated for 1 minute. The mixture was then heated to reflux for 4 hours. The reaction mixture was then evaporated in-vacuo gave the crude material which was purified by column chromatography over silica gel eluting with 0-20% ethyl acetate:petroleum ether. Evaporation of the eluents gave the title compound as a yellow glass (160 mg, 90%).

$\delta_H$ (CDCl$_3$, 400 MHz) 7.57 (s, 4H), 7.44 (d, J 15.5, 1H), 7.29 (s, 1H), 7.14 (d, J 15.5, 1H), 3.18-3.14 (m, 2H), 3.00 (d, J 7.5, 2H), 1.96 (sept. J 6.7, 1H), 1.68-1.62 (m, 2H), 1.32 (s, 6H), 0.90 (d, J 6.7, 6H).

$\delta_C$ (CDCl$_3$, 100 MHz) 185.8, 160.4, 148.5, 138.2, 129.3, 122.2, 117.0, 114.2, 114.0, 64.5, 55.5, 43.7, 39.3, 30.5, 28.0, 27.8, 20.0. HRMS (ES): calc. for $C_{21}H_{30}NO_2$ [MH$^+$], 328.2271. Found, 328.2271 [MH$^+$]. UV $\lambda_{max}$ 364 nm, $\epsilon$ 16150 M$^{-1}$ cm$^{-1}$.

Example 26—Preparation of (2E,4E/Z)-1-(1-isobutyl-4,4-dimethyl-1,4,5,6-tetrahydropyridin-3-yl)-5-phenylpenta-2,4-dien-1-one, 35

Prepared according to the procedure above for the preparation of (E)-1-(1-isobutyl-4,4-dimethyl-1,4,5,6-tetrahydropyridin-3-yl)-3-(4-methoxyphenyl)prop-2-en-1-one, 34 as a yellow oil (110 mg, 63%). Analytical data were complicated by the presence of double bond isomers about the styrenyl double bond (also present in (2-bromovinyl)benzene starting material).

$\delta_H$ (CDCl$_3$, 400 MHz) 7.48-7.24 (m, 7H), 6.99-6.71 (m, 3H), 3.22-3.13 (m, 2H), 3.04-2.99 (m, 2H), 2.04-2.99 (m, 1H), 1.65 (t, J 5.9, 2H), 1.36-1.34 (m, 6H), 0.95-0.92 (m, 6H). $\delta_C$ (CDCl$_3$, 100 MHz) 185.4, 148.6, 138.6, 137.5, 137.1, 134.0, 129.3, 128.8, 128.7, 128.5, 128.3, 127.7, 126.9, 123.3, 117.1, 64.5, 43.8, 39.2, 30.5, 27.9, 27.6, 20.0. HRMS (ES): calc. for $C_{22}H_{30}NO$ [MH$^+$], 324.2322. Found, 324.2321 [MH$^+$]. UV $\lambda_{max}$ 318 nm, $\epsilon$ 14800 M$^{-1}$ cm$^{-1}$ and 370 nm, $\epsilon$ 13200 M$^{-1}$ cm$^{-1}$.

Example 27—Preparation of 1-(1-Isobutyl-4,4-dimethyl-1,4,5,6-tetrahydropyridin-3-yl)methylprop-2-en-1-one, 36

Prepared according to the procedure above for the preparation of 1-(1-isobutyl-4,4-dimethyl-1,4,5,6-tetrahydropyridin-3-yl)-3-methyl but-2-en-1-one, 26 as a yellow oil (24 mg, 9%).

$\delta_H$ (CDCl$_3$, 400 MHz) 7.14 (s, 1H), 5.17-5.14 (m, 1H), 4.96-4.93 (m, 1H), 3.11-3.06 (m, 2H), 2.89 (d, J 7.4, 2H), 1.90-1.87 (m, 3H), 1.62-1.57 (m, 1H), 1.26 (s, 6H), 0.85 (d, J 6.7, 6H). $\delta_C$ (CDCl$_3$, 100 MHz) 195.5, 151.8, 146.5, 116.3, 113.9, 64.3, 43.7, 39.1, 30.1, 27.8, 27.6, 20.9, 20.0. HRMS (ES): calc. for $C_{15}H_{26}NO$ [MH$^+$], 236.2009. Found, 236.2008 [MH$^+$]. UV $\lambda_{max}$ 310 nm, $\epsilon$ 18950 M$^{-1}$ cm$^{-1}$.

Example 28—Preparation of (2E/Z) 1-(1-isobutyl-4,4-dimethyl-1,4,5,6-tetrahydropyridin-3-yl)penta-2,4-dien-1-one, 38

Prepared according to the procedure above for the preparation of 1-(1-isobutyl-4,4-dimethyl-1,4,5,6-tetrahydropyridin-3-yl)-3-methyl but-2-en-1-one, 26 as a yellow oil (170 mg, 29%). Analytical data suggested the presence of an approximately 75:25 mixture of E/Z double bond isomers.

$\delta_H$ (CDCl$_3$, 400 MHz) 7.23 (s, 1H), 7.16-6.89 (m, 1H), 6.62-6.11 (m, 2H), 5.52-5.20 (m, 2H), 3.20-3.14 (m, 2H), 3.00 (d, J 7.5, 1.5H), 2.95 (d, J 7.5, 0.5H), 2.02-1.91 (m, 1H), 1.66 (t, J 5.9, 2H), 1.35-1.34 (m, 6H), 0.94-0.89 (m, 6H). $\delta_C$ (CDCl$_3$, 100 MHz) 185.6, 151.4, 148.8, 138.7, 136.2, 135.1, 134.3, 129.2, 128.3, 122.4, 120.6, 117.0, 64.5, 64.4, 43.7, 39.2, 30.4, 30.3, 27.9, 27.6, 27.5, 20.0. HRMS (ES): calc. for $C_{16}H_{26}NO$ [MH$^+$], 248.2009. Found, 248.2009 [MH$^+$]. UV $\lambda_{max}$ 352 nm, $\epsilon$ 18000 M$^{-1}$ cm$^{-1}$.

Example 29—Preparation of 1-(1-isobutyl-4,4-dimethyl-1,4,5,6-tetrahydropyridine-3-carbonyl)-2-cyano-3,3-diphenylprop-2-en-1-one, 39

Prepared according to the procedure above for the preparation of 1-(1-isobutyl-4,4-dimethyl-1,4,5,6-tetrahydropyridin-3-yl)-3-methyl but-2-en-1-one, 26 as a bright yellow solid (137 mg, 25%).

$\delta_H$ (CDCl$_3$, 400 MHz) 7.42 (m, 5H), 7.33-7.15 (m, 5H), 3.03 (m, 2H), 2.91 (d, J 7.6, 2H), 1.85 (m, 1H), 1.44 (m, 2H), 1.18 (s, 6H), 0.82 (d, J 6.5, 6H). $\delta_C$ (CDCl$_3$, 100 MHz)

182.8, 158.8, 152.7, 139.1, 138.8, 130.1, 129.9, 129.9, 129.5, 128.7, 128.6, 128.2, 118.8, 114.0, 112.9, 64.8, 43.9, 38.6, 30.2, 27.5, 27.2, 20.0. HRMS (ES): calc. for $C_{27}H_{31}N_2O$ [MH$^+$], 399.2431. Found, 399.2432 [MH$^+$]. UV $\lambda_{max}$ 297 nm, $\epsilon$ 15750 M$^{-1}$ cm$^{-1}$ and 317 nm, $\epsilon$ 16150 M$^{-1}$ cm$^{-1}$.

Example 30—Preparation of 3,3-dimethyl-5-oxo-5-(phenylamino)pentanoic acid, 41a A solution of 4,4-dimethyldihydro-2H-pyran-2,6(3H)-dione (2.1 g, 14.8 mmol) in chloroform (20 mL) was treated drop-wise with aniline (2.7 mL, 29.5 mmol) and the mixture stirred at room temperature for 1 hour. The mixture was then diluted with DCM (20 mL), washed with hydrochloric acid solution (2 M, 30 mL), dried with magnesium sulfate and evaporated in-vacuo to give the title compound as a colourless solid (3.5 g, 100%).

$\delta_H$ (CDCl$_3$, 400 MHz) 8.01 (s, br, 1H), 7.55 (d, J 8.4, 2H), 7.38 (t, J 7.6, 2H), 7.20 (t, J 6.4, 1H), 2.53 (s, 2H), 2.50 (s, 2H), 1.20 (s, 6H).

Example 31—Preparation of 5-((4-methoxyphenyl)amino)-3,3-dimethyl-5-oxopentanoic acid, 41b Prepared according to the procedure above for the preparation of 3,3-dimethyl-5-oxo-5-(phenylamino)pentanoic acid, 41a as a grey solid (3.5 g, 93%).

$\delta_H$ (CDCl$_3$, 400 MHz) 7.69 (s, br, 1H), 7.43 (d, J 9.0, 2H), 6.92 (d, J 9.0, 2H), 3.83 (s, 3H), 2.52 (s, 2H), 2.47 (s, 2H), 1.21 (s, 6H).

Example 32—Preparation of 4,4-dimethyl-1-phenylpiperidine-2,6-dione, 42a

A suspension of 3,3-dimethyl-5-oxo-5-(phenylamino)pentanoic acid, 41a (3.5 g, 14.9 mmol) in chloroform (20 mL) was treated drop-wise with thionyl chloride (1.63 mL, 22.3 mmol) and the mixture stirred at room temperature for 10 minutes. After this time all material had dissolved and the mixture was heated in a sealed vessel under microwave irradiation at 100° C. for 10 minutes. The mixture was then diluted with DCM (20 mL), washed with water (2×50 mL) and 10% Na$_2$CO$_3$ solution (50 mL), dried with magnesium sulfate and evaporated in-vacuo to give the title compound as a cream solid (3.12 g, 97%).

$\delta_H$ (CDCl$_3$, 400 MHz) 7.51-7.38 (m, 3H), 7.10 (d, J 6.8, 2H), 2.71 (s, 4H), 1.24 (s, 6H).

Example 33—Preparation of 1-(4-methoxyphenyl)-4,4-dimethylpiperidine-2,6-dione, 42b Prepared according to the procedure above for the preparation of 4,4-dimethyl-1-phenylpiperidine-2,6-dione, 42a as a yellow solid (3.5 g, 100%).

$\delta_H$ (CDCl$_3$, 400 MHz) 7.03-6.98 (m, 4H), 3.83 (s, 3H), 2.69 (s, 4H), 1.23 (s, 6H).

Example 34—Preparation of 4,4-dimethyl-1-phenyl-3,4-dihydropyridin-2(1H)-one, 43a A suspension of 4,4-dimethyl-1-phenylpiperidine-2,6-dione, 42a (1.5 g, 6.9 mmol) in THF (20 mL) was cooled on an ice bath and treated drop-wise with lithium aluminium hydride (1 M solution in diethyl ether, 3.8 mL, 3.8 mmol) and the mixture stirred for 15 minutes. The reaction was then quenched by addition of 2 M hydrochloric acid solution until effervescence ceased followed by 4 M hydrochloric acid solution until a clear aqueous phase of pH<2 was formed. The biphasic mixture was then stirred for 15 minutes, the organic phase separated, dried with magnesium sulfate and evaporated in-vacuo to give a mixture of the title compound and starting dione as an orange liquid (0.82 g, 91% by wt, 54%).

$\delta_H$ (CDCl$_3$, 400 MHz) 7.46-7.39 (m, 2H), 7.33-7.25 (m, 3H), 6.18 (d, J 7.1, 1H), 5.16 (d, J 7.8, 1H), 2.57 (s, 2H), 1.21 (s, 6H).

Example 35—Preparation of 1-(4-methoxyphenyl)-4,4-dimethyl-3,4-dihydropyridin-2(1H)-one, 43b Prepared according to the procedure above for the preparation of 4,4-dimethyl-1-phenyl-3,4-dihydropyridin-2(1H)-one, 43a as an orange oil (1.7 g, 61%).

$\delta_H$ (CDCl$_3$, 400 MHz) 7.18 (d, J 8.9, 2H), 6.93 (d, J 8.9, 2H), 6.13 (d, J 7.7, 1H), 5.11 (d, J 7.7, 1H), 3.83 (s, 3H), 2.55 (s, 2H), 1.19 (s, 6H).

Example 36—Preparation of 4,4-dimethyl-1-phenyl-1,2,3,4-tetrahydropyridine, 46

A suspension of 4,4-dimethyl-1-phenyl-3,4-dihydropyridin-2(1H)-one, 43a (0.45 g, 2.24 mmol) in diethyl ether (20 mL) was treated drop-wise with lithium aluminium hydride (1 M solution in diethyl ether, 2.24 mL, 2.24 mmol) and the mixture heated to reflux for 1 hour. Heating was then discontinued and after 10 minutes the reaction quenched by addition of sodium sulfate decahydrate (0.15 g, 4.74 mmol). Once addition was complete the mixture was stirred for 20 minutes, treated with anhydrous sodium sulfate (300 mg) and stirred for a further 10 minutes. The mixture was then filtered through Celite into a flask containing BHT (4 g, 1 wt % assuming 100% yield), the filter cake washed with diethyl ether and the combined filtrates evaporated in-vacuo to give a mixture of the title compound and fully reduced amine, 4,4-dimethyl-1-phenylpiperidine as a golden liquid (321 mg, 70% by wt, 54%).

$\delta_H$ (CDCl$_3$, 400 MHz) 7.30-7.25 (m, 2H), 6.92 (d, J 7.9, 2H), 6.85 (t, J 6.5, 1H), 6.49 (d, J 8.1, 1H), 4.54 (d, J 8.1, 1H), 3.54-3.49 (m, 2H), 1.76 (t, J 5.7, 2H), 1.09 (s, 6H). UV $\lambda_{max}$ 278 nm, $\epsilon$ 22550 M$^{-1}$ cm$^{-1}$.

Example 37—Preparation of 1-(4,4-dimethyl-1-phenyl-1,4,5,6-tetrahydropyridin-3-yl)propan-1-one, 47

A solution of 4,4-dimethyl-1-phenyl-1,2,3,4-tetrahydropyridine, 46 (320 mg, 80% by wt, 1.37 mmol) and triethylamine (229 μL, 1.64 mmol) in DCM (10 mL) was cooled on an ice bath and treated drop wise with a solution of propionyl chloride (120 μL, 1.37 mmol) in DCM (10 mL). Once addition was complete the mixture was stirred for 1 hour at room temperature and heated to reflux for 1 hour after which time $^1$H NMR analysis suggested approximately 50% conversion. The mixture was then cooled to room temperature, diluted with water (10 mL) and the organic phase separated. The organic phase was then washed with sodium carbonate solution (10% w/w, 20 mL) and dried with magnesium sulfate. Evaporation in-vacuo gave the crude material as a brown oil (400 mg) which was purified by column chromatography over silica gel eluting with 0-10% ethyl acetate petroleum ether. Evaporation of the eluents gave the title compound as a pale yellow oil (110 mg, 33%).

$\delta_H$ (CDCl$_3$, 400 MHz) 7.72 (s, 1H), 7.42 (t, J 8.1, 2H), 7.17-7.10 (m, 3H), 3.64 (t, J 5.7, 2H), 2.63 (q, J 7.4, 2H), 1.81 (t, J 5.7, 2H), 1.40 (s, 6H), 1.16 (t, J 7.4, 2H). $\delta_C$ (CDCl$_3$, 100 MHz) 198.1, 146.0, 141.8, 129.7, 123.3, 121.0, 117.8, 43.4, 39.6, 30.7, 30.4, 28.2, 9.9. FIRMS (APCI): calc. for C$_{16}$H$_{22}$NO [MH$^+$], 244.1696. Found, 244.1706 [MH$^+$]. UV $\lambda_{max}$ 321 nm, $\epsilon$ 23000 M$^{-1}$ cm$^{-1}$.

Example 38—Preparation of 1-(4,4-dimethyl-1-phenyl-1,4,5,6-tetrahydropyridin-3-yl)prop-2-en-1-one, 48

Prepared according to the procedure above for the preparation of 1-(4,4-dimethyl-1-phenyl-1,4,5,6-tetrahydropyridin-3-yl)propan-1-one, 47 as a yellow oil (122 mg, 38%).

$\delta_H$ (CDCl$_3$, 400 MHz) 7.77 (s, 1H), 7.40 (t, J 7.4, 2H), 7.17-7.11 (m, 3H), 6.87 (dd, J 14.6 and 10.6, 1H), 6.13 (d, J 16.9, 1H), 5.60 (d, J 10.6, 1H), 3.67 (1, J 5.8, 2H), 1.84 (t, J 4.4, 2H), 1.42 (s, 6H). $\delta_C$ (CDCl$_3$, 100 MHz) 188.3, 145.8, 143.7, 133.9, 129.7, 124.8, 123.7, 121.7, 118.0, 43.7, 39.3, 30.8, 27.8. HRMS (ES): calc. for C$_{16}$H$_{20}$NO [MH$^+$], 242.1539. Found, 242.1540 [MH$^+$]. UV $\lambda_{max}$ 346 nm, 21000 M$^{-1}$ cm$^{-1}$.

Example 39—Preparation of (4-bromophenyl)(1-(phenyl)-4,4-dimethyl-1,4,5,6-tetrahydropyridin-3-yl)methanone, 49

A solution of 4,4-dimethyl-1-phenyl-1,2,3,4-tetrahydropyridine, 46 (450 mg, 55% by wt, 1.32 mmol) and triethylamine (313 µL, 2.25 mmol) in DCM (10 mL) was cooled on an ice bath and treated drop wise with a solution of 4-bromobenzoyl chloride (435 mg, 1.98 mmol) in DCM (10 mL). Once addition was complete the mixture was heated to reflux for 2 hour after which time $^1$H NMR analysis suggested that significant starting material remained. The mixture was then heated in a sealed vessel under microwave irradiation at 110° C. for 30 minutes, a further portion of triethylamine (313 µL, 2.25 mmol) and 4-bromobenzoyl chloride (435 mg, 1.98 mmol) added and the mixture heated to 140° C. for 30 minutes. The reaction mixture was then evaporated in-vacuo and the residue purified by column chromatography over silica gel eluting with 0-10% ethyl acetate:petroleum ether. Evaporation of the eluents gave the title compound as an off white crystalline solid (110 mg, 23%).

$\delta_H$ (CDCl$_3$, 400 MHz) 7.56 (d, J 8.4, 2H), 7.47 (d, J 8.5, 2H), 7.36-7.28 (m, 3H), 7.08 (t, J 7.4, 1H), 6.95 (d, J 8.7, 2H), 3.69 (t, J 5.9, 2H), 1.90 (t, 5.8, 2H), 1.46 (s, 6H). $\delta_C$ (CDCl$_3$, 100 MHz) 193.5, 146.5, 145.4, 140.6, 131.4, 130.5, 129.7, 124.5, 123.7, 120.4, 117.7, 43.7, 39.0, 30.9, 27.8. HRMS (ES): calc. for C$_{20}$H$_{21}$BrNO [MH$^+$], 370.0801. Found, 370.0802 [MH$^+$]. UV $\lambda_{max}$ 338 nm, $\epsilon$ 23300 M$^{-1}$ cm$^{-1}$.

Example 40—Preparation of 4,4-dimethyl-1-phenyl-1,4-dihydropyridine, 50

Bis enamine, 50 was isolated from an unsuccessful acylation reaction as a yellow oil.

$\delta_H$ (CDCl$_3$, 400 MHz) 7.33-7.28 (m, 2H), 7.05-6.99 (m, 3H), 6.42 (d, J 8.2, 1H), 4.60 (d, J 8.2, 1H), 1.14 (s, 6H). UV $\lambda_{max}$ 285 nm, $\epsilon$ 16000 M$^{-1}$ cm$^{-1}$.

Example 41—Preparation of 1-(4-methoxyphenyl)-4,4-dimethyl-1,2,3,4-tetrahydropyridine, 51

Prepared according to the procedure above for the preparation of 4,4-dimethyl-1-phenyl-1,2,3,4-tetrahydropyridine, 46, as pale yellow solid containing the title compound and fully reduced amine 1-(4-methoxyphenyl)-4,4-dimethylpiperidine (1.32 g, 85% by wt, 70%).

$\delta_H$ (CDCl$_3$, 400 MHz) 6.89-6.85 (m, 4H), 6.38 (d, J 8.1, 1H), 4.48 (d, J 8.1, 1H), 3.81 (s, 3H), 3.46 (t, J 5.8, 2H), 1.74 (t, J 6.3, 2H), 1.09 (s, 6H). UV $\lambda_{max}$ 278 nm, $\epsilon$ 22550 M$^{-1}$ cm$^{-1}$.

Example 42—Preparation of 1-(1-(4-methoxyphenyl)-4,4-dimethyl-1,4,5,6-tetrahydropyridin-3-yl)propan-1-one, 52

Prepared according to the procedure above for the preparation of 1-(4,4-dimethyl-1-phenyl-1,4,5,6-tetrahydropyridin-3-yl)propan-1-one, 47 as a pale yellow oil (178 mg, 40%).

$\delta_H$ (CDCl$_3$, 400 MHz) 7.59 (s, 1H), 7.05 (d, J 9.1, 2H), 6.92 (d, J 9.1, 2H), 3.82 (s, 3H), 3.58 (t, J 5.4, 2H), 2.56 (q, J 7.4, 2H), 1.77 (t, J 5.8, 2H), 1.36 (s, 6H), 1.13 (t, J 7.5, 2H). $\delta_C$ (CDCl$_3$, 100 MHz) 197.8, 156.2, 142.9, 140.0, 119.9, 119.8, 114.9, 55.8, 44.1, 39.7, 30.6, 30.3, 28.2, 10.1. HRMS (APCI): calc. for C$_{17}$H$_{24}$NO$_2$[MH$^+$], 274.1802. Found, 274.1803 [MH$^+$]. UV $\lambda_{max}$ 328 nm, $\epsilon$ 23500 M$^{-1}$ cm$^{-1}$.

Example 43—Preparation of 1-(1-(4-methoxyphenyl)-4,4-dimethyl-1,4,5,6-tetrahydropyridin-3-yl)prop-2-en-1-one, 53

Prepared according to the procedure above for the preparation of 1-(4,4-dimethyl-1-phenyl-1,4,5,6-tetrahydropyridin-3-yl)propan-1-one, 47 as a bright yellow oil (230 mg, 54%).

$\delta_H$ (CDCl$_3$, 400 MHz) 7.67 (s, 1H), 7.06 (d, J 9.1, 2H), 6.94 (d, J 9.1, 2H), 6.84 (dd, J 16.9 and 10.6, 1H), 6.11 (d, J 16.9, 1H), 5.54 (d, J 10.6, 1H), 3.83 (s, 3H), 162 (t, J 5.8, 2H), 1.80 (t, J 7.1, 2H), 1.40 (s, 6H). $\epsilon_C$ (CDCl$_3$, 100 MHz) 187.8, 156.5, 144.7, 139.7, 133.9, 124.4, 120.7, 120.1, 114.9, 55.8, 44.4, 39.4, 30.6, 27.9. HRMS (APCI): calc. for C$_{17}$H$_{22}$NO$_2$ [MH$^+$], 272.1645. Found, 272.1644 [MH$^+$]. UV $\lambda_{max}$ 350 nm, $\epsilon$ 21500 M$^{-1}$ cm$^{-1}$.

Example 44—Preparation of (4-fluorophenyl)(1-(4-methoxyphenyl)-4,4-dimethyl-1,4,5,6-tetrahydropyridin-3-yl)methanone, 54

Prepared according to the procedure above for the preparation of (4-bromophenyl)(1-(cyclohexa-1,5-dien-1-yl)-4,4-dimethyl-1,4,5,6-tetrahydropyridin-3-yl)methanone, 49 as a cream gum (35 mg, 11%).

$\delta_H$ (CDCl$_3$, 400 MHz) 7.59 (t, J 8.9, 2H), 7.23 (s, 1H), 7.08 (t, J 8.6, 2H), 6.90-6.85 (m, 4H), 3.79 (s, 3H), 3.65 (t, J 5.8, 2H), 1.89 (t, J 5.9, 2H), 1.46 (s, 6H). $\delta_C$ (CDCl$_3$, 100 MHz) 193.4, 165.1, 162.6, 156.3, 147.2, 139.4, 138.1, 131.0, 129.2, 126.1, 119.7, 119.4, 115.2, 115.0, 114.9, 55.7, 44.3, 39.1, 30.7, 28.1, 27.8. HRMS (APCI): calc. for C$_{21}$H$_{22}$FNO$_2$ [M$^+$], 339.1629. Found, 339.1628 [M$^+$]. UV $\lambda_{max}$ 341 nm, $\epsilon$ 19350 M$^{-1}$ cm$^{-1}$.

Example 45—Preparation of 1-isobutyl-4,4,6-trimethyl-3,4-dihydropyridin-2(1H)-one, 56a A solution of 1-isobutyl-4,4-dimethylpiperidine-2,6-dione, 55 (2.0 g, 10.14 mmol) in diethyl ether (20 mL) was treated drop-wise with methylmagnesium bromide (3 M solution in diethyl ether, 6.8 mL, 20.28 mmol) and the mixture heated to reflux for 18 hours. Heating was then discontinued and the reaction mixture cooled to room temperature and quenched by addition of 2 M hydrochloric acid solution until a separate aqueous phase with pH<2 was seen. The mixture was then stirred for 15 minutes, the organic phase separated, dried with magnesium sulfate and evaporated in-vacuo to give a pale yellow oil (1.7 g). Examination by $^1$H NMR suggested a composition of 50% starting material, 16% intermediate hydroxyl compound 6-hydroxy-1-isobutyl-4,4,6-trimethylpiperidin-2-one and 34% title compound. The residue was then purified by column chromatography over silica gel eluting with 0-4% ethyl acetate: petroleum ether to give a mixture of the title compound and starting material 1-isobutyl-4,4-dimethylpiperidine-2,6-dione, 55 as a colourless oil (0.69 g, 60% by wt, 21%).

$\delta_H$ (CDCl$_3$, 400 MHz) 4.83 (s, 1H), 3.44 (d, J 7.2, 2H), 2.34 (s, 2H), 1.96-1.88 (m, 4H), 1.04 (s, 6H), 0.93 (d, J 6.7, 6H).

Example 46—Preparation of 1-isobutyl-4,4-dimethyl-6-phenyl-3,4-dihydropyridin-2(1H)-one, 56b Hydroxy intermediate 6-hydroxy-1-isobutyl-4,4-dimethyl-6-phenylpiperidin-2-one was prepared according to the procedure above for the preparation of 1-isobutyl-4,4,6-trimethyl-3,4-dihydropyridin-2(1H)-one, 56a as a golden oil (430 mg, 34%).

$\delta_H$ (CDCl$_3$, 400 MHz) 7.99 (d, J 7.3, 2H), 7.58 (t, J 7.4, 1H), 7.49 (t, J 7.8, 2H), 6.62 (s, br, 1H), 3.12-3.06 (m, 4H), 2.38 (s, 2H), 1.83-1.71 (m, 1H), 1.16 (s, 6H), 0.92 (d, J 6.7, 6H).

A solution of 6-hydroxy-1-isobutyl-4,4-dimethyl-6-phenylpiperidin-2-one (0.4 g, 1.45 mmol) in toluene (20 mL) was treated with p-toluenesulfonic acid (55 mg, 0.29 mmol) and heated to reflux for 3 hours. The mixture was then cooled to room temperature, diluted with diethyl ether, washed with water (20 mL) and sodium carbonate solution (10% w/w, 20 mL) and dried with magnesium sulfate. The organic layer was then evaporated in-vacuo to give the title compound as a yellow oil (348 mg, 93%).

$\delta_H$ (CDCl$_3$, 400 MHz) 7.40-7.22 (m, 5H), 5.10 (s, 1H), 3.37 (d, J 7.0, 2H), 2.46 (s, 2H), 1.82-1.75 (m, 1H), 1.17 (s, 6H), 0.73 (d, J 6.7, 6H).

Example 47—Preparation of 1-isobutyl-4,4,6-trimethyl-1,2,3,4-tetrahydropyridine, 57a Lithium aluminium hydride (1 M solution in diethyl ether, 2.0 mL, 2.0 mmol) was added to diethyl ether (10 mL) and treating drop-wise with a solution of 1-isobutyl-4,4,6-trimethyl-3,4-dihydropyridin-2(1H)-one, 56a (0.65 g, 60% by wt, 2.0 mmol) in diethyl ether (10 mL). The mixture was then heated to reflux for 1 hour and the mixture then quenched by portion wise addition of sodium sulfate decahydrate (0.14 g, 4.2 mmol). The resulting suspension was then stirred for 20 minutes, treated with anhydrous sodium sulfate (0.30 g) and stirred for a further 10 minutes before being filtered into a flask containing BHT (4 mg, 1 wt % assuming 100% yield). The filter pad was washed with diethyl ether (2×20 mL) and the combined filtrates evaporated in-vacuo to give a mixture of the title compound and fully reduced amine, 1-isobutyl-4,4-dimethylpiperidine as a colourless liquid (0.54 g, 67% by wt, 97%).

$\delta_H$ (CDCl$_3$, 400 MHz) 3.98 (s, 1H), 2.99 (t, J 5.6, 2H), 2.74 (d, J 7.3, 2H), 1.89-1.84 (m, 1H), 1.76 (s, 3H), 1.51 (t, J 5.5, 2H), 0.99 (s, 6H), 0.89 (d, J 6.2, 6H).

Example 48—Preparation of 1-isobutyl-4,4-dimethy-6-phenyl-1,2,3,4-tetrahydropyridine, 57b Prepared according to the procedure above for the preparation of 1-isobutyl-4,4,6-trimethyl-1,2,3,4-tetrahydropyridine, 57a as a pale yellow liquid (0.28 g, 97%).

$\delta_H$ (CDCl$_3$, 400 MHz) 7.41-7.24 (m, 5H), 4.61 (s, 1H), 3.11 (t, J 8.1, 2H), 2.49 (d, J 7.4, 2H), 1.95-1.87 (m, 1H), 1.58-1.54 (m, 2H), 1.09 (s, 6H), 0.83 (d, J 6.9, 6H).

Example 49—Preparation of 1-(1-isobutyl-4,4-dimethyl-2-phenyl-1,4,5,6-tetrahydropyridin-3-yl)propan-1-one, 58

A solution of 1-isobutyl-4,4-dimethy-6-phenyl-1,2,3,4-tetrahydropyridine, 57b (270 mg, 1.1 mmol) and triethylamine (155 µL, 1.1 mmol) in DCM (5 mL) was cooled on an ice bath and treated drop wise with propionyl chloride (97 µL, 1.1 mmol). Once addition was complete the mixture was stirred for a further 2 hours before quenching by pouring into water (10 mL). The organic phase was then separated, washed with sodium carbonate solution (10% w/w, 10 mL) and dried with magnesium sulfate. Evaporation in-vacuo gave the crude material as a purple oil which was purified by column chromatography over silica gel eluting with 0-5% ethyl acetate:petroleum ether. Evaporation of the eluents gave the title compound as a pale yellow oil (30 mg, 9%).

$\delta_H$ (CDCl$_3$, 400 MHz) 7.37-7.26 (m, 5H), 3.23 (t, J 5.9, 2H), 2.62 (d, J 7.5, 1.5H), 1.94-1.85 (m, 1H), 1.71 (t, J 6.0, 2H), 1.52 (q, J 7.4, 2H), 1.26 (s, 6H), 0.74 (d, J 6.7, 6H), 0.61 (t, J 7.4, 3H). HRMS (APCI): calc. for C$_{20}$H$_{30}$NO [MH$^+$], 300.2322. Found, 300.2322 [MH$^+$]. UV $\lambda_{max}$ 338 nm, $\epsilon$ 8000 M$^{-1}$ cm$^{-1}$.

Example 50—Preparation of 1-(1-isobutyl-4,4-dimethyl-1,4,5,6-tetrahydropyridin-2-yl)butan-2-one, 59 and 1-(1-isobutyl-4,4-dimethyl-1,4,5,6-tetrahydropyridin-2-yl)but-1-en-2-yl propionate, 60

Prepared according to the procedure above for the preparation of 1-(1-isobutyl-4,4-dimethyl-2-phenyl-1,4,5,6-tetrahydropyridin-3-yl)propan-1-one, 58 to give: 1-(1-(1-isobutyl-4,4-dimethyl-1,4,5,6-tetrahydropyridin-2-yl)butan-2-one, 59 as a pale yellow oil (100 mg, 24%).

$\delta_H$ (CDCl$_3$, 400 MHz) 5.06 (s, 1H), 3.32 (t, J 6.5, 2H), 3.08 (s, 2H), 3.04 (d, J 7.4, 2H), 2.31 (q, J 7.5, 2H), 2.24-2.17 (m, 1H), 1.57 (t, J 6.4, 2H), 1.09 (t, J 7.5, 3H), 1.00 (s, 6H), 0.95 (d, J 6.7, 6H). $\delta_C$ (CDCl$_3$, 100 MHz) 197.5, 162.2, 93.2, 59.8, 49.2, 40.8, 37.3, 36.3, 28.5, 27.5, 26.1, 20.7, 10.2. HRMS (APCI): calc. for C$_{15}$H$_{25}$NO [MH$^+$], 238.2165. Found, 238.2166 [MH$^+$]. UV $\lambda_{max}$ 312 nm, $\epsilon$ 16000 M$^{-1}$ cm$^{-1}$.

1-(1-isobutyl-4,4-dimethyl-1,4,5,6-tetrahydropyridin-2-yl)but-1-en-2-yl propionate, 60 as a pale yellow oil (75 mg, 15%). Analytical data were complicated by the presence of enol double bond isomers.

$\delta_H$ (CDCl$_3$, 400 MHz) 5.28 (s, 1H), 5.05 (s, 1H), 3.49-2.74 (m, 6H), 2.37-2.07 (m, 3H), 1.31-0.93 (m, 18H). $\delta_C$ (CDCl$_3$, 100 MHz) 196.9, 158.3, 148.0, 114.8, 94.4, 64.4, 60.0, 57.2, 49.4, 43.6, 40.4, 39.5, 37.3, 30.8, 30.6, 30.2, 30.0, 28.7, 28.2, 27.6, 27.2, 25.8, 20.6, 20.5, 20.0, 10.5. HRMS (APCI): calc. for $C_{18}H_{32}NO_2[MH^+]$, 294.2428. Found, 294.2442 [MH$^+$]. UV $\lambda_{max}$ 323 nm, $\epsilon$ 20000 M$^{-1}$ cm$^{-1}$.

Example 51—Preparation of 3-(3,5,7,9,11,13,15-Heptaisobutyl-2,4,6,8,10,12,14,16,18,20-dodecaoxa-1,3,5,7,9,11,13,15-octasilapentcyclo[9.5.1.1$^{3,9}$.1$^{5,15}$.1$^{7,13}$]icosan-1-yl)propyl 4-(1-isobutyl-4,4-dimethyl-1,4,5,6-tetrahydropyridin-3-yl)-4-oxobutanoate, 63

A solution of 1-isobutyl-4,4-dimethyl-1,2,3,4-tetrahydropyridine (200 mg, 1.2 mmol) and triethylamine (170 µL, 1.2 mmol) in DCM (4 mL) was cooled to −50° C. and treated drop wise with a solution of 3-(3,5,7,9,11,13,15-Heptaisobutyl-2,4,6,8,10,12,14,16,18,20-dodecaoxa-1,3,5,7,9,11,13,15-octasilapentcyclo[9.5.1.1$^{3,9}$.1$^{5,15}$.1$^{7,13}$]icosan-1-yl)propyl-4-chloro-4-oxobutanoate (1.19 g, 1.2 mmol) in DCM. Once addition was complete the mixture was allowed to warm slowly to room temperature with stirring over 6 hours. The reaction mixture was then evaporated in-vacuo and the residue partitioned between water and diethyl ether. The organic phase was then separated, washed with water and dried with magnesium sulfate. Evaporation in-vacuo gave the crude material as an oily solid which was triturated with methanol, the liquors evaporated in-vacuo and purified by column chromatography over silica gel eluting with 0-100% ethyl acetate:heptane. Evaporation of the eluents gave the title compound as a pale orange oil (228 mg, 17%).

$\delta_H$ (CDCl$_3$, 400 MHz) 7.15 (s, 1H), 4.03-3.95 (m, 2H), 3.09-3.04 (m, 2H), 2.92 (d, J 7.5, 2H), 2.76-2.70 (m, 2H), 2.61-2.54 (m, 2H), 2.01-1.73 (m, 8H), 1.73-1.62 (m, 2H), 1.62-1.49 (m, 2H), 1.22 (s, 6H), 0.92 (d, J 6.6, 42H), 0.87 (d, J 6.6, 6H), 0.57 (dd, J 7.0, 3.0, 16H). $\delta_C$ (CDCl$_3$, 100 MHz) 192.5, 174.2, 148.2, 115.0, 66.5, 64.4, 43.6, 39.4, 31.4, 30.3, 29.7, 28.2, 27.7, 25.9, 24.1, 24.0, 22.7, 22.6, 22.3, 20.0, 8.5. HRMS (ES): calc. for $C_{46}H_{94}NO_{15}Si_8$ [MH$^+$], 1124.4772. Found, 1124.4775 [MH$^+$]. UV $\lambda_{max}$ 308 nm, $\epsilon$ 21800 M$^{-1}$ cm$^{-1}$.

Example 52—Preparation of 1-isobutyl-4,4-dimethyl-5-propionyl-3,4-dihydropyridin-2(1H)-one, 64

1-(1-isobutyl-4,4-dimethyl-1,4,5,6-tetrahydropyridin-3-yl)propan-1-one (1 g, 4.48 mmol) was placed in an open vessel and heated at 120° C. for 90 minutes. The temperature was then increased to 160° C. and heating continued for a 4 days. The mixture was weighed and was found to have lost 10% of its mass (total mass after heating 0.9 g). A portion of this material (0.45 g) was purified by column chromatography eluting with 0-20% ethyl acetate:petroleum ether to give the title compound as an orange oil (0.032 g, 6.4%).

$\delta_H$ (CDCl$_3$, 400 MHz) 6.87 (s, 1H), 5.62 (d, J 7.9, 1H), 4.51 (d, J 7.9, 1H), 2.95 (d, J 7.4, 2H), 2.51 (q, J 7.4, 2H), 1.93-1.84 (m, 1H), 1.41 (s, 6H), 1.10 (t, J 7.4, 3H), 0.94 (d, J 6.7, 6H). $\delta_C$ (CDCl$_3$, 100 MHz) 199.1, 142.4, 124.3, 118.1, 116.3, 62.1, 32.9, 31.7, 30.5, 29.5, 19.8, 9.8. HRMS (ES): calc. for $C_{14}H_{24}ON$ [MH$^+$], 222.1852. Found, 222.1854 [MH$^+$]. UV $\lambda_{max}$ 367 nm.

Example 53—Preparation of 1-(1-isobutyl-4,4-dimethyl-1,4-dihydropyridin-3-yl)propan-1-one, 65

Prepared according to the procedure set out for compound 64 with purification by column chromatography eluting with 0-2% diethyl ether:dichloromethane to give the title compound (0.16 g, 32% recovery).

$\delta_H$ (CDCl$_3$, 400 MHz) 6.96 (s, 1H), 3.42 (d, J 7.5, 2H), 2.60 (q, J 5.0, 2H), 2.41 (s, 2H), 2.03-1.95 (m, 1H), 1.26 (s, 6H), 1.12 (t, J 7.4, 3H), 0.94 (d, J 6.7, 6H). MS (EI): 237.2 [M$^+$]. UV $\lambda_{max}$ 291 nm.

Example 54—Preparation of 4-(1-isobutyl-4,4-dimethyl-1,4,5,6-tetrahydropyridin-3-yl)-4-oxobutanoic acid, 70

A suspension of aluminium chloride (400 mg, 2.99 mmol) in DCM (10 mL) was treated with succinic anhydride (150 mg, 1.5 mmol) and stirred at room temperature for 15 minutes. The mixture was then cooled on an ice-bath and treated with a solution of 1-isobutyl-4,4-dimethyl-1,2,3,4-tetrahydropyridine (250 mg, 1.5 mmol) in DCM (5 mL). The mixture was then allowed to warm to room temperature over 1.5 hours and poured onto crushed ice. The organic phase was separated, extracted with sodium carbonate solution (5% w/v) and the basic phase acidified with 1M hydrochloric acid solution. The aqueous phase was then extracted with DCM, the extracts dried with magnesium sulfate and evaporated in-vacuo to give the title compound as a cream solid (10 mg, 3%).

$\delta_H$ (CDCl$_3$, 200 MHz) 7.32 (s, 1H), 3.21 (t, J 5.8, 2H), 3.07 (d, J 7.5, 2H), 2.89-2.62 (m, 4H), 2.11-1.91 (m, 1H), 1.67 (t, J 5.9, 2H), 1.30 (s, 6H), 0.95 (d, J 6.7, 6H). $\delta_C$ (CDCl$_3$, 100 MHz) 194.7, 175.5, 150.8, 114.5, 64.9, 43.9, 39.0, 31.8, 30.3, 29.9, 27.8, 27.5, 19.9. HRMS (ES): calc. for $C_{15}H_{26}NO_3$ [MH$^+$], 268.1918. Found, 268.1907 [MH$^+$]. UV $\lambda_{max}$ 308 nm.

Example 55—Preparation of 1-(1-isobutyl-4,4-dimethyl-1,4,5,6-tetrahydropyridin-3-yl)-2,2-diphenylethanone, 71

A solution of 1-isobutyl-4,4-dimethyl-1,2,3,4-tetrahydropyridine (400 mg, 2.39 mmol) and triethylamine (400 µL, 2.87 mmol) in DCM (10 mL) was cooled on an ice bath and treated drop wise with a solution of 2,2-diphenylacetyl chloride (552 mg, 2.39 mmol) in DCM (10 mL). Once addition was complete the mixture was stirred for a further 18 hours before quenching by pouring into water (10 mL). The organic phase was then separated, washed with sodium carbonate solution (10% w/v), water and dried with magnesium sulfate. Evaporation in-vacuo gave the crude material as a brown oil (790 mg) which was purified by column chromatography over silica gel eluting with 10-10% ethyl acetate:petroleum ether. Evaporation of the eluents gave the title compound as a pale yellow oil (280 mg, 32%).

$\delta_H$ (CDCl$_3$, 400 MHz) 7.47 (m, 2H), 7.33 (m, 2H), 6.72 (s, 1H), 3.16 (m, 2H), 2.83 (d, J 7.6, 2H), 1.89 (m, 1H), 1.69 (m, 2H), 1.36 (s, 6H), 0.83 (d, J 6.6, 6H). $\delta_C$ (CDCl$_3$, 100 MHz) 192.4, 149.3, 142.0, 129.2, 128.4, 126.4, 114.5, 64.6, 57.6, 43.6, 39.3, 30.4, 28.0, 27.4, 19.7. HRMS (ES): calc. for $C_{25}H_{32}NO$ [MH$^+$], 362.2478. Found 362.2478 [MH$^+$]. UV $\lambda_{max}$ 314 nm, $\epsilon$ 26000 M$^{-1}$ cm$^{-1}$.

Example 56—Preparation of 1-Isobutyl-4,4-dimethyl-5-(phenylsulfonyl)-1,2,3,4-tetrahydropyridine, 72

Prepared according to the procedure above for the preparation of 3-(3,5,7,9,11,13,15-Heptaisobutyl-2,4,6,8,10,12,14,16,18,20-dodecaoxa-1,3,5,7,9,11,13,15-octasilapentcyclo[9.5.1.1$^{3,9}$.1$^{5,15}$.1$^{7,13}$]icosan-1-yl)propyl 4-(1-isobutyl-4,4-dimethyl-1,4,5,6-tetrahydropyridin-3-yl)-4-oxobutanoate, 63 as a pale orange oil (58 mg, 8%).

$\delta_H$ (CDCl$_3$, 400 MHz) 7.81-7.75 (m, 2H), 7.45-7.36 (m, 3H), 3.17-3.10 (m, 2H), 2.98 (d, J 7.5, 2H), 1.94 (sept, J 6.7, 1H), 1.52-1.47 (m, 2H), 1.03 (s, 6H), 0.90 (d, J 6.7, 6H). $\delta_C$ (CDCl$_3$, 100 MHz) 146.7, 146.2, 131.3, 128.7, 126.8, 105.6, 64.0, 43.5, 38.4, 31.1, 28.8, 27.6, 20.0. HRMS (ES): calc. for C$_{17}$H$_{26}$O$_2$NS [MH$^+$], 308.1679. Found, 308.1677 [MH$^+$]. UV $\lambda_{max}$ 285 nm, $\epsilon$ 11000 M$^{-1}$ cm$^{-1}$.

Example 57—Preparation of 5-(tert-butylamino)-2,2-dimethyl-5-oxopentanoic acid, 107 and 5-(tert-butylamino)-4,4-dimethyl-5-oxopentanoic acid, 108

A solution of triethylamine (5.39 mL, 38.7 mmol) and t-butylamine (3.70 mL, 35.2 mmol) in DCM (30 mL) was treated dropwise with a solution of 3,3-dimethyldihydro-2H-pyran-2,6(3H)-dione (5.0 g, 35.2 mmol) in DCM (30 mL) at room temperature. The mixture was then stirred for 72 hours, diluted with DCM (30 mL, washed with 1M aqueous HCl solution (2×75 mL) and dried with magnesium sulfate. Evaporation in-vacuo gave the title compounds (85:15 mixture 107:108) as a colourless oil (1.3 g, 17%).

$\delta_H$ (107, 400 MHz) 5.34 (br s, 1H), 2.11 (t, J 8.5, 2H), 1.85 (t, J 8.2, 2H), 1.32 (s, 9H), 1.19 (s, 6H).

Example 58—Preparation of 5-((4-methoxyphenyl)amino)-3,3-dimethyl-5-oxopentanoic acid, 144b Prepared according to the procedure above for the preparation of 5-(tert-butylamino)-2,2-dimethyl-5-oxopentanoic acid, 108, as a brown solid in 97% yield. $\delta_H$ (400 MHz) 7.69 (br s, 1H), 7.43 (d, J 9.0, 2H), 6.92 (d, J 9.0, 2H), 3.83 (s, 3H), 2.52 (s, 2H), 2.47 (s, 2H), 1.21 (s, 6H).

Example 59—Preparation of 5-(ethoxyamino)-3,3-dimethyl-5-oxopentanoic acid, 144i A suspension of O-ethylhydroxylamine hydrochloride (3.77 g, 38.70 mmol) in DCM (60 mL) was cooled on an ice bath and treated dropwise with triethylamine (5.39 mL, 38.70 mmol). The resulting suspension was then treated dropwise with a solution of 4,4-dimethyldihydro-2H-pyran-2,6(3H)-dione (5.00 g, 35.20 mmol) in DCM (30 mL) and the resulting turbid solution left to stir for 18 hours. The mixture was washed with 1M HCl solution (50 mL), the aqueous phase saturated with sodium chloride and extracted with ethyl acetate (2×50 mL). The combined organic extracts were then evaporated in-vacuo to give the title compound as a colourless gum (5.17 g, 72%).

$\delta_H$ (400 MHz) 9.20 (br s, 1H), 3.99 (q, J 7.1, 2H), 2.42 (s, 2H), 2.22 (s, 2H), 1.27 (t, J 7.1, 3H), 1.13 (s, 6H).

Example 60—Preparation of 5-(adamantan-1-ylamino)-3,3-dimethyl-5-oxopentanoic acid, 144j Prepared according to the procedure above for the preparation of 5-(tert-butylamino)-2,2-dimethyl-5-oxopentanoic acid, 107, as a white solid in 98% yield.

$\delta_H$ (400 MHz) 13.34 (br s, 1H), 5.66 (br s, 1H), 2.41 (s, 2H), 2.19 (s, 2H), 2.10 (m, 3H), 2.02 (d, J 3.0, 6H), 1.69 (t, J 3.0, 6H), 1.09 (s, 6H).

Example 61—Preparation of 1-(4-methoxyphenyl)-4,4-dimethylpiperidine-2,6-dione, 145b A suspension of 5-((4-methoxyphenyl)amino)-3,3-dimethyl-5-oxopentanoic acid, 144b (18.10 g, 68.20 mmol) in CHCl$_3$ (50 mL) was treated drop-wise with thionyl chloride (7.47 mL, 102.00 mmol) and the mixture stirred at room temperature for 10 minutes. After this time all material had dissolved and the mixture was heated in a sealed vessel under microwave irradiation at 100° C. for 10 minutes. The mixture was then diluted with DCM (75 mL), washed with water (2×50 mL) and 10% Na$_2$CO$_3$ solution (50 mL), dried with magnesium sulfate and evaporated in-vacuo to give the title compound as a brown solid in 82% yield.

$\delta_H$ (400 MHz) 7.03-6.98 (m, 4H), 3.83 (s, 3H), 2.69 (s, 4H), 1.23 (s, 6H).

Example 62—Preparation of 1-(4-(dimethylamino)phenyl)-4,4-dimethylpiperidine-2,6-dione, 145c A solution of 4,4-dimethyldihydro-2H-pyran-2,6(3H)-dione (2.00 g, 14.07 mmol) in CHCl$_3$ (20 mL) was treated with N,N-dimethylbenzene-1,4-diamine (1.92 g, 14.07 mmol) and stirred at room temperature for 18 hours. Analysis of an aliquot by $^1$H NMR show a 66:33 ratio of ring opened intermediate to starting anhydride. The mixture was treated with a further portion of N,N-dimethylbenzene-1,4-diamine (0.96 g, 7.05 mmol) and stirred for a further 2 hours. The mixture was then treated with thionyl chloride (1.54 mL, 21.10 mmol) and stirred for 15 minutes before heating to 100° C. for 10 min under microwave irradiation. The reaction mixture was then diluted with CHCl$_3$ (30 mL), treated with potassium carbonate (9.72 g, 70.30 mmol), stirred for 15 minutes and then sufficient MeOH added to dissolve any remaining purple solid. The mixture was then stirred for 18 hours, filtered through a pad of celite and evaporated in-vacuo to a black solid (4.9 g). The crude material was then purified by column chromatography over silica gel eluting with 0-10% diethyl ether:DCM. Evaporation of the eluents gave the title compound as a pale yellow solid (2.49 g, 68%).

$\delta_H$ (400 MHz) 6.94-6.87 (m, 2H), 6.77 (br s, 2H), 2.96 (s, 6H), 2.64 (s, 4H), 1.18 (s, 6H).

Example 63—Preparation of 4,4-dimethyl-1-(naphthalen-1-yl)piperidine-2,6-dione, 145d Prepared according to the procedure above for the preparation of 1-isobutyl-3,3-dimethylpyrrolidine-2,5-dione, 118, as a purple solid in 89% yield.

$\delta_H$ (400 MHz) 7.91-7.86 (m, 2H), 7.54-7.45 (m, 4H), 7.22 (d, J 7.3, 1H), 2.73 (dd, J 16.6, 25.0, 4H), 1.33 (s, 3H), 1.24 (s, 3H).

Example 64—Preparation of 4,4-dimethyl-1-(p-tolyl)piperidine-2,6-dione, 145e Prepared according to the procedure above for the preparation of 1-isobutyl-3,3-dimethylpyrrolidine-2,5-dione, 118, as a cream solid in >99% yield.

$\delta_H$ (400 MHz) 7.24 (d, J 9.1, 2H), 6.95 (d, J 8.5, 2H), 2.65 (s, 4H), 2.36 (s, 3H), 1.19 (s, 6H).

Example 65—Preparation of 4,4-dimethyl-1-(pyridin-4-yl)piperidine-2,6-dione, 145f Prepared according to the procedure above for the preparation of 1-isobutyl-3,3-dimethylpyrrolidine-2,5-dione, 118, as a brown solid in 21% yield.

$\delta_H$ (DMSO-d$_6$, 400 MHz) 8.63 (d, J 6.1, 2H), 7.20 (d, J 6.1, 2H), 2.65 (s, 4H), 1.08 (s, 6H).

Example 66—Preparation of 1-(1,3-dimethyl-1H-pyrazol-5-yl)-4,4-dimethylpiperidine-2,6-dione, 145g Prepared according to the procedure above for the preparation of 1-isobutyl-3,3-dimethylpyrrolidine-2,5-dione, 118, as a black oil in 60% yield.

$\delta_H$ (400 MHz) 5.93 (s, 1H), 3.57 (s, 3H), 2.68 (s, 4H), 2.28 (s, 3H), 1.20 (s, 3H), 1.18 (s, 3H).

Example 67—Preparation of 1-(4-(tert-butyl)phenyl)-4,4-dimethylpiperidine-2,6-dione, 145h Prepared according to the procedure above for the preparation of 1-isobutyl-3,3-dimethylpyrrolidine-2,5-dione, 118, as a cream solid in 83% yield.

$\delta_H$ (400 MHz) 7.48 (d, J 8.6, 2H), 7.01 (d, J 8.6, 2H), 2.69 (s, 4H), 2.28 (s, 3H), 1.35 (s, 9H), 1.23 (s, 6H).

Example 68—Preparation of 1-ethoxy-4,4-dimethylpiperidine-2,6-dione, 145i

Prepared according to the procedure above for the preparation of 1-(4-methoxyphenyl)-4,4-dimethylpiperidine-2,6-dione, 145b as a white solid in 62% yield.

$\delta_H$ (400 MHz) 4.08 (q, J 7.1, 2H), 2.61 (s, 4H), 1.36 (t, J 7.1, 3H), 1.13 (s, 6H).

Example 69—Preparation of 1-(4-(dimethylamino)phenyl)-6-hydroxy-4,4-dimethylpiperidin-2-one, 146c A suspension of 1-(4-(dimethylamino)phenyl)-4,4-dimethylpiperidine-2,6-dione, 145c (1.00 g, 3.84 mmol) in THF (25 mL) was cooled on an ice bath and treated drop-wise with lithium aluminium hydride (1 M solution in diethyl ether, 2.00 mL, 2.00 mmol) and the mixture stirred for 15 minutes. The reaction was then quenched by addition of 2 M hydrochloric acid solution until effervescence ceased followed by 4 M hydrochloric acid solution until a clear aqueous phase of pH<2 was formed. The biphasic mixture was then stirred for 30 minutes, diluted with diethyl ether (30 mL) and water (30 mL) and the pH of the aqueous phase adjusted to 5-6 with sodium carbonate solution (10% w/w). The mixture was then extracted with diethyl ether (2×30 mL). The pH of the aqueous phase was then adjusted to 10 with sodium carbonate solution (10% w/w) and a further extraction with diethyl ether performed (2×30 mL). The organic extracts were then combined, dried with magnesium sulfate and evaporated in-vacuo to give the title compound as a cream solid (0.90 g, 90%).

$\delta_H$ (400 MHz) 7.02 (d, J 8.8, 2H), 6.73 (d, J 8.9, 2H) 5.22-5.18 (m, 1H), 2.94 (s, 6H), 2.52-2.29 (m, 3H), 2.08-2.03 (m, 1H), 1.74 (dd, J 7.0, 20.7), 1.14 (s, 3H), 1.10 (s, 2H).

Example 70—Preparation of 1-(1,3-dimethyl-1H-pyrazol-5-yl)-6-hydroxy-4,4-dimethylpiperidin-2-one, 146g Prepared according to the procedure above for the preparation of 1-(4-(dimethylamino)phenyl)-6-hydroxy-4,4-dimethylpiperidin-2-one, 146c, as brown oil in 62% yield.

$\delta_H$ (400 MHz) 4.82 (s, 1H), 5.24 (t, J 5.6, 1H), 3.63 (s, 1H) 2.48-2.10 (m, 3H), 2.20 (s, 3H), 1.86-1.68 (m, 1H), 1.19 (s, 3H), 1.13 (s, 2H).

Example 71—Preparation of 1-(tert-butyl)-4,4-dimethyl-3,4-dihydropyridin-2(1H)-one, 147a Prepared according to the procedure above for the preparation of 1-isobutyl-3,3-dimethyl-3,4-dihydropyridin-2(1H)-one, 114, as yellow oil in 94% yield.

$\delta_H$ (400 MHz) 6.24 (d, J 8.1, 1H), 4.95 (d, J 8.1, 1H), 2.32 (s, 2H), 1.48 (s, 9H), 1.04 (s, 6H).

Example 72—Preparation of 1-(4-methoxyphenyl)-4,4-dimethyl-3,4-dihydropyridin-2(1H)-one, 147b A suspension of 1-(4-methoxyphenyl)-4,4-dimethylpiperidine-2,6-dione, 145b (13.80 g, 27.9 mmol) in THF (200 mL) was cooled on an ice bath and treated drop-wise with lithium aluminium hydride (1 M solution in diethyl ether, 27.9 mL, 27.9 mmol) and the mixture stirred for 15 minutes. The reaction was then quenched by addition of 2 M hydrochloric acid solution until effervescence ceased followed by 4 M hydrochloric acid solution until a clear aqueous phase of pH<2 was formed. The biphasic mixture was then stirred for 15 minutes, diluted with diethyl ether (100 mL) and the organic phase separated and combined with a further diethyl ether extract. The organic extracts were then dried with magnesium sulfate and evaporated in-vacuo to give the title compound as a brown oil which on standing solidified (8.53 g, 66%).

$\delta_H$ (400 MHz) 7.18 (d, J 8.9, 2H), 6.93 (d, J 8.9, 2H), 6.13 (d, J 7.7, 1H), 5.11 (d, J 7.7, 1H), 3.83 (s, 3H), 2.55 (s, 2H), 1.19 (s, 6H).

Example 73—Preparation of 1-(4-(dimethylamino)phenyl)-4,4-dimethyl-3,4-dihydropyridin-2(1H)-one, 147c A mixture of 1-(4-(dimethylamino)phenyl)-6-hydroxy-4,4-dimethylpiperidin-2-one, 146c (0.90 g, 3.43 mmol) and p-toluenesulfonic acid (0.13 g, 0.69 mmol) in toluene (50 mL) was heated to reflux for 30 minutes. The mixture was then cooled to room temperature, diluted with diethyl ether (50 mL) and washed with sodium carbonate solution (10% w/w, 30 mL). The mixture was then dried with magnesium sulfate and evaporated in-vacuo to give the title compound as a pale brown solid (0.76 g, 91%).

$\delta_H$ (400 MHz) 7.07 (d, J 9.0, 2H), 6.70 (d, J 8.9, 2H), 6.08 (d, J 7.7, 1H), 5.03 (d, J 7.7, 1H), 2.93 (s, 6H), 2.50 (s, 2H), 1.19 (s, 6H).

Example 74—Preparation of 4,4-dimethyl-1-(naphthalen-1-yl)-3,4-dihydropyridin-2(1H)-one, 147d Prepared according to the procedure above for the preparation of 1-(4-methoxyphenyl)-4,4-dimethyl-3,4-dihydropyridin-2(1H)-one, 147b, as a tan solid in 55% yield.

$\delta_H$ (400 MHz) 7.91-7.82 (m, 2H), 7.72 (t, J 4.5, 1H), 7.53-7.47 (m, 3H), 7.35 (d, J 7.3, 1H), 6.07 (d, J 7.7, 1H), 5.11 (d, J 7.7, 1H), 2.65 (dd, J 15.4, 35.6, 2H), 1.29 (s, 3H), 1.24 (s, 3H).

Example 75—Preparation of 4,4-dimethyl-1-(p-tolyl)-3,4-dihydropyridin-2(1H)-one, 147e Prepared according to the procedure above for the preparation of 1-(4-methoxyphenyl)-4,4-dimethyl-3,4-dihydropyridin-2(1H)-one, 147b, as a light orange solid in 63% yield.

δ$_H$ (400 MHz) 7.17 (d, J 8.3, 2H), 7.11 (d, J 8.4, 2H), 6.11 (d, J 7.7, 1H), 5.08 (d, J 7.7, 1H), 2.51 (s, 2H), 2.33 (s, 3H), 1.13 (s, 6H).

Example 76—Preparation of 1-(1,3-dimethyl-1H-pyrazol-5-yl)-4,4-dimethyl-3,4-dihydropyridin-2(1H)-one, 147g Prepared according to the procedure above for the preparation of 1-(4-(dimethylamino)phenyl)-4,4-dimethyl-3,4-dihydropyridin-2(1H)-one, 147c, as a pale green oil in 40% yield.
δ$_H$ (400 MHz) 5.98 (d, J 7.7, 1H), 5.92 (s, 1H), 5.13 (d, J 7.7, 1H), 3.63 (s, 3H), 2.55 (s, 2H), 2.26 (s, 3H), 1.18 (s, 6H).

Example 77—Preparation of 1-(4-(tert-butyl)phenyl)-4,4-dimethylpiperidine-2,6-dione, 147h Prepared according to the procedure above for the preparation of 1-(4-methoxyphenyl)-4,4-dimethyl-3,4-dihydropyridin-2(1H)-one, 147b, as a pale brown solid in 66% yield.
δ$_H$ (400 MHz) 7.38 (d, J 8.8, 2H), 7.14 (d, J 8.8, 2H), 6.14 (d, J 7.7, 1H), 5.08 (d, J 7.7, 1H), 2.51 (s, 2H), 1.30 (s, 9H), 1.13 (s, 6H).

Example 78—Preparation of 1-ethoxy-4,4-dimethyl-3,4-dihydropyridin-2(1H)-one, 147i Prepared according to the procedure above for the preparation of 1-(4-(dimethylamino)phenyl)-4,4-dimethyl-3,4-dihydropyridin-2(1H)-one, 147c, as a straw coloured liquid in 31% yield.
δ$_H$ (400 MHz) 6.10 (d, J 7.9, 1H), 4.91 (d, J 7.8, 1H), 4.04 (q, J 7.1, 2H), 2.40 (s, 2H), 1.27 (t, J 7.3, 3H), 1.07 (s, 6H).

Example 79—Preparation of 1-(tert-butyl)-4,4-dimethyl-1,2,3,4-tetrahydropyridine, 148a Lithium aluminium hydride (1M solution in ether, 29.6 mL, 29.6 mmol) was added to ether (30 mL). The mixture was then treated dropwise with a solution of 1-(tert-butyl)-4,4-dimethyl-3,4-dihydropyridin-2(1H)-one, 147a (5.36 g, 29.6 mmol) in ether (30 mL) at a rate sufficient to maintain a gentle reflux. The resulting milky suspension was then refluxed for a further 1 hour, heating discontinued and the mixture allowed to cool in the oil bath for 10 minutes before being quenched by addition of sodium sulfate decahydrate (2.02 g, 62.7 mmol). Once addition was complete the mixture was stirred for 20 minutes and treated with anhydrous sodium sulfate (1.00 g), stirred for a further 10 minutes and filtered into a receiving flask was preloaded with BHT (50 mg). The filter pad was then washed with ether and the combined organics evaporated to a pale yellow liquid (4.70 g, 95%).
δ$_H$ (400 MHz) 6.05 (d, J 8.3, 1H), 4.24 (d, J 8.3, 1H), 2.92 (t, J 5.7, 2H), 1.58 (t, J 5.6, 2H), 1.14 (s, 9H), 0.96 (s, 6H).

Example 80—Preparation of 4-(4,4-dimethyl-1,2,3,4-tetrahydropyridin-1(2H)-yl)-N,N-dimethylaniline, 148c Prepared according to the procedure above for the preparation of 1-(tert-butyl)-4,4-dimethyl-1,2,3,4-tetrahydropyridine, 148a, as a pale yellow solid in 95% yield.
δ$_H$ (400 MHz) 6.85-6.73 (m, 4H), 6.33 (d, J 8.1, 1H), 4.40 (d, J 8.1, 1H), 3.41 (t, J 5.8, 2H), 2.85 (s, 6H), 1.68 (t, J 6.3, 2H), 1.04 (s, 6H).

Example 81—Preparation of 4,4-dimethyl-1-(naphthalen-1-yl)-1,2,3,4-tetrahydropyridine, 148d Prepared according to the procedure above for the preparation of 1-(tert-butyl)-4,4-dimethyl-1,2,3,4-tetrahydropyridine, 148a, as a pale yellow solid in 96% yield.
δ$_H$ (400 MHz) 8.18-7.39 (m, 6H), 7.12 (d, J 7.0, 1H), 6.25 (d, J 7.9, 1H), 4.59 (d, J 7.9, 1H), 3.56 (t, J 5.2, 2H), 1.81 (t, J 4.6, 2H), 1.16 (s, 6H).

Example 82—Preparation of 4,4-dimethyl-1-(p-tolyl)-1,2,3,4-tetrahydropyridine, 148e Prepared according to the procedure above for the preparation of 1-(tert-butyl)-4,4-dimethyl-1,2,3,4-tetrahydropyridine, 148a, as a white solid in 93% yield.
δ$_H$ (400 MHz) 7.04 (d, J 8.21, 2H), 6.79 (d, J 8.4, 2H), 6.40 (d, J 8.1, 1H), 4.46 (d, J 8.1, 1H), 3.44 (t, J 5.9, 2H), 2.25 (s, 3H), 1.70 (t, J 5.7, 2H), 1.05 (s, 6H).

Example 83—Preparation of 1-(4-(tert-butyl)phenyl)-4,4-dimethyl-1,2,3,4-tetrahydropyridine, 148h Prepared according to the procedure above for the preparation of 1-(tert-butyl)-4,4-dimethyl-1,2,3,4-tetrahydropyridine, 148a, as a cream solid in 84% yield.
δ$_H$ (400 MHz) 7.26 (d, J 8.5, 2H), 6.83 (d, J 8.4, 2H), 6.43 (d, J 8.3, 1H), 4.46 (d, J 8.2, 1H), 3.45 (t, J 5.4, 2H), 1.69 (t, J 5.6, 2H), 1.27 (s, 9H), 1.04 (s, 6H).

Example 84—Preparation of 1-(1-(tert-butyl)-4,4-dimethyl-1,4,5,6-tetrahydropyridin-3-yl)prop-2-en-1-one, 154

A solution of 1-(tert-butyl)-4,4-dimethyl-1,2,3,4-tetrahydropyridine (1.58 g, 9.4 mmol) and triethylamine (1.32 mL, 9.4 mmol) in DCM (80 mL) was cooled to −50° C. and treated drop wise with a solution of acryloyl chloride (764 μL, 9.4 mmol) in DCM (16 mL), under an inert atmosphere. Once addition was complete the mixture was stirred with the cold bath in place, and allowed to warm to room temperature over 6 hours, then stirred for a further 2 hours before quenching by pouring into water (80 mL). The organic phase was then separated, and the aqueous phase extracted with DCM (2×80 mL). The combined organic extracts were washed with water (2×80 mL) and brine (80 mL), and dried with magnesium sulfate. Evaporation in-vacuo gave the crude material as a dark red oil which was purified by column chromatography over silica gel, eluting with 0-2% ethyl acetate:DCM. Evaporation of the eluent gave the title compound as an orange/red solid (1.70 g, 81%), m.pt. 68-69° C.
δ$_H$ (400 MHz) 7.63 (s, 1H), 6.73 (dd, J 10.7, 17.0, 1H), 6.00 (dd, J 2.3, 17.0, 1H), 5.45 (dd, J 2.3, 10.6, 1H), 3.19 (m, 2H), 1.59 (m, 2H), 1.31 (s, 9H), 1.29 (s, 6H). δ$_C$ (100 MHz) 186.6, 145.2, 134.3, 123.1, 116.9, 57.4, 40.0, 38.9, 30.5, 28.4, 27.9. HRMS (ES): calc. for C$_{14}$H$_{24}$NO [MH$^+$], 222.1858. Found, 222.1849 [MH$^+$]. UV λ$_{max}$ 328 nm, ε 24907 M$^{-1}$ cm$^{-1}$.

Example 85—Preparation of (E)-1-(1-(tert-butyl)-4,4-dimethyl-1,4,5,6-tetrahydropyridin-3-yl)-3-phenylprop-2-en-1-one, 155

A mixture of 1-(1-(tert-butyl)-4,4-dimethyl-1,4,5,6-tetrahydropyridin-3-yl)prop-2-en-1-one (0.70 g, 3.2 mmol) and iodobenzene (0.71 mL, 6.4 mmol) in acetonitrile (30 mL) was treated with triethylamine (1.06 mL, 7.6 mmol) and a mixture of palladium(II)acetate (71 mg, 0.32 mmol) and tris(o-tolyl)phosphine (193 mg, 0.64 mmol) in acetonitrile (5 mL) which had been previously sonicated for 1 minute. The mixture was then heated to reflux for 4 hours under an inert atmosphere. The reaction mixture was then evaporated in-vacuo to give the crude material which was purified by column chromatography over silica gel eluting with 5% ethyl acetate:petroleum ether, followed by radial chromatography eluting with 0-5% ethyl acetate:DCM. Evaporation of the eluent gave the title compound as a yellow solid (0.45 g, 47%), m.pt. 117-119° C.

$\delta_H$ (400 MHz) 7.73 (s, 1H), 7.56-7.42 (m, 3H), 7.38-7.27 (m, 3H), 7.12 (d, J 15.5, 1H), 3.23 (m, 2H), 1.64 (m, 2H), 1.35 (s, 9H), 1.34 (s, 6H). $\delta_C$ (100 MHz) 185.8, 144.5, 138.3, 136.7, 128.9, 128.9, 127.7, 124.6, 117.8, 57.5, 40.1, 39.0, 30.8, 28.4, 28.1. HRMS (ES): calc. for $C_{20}H_{28}NO$ [MH$^+$], 298.2165. Found, 298.2165 [MH$^+$]. UV $\lambda_{max}$ 360 nm, $\epsilon$ 23198 M$^{-1}$ cm$^{-1}$.

Example 86—Preparation of (4-bromophenyl)(1-(tert-butyl)-4,4-dimethyl-1,4,5,6-tetrahydropyridin-3-yl)methanone, 156

A solution of 1-(tert-butyl)-4,4-dimethyl-1,2,3,4-tetrahydropyridine, 148a (1.02 g, 6.10 mmol) and triethylamine (0.85 mL, 6.10 mmol) in DCM (15 mL) was cooled on an ice bath and treated dropwise with a solution of 4-bromobenzoyl chloride (1.34 g, 6.10 mmol) in DCM (20 Once addition was complete the mixture was stirred for a further 18 hours before quenching by pouring into water (30 mL). The organic phase was then separated, combined with two further DCM extracts and the combined organic layers washed with water and dried with magnesium sulfate. Evaporation in-vacuo gave the crude material as a brown solid (2.12 g) which was purified by column chromatography over silica gel eluting with 10% ethyl acetate:petroleum ether. Evaporation of the eluent gave a yellow solid which was recrystallised from ethyl acetate:petroleum ether. The crystals were collected by filtration and dried in-vacuo to afford the title compound as a yellow solid (0.56 g, 26%), m.pt. 98-99° C.

$\delta_H$ (400 MHz) 7.46 (m, 2H), 7.33 (m, 2H), 7.15 (s, 1H), 3.21 (m, 2H), 1.66 (m, 2H), 1.35 (s, 6H), 1.18 (s, 9H). $\delta_C$ (100 MHz) 192.2, 148.7, 141.6, 131.0, 130.3, 123.4, 115.7, 57.3, 39.7, 38.9, 30.5, 28.2, 27.8. HRMS (ES): calc. for $C_{18}H_{25}NOBr$ [MH$^+$], 350.1114. Found, 350.1119 [MH$^+$]. UV $\lambda_{max}$ 317 nm, $\epsilon$ 27506 M$^{-1}$ cm$^{-1}$.

Example 87—Preparation of (1-(tert-butyl)-4,4-dimethyl-1,4,5,6-tetrahydropyridine-3-yl)(4-(dimethylamino)phenyl)methanone, 157 and (4-(tert-butoxy)phenyl)(1-(tert-butyl)-4,4-dimethyl-1,4,5,6-tetrahydropyridin-3-yl)methanone, 158

In a Schlenk tube, toluene (10 mL; previously dried over sodium wire) was degassed with a stream of argon. Sodium tert-butoxide (593 mg, 6.2 mmol) was added followed by dimethylamine hydrochloride (231 mg, 2.8 mmol), and the mixture stirred for 5 mins. The remaining materials were added in the following order: (4-bromophenyl)(1-(tert-butyl)-4,4-dimethyl-1,4,5,6-tetrahydropyridin-3-yl)methanone, 156 (900 mg, 2.6 mmol), BINAP (96 mg, 0.15 mmol) and tris(dibenzylidene)dipalladium(0) (80 mg, 0.077 mmol). The Schlenk tube was sealed and the reaction stirred at 80° C. for 18 h. The reaction was then cooled, diluted with ethyl acetate and filtered through Celite, washing thoroughly with extra ethyl acetate. The filtrate was then washed with water (20 mL), sat. NaHCO$_3$ (20 mL) and brine (20 mL), then dried (MgSO$_4$) and concentrated in-vacuo. The crude material was purified by radial chromatography over silica gel eluting with 20% ethyl acetate petroleum ether to afford (1-(tert-butyl)-4,4-dimethyl-1,4,5,6-tetrahydropyridine-3-yl)(4-(dimethylamino)phenyl)methasone, 57, as a yellow solid (157 mg, 19%), m.pt. 162-163° C.

$\delta_H$ (400 MHz) 7.48 (m, 2H), 7.26 (s, t 1H), 6.64 (m, 2H), 3.21 (m, 2H), 2.99 (s, 6H), 1.67 (m, 2H), 1.34 (s, 6H), 1.20 (s, 9H). $\delta_C$ (100 MHz) 193.6, 151.7, 146.8, 131.0, 130.1, 115.7, 111.0, 56.7, 40.5, 39.9, 38.7, 30.6, 28.4, 28.2. HRMS (ES): calc. for $C_{20}H_{31}N_2O$ [MH$^+$], 315.2431. Found, 315.2432 [MH$^+$]. UV $\lambda_{max}$ 333 nm, $\epsilon$ 24966 M$^{-1}$ cm$^{-1}$.

Also isolated was (4-(tert-butoxy)phenyl)(1-(tert-butyl)-4,4-dimethyl-1,4,5,6-tetrahydropyridin-3-yl)methanone, 158 as a yellow solid (0.33 g, 40%), m.pt. 98-101° C.

$\delta_H$ (CDCl$_3$, 400 MHz) 7.39 (m, 2H), 7.19 (s, 1H), 6.96 (m, 2H), 3.20 (m, 2H), 1.66 (m, 2H), 1.35 (s, 6H), 1.34 (s, 9H), 1.16 (s, 9H). $\delta_C$ (CDCl$_3$, 100 MHz) 193.5, 156.4, 148.6, 137.9, 129.7, 123.4, 115.8, 79.1, 57.1, 39.8, 38.8, 30.5, 29.1, 28.2, 28.0. HRMS (ES): calc. for $C_{22}H_{34}NO_2$ [MH$^+$], 344.2584. Found, 344.2585 [MH$^+$]. UV $\lambda_{max}$ 317 nm, $\epsilon$ 32556 M$^{-1}$ cm$^{-1}$.

Example 88—Preparation of 1,4-phenylenebis((1-(tert-butyl)-4,4-dimethyl-1,4,5,6-tetrahydropyridin-3-yl)methanone), 159 and 4-(1-(tert-butyl)-4,4-dimethyl-1,4,5,6-tetrahydropyridine-3-carbonyl)benzoic acid, 160

A solution of 1-(tert-butyl)-4,4-dimethyl-1,2,3,4-tetrahydropyridine (1.01 g, 6.00 mmol) and triethylamine (0.80 mL, 5.80 mmol) in DCM (20 mL) was cooled on an ice bath and treated dropwise with a solution of terephthaloyl chloride (0.58 g, 2.90 mmol) in DCM (5 mL). Once addition was complete the mixture was stirred at 0° C. for 1 hour, then allowed to warm to room temperature and stirred for a further 18 hours before quenching by pouring into water (30 mL). The organic phase was then separated, combined with two further DCM extracts and the combined organic layers washed with water and dried with magnesium sulfate. Evaporation in-vacuo gave the crude material as a dark red solid (0.54 g) which was purified by radial chromatography eluting with 30% ethyl acetate:petroleum ether. Evaporation of the eluents gave 1,4-phenylenebis((1-(tert-butyl)-4,4-dimethyl-1,4,5,6-tetrahydropyridin-3-yl)methanone), 159 as a yellow solid (0.07 g, 5%), m.pt. 243° C. (decamp).

$\delta_H$ (400 MHz) 7.44 (s, 4H), 7.23 (s, 2H), 3.21 (m, 4H), 1.67 (m, 4H), 1.37 (s, 12H), 1.16 (s, 18H). $\delta_C$ (100 MHz) 193.4, 149.1, 143.3, 128.2, 115.8, 57.3, 39.8, 38.9, 30.6, 28.3, 27.9. HRMS (ES): calc. for $C_{30}H_{45}N_2O_2$ [MH$^+$], 465.3476. Found, 465.3485 [MH$^+$]. UV $\lambda_{max}$ 317 nm, $\epsilon$ 33982 M$^{-1}$ cm$^{-1}$.

Also isolated was 4-(1-(tert-butyl)-4,4-dimethyl-1,4,5,6-tetrahydropyridine-3-carbonyl)benzoic acid, 160 as an orange solid (0.05 g, 5%), m.pt. 80-83° C.

$\delta_H$ (CDCl$_3$, 400 MHz) 8.07 (d, J 8.2, 2H), 7.50 (d, J 8.2, 2H), 7.14 (s, 1H), 3.23 (m, 2H), 1.67 (m, 2H), 1.38 (s, 6H), 1.16 (s, 9H). $\delta_C$ (CDCl$_3$, 100 MHz) 192.8, 171.0, 149.7, 146.8, 132.0, 129.8, 128.3, 115.8, 57.5, 39.8, 39.0, 30.5, 28.2, 27.8. HRMS (ES): calc. for $C_{19}H_{26}NO_3$[MH$^+$], 316.1907. Found, 316.1907 [MH$^+$]. UV $\lambda_{max}$ 317 nm, $\epsilon$ 17300 M$^{-1}$ cm$^{-1}$.

Example 89—Preparation of 1,10-bis(1-(tert-butyl)-4,4-dimethyl-1,4,5,6-tetrahydropyridin-3-yl)decane-1,10-dione, 166

A solution of 1-(tert-butyl)-4,4-dimethyl-1,2,3,4-tetrahydropyridine, 148a (0.25 g, 1.47 mmol) and triethylamine (0.21 mL, 1.54 mmol) in DCM (10 mL) was treated dropwise with sebacoyl chloride (0.16 g, 0.67 mmol) at room temperature. The mixture was then stirred for 18 hours. The mixture was diluted with water (20 mL) and DCM (20 mL) and the organic phase separated, washed with sodium carbonate solution (10% w/w, 30 mL) and dried with magnesium sulfate. Evaporation in-vacuo gave the crude material as a dark red oil which was purified by column chromatography over silica gel, eluting with 0-30% ethyl acetate: petroleum ether. Evaporation of the eluents gave the title compound as cream solid (0.15 g, 45%). m.pt. 72-74° C.

$\delta_H$ (400 MHz) 6.87 (s, 2H), 3.09 (t, J, 5.9, 4H), 2.37 (t, J 7.8, 4H), 1.59-1.52 (m, 8H), 1.30-1.22 (m, 38H). $\delta_C$ (100 MHz) 196.4, 143.6, 116.2, 56.9, 40.3, 38.7, 37.5, 30.5, 29.9, 28.4, 28.3, 26.9, HRMS (ES): calc. for $C_{32}H_{56}N_2O_2$ [M$^+$], 500.4336. Found, 500.4340 [M$^+$]. UV $\lambda_{max}$ 307 nm, $\epsilon$ 54797 M$^{-1}$ cm$^{-1}$.

Example 90—Preparation of bis(1-(tert-butyl)-4,4-dimethyl-1,4,5,6-tetrahydropyridin-3-yl)methanone, 167

Prepared according to the procedure above for the preparation of 1,10-bis(1-(tert-butyl)-4,4-dimethyl-1,4,5,6-tetrahydropyridin-3-yl)decane-1,10-dione, 166 as a pale yellow in 14% yield. m.pt. 134-137° C.

$\delta_H$ (400 MHz) 7.48 (s, 2H), 3.12 (t, J, 5.7, 4H), 1.57 (t, J 5.7, 4H), 1.19-1.23 (m, 30H). $\delta_C$ (100 MHz) 196.5, 141.2, 117.6, 55.5, 40.0, 38.5, 30.7, 29.6, 28.3. HRMS (ES): calc. for $C_{23}H_{40}N_2O$ [M$^+$], 360.3141. Found, 360.3133 [M$^+$]. UV $\lambda_{max}$ 305 nm, $\epsilon$ 15425 M$^{-1}$ cm$^{-1}$.

Example 91—Preparation of 1-(1-(tert-butyl)-4,4-dimethyl-1,4,5,6-tetrahydropyridin-3-yl)-2-phenoxyethanone, 168

Prepared according to the procedure above for the preparation of 1,10-bis(1-(tert-butyl)-4,4-dimethyl-1,4,5,6-tetrahydropyridin-3-yl)decane-1,10-dione, 166 as a dark yellow solid in 36% yield. m.pt. 87-88° C.

$\delta_H$ (400 MHz) 7.93 (s, 1H), 7.25-7.21 (m, 2H), 6.93-6.87 (m, 3H), 4.67 (s, 2H), 3.14 (t, J 5.8, 2H), 1.52 (t, J 5.7, 4H), 1.28 (s, 9H), 1.22 (s, 6H). $\delta_C$ (100 MHz) 189.6, 158.5, 145.8, 129.6, 121.0, 114.9, 72.7, 57.6, 39.8, 38.8, 30.3, 28.4, 27.8. HRMS (ES): calc. for $C_{19}H_{28}NO_2$ [MH$^+$], 302.2115. Found, 302.2114 [MH$^+$]. UV $\lambda_{max}$ 313 nm, $\epsilon$ 26154 M$^{-1}$ cm$^{-1}$.

Example 92—Preparation of (1-(tert-butyl)-4,4-dimethyl-1,4,5,6-tetrahydropyridin-3-yl)(pyridin-4-yl)methanone, 169

Prepared according to the procedure above for the preparation of 1,10-bis(1-(tert-butyl)-4,4-dimethyl-1,4,5,6-tetrahydropyridin-3-yl)decane-1,10-dione, 166 as a dark cream solid in 25% yield. m.pt. 134-135° C.

$\delta_H$ (400 MHz) 8.61 (d, J 6.0, 2H), 7.30 (d, J 6.0, 2H), 7.08 (s, 1H), 3.22 (t, J 5.8, 2H), 1.64 (t, J 5.7, 4H), 1.35 (s, 6H), 1.15 (s, 9H). $\delta_C$ (100 MHz) 190.8, 149.4, 115.5, 57.7, 39.6, 39.0, 30.5, 28.1, 27.7. HRMS (ES): calc. for $C_{17}H_{24}N_2O$ [M$^+$], 272.1883. Found, 272.1882 [M$^+$]. UV $\lambda_{max}$ 316 nm, $\epsilon$ 23556 M$^{-1}$ cm$^{-1}$.

Example 93—Preparation of 1-(1-(tert-butyl)-4,4-dimethyl-1,4,5,6-tetrahydropyridin-3-yl)-3-phenyl-propane-1,3-dione, 170

A solution of 1-(tert-butyl)-4,4-dimethyl-1,2,3,4-tetrahydropyridine (0.23 g, 1.40 mmol) and triethylamine (0.23 mL, 1.60 mmol) in DCM (2 mL) was cooled on an ice bath and treated drop wise with a solution of 3-oxo-3-phenyl-propanoyl chloride (0.25 g, 1.40 mmol) in DCM (3 mL). Once addition was complete the mixture was stirred for a further 18 hours. Analysis by tlc (5% ethyl acetate:petroleum ether) showed starting material still present. The reaction was stirred for 20 hours at 40° C., before quenching by pouring into water (10 mL). The organic phase was then separated, combined with two further DCM extracts and the combined organic layers washed with water and dried with magnesium sulfate. Evaporation in-vacuo gave the crude material as a dark red oil (0.33 g) which was purified by column chromatography over silica gel eluting with 5% ethyl acetate petroleum ether, followed by radial chromatography eluting with 5% ethyl acetate:petroleum ether. Evaporation of the eluent in-vacuo gave the title compound as a yellow solid (0.11 g, 25%), m.pt. 103-104° C. Analytical data indicated the presence of an approximately 3:7 mixture of the keto and enol forms.

$\delta_H$ (400 MHz) 8.19-8.14 (m, 0.6H), 7.84 (s, 0.3H), 7.83-7.78 (m, 1.4H), 7.74 (s, 0.7H), 7.56-7.50 (m, 0.3H), 7.48-7.37 (m, 2.7H), 6.15 (s, 0.7H), 4.12 (s, 0.6H), 3.24 (m, 1.4H), 3.14 (m, 0.6H), 1.65 (m, 1.4H), 1.52 (m, 0.6H), 1.36 (s, 9H), 1.35 (s, 4.3H), 1.18 (s, 1.7H). $\delta_C$ (100 MHz) 196.4, 188.9, 186.6, 175.7, 147.3, 142.3, 137.1, 137.0, 133.1, 130.4, 129.5, 128.5, 128.4, 126.2, 116.3, 112.3, 91.7, 57.7, 57.5, 53.0, 40.3, 39.9, 38.9, 38.8, 30.4, 30.2, 28.5, 28.4, 28.3, 27.8. HRMS (ES): calc. for $C_{20}H_{28}NO_2$ [MH$^+$], 314.2115. Found, 314.2114 [MH$^+$]. UV $\lambda_{max}$ 309, 396 nm, $\epsilon$ 19993, 8961 M$^{-1}$ cm$^{-1}$.

Example 94—Preparation of 2-(1-(4-methoxyphenyl)-4,4-dimethyl-1,4,5,6-tetrahydropyridine-3-carbonyl)cyclopentanone, 171

Prepared according to the procedure above for the preparation of 1,10-bis(1-(tert-butyl)-4,4-dimethyl-1,4,5,6-tetrahydropyridin-3-yl)decane-1,10-dione, 166 as a dark yellow gum in 16% yield.

$\delta_H$ (400 MHz) 7.65 (s, 1H), 7.11 (d, J 9.1, 2H), 6.88 (d, J 9.1, 2H), 3.78 (s, 3H), 3.74-3.52 (m, 3H), 2.60-1.67 (m, 8H), 1.29 (s, 6H). $\delta_C$ (100 MHz) 189.8, 156.5, 147.2, 139.9, 120.5, 119.9, 119.8, 114.9, 114.8, 114.7, 55.9, 55.8, 44.4, 39.6, 39.5, 39.2, 30.7, 28.2, 28.1, 27.9, 27.3, 21.4. HRMS (ES): calc. for $C_{20}H_{26}NO_3$ [MH$^+$], 328.1907. Found, 328.1904 [MH$^+$]. UV $\lambda_{max}$ 332 nm, $\epsilon$ 30675 M$^{-1}$ cm$^{-1}$.

Example 95—Preparation of 1,10-bis(4,4-dimethyl-1-(p-tolyl)-1,4,5,6-tetrahydropyridin-3-yl)decane-1,10-dione, 172

Prepared according to the procedure above for the preparation of 1,10-bis(1-(tert-butyl)-4,4-dimethyl-1,4,5,6-tetrahydropyridin-3-yl)decane-1,10-dione, 166 as a cream solid in 15% yield. m.pt. 131-132° C.

$\delta_H$ (400 MHz) 7.59 (s, 2H), 7.14 (d, J 9.1, 4H), 6.97 (d, J 8.9, 4H), 3.55 (t, J 5.8, 4H), 2.31 (s, 6H), 1.73 (t, J 5.8, 4H), 1.63-1.53 (n, 4H), 1.33-1.24 (m, 20H). $\delta_C$ (100 MHz) 197.7, 143.8, 142.4, 133.0, 130.2, 120.8, 117.9, 43.6, 39.7, 37.6, 30.7, 29.7, 29.6, 28.2, 26.3, 20.8. HRMS (ES): calc. for $C_{38}H_{52}N_2O_2$ [M$^+$], 568.4023. Found, 568.4026 [M$^+$]. UV $\lambda_{max}$ 328 nm, $\epsilon$ 52737 M$^{-1}$ cm$^{-1}$.

Example 96—Preparation of 1-(1-(4-methoxyphenyl)-4,4-dimethyl-1,4,5,6-tetrahydropyridine-3-yl)-2-phenoxyethanone, 173

Prepared according to the procedure above for the preparation of 1,10-bis(1-(tert-butyl)-4,4-dimethyl-1,4,5,6-tetrahydropyridin-3-yl)decane-1,10-dione, 166 as a golden oil in 68% yield.

$\delta_H$ (400 MHz) 7.99 (s, 1H), 7.29-7.23 (m, 2H), 7.03 (d, J 9.1, 4H), 6.95-6.88 (m, 5H), 4.81 (s, 2H), 3.79 (a, 3H), 3.58 (t, J 5.8, 2H), 1.72 (t, J 5.8, 2H), 1.29 (s, 6H). $\delta_C$ (100 MHz) 191.4, 158.4, 156.6, 145.1, 139.6, 129.7, 121.3, 120.0, 117.9, 114.9, 114.9, 55.8, 44.2, 39.2, 30.3, 27.8. HRMS (ES): calc. for $C_{22}H_{26}NO_3$[MH$^+$], 352.1907. Found, 352.1907 [MH$^+$]. UV $\lambda_{max}$ 339 nm, $\epsilon$ 26633 M$^{-1}$ cm$^{-1}$.

Example 97—Preparation of 1-(1-(4-methoxyphenyl)-4,4-dimethyl-1,4,5,6-tetrahydropyridin-3-yl)-2-phenylethanone, 174

Prepared according to the procedure above for the preparation of 1,10-bis(1-(tert-butyl)-4,4-dimethyl-1,4,5,6-tetrahydropyridin-3-yl)decane-1,10-dione, 166 as a cream solid in 40% yield. m.pt. 86-88° C.

$\delta_H$ (400 MHz) 7.60 (s, 1H), 7.29-7.17 (m, 5H), 6.88 (s, 4H), 3.83 (s, 2H), 3.79 (s, 3H), 3.52 (t, J 5.8, 2H), 1.71 (t, J 5.8, 2H), 1.30 (s, 6H). $\delta_C$ (100 MHz) 194.3, 156.3, 144.8, 139.8, 137.8, 129.0, 128.7, 126.4, 119.9, 119.4, 114.9, 55.8, 45.4, 44.2, 39.5, 30.6, 28.0. HRMS (ES): calc. for $C_{22}H_{26}NO_2$ [MH$^+$], 336.1958. Found, 336.1958 [MH$^+$]. UV $\lambda_{max}$ 334 nm, $\epsilon$ 33786 M$^{-1}$ cm$^{-1}$.

Example 98—Preparation of 1-(1-(4-(dimethylamino)phenyl)-4,4-dimethyl-1,4,5,6-tetrahydropyridin-3-yl)octan-1-one, 175

Prepared according to the procedure above for the preparation of 1,10-bis(1-(tert-butyl)-4,4-dimethyl-1,4,5,6-tetrahydropyridin-3-yl)decane-1,10-dione, 166 as a yellow oil in 22% yield. m.pt. 55° C.

$\delta_H$ (400 MHz) 7.52 (s, 1H), 6.97 (d, J 9.1, 2H), 6.74 (d, J 9.0, 2H), 3.52 (t, J 5.8, 2H), 2.91 (s, 6H), 2.45 (t, J 7.8, 2H), 1.72 (t, J 5.8, 2H), 1.62-1.53 (m, 2H), 1.33-1.20 (m, 14H), 0.85 (t, J 7.0, 3H). $\delta_C$ (100 MHz) 197.3, 147.8, 143.5, 136.9, 120.0, 119.5, 113.7, 44.3, 41.2, 44.2, 39.7, 37.6, 31.9, 30.6, 29.7, 29.4, 28.2, 26.5, 22.8, 14.3. HRMS (ES): calc. for $C_{23}H_{36}N_2O_2$ [M$^+$], 356.2822. Found, 356.2822 [M$^+$]. UV $\lambda_{max}$ 338 nm, $\epsilon$ 28040 M$^{-1}$ cm$^{-1}$.

Example 99—Preparation of 1-(4,4-dimethyl-1-(p-tolyl)-1,4,5,6-tetrahydropyridin-3-yl)propan-1-one, 176

Prepared according to the procedure above for the preparation of 1,10-bis(1-(tert-butyl)-4,4-dimethyl-1,4,5,6-tetrahydropyridin-3-yl)decane-1,10-dione, 166 as a cream solid in 47% yield.

$\delta_H$ (400 MHz) 7.65 (s, 1H), 7.17 (d, J 9.1, 2H), 7.00 (d, J 9.0, 2H), 3.59 (t, J 5.7, 2H), 2.58 (q, J 7.4, 2H), 2.35 (s, 3H), 1.77 (t, J 5.8, 2H), 1.34 (s, 6H), 1.13 (t, J 7.5, 3H). $\delta_C$ (100 MHz) 197.4, 143.2, 141.7, 132.5, 129.6, 119.9, 117.3, 43.1, 39.1, 30.1, 29.8, 27.7, 20.3, 9.5. HRMS (ES): calc. for $C_{17}H_{24}NO$ [MH$^+$], 258.1852. Found, 258.1851 [MH$^+$]. UV $\lambda_{max}$ 327 nm, $\epsilon$ 34608 M$^{-1}$ cm$^{-1}$.

Example 100—Preparation of 1-(1-(4-(tert-butyl)phenyl)-4,4-dimethyl-1,4,5,6-tetrahydropyridin-3-yl)propan-1-one, 177

Prepared according to the procedure above for the preparation of 1,10-bis(1-(tert-butyl)-4,4-dimethyl-1,4,5,6-tetrahydropyridin-3-yl)decane-1,10-dione, 166 as a pale yellow gum in 54% yield.

$\delta_H$ (400 MHz) 7.68 (s, 1H), 7.42 (d, J 8.8, 2H), 7.04 (d, J 8.7, 2H), 3.61 (t, J 5.8, 2H), 2.59 (q, J 7.4, 2H), 1.77 (t, J 5.7, 2H), 1.34 (s, 6H), 1.13 (t, J 7.5, 3H). $\delta_C$ (100 MHz) 198.0, 146.4, 143.6, 142.2, 126.5, 120.5, 117.5, 43.5, 39.7, 34.4, 31.5, 30.7, 30.4, 28.2, 10.0. HRMS (ES): calc. for $C_{20}H_{29}NO$ [M$^+$], 299.2244. Found, 299.2244 [M$^+$]. UV $\lambda_{max}$ 329 nm, $\epsilon$ 31955 M$^{-1}$ cm$^{-1}$.

Example 101—Preparation of 1-(4,4-dimethyl-1-(naphthalen-1-yl)-1,4,5,6-tetrahydropyridin-3-yl)propan-1-one, 178

Prepared according to the procedure above for the preparation of 1,10-bis(1-(tert-butyl)-4,4-dimethyl-1,4,5,6-tetrahydropyridin-3-yl)decane-1,10-dione, 166 as a pale yellow oil in 44% yield.

$\delta_H$ (400 MHz) 7.95 (t, J 8.0, 2H), 7.79 (d, J 8.2, 1H), 7.61-7.47 (m, 4H), 7.33 (d, J 7.4, 1H), 3.66 (t, J 5.8, 2H), 2.46 (q, J 7.4, 2H), 1.91 (br s, 2H), 1.44 (s, 6H), 1.07 (t, J 7.5, 3H). $\delta_C$ (100 MHz) 197.9, 146.6, 143.9, 135.0, 129.4, 128.9, 127.1, 126.9, 126.7, 125.9, 122.9, 122.2, 119.0, 47.0, 40.1, 30.8, 30.3, 28.5, 10.1. HRMS (ES): calc. for $C_{20}H_{23}NO$ [M$^+$], 293.1774. Found, 293.1776 [M$^+$]. UV $\lambda_{max}$ 321 nm, $\epsilon$ 23247 M$^{-1}$ cm$^{-1}$.

Example 102—Preparation of 1-(tert-butyl)-4,4-dimethyl-N-phenyl-1,4,5,6-tetrahydropyridine-3-carboxamide, 179

A solution of 1-(tert-butyl)-4,4-dimethyl-1,2,3,4-tetrahydropyridine, 148a (0.18 g, 1.08 mmol) in DCM (10 mL) was treated dropwise with phenyl isocyanate (0.12 mL, 1.08 mmol) at room temperature. The mixture was then stirred at room temperature for 18 hours and evaporated in-vacuo to a white solid which was washed with petroleum ether and diethyl ether before drying to give the title compound as a white solid (0.28 g, 90%). m.pt. 232-234° C.

$\delta_H$ (400 MHz) 7.45 (d, J 7.5, 2H), 7.32 (s, 1H), 7.30-7.24 (m, 2H), 7.01-6.94 (m, 2H), 3.15 (t, J 5.9, 2H), 1.63 (t, J 5.8, 2H), 1.29 (s, 6H), 1.27 (s, 9H). $\delta_C$ (100 MHz) 168.1, 139.6, 138.0, 129.0, 122.9, 119.7, 108.5, 56.2, 40.0, 38.5, 30.0, 29.4, 28.3. HRMS (ES): calc. for $C_{18}H_{26}N_2O$ [MH$^+$], 286.2040. Found, 286.2042 [MH$^+$]. UV $\lambda_{max}$ 308 nm, $\epsilon$ 34834 M$^{-1}$ cm$^{-1}$.

Example 103—Preparation of 1-(tert-butyl)-N,4,4-trimethyl-N-phenyl-1,4,5,6-tetrahydropyridine-3-carboxamide, 180

A solution of 1-(tert-butyl)-4,4-dimethyl-N-phenyl-1,4,5,6-tetrahydropyridine-3-carboxamide, 179 (0.1 g, 0.35 mmol) in DMF (10 mL) was treated with sodium hydride (50% weight in mineral oil, 0.03 g, 0.70 mmol) and stirred at room temperature for 1 hour. Iodomethane (0.03 mL, 0.52 mmol) was then added dropwise and the mixture stirred at room temperature for 18 hours. The reaction mixture was then diluted with water (30 mL), extracted into MTBE (2×30 mL) and the combined organics washed with water (20 mL), dried with magnesium sulfate and evaporated in-vacuo to give the crude material as a yellow oil which was purified by column chromatography over silica gel, eluting with 0-20% ethyl acetate:petroleum ether. Evaporation of the eluents gave the title compound as cream solid (0.09 g, 84%), m.pt. 83-84° C.

$\delta_H$ (400 MHz) 7.45 (d, J 7.5, 2H), 7.32 (s, 1H), 7.30-7.24 (m, 2H), 7.01-6.94 (m, 2H), 3.15 (t, J 5.9, 2H), 1.63 (t, J 5.8, 2H), 1.29 (s, 6H), 1.27 (s, 9H). $\delta_C$ (100 MHz) 172.7, 149.1, 141.8, 129.1, 126.2, 124.4, 55.6, 39.2, 38.2, 38.0, 30.2, 28.7, 28.0. HRMS (ES): calc. for $C_{19}H_{28}N_2O$ [MH$^+$], 301.2274. Found, 301.2276 [MH$^+$]. UV $\lambda_{max}$ 312 nm, $\epsilon$ 15174 M$^{-1}$ cm$^{-1}$.

Example 104—Preparation of N,N'-(hexane-1,6-diyl)bis(1-(tert-butyl)-4,4-dimethyl-1,4,5,6-tetrahydropyridine-3-carboxamide), 181

A solution of 1-(tert-butyl)-4,4-dimethyl-1,2,3,4-tetrahydropyridine, 148a (0.20 g, 1.19 mmol) in DCM (10 mL) was treated dropwise with 1,6-diisocyanatohexane (0.10 mL, 0.60 mmol) at room temperature. The mixture was then stirred for 18 hours before and heating to 100° C. for 30 minutes under microwave irradiation. The crude mixture was then treated with water (10 mL) and stirred for 30 minutes before separation of the organic phase. The aqueous layer was then extracted with CHCl$_3$ (2×10 mL) and the combined organic layers dried with magnesium sulfate and evaporated in-vacuo to a yellow oil which was purified by column chromatography over silica gel, eluting with 0-100% ethyl acetate:petroleum ether. Evaporation of the eluents gave the title compound as white solid (0.02 g, 5%), m.pt. 191-193° C.

$\delta_H$ (400 MHz) 7.19 (s, 2H), 5.21 (br s, 2H), 3.25 (q, J 6.0, 4H), 3.07 (t, J 5.8, 4H), 1.67-1.28 (m, 12H), 1.22 (s, 18H), 1.20 (s, 12H). $\delta_C$ (100 MHz) 170.2, 136.9, 108.7, 55.8, 40.2, 39.4, 38.4, 30.2, 29.8, 29.7, 29.5, 28.3, 26.9. HRMS (ES): calc. for $C_{30}H_{55}N_4O_2$ [MH$^+$], 503.4320. Found, 503.4323 [MH$^+$]. UV $\lambda_{max}$ 289 nm, $\epsilon$ 31072 M$^{-1}$ cm$^{-1}$.

Example 105—Preparation of 1-(tert-butyl)-4,4-dimethyl-N-phenyl-1,4,5,6-tetrahydropyridine-3-carbothioamide, 182

Prepared according to the procedure above for the preparation of 1-(tert-butyl)-4,4-dimethyl-N-phenyl-1,4,5,6-tetrahydropyridine-3-carboxamide, 179, with final purification by column chromatography over silica gel, eluting with 0-30% ethyl acetate petroleum ether to give the title compound as a yellow solid in 59% yield. m.pt. 144-146° C.

$\delta_H$ (400 MHz) 8.50 (s, 1H), 7.96 (br s, 1H), 7.51 (d, J 8.7, 2H), 7.33 (t, J 8.3, 2H), 7.15 (t, J 8.5, 1H), 3.22 (t, J 7.7, 2H), 1.66 (t, J 7.5, 2H), 1.40 (s, 6H), 1.30 (s, 9H). $\delta_C$ (100 MHz) 194.6, 147.3, 140.7, 128.8, 124.9, 114.2, 57.9, 40.7, 38.7, 30.8, 29.1, 28.4. HRMS (ES): calc. for $C_{18}H_{26}N_2S$ [M$^+$], 302.1811. Found, 302.1811 [M$^+$]. UV $\lambda_{max}$ 363 nm, $\epsilon$ 20881 M$^{-1}$ cm$^{-1}$.

Example 106—Preparation of 1-(tert-butyl)-N-butyl-4,4-dimethyl-1,4,5,6-tetrahydropyridine-3-carboxamide, 183

Prepared according to the procedure above for the preparation of N,N'-(hexane-1,6-diyl)bis(1-(tert-butyl)-4,4-dimethyl-1,4,5,6-tetrahydropyridine-3-carboxamide), 181, as a pale yellow solid in 7% yield. m.pt. 115-116° C.

$\delta_H$ (400 MHz) 7.19 (s, 1H), 5.17 (br s, 1H), 3.26 (q, J 6.0, 2H), 3.07 (t, J 5.8, 2H), 1.61-1.19 (m, 21H), 0.90 (t, J 7.3, 3H). $\delta_C$ (100 MHz) 170.2, 136.9, 108.7, 55.8, 40.2, 39.4, 38.4, 32.3, 29.7, 29.5, 28.2, 20.5, 14.0. HRMS (ES): calc. for $C_{16}H_{31}N_2O$ [MH$^+$], 267.2436. Found, 267.2429 [MH$^+$]. UV $\lambda_{max}$ 288 nm, $\epsilon$ 22531 M$^{-1}$ cm$^{-1}$.

Example 107—Preparation of N,N'-(4-methyl-1,3-phenylene)bis(1-(tert-butyl)-4,4-dimethyl-1,4,5,6-tetrahydropyridine-3-carboxamide), 184

Prepared according to the procedure above for the preparation of 1-(tert-butyl)-4,4-dimethyl-N-phenyl-1,4,5,6-tetrahydropyridine-3-carboxamide, 179, with final purification by column chromatography over silica gel, eluting with 0-30% ethyl acetate petroleum ether to give the title compound as a white solid in 84% yield. m.pt. 91-92° C.

$\delta_H$ (400 MHz) 7.83 (s, 1H), 7.57 (dd, J 2.3, 8.2, 1H), 7.39 (s, 1H), 7.21 (s, 1H), 7.05 (d, J 8.5, 1H), 6.98 (br a, 1H), 6.83 (br s, 1H), 3.17-3.11 (m, 4H), 2.20 (s, 3H), 1.61-1.59 (m, 4H), 1.32-1.23 (m, 30H). $\delta_C$ (100 MHz) 167.7, 167.6, 137.9, 137.6, 137.2, 136.7, 130.1, 120.6, 114.8, 112.0, 108.6, 107.9, 55.7, 55.6, 39.6, 39.5, 37.9, 29.5, 29.33, 28.85, 28.73, 27.8, 17.2. HRMS (ES): calc. for $C_{31}H_{48}N_4O_2$ [M$^+$], 508.3772. Found, 508.3776 [M$^+$]. UV $\lambda_{max}$ 308 nm, $\epsilon$ 59763 M$^{-1}$ cm$^{-1}$.

Example 108—Preparation of N,N'-(methylenebis(4,1-phenylene))bis(1-(tert-butyl)-4,4-dimethyl-1,4,5,6-tetrahydropyridine-3-carboxamide), 185

A solution of 1-(tert-butyl)-4,4-dimethyl-1,2,3,4-tetrahydropyridine, 148a (0.20 g, 1.20 mmol) in CHCl$_3$ (10 mL) was treated with bis(4-isocyanatophenyl)methane (0.17 g, 0.68 mmol) and stirred at room temperature for 18 hours. The resulting thick suspension was then evaporated in-vacuo and the white solid residue heated to reflux in ethyl acetate (50 mL), left to stand for 1 hour and filtered. The precipitate was then heated to reflux in CHCl$_3$ (15 mL) and the resulting turbid solution treated with petroleum ether until a precipitate started to form. The mixture was then left to stand for 2 hours, after which time the precipitate was filtered and discarded (heavily enriched with monoacylated product). Evaporation of the liquors in-vacuo gave the title compound as a white solid in 40% yield. m.pt. 235° C.

$\delta_H$ (400 MHz) 7.35 (d, J 8.5, 4H), 7.29 (s, 2H), 7.07 (d, J 8.5, 4H), 6.92 (br s, 2H), 6.83 (br 5, 1H), 3.85 (s, 2H), 3.14 (t, J 5.8, 4H), 1.61 (t, J 5.8, 4H), 1.29-1.24 (m, 30H). $\delta_C$ (100 MHz) 168.1, 137.8, 137.5, 136.1, 129.4, 119.9, 108.6, 56.2, 40.8, 40.0, 38.5, 30.0, 29.4, 28.3. HRMS (ES): calc. for $C_{37}H_{52}N_4O_2$ [M$^+$], 584.4085. Found, 584.4089 [M$^+$]. UV $\lambda_{max}$ 310 nm, $\epsilon$ 64589 M$^{-1}$ cm$^{-1}$.

Example 109—Preparation of 1-(tert-butyl)-4,4-dimethyl-N-tosyl-1,4,5,6-tetrahydropyridine-3-carboxamide, 186

Prepared according to the procedure above for the preparation of 1-(tert-butyl)-4,4-dimethyl-N-phenyl-1,4,5,6-tetrahydropyridine-3-carboxamide, 179, with final purification by column chromatography over silica gel, eluting with 0-30% ethyl acetate:petroleum ether to give the title compound as a white solid in 94% yield. m.pt. 58-60° C.

$\delta_H$ (400 MHz) 7.88 (d, J 8.3, 2H), 7.69 (br s, 1H), 7.44 (s, 1H), 7.29-7.23 (m, 2H), 3.14 (t, J 5.8, 2H), 2.39 (s, 3H), 1.50

(t, J 5.8, 2H), 1.25 (s, 9H), 1.09 (s, 6H). $\delta_C$ (100 MHz) 164.8, 144.4, 142.8, 129.9, 129.4, 128.1, 104.9, 57.4, 53.6, 39.5, 38.7, 29.7, 28.4, 28.3, 21.8. HRMS (ES): calc. for $C_{19}H_{28}N_2O_3S$ [M$^+$], 364.1815. Found, 364.1816 [M$^+$]. UV $\lambda_{max}$ 304 nm, $\epsilon$ 34588 M$^{-1}$ cm$^{-1}$.

Example 110—Preparation of N,N'-(1,4-phenylene) bis(1-(tert-butyl)-4,4-dimethyl-1,4,5,6-tetrahydropyridine-3-carboxamide), 187

Prepared according to the procedure above for the preparation of 1-(tert-butyl)-4,4-dimethyl-N-phenyl-1,4,5,6-tetrahydropyridine-3-carboxamide, 179, to give the title compound as a white solid in 86% yield. m.pt. 324° C. (dec).
$\delta_H$ (DMSO-d$_6$, 400 MHz) 8.93 (br s, 2H), 7.40-7.22 (m, 4H), 7.03 (br s, 2H), 3.09 (br s, 2H), 1.50 (br s, 4H), 1.22 (s, 18H), 1.15 (s, 12H). $\delta_C$ (DMSO-d$_6$, 100 MHz) 167.8, 137.6, 135.8, 135.5, 120.0, 108.9, 56.3, 38.4, 30.4, 29.1, 28.4. HRMS (ES): calc. for $C_{30}H_{46}N_4O_2$ [M$^+$], 494.3615. Found, 494.3619 [M$^+$]. UV $\lambda_{max}$ 322 nm, $\epsilon$ 71962 M$^{-1}$ cm$^{-1}$.

Example 111—Preparation of N,N'-(1,3-phenylene) bis(1-(tert-butyl)-4,4-dimethyl-1,4,5,6-tetrahydropyridine-3-carboxamide), 188

Prepared according to the procedure above for the preparation of 1-(tert-butyl)-4,4-dimethyl-N-phenyl-1,4,5,6-tetrahydropyridine-3-carboxamide, 179, with final purification by column chromatography over silica gel, eluting with 0-30% ethyl acetate:petroleum ether to give the title compound as a white solid in 95% yield. m.pt. 194-196° C.
$\delta_H$ (400 MHz) 7.72 (s, 1H), 7.27 (s, 2H), 7.17 (s, 3H), 6.99 (s, 2H), 3.16-3.09 (m, 4H), 1.62-1.57 (m, 4H), 1.25 (s, 30H). $\delta_C$ (100 MHz) 168.2, 140.1, 137.8, 129.3, 114.0, 110.5, 108.6, 56.2, 40.0, 38.5, 30.0, 29.3, 28.4. HRMS (ES): calc. for $C_{30}H_{47}N_4O_2$ [MH$^+$], 495.3694. Found, 495.3690 [MH$^+$]. UV $\lambda_{max}$ 313 nm, $\epsilon$ 55779 M$^{-1}$ cm$^{-1}$.

Example 112—Preparation of N-(3-isocyanato-4-methylphenyl)-4,4-dimethyl-1-(p-tolyl)-1,4,5,6-tetrahydropyridine-3-carboxamide, 189

Prepared according to the procedure above for the preparation of 1-(tert-butyl)-4,4-dimethyl-N-phenyl-1,4,5,6-tetrahydropyridine-3-carboxamide, 179, with final purification by column chromatography over silica gel, eluting with 0-10% ethyl acetate:petroleum ether to give the title compound as a white solid in 5% yield.
$\delta_H$ (400 MHz) 7.42 (s, 1H), 7.37 (s, 1H), 7.13-7.07 (m, 5H), 6.96-6.92 (m, 3H), 3.58 (t, J 5.8, 2H), 2.29 (s, 3H), 2.25 (s, 2H), 1.79 (t, J 5.8, 2H), 1.35 (s, 6H).

Example 113—Preparation of 1-(tert-butyl)-N-(5-(4,4-dimethyl-1-(p-tolyl)-1,4,5,6-tetrahydropyridine-3-carboxamido)-2-methylphenyl)-4,4-dimethyl-1,4,5,6-tetrahydropyridine-3-carboxamide, 190

Prepared according to the procedure above for the preparation of 1-(tert-butyl)-4,4-dimethyl-N-phenyl-1,4,5,6-tetrahydropyridine-3-carboxamide, 179, with final purification by column chromatography over silica gel, eluting with 0-30% ethyl acetate:petroleum ether to give the title compound as a white solid in 64% yield.
$\delta_H$ (400 MHz) 7.89 (s, 1H), 7.60 (dd, J 2.2, 8.3, 1H), 7.41 (s, 1H), 7.33 (s, 1H), 7.18 (s, 1H), 7.12-6.92 (m, 5H), 6.85 (s, 1H), 3.55 (t, J 5.9, 2H), 3.16 (t, J 5.8, 2H), 2.29 (s, 3H), 2.21 (s, 3H), 1.81 (t, J 5.7, 2H), 1.61 (t, J 5.8, 2H), 1.36-1.24 (m, 21H). $\delta_C$ (100 MHz) 167.7, 143.7, 138.6, 134.8, 131.8, 130.7, 130.0, 121.5, 116.9, 115.3, 114.8, 112.6, 108.2, 56.3, 43.2, 40.1, 39.1, 38.5, 30.7, 29.9, 28.8, 28.3, 20.7, 17.8. HRMS (ES): calc. for $C_{34}H_{47}N_4O_2$ [MH$^+$], 543.3694. Found, 543.3696 [MH$^+$]. UV $\lambda_{max}$ 314 nm, $\epsilon$ 51743 M$^{-1}$ cm$^{-1}$.

Example 114—Preparation of N,N'-(1,4-phenylene) bis(1-(4-(tert-butyl)phenyl)-4,4-dimethyl-1,4,5,6-tetrahydropyridine-3-carboxamide), 191

Prepared according to the procedure above for the preparation of N,N'-(hexane-1,6-diyl)bis(1-(tert-butyl)-4,4-dimethyl-1,4,5,6-tetrahydropyridine-3-carboxamide), 181 as a sandy coloured solid in 23% yield. m.pt. 355° C. (dec).
$\delta_H$ (DMSO-d$_6$, 400 MHz) 9.36 (s, 2H), 7.45 (br s, 4H), 7.39-7.12 (m, 10H), 3.53 (br t, J 5.6, 4H), 1.70 (br t, J 5.4, 4H), 1.29-1.19 (m, 31H). $\delta_C$ (DMSO-d$_6$, 100 MHz) 167.2, 144.4, 143.8, 135.5, 135.0, 126.5, 120.4, 116.4, 114.2, 49.1, 42.3, 34.3, 30.9, 29.0. HRMS (ES): calc. for $C_{42}H_{54}N_4O_2$ [M$^+$], 646.4241. Found, 646.4241 [M$^+$]. UV $\lambda_{max}$ 331 nm, $\epsilon$ 68095 M$^{-1}$ cm$^{-1}$.

Example 115—Preparation of 4,4-dimethyl-N-phenyl-1-(p-tolyl)-1,4,5,6-tetrahydropyridine-3-carboxamide, 192

Prepared according to the procedure above for the preparation of 1-(tert-butyl)-4,4-dimethyl-N-phenyl-1,4,5,6-tetrahydropyridine-3-carboxamide, 179, with final purification by column chromatography over silica gel, eluting with 0-10% ethyl acetate:petroleum ether to give the title compound as a white solid in 56% yield. m.pt. 199-200° C.
$\delta_H$ (400 MHz) 7.48 (d, J 7.8, 2H), 7.40 (s, 1H), 7.29 (t, J 8.5, 2H), 7.17-6.91 (m, 6H), 3.59 (t, J 5.6, 2H), 2.29 (s, 3H), 1.80 (t, J 5.7, 2H), 1.37 (s, 6H). $\delta_C$ (100 MHz) 167.7, 143.6, 139.1, 135.5, 132.1, 130.1, 129.1, 123.5, 120.0, 117.1, 114.5, 43.3, 39.1, 30.6, 28.8, 20.7. HRMS (ES): calc. for $C_{21}H_{25}N_2O$ [MH$^+$], 321.1961. Found, 321.1961 [MH$^+$]. UV $\lambda_{max}$ 323 nm, $\epsilon$ 33948 M$^{-1}$ cm$^{-1}$.

Example 116—Preparation of 1-(4-(tert-butyl)phenyl)-4,4-dimethyl-N-phenyl-1,4,5,6-tetrahydropyridine-3-carboxamide, 193

Prepared according to the procedure above for the preparation of 1-(tert-butyl)-4,4-dimethyl-N-phenyl-1,4,5,6-tetrahydropyridine-3-carboxamide, 179, as a white solid in 36% yield. m.pt. 228° C.
$\delta_H$ (400 MHz) 7.47 (d, J 7.6, 2H), 7.41 (s, 1H), 7.36-7.26 (m, 5H), 7.08 (br s, 1H), 7.05-6.97 (m, 3H), 3.60 (t, J 5.7, 2H), 1.79 (t, J 5.7, 2H), 1.37 (s, 6H), 1.29 (s, 9H). $\delta_C$ (100 MHz) 167.6, 145.5, 143.4, 139.1, 135.3, 129.1, 126.4, 123.5, 119.9, 116.7, 114.7. HRMS (ES): calc. for $C_{24}H_{30}N_2O$ [M$^+$], 362.2353. Found, 362.2364 [M$^+$]. UV $\lambda_{max}$ 324 nm, $\epsilon$ 35759 M$^{-1}$ cm$^{-1}$.

Example 117—Preparation of 1-(1-(4-(tert-butyl)phenyl)-4,4-dimethyl-1,4,5,6-tetrahydropyridin-3-yl)-2,2,2-trifluoroethanone, 194

A solution of 1-(4-(tert-butyl)phenyl)-4,4-dimethyl-1,2,3,4-tetrahydropyridine, 148h (1.00 g, 4.11 mmol) and triethylamine (0.69 mL, 4.93 mmol) in DCM (40 mL) was cooled on an ice bath and treated dropwise with trifluoroacetic anhydride (0.61 mL, 4.31 mmol). The mixture was then stirred for 1.5 hours. The mixture was then diluted with water (40 mL) and DCM (40 mL) and the organic phase separated, washed with sodium carbonate solution (10% w/w, 50 mL) and dried with magnesium sulfate. Evaporation in-vacuo gave the crude material as a yellow oil which was purified by column chromatography over silica gel, eluting with 0-5% ethyl acetate:petroleum ether. Evaporation of the eluents gave the title compound as cream solid (1.19 g, 85%), m.pt. 95° C.

$\delta_H$ (400 MHz) 7.80 (s, 1H), 7.42 (d, J 8.9, 2H), 7.05 (d, J 8.9, 2H), 3.67 (t, J 5.8, 2H), 1.81 (t, J 5.7, 2H), 1.34 (s, 6H), 1.30 (s, 9H). $\delta_C$ (100 MHz) 176.5, 148.6, 147.7, 147.6, 142.8, 126.8, 118.8, 114.0, 44.3, 38.9, 34.6, 31.5, 30.5, 27.3. HRMS (ES): calc. for $C_{19}H_{24}NOF_3$ [MH$^+$], 339.1805. Found, 339.1806 [MH$^+$]. UV $\lambda_{max}$ 337 nm, $\epsilon$ 42723 M$^{-1}$ cm$^{-1}$.

Example 118—Preparation of 2,2,2-trifluoro-1-(1-(4-methoxyphenyl)-4,4-dimethyl-1,4,5,6-tetrahydro-pyridin-3-yl)ethanone, 195

Prepared according to the procedure above for the preparation of 1-(1-(4-(tert-butyl)phenyl)-4,4-dimethyl-1,4,5,6-tetrahydropyridin-3-yl)-2,2,2-trifluoroethanone, 194, as a cream solid in 59% yield. m.pt. 64-65° C.

$\delta_H$ (400 MHz) 7.71 (s, 1H), 7.04 (d, J 9.1, 2H), 6.93 (d, J 9.0, 2H), 3.80 (s, 3H), 3.65 (t, J 5.8, 2H), 1.81 (t, J 5.7, 2H), 1.34 (s, 6H). $\delta_C$ (100 MHz) 175.6, 157.5, 148.2, 148.1, 139.0, 121.0, 115.0, 55.8, 44.8, 33.9, 30.4, 27.3. HRMS (ES): calc. for $C_{16}H_{19}NO_2F_3$ [MH$^+$], 314.1362. Found, 314.1361 [MH$^+$]. UV $\lambda_{max}$ 339 nm, $\delta$ 24235 M$^{-1}$ cm$^{-1}$.

Example 119—Preparation of 1-(1-(4-(dimethyl-amino)phenyl)-4,4-dimethyl-1,4,5,6-tetrahydropyri-din-3-yl)-2,2,2-trifluoroethanone, 196

Prepared according to the procedure above for the preparation of 1-(1-(4-(tert-butyl)phenyl)-4,4-dimethyl-1,4,5,6-tetrahydropyridin-3-yl)-2,2,2-trifluoroethanone, 194, as a yellow solid in 71% yield. m.pt. 72-73° C.

$\delta_H$ (400 MHz) 7.70 (s, 1H), 7.02 (d, J 9.0, 2H), 6.77 (br s, 2H), 3.63 (t, J 5.7, 2H), 2.96 (s, 6H), 1.80 (t, J 5.7, 2H), 1.33 (s, 6H). $\delta_C$ (100 MHz) 176.8, 148.8, 148.4, 135.5, 121.0, 113.3, 112.7, 45.0, 40.9, 38.9, 30.4, 27.3. HRMS (ES): calc. for $C_{17}H_{21}N_2OF_3$ [M$^+$], 326.1600. Found, 326.1602 [M$^+$]. UV $\lambda_{max}$ 354 nm, $\epsilon$ 32744 M$^{-1}$ cm$^{-1}$.

Example 120—Preparation of 1-(4,4-dimethyl-1-(p-tolyl)-1,4,5,6-tetrahydropyridin-3-yl)-2,2,2-trifluoroethanone, 197

Prepared according to the procedure above for the preparation of 1-(1-(4-(tert-butyl)phenyl)-4,4-dimethyl-1,4,5,6-tetrahydropyridin-3-yl)-2,2,2-trifluoroethanone, 194, as a pale yellow solid in 50% yield. m.pt. 105-106° C.

$\delta_H$ (400 MHz) 7.81 (s, 1H), 7.22 (d, J 8.6, 2H), 7.05 (d, J 8.7, 2H), 3.69 (t, J 5.7, 2H), 2.37 (s, 3H), 1.85 (t, J 5.7, 2H), 1.37 (s, 6H). $\delta_C$ (100 MHz) 176.4, 147.2, 142.5, 134.8, 129.9, 118.9, 113.4, 43.8, 38.3, 29.9, 26.7, 20.4. HRMS (ES): calc. for $C_{16}H_{13}NOF_3$ [M$^+$], 297.1335. Found, 297.1335 [M$^+$]. UV $\lambda_{max}$ 337 nm, $\epsilon$ 43513 M$^{-1}$ cm$^{-1}$.

Example 121—Preparation of 1-(4,4-dimethyl-1-(naphthalen-1-yl)-1,4,5,6-tetrahydropyridine-3-yl)-2,2,2-trifluoroethanone, 198

Prepared according to the procedure above for the preparation of 1-(1-(4-(tert-butyl)phenyl)-4,4-dimethyl-1,4,5,6-tetrahydropyridin-3-yl)-2,2,2-trifluoroethanone, 194, as an off-white solid in 46% yield. m.pt. 113-114° C.

$\delta_H$ (400 MHz) 7.94-7.79 (m, 3H), 7.61 (s, 1H), 7.60-7.47 (m, 3H), 7.33 (d, J 8.4, 1H), 3.71 (t, J 5.7, 2H), 1.96 (br s, 2H), 1.44 (s, 6H). $\delta_C$ (100 MHz) 177.0, 151.7, 151.6, 142.6, 134.9, 129.0, 128.6, 127.6, 127.1, 125.8, 123.0, 122.2, 119.3, 116.4, 112.5, 47.4, 39.3, 30.6, 27.5. HRMS (ES): calc. for $C_{19}H_{19}NOF_3$ [MH$^+$], 334.1413. Found, 334.1409 [MH$^+$]. UV $\lambda_{max}$ 325 nm, $\epsilon$ 32790 M$^{-1}$ cm$^{-1}$.

Example 122—Preparation of 1-(4,4-dimethyl-1-(p-tolyl)-1,4-dihydropyridin-3-yl)-2,2,2-trifluoroethanone, 199

Prepared according to the procedure above for the preparation of 1-(1-(4-(tert-butyl)phenyl)-4,4-dimethyl-1,4,5,6-tetrahydropyridin-3-yl)-2,22-trifluoroethanone, 194, as a yellow solid in 93% yield. m.pt. 90° C.

$\delta_H$ (400 MHz) 7.42 (s, 1H), 7.20 (d, J 9.1, 1H), 7.04 (d, J 8.9, 2H), 6.11 (d, J 8.1, 1H), 4.82 (d, J 8.1, 1H), 2.34 (s, 3H), 1.48 (s, 6H). $\delta_C$ (100 MHz) 178.2, 144.3, 141.1, 136.6, 130.6, 122.8, 121.3-120.5, 119.1, 118.9, 113.3, 32.9, 30.5, 30.3, 27.3, 21.0. HRMS (ES): calc. for $C_{16}H_{17}NOF_3$[MH$^+$], 296.1257. Found, 296.1257 [MH$^+$]. UV $\lambda_{max}$ 388 nm, $\epsilon$ 14911 M$^{-1}$ cm$^{-1}$.

Example 123—Preparation of 1-(5-(4,4-dimethyl-pyridin-1(4H)-yl)-1,3-dimethyl-1H-pyrazol-4-yl)-2,2,2-trifluoroethan one, 200 and 1-(1,3-dimethyl-1H-pyrazol-5-yl)-4,4-dimethyl-1,4-dihydropyridine, 152

1-(5-(4,4-dimethylpyridin-1(4H)-yl)-1,3-dimethyl-1H-pyrazol-4-yl)-2,2,2-trifluoroethanone, 200 was prepared according to the procedure above for the preparation of 1-(1-(4-(tert-butyl)phenyl)-4,4-dimethyl-1,4,5,6-tetrahydro-pyridin-3-yl)-2,2,2-trifluoroethanone, 194, as a pale yellow solid in 39% yield.

$\delta_H$ (400 MHz) 5.90 (d, J 6.6, 2H), 5.77 (s, 1H), 4.56 (d, J 8.0, 2H), 3.72 (s, 3H), 2.25 (s, 3H), 1.13 (s, 6H). UV $\lambda_{max}$ 253 nm, $\epsilon$ 10016 M$^{-1}$ cm$^{-1}$.

Also isolated was 1-(1,3-dimethyl-1H-pyrazol-5-yl)-4,4-dimethyl-1,4-dihydropyridine, 152, as a cream solid in 22% yield.

$\delta_H$ (400 MHz) 5.74 (d, J 7.9, 2H), 4.63 (d, J 8.2, 2H), 3.72 (s, 3H), 2.45 (s, 3H), 1.16 (s, 6H). UV $\lambda_{max}$ 253 nm, $\epsilon$ 11371 M$^{-1}$ cm$^{-1}$.

Example 124—Preparation of 1-(1-(4-(tert-butyl) phenyl)-4,4-dimethyl-1,4,5,6-tetrahydropyridine-3-yl)-2,2-diphenylethanone, 204

A solution of 2,2-diphenylacetic acid (0.23 g, 1.09 mmol) in DCM (2 mL) was treated with trifluoroacetic anhydride (0.14 mL, 0.99 mmol) and stirred at room temperature for 20 minutes. The solution was then added dropwsise to a solution of 1-(4-(tert-butyl)phenyl)-4,4-dimethyl-1,2,3,4-tetra-hydropyridine, 148h (0.12 g, 0.49 mmol) and triethylamine (0.24 mL, 1.73 mmol) in DCM (5 mL) and the mixture was then stirred at room temperature for 18 hours. The mixture was then diluted with water (10 mL) and DCM (10 mL) and the organic phase separated, washed with sodium carbonate solution (10% w/w, 10 mL) and dried with magnesium sulfate. Evaporation in-vacuo gave the crude material as a yellow oil which was purified by column chromatography over silica gel, eluting with 0-5% ethyl acetate:petroleum ether. Evaporation of the eluents gave the title compound as a pale yellow gum (0.15 g, 70%).

δ$_H$ (400 MHz) 7.76 (s, 1H), 7.32-7.18 (m, 12H), 6.78 (d, J 6.7, 2H), 5.57 (s, 1H), 3.54 (t, J 5.8, 2H), 1.70 (t, J 5.8, 2H), 1.32 (s, 6H), 1.30 (s, 9H). δ$_C$ (100 MHz) 194.4, 146.6, 143.7, 143.4, 141.4, 129.3, 128.6, 126.6, 126.5, 119.9, 117.6. HRMS (ES): calc. for $C_{31}H_{36}NO$ [MH$^+$], 438.2791. Found, 438.2792 [MH$^+$]. UV λ$_{max}$ 337 nm, ε 17793 M$^{-1}$ cm$^{-1}$.

Example 125—Preparation of (1-(4-(tert-butyl)phenyl)-4,4-dimethyl-1,4,5,6-tetrahydropyridin-3-yl)(9H-fluoren-9-yl)methanone, 205 and (1-(4-(tert-butyl)phenyl)-4,4-dimethyl-1,4,5,6-tetrahydropyridin-3-yl)(9H-fluoren-9-ylidene)methyl 9H-fluorene-9-carboxylate, 206

(1-(4-(tert-butyl)phenyl)-4,4-dimethyl-1,4,5,6-tetrahydropyridin-3-yl)(9H-fluoren-9-yl)methanone, 205, was prepared according to the procedure above for the preparation of 1-(1-(4-(tert-butyl)phenyl)-4,4-dimethyl-1,4,5,6-tetrahydropyridine-3-yl)-2,2-diphenylethanone, 204, as a pale yellow gum in 15% yield.

δ$_H$ (400 MHz) 7.79 (d, J 7.6, 2H), 7.53-7.21 (m, 7H), 7.17 (d, J 8.7, 2H), 6.42 (br s, 2H), 5.13 (s, 1H), 3.46 (t, J 5.8, 2H), 1.70 (t, J 5.8, 2H), 1.32 (s, 6H), 1.26 (s, 9H). δ$_C$ (100 MHz) 194.0, 146.2, 144.9, 143.7, 142.7, 140.9, 127.7, 127.5, 126.1, 125.8, 124.9, 120.5, 116.7, 43.1, 39.3, 34.4, 31.5, 30.7, 27.9. HRMS (ES): calc. for $C_{31}H_{34}NO$ [MH$^+$], 436.2635. Found, 436.2635 [MH$^+$]. UV λ$_{max}$ 339 nm, ε 30745 M$^{-1}$ cm$^{-1}$. Also isolated was (1-(4-(tert-butyl)phenyl)-4,4-dimethyl-1,4,5,6-tetrahydropyridin-3-yl)(9H-fluoren-9-ylidene)methyl 9H-fluorene-9-carboxylate, 206 as a bright yellow solid in 48% yield. m.pt. 145° C.

δ$_H$ (400 MHz) 8.08 (d, J 8.0, 2H), 7.93-6.91 (m, 19H), 5.14 (brs, 1H), 3.77-3.60 (m, 2H), 2.07-2.01 (m, 2H), 1.28 (s, 9H), 1.14 (s, 3H), 1.10 (s, 3H). δ$_C$ (100 MHz) 168.3, 151.9, 144.5, 143.5, 141.7, 141.6, 140.0, 139.8, 139.6, 139.3, 138.2, 136.8, 136.3, 134.9, 129.3, 128.5, 1276, 127.5, 127.3, 127.2, 127.1, 126.7, 126.3, 126.2, 126.0, 125.1, 124.5, 123.7, 120.5, 120.2, 120.1, 199.7, 115.6, 110.0, 54.2, 43.0, 38.7, 34.2, 31.7, 31.5, 30.1, 27.6. HRMS (ES): calc. for $C_{45}H_{42}NO_2$ [MH$^+$], 628.3210. Found, 628.3214 [MH$^+$]. UV λ$_{max}$ 407 nm, ε 6635 M$^{-1}$ cm$^{-1}$.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Unless defined otherwise, all technical and scientific terms used herein have the same meaning as would be commonly understood by those of ordinary skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. It is expected that skilled artisans will employ such variations as appropriate and it is considered within the scope and spirit of the present invention for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

ITEMISED LISTING OF EMBODIMENTS

1. A compound of formula I, or a salt thereof:

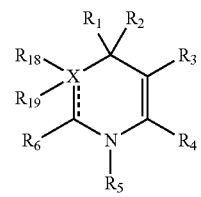

formula I wherein, the dashed line may represent a bond and X, if present, is one or two carbon atoms forming part of the ring structure;

$R_1$ and $R_2$ are independently selected from the group consisting of hydrogen, $C_1$ to $C_{10}$ alkyl, $C_1$ to $C_{10}$ alkenyl and $C_1$ to $C_{10}$ alkoxy, each of which groups may be substituted or unsubstituted;

$R_3$ is selected from the group consisting of hydrogen, hydroxyl, sulfonyl, substituted or unsubstituted $C_1$ to $C_6$ alkyl, substituted or unsubstituted $C_1$ to $C_6$ alkenyl, substituted or unsubstituted $C_1$ to $C_6$ alkoxy and

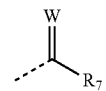

wherein W is sulphur or oxygen and $R_7$ is selected from the group consisting of $C_1$ to $C_{20}$ alkyl, $C_2$ to $C_a$ alkenyl, $C_2$ to $C_{20}$ alkynyl, aryl, heteroaryl, aroyl, $C_2$ to $C_{20}$ alkanone, $C_5$ to $C_7$ cycloalkyl, $C_4$ to $C_7$ cycloalkanone, $C_5$ to $C_7$ cycloalkenyl, $C_2$ to $C_{20}$ alkanoyl, $C_2$ to $C_{20}$ alkanoyloxy, $C_2$ to $C_{20}$ alkoxycarbonyl, $C_2$ to $C_{20}$ carbamoyl, $C_2$ to $C_{20}$ carboxyl, haloalkyl, N-alkyl, N-aryl, N-heterocyclyl, N—SO$_2$—R$_{20}$ and heterocyclic all of which groups may be substituted or unsubstituted and wherein $R_{20}$ is selected from the group consisting of $C_1$ to $C_6$ alkyl and phenyl each of which may be substituted or unsubstituted;

$R_4$ is selected from the group consisting of hydrogen, $C_1$ to $C_{12}$ alkyl, $C_2$ to $C_{12}$ alkenyl, aryl, heteroaryl, $C_5$ to $C_7$ cycloalkyl, $C_5$ to $C_7$ cycloalkenyl, $C_1$ to $C_{12}$ alkanoyl, $C_1$ to $C_{12}$ alkanoyloxy, $C_1$ to $C_{12}$ carboalkoxy and $C_1$ to $C_{12}$ alkanone all of which groups may be substituted or unsubstituted;

$R_5$ is selected from the group consisting of $C_1$ to $C_{12}$ alkyl, $C_2$ to $C_{12}$ alkenyl, $C_2$ to $C_{12}$ alkynyl, aryl, heteroaryl, $C_5$ to $C_9$ cycloalkyl, $C_5$ to $C_7$ cycloalkenyl, $C_2$ to $C_9$ alkanoyl, $C_2$ to $C_9$ alkanoyloxy and carbamoyl all of which groups may be substituted or unsubstituted;

$R_6$ is selected from the group consisting of hydrogen, oxo, substituted or unsubstituted $C_1$ to $C_6$ alkyl, substituted or unsubstituted $C_2$ to $C_6$ alkenyl and substituted or unsubstituted $C_2$ to $C_6$ alkanoyl; and $R_{18}$ and $R_{19}$ are independently selected from the group consisting of hydrogen, $C_1$ to $C_6$ alkyl, $C_1$ to $C_6$ alkenyl and $C_1$ to $C_6$ alkoxy, each of which groups may be substituted or unsubstituted, with the proviso that when $R_5$ is alkyl or cycloalkyl and the dashed line is not a bond and $R_4$ is hydrogen then $R_7$ is not an unsubstituted alkyl chain, an ester or an ether; and when $R_5$ is unsubstituted benzyl then $R_7$ is not hexyl.

2. The compound of item 1 wherein the compound is a compound of formula IIa or IIb:

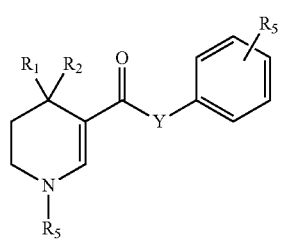

formula IIa

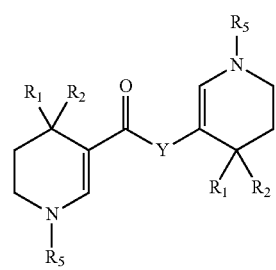

formula IIb wherein $R_1$, $R_2$ and $R_6$ are as described in item 1;

Y, when present, may be nitrogen, N-alkyl $C_1$ to $C_{18}$ alkyl optionally substituted with oxo, hydroxyl, alkoxy and halo and may be oxygen linked to the ring;

$R_8$, when present, may be selected from the group consisting of $C_1$ to $C_6$ alkyl, substituted or unsubstituted, aryl, alkoxy, halo and amino.

3. The compound of item 1 or item 2 wherein the compound is a compound of formula III:

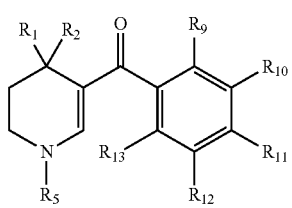

formula III wherein, $R_1$, $R_2$ and $R_5$ are as described in item 1;

$R_9$, $R_{10}$, $R_{12}$ and $R_{13}$ may be independently selected from the group consisting of hydrogen, $C_1$ to $C_6$ alkyl substituted or unsubstituted, aryl, aroyl such as benzoyl, alkoxy, halo, amino and a further substituted cyclic enamine linked to the benzene ring of formula III by a carbonyl moiety; and $R_{10}$ and $R_{11}$ may be joined to form a cyclic aryl or heterocycle.

4. The compound of any one of the preceding items wherein the compound is a compound of formula IV:

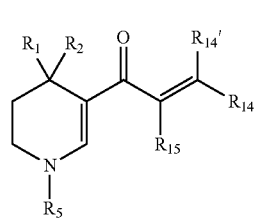

formula IV wherein, $R_1$, $R_2$ and $R_5$ are as described in item 1;

$R_{14}$, $R_{14}'$ and $R_{15}$, when present, may be independently selected from the group consisting of amino, cyano, $C_1$ to $C_6$ alkyl substituted or unsubstituted, $C_1$ to $C_6$ alkenyl substituted or unsubstituted and aryl substituted or unsubstituted.

5. The compound of any one of the preceding items wherein the compound is a compound of formula V:

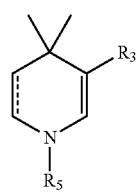

formula V wherein, $R_3$ is as described in item 1;

$R_5$ is aryl substituted or unsubstituted and the dashed line may be a bond.

6. The compound of item 6 wherein the aryl group is substituted with $C_1$ to $C_6$ alkoxy or halo.

7. The compound of any one of the preceding items wherein the compound is a compound of formula VI:

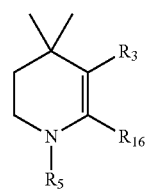

formula VI wherein, $R_3$ and $R_5$ are as described in item 1;

$R_{16}$ may be aryl substituted or unsubstituted, alkenyl substituted or unsubstituted, carboxy substituted or unsubstituted or alkanoyl substituted or unsubstituted.

8. The compound of any one of the preceding items wherein $R_1$ and $R_2$ are independently selected from the group consisting of $C_1$ to $C_6$ alkyl, $C_1$ to $C_6$ alkenyl and $C_1$ to $C_6$ alkoxy, each of which groups may be substituted or unsubstituted.

9. The compound of any one of the preceding items wherein $R_1$ and $R_2$ are independently selected from $C_1$ to $C_4$ alkyl substituted or unsubstituted.

10. The compound of any one of the preceding items wherein $R_1$ and $R_2$ are methyl, ethyl or propyl.

11. The compound of any one of the preceding items wherein $R_3$ is selected from the group consisting of hydrogen, sulfonyl, substituted or unsubstituted $C_1$ to $C_6$ alkyl, substituted or unsubstituted $C_1$ to $C_6$ alkenyl, substituted or unsubstituted $C_1$ to $C_6$ alkoxy, and

wherein W is sulphur or oxygen and $R_7$ is selected from the group consisting of $C_1$ to $C_6$ alkyl, trihaloalkyl, $C_2$ to $C_6$ alkenyl, $C_2$ to $C_6$ alkynyl, aryl, aroyl, $C_2$ to $C_{12}$ alkanone, $C_2$ to $C_9$ alkanoyl, $C_2$ to $C_9$ alkanoyloxy, $C_2$ to $C_9$ alkoxycarbonyl, $C_2$ to $C_6$ carboxyl, $C_1$ to $C_6$ haloalkyl, $C_4$ to $C_7$ cycloalkanone, N—$C_1$ to $C_6$ alkyl, N— $C_5$ to $C_7$ aryl, N— $C_5$ to $C_7$ heterocycyl, N—SO$_2$—R$_{20}$ and $C_5$ or $C_6$ heterocyclic all of which groups may be substituted or unsubstituted and wherein $R_{20}$ is selected from the group consisting of $C_1$ to $C_6$ alkyl and phenyl each of which may be substituted or unsubstituted.

12. The compound of any one of the preceding items wherein $R_3$ is selected from the group consisting of hydrogen, arylsulfonyl and

wherein W is sulphur or oxygen and $R_7$ is selected from the group consisting of $C_1$ to $C_4$ alkyl, trifluoro substituted $C_1$ to $C_4$ alkyl, $C_2$ to $C_6$ alkenyl, phenyl, phenylheterocyclic, alkylbenzoyl, phenyl substituted alkanone, $C_2$ to $C_9$ alkanoyloxy, $C_2$ to $C_9$ alkoxycarbonyl, $C_2$ to $C_4$ carboxyl, $C_5$ or $C_6$ heterocyclic, N— $C_1$ to $C_6$ alkyl, N— $C_6$ aryl, N—SO$_2$—R$_{20}$, POSS substituted alkanoyloxy and POSS substituted carboalkoxy all of which groups may be substituted or unsubstituted and wherein $R_{20}$ is selected from the group consisting of $C_1$ to $C_6$ alkyl and phenyl each of which may be substituted or unsubstituted.

13. The compound of any one of the preceding items wherein $R_3$ is selected from the group consisting of hydrogen, benzenesulfonyl and

wherein W is sulphur or oxygen and $R_7$ is selected from the group consisting of

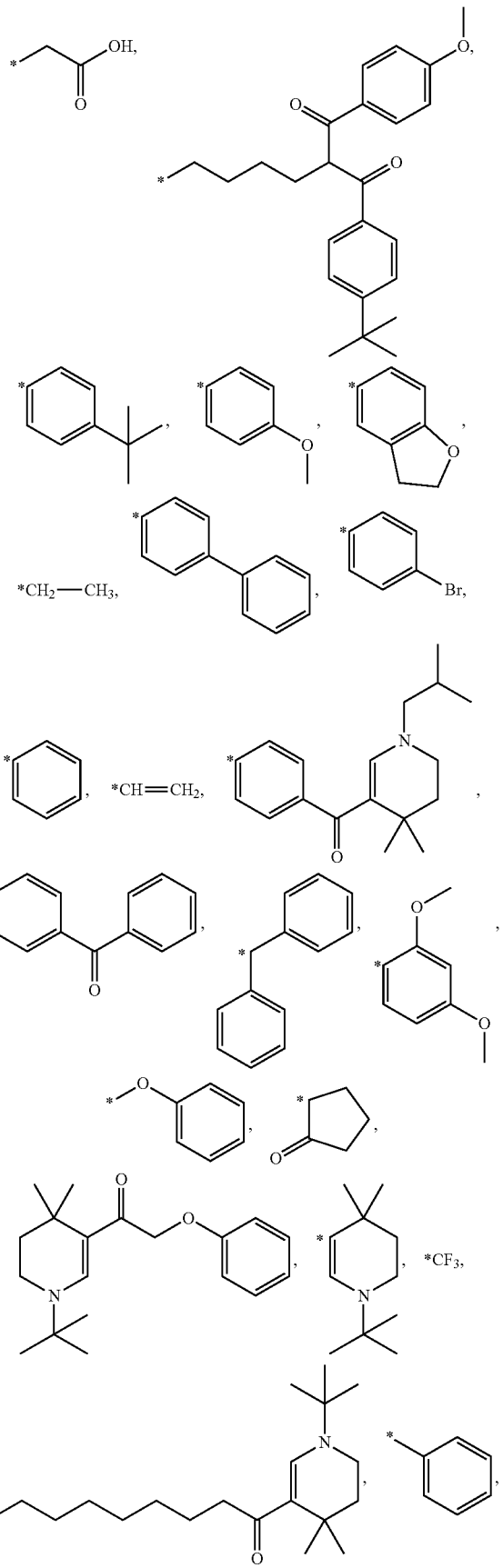

147
-continued
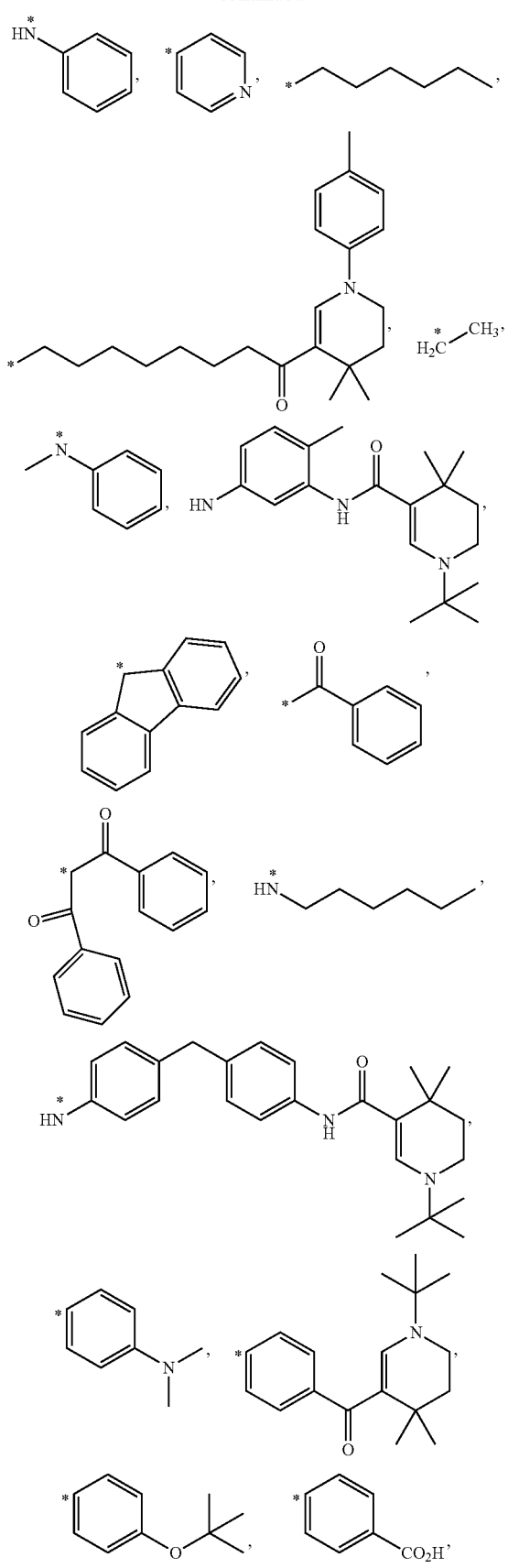
148
-continued
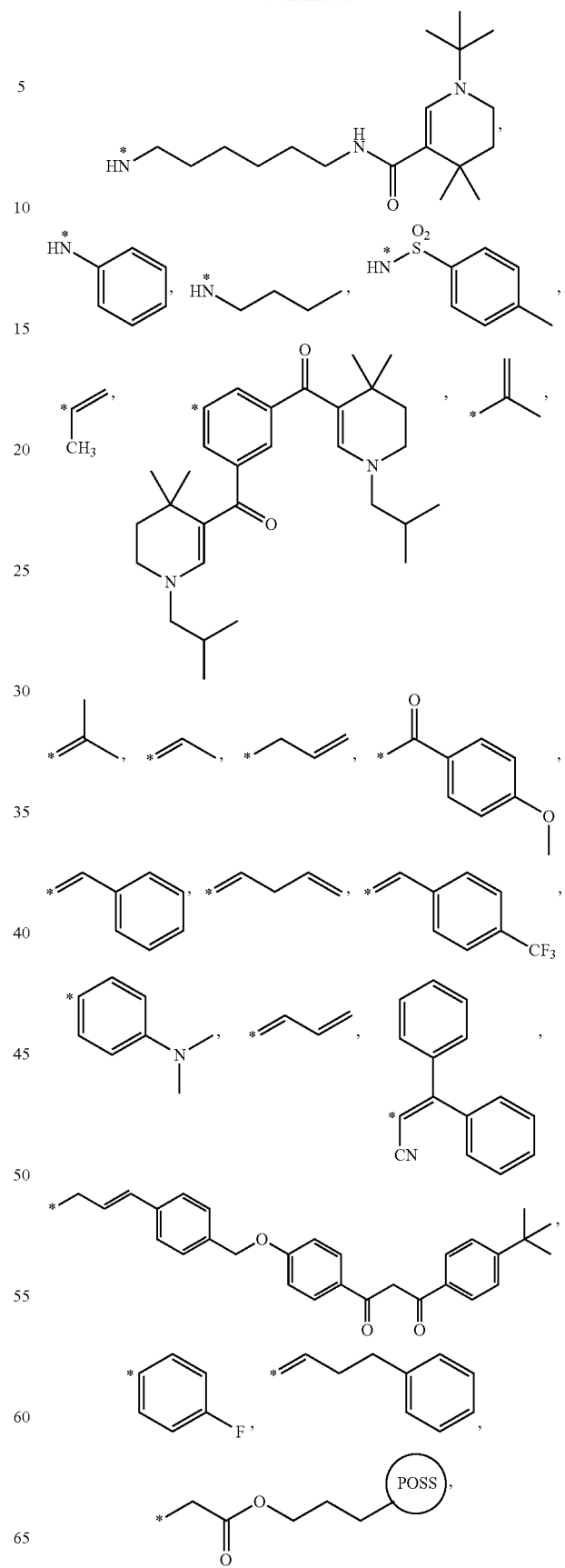

-continued

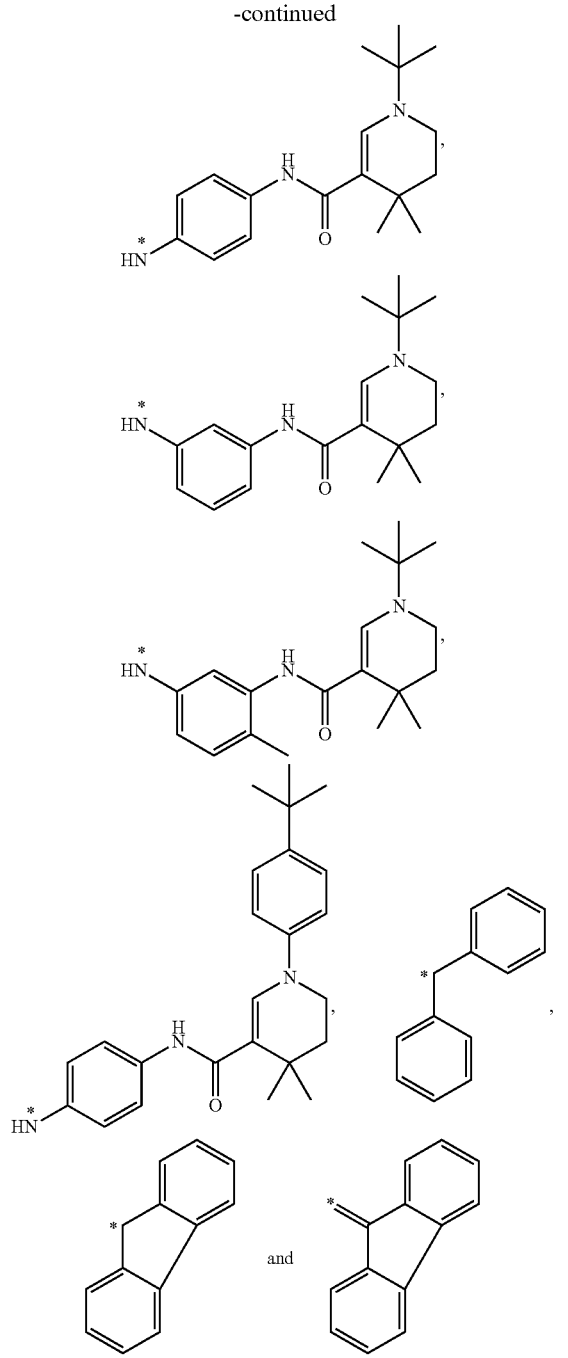

wherein * represents the carbon atom which is attached to the carbonyl carbon.

14. The compound of any one of the preceding items wherein when $R_3$ is $N-SO_2-R_{20}$ then $R_{20}$ is selected from the group consisting of methyl, ethyl, propyl, butyl, phenyl and benzyl each of which may be substituted with of methyl, ethyl and propyl.

15. The compound of any one of the preceding items wherein $R_4$ is selected from the group consisting of hydrogen, $C_1$ to $C_6$ alkyl, $C_2$ to $C_6$ alkenyl, phenyl, heteroaryl, $C_6$ cycloalkyl, $C_1$ to $C_{12}$ alkanoyl, $C_1$ to $C_9$ alkanoyloxy, $C_1$ to $C_9$ carboalkoxy and $C_1$ to $C_6$ alkanone all of which groups may be substituted or unsubstituted.

16. The compound of any one of the preceding items wherein $R_4$ is selected from the group consisting of hydrogen, $C_1$ to $C_6$ alkyl, $C_2$ to $C_6$ alkenyl, phenyl, $C_6$ cycloalkyl, $C_1$ to $C_{12}$ alkanoyl and $C_1$ to $C_{12}$ alkanoyloxy all of which groups may be substituted or unsubstituted.

17. The compound of any one of the preceding items wherein $R_4$ is selected from the group consisting of hydrogen, phenyl, butan-2-one and but-1-ene-2-yl propionate.

18. The compound of any one of the preceding items wherein $R_5$ is selected from the group consisting of $C_1$ to $C_6$ alkyl, $C_2$ to $C_6$ alkenyl, phenyl, naphthyl, $C_6$ cycloalkyl, $C_2$ to $C_6$ alkanoyl and $C_2$ to $C_6$ alkanoyloxy all of which groups may be substituted or unsubstituted.

19. The compound of any one of the preceding items wherein $R_5$ is selected from the group consisting of $C_1$ to $C_6$ alkyl, phenyl, naphtyl and $C_6$ cycloalkyl all of which groups may be substituted or unsubstituted.

20. The compound of any one of the preceding items wherein $R_5$ is selected from the group consisting of

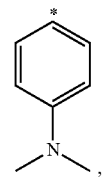

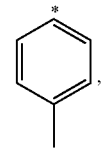

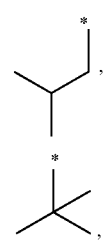

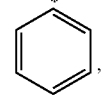

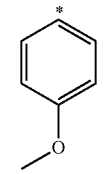

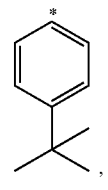

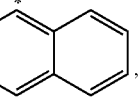

-continued

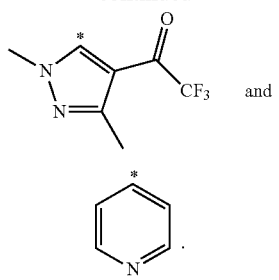 and

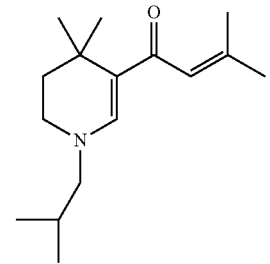

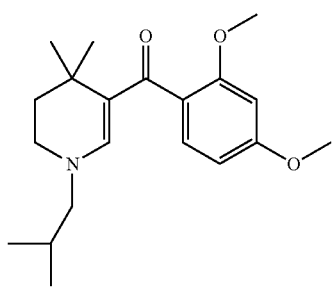

21. The compound of any one of the preceding items wherein $R_6$ is selected from the group consisting of hydrogen, oxo and substituted or unsubstituted $C_1$ to $C_6$ alkyl.

22. The compound of any one of the preceding items wherein $R_6$ is hydrogen or oxo.

23. The compound of any one of the preceding items wherein $R_{18}$ and $R_{19}$ are independently selected from the group consisting of hydrogen and $C_1$ to $C_6$ alkyl, each of which groups may be substituted or unsubstituted.

24. The compound of any one of the preceding items wherein $R_{18}$ and $R_{19}$ are hydrogen.

25. The compound of any one of the preceding items wherein substituted refers to substitution with a group selected from alkyl, alkenyl, aryl, heteroaryl, heterocyclyl, alkynyl, aroyl, alkanone, cycloalkyl, cycloalkanone, cycloalkenyl, alkanoyl, alkanoyloxy, alkoxycarbonyl, carbamoyl, carboxyl, haloalkyl, N-alkyl, N-aryl and N-heterocyclyl.

26. The compound of any one of the preceding items wherein X is one carbon atom.

27. The compound of any one of the preceding items wherein W is oxygen (oxo).

28. The compound of any one of the preceding items wherein the compound is selected from the group consisting of:

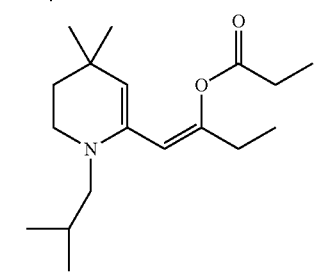

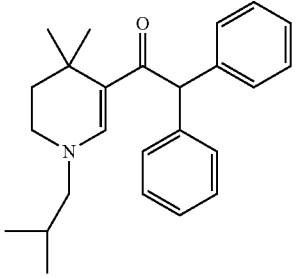 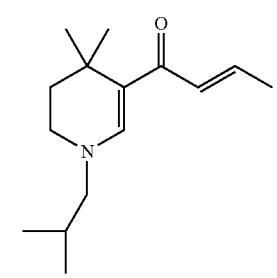

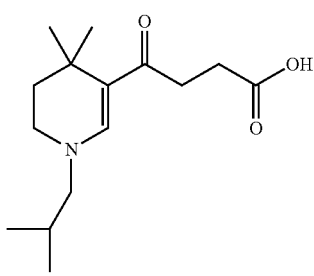 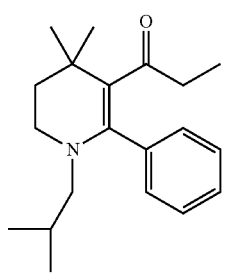 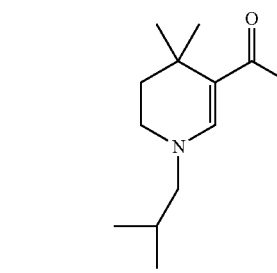

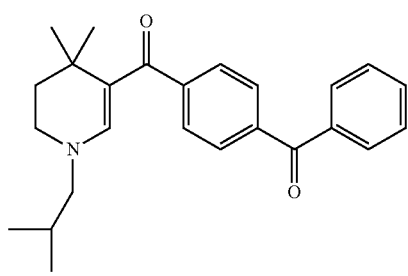 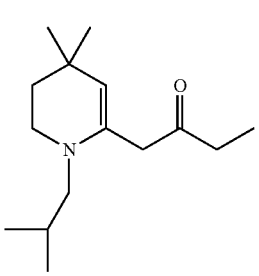 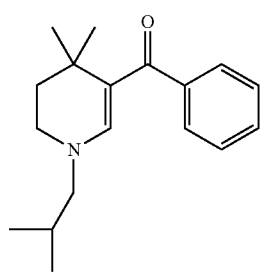

153
-continued
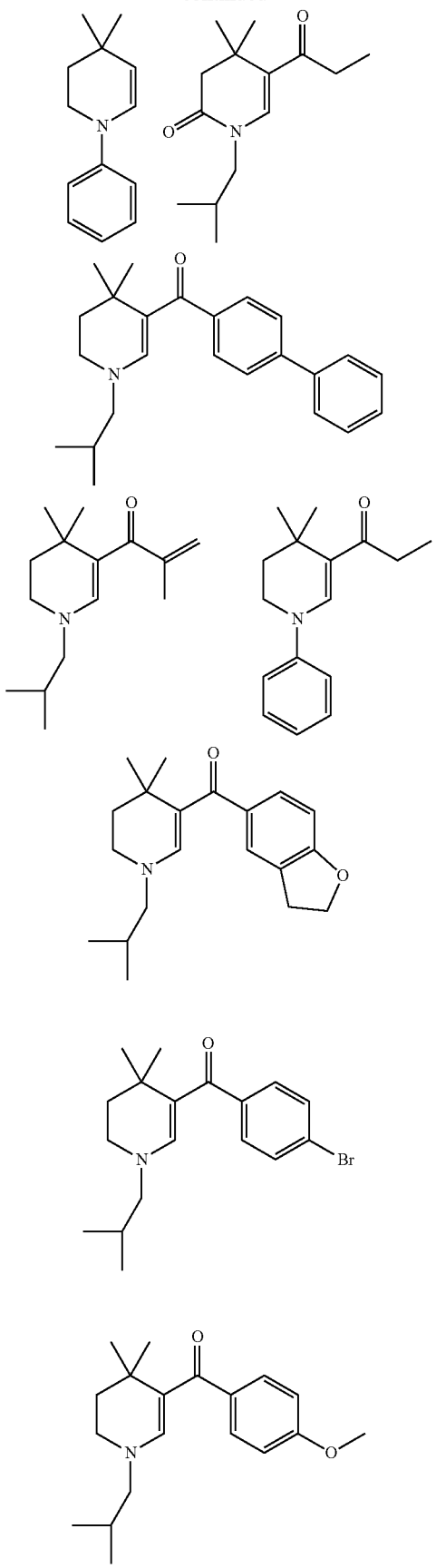
154
-continued
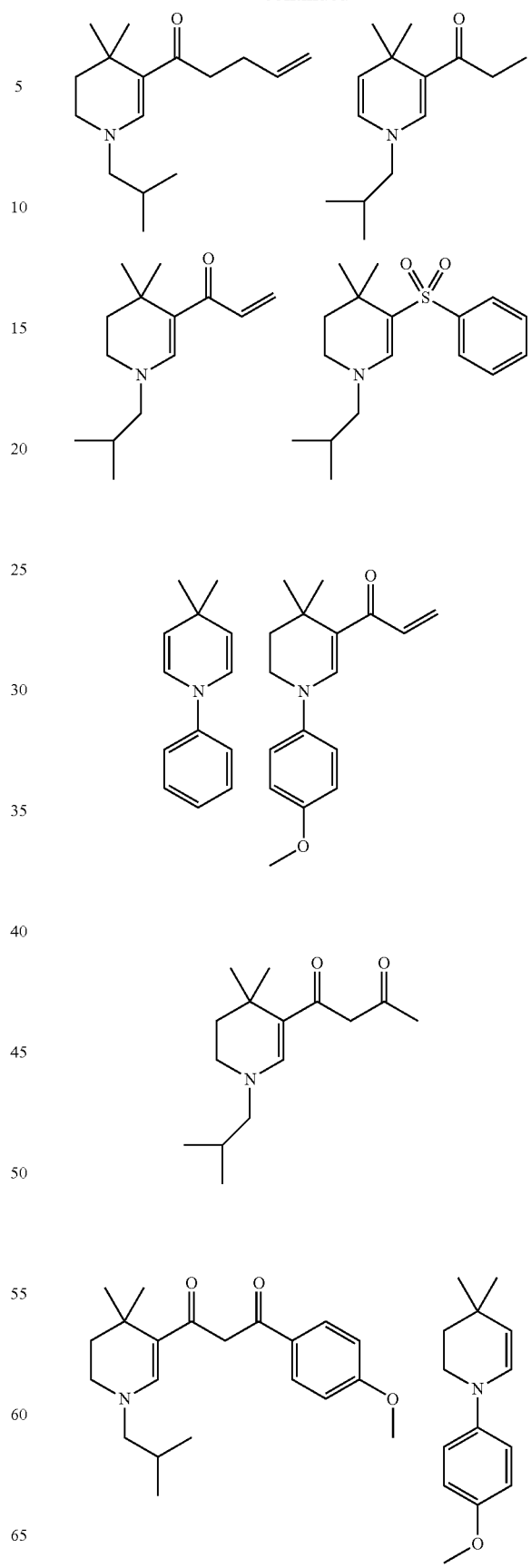

155
-continued
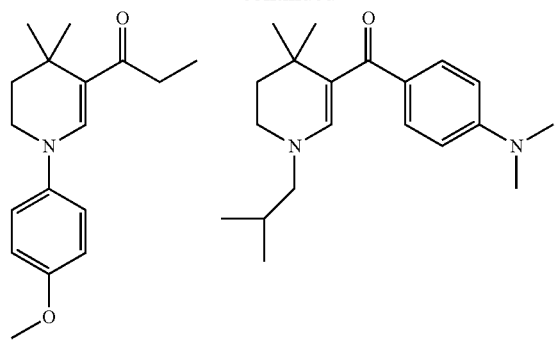
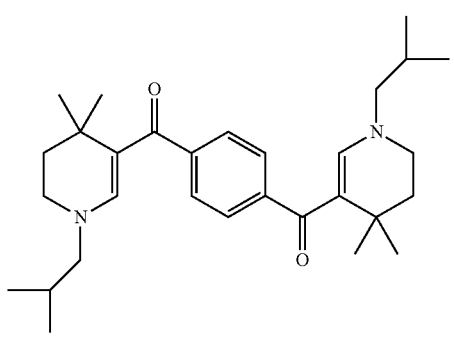
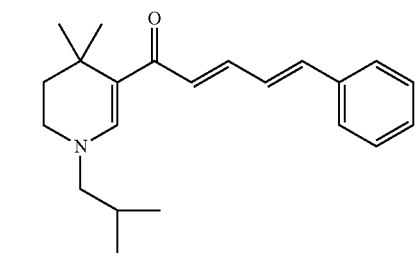
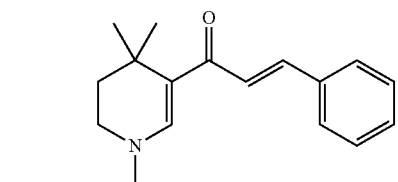
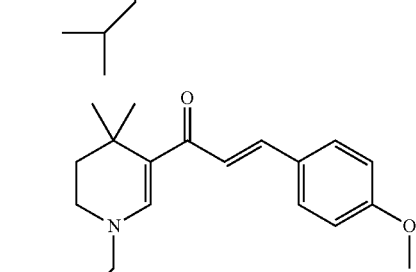
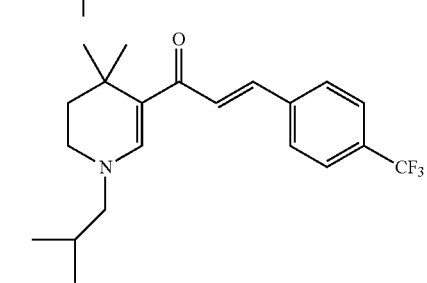
156
-continued
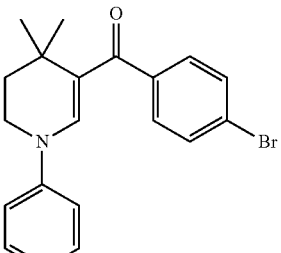
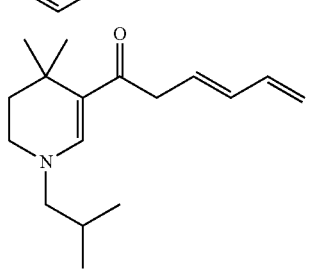
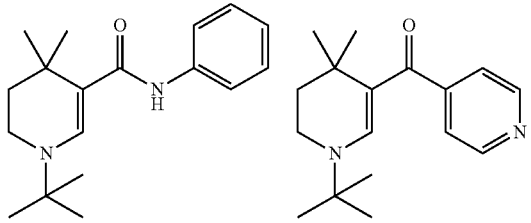
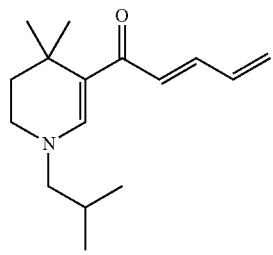
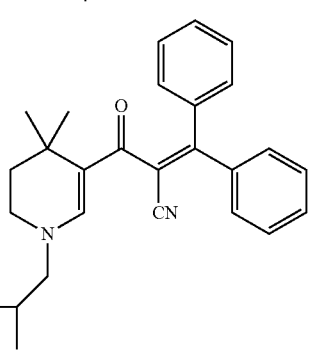
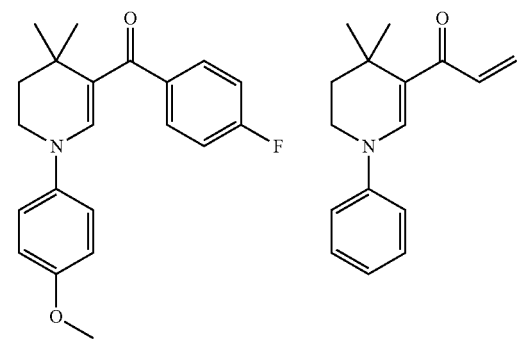

157
-continued
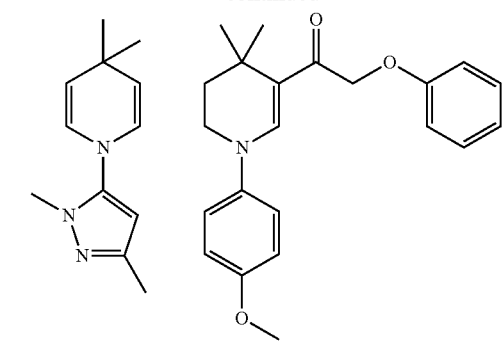
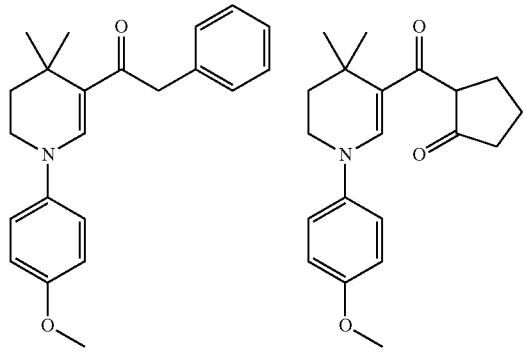
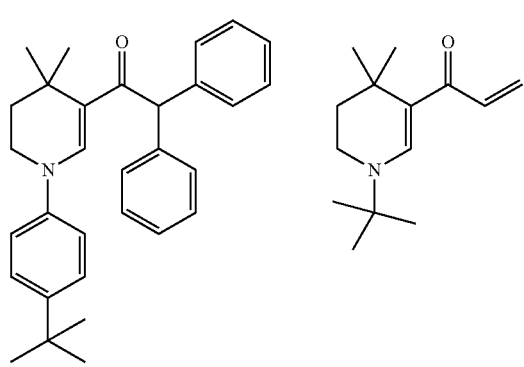
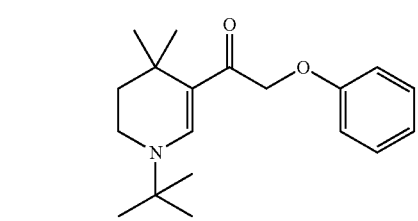
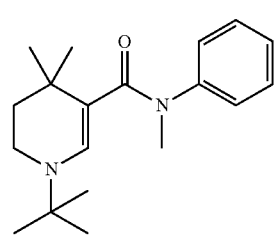
158
-continued
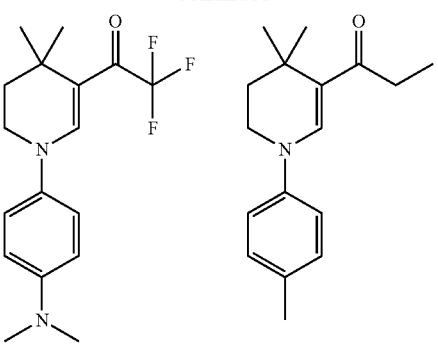
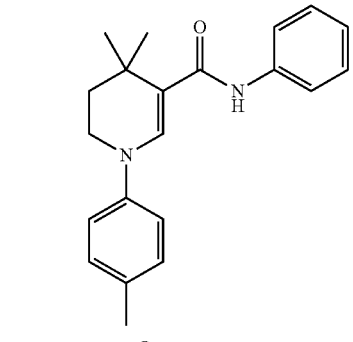
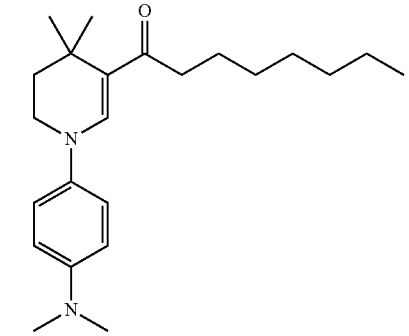
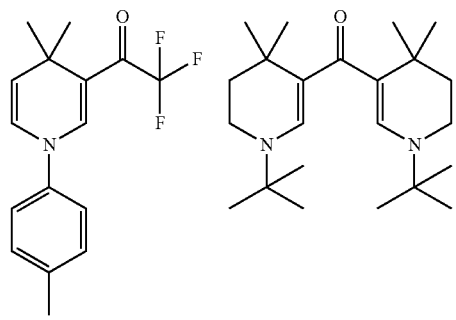
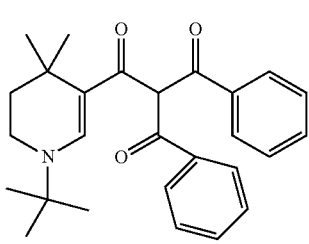

159
-continued
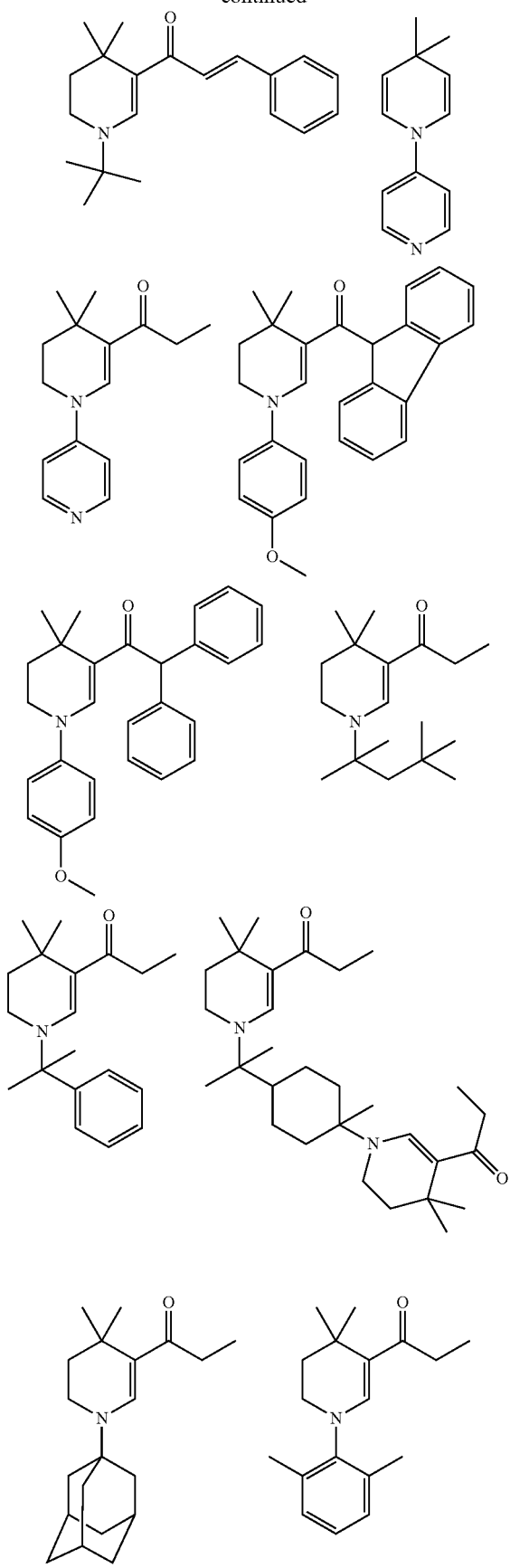
160
-continued
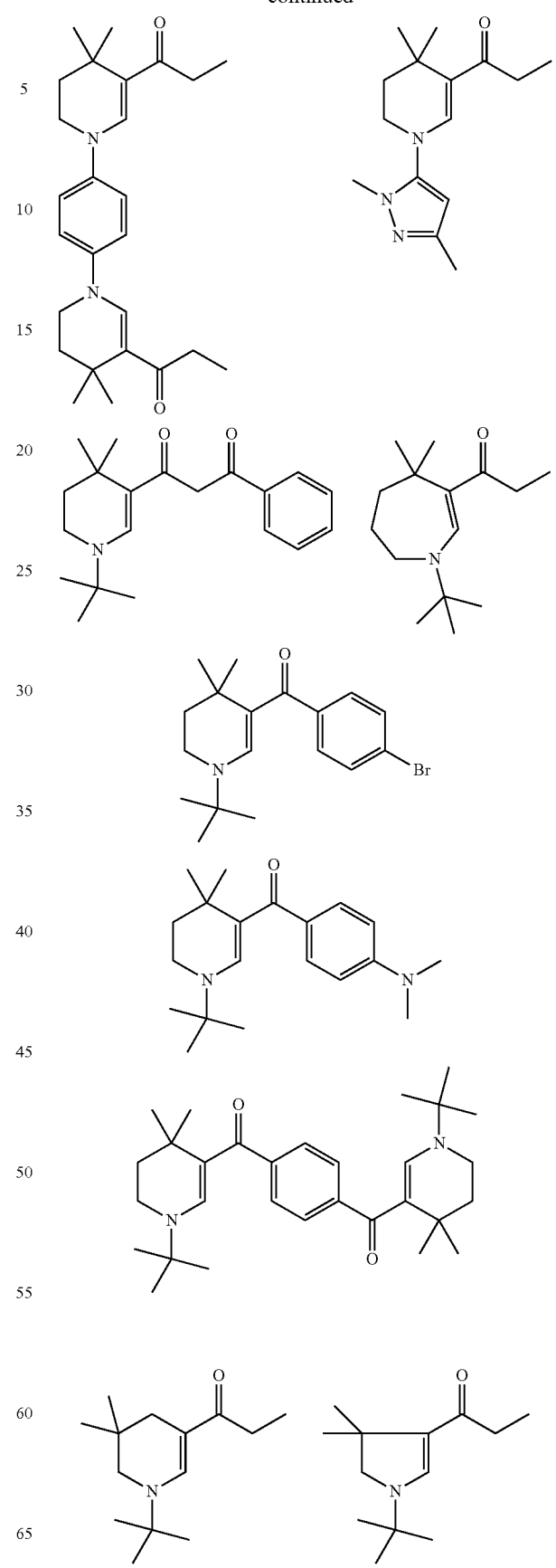

161
-continued
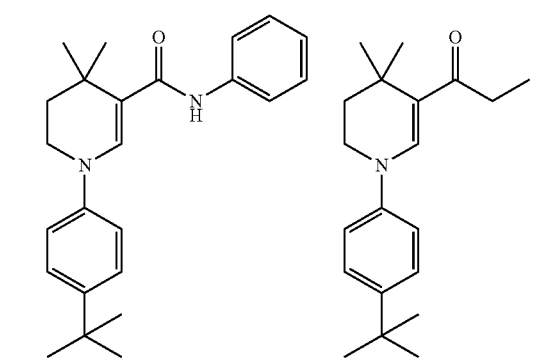
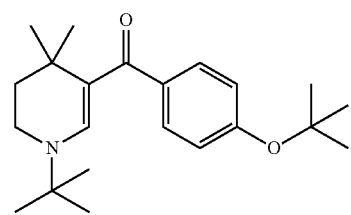
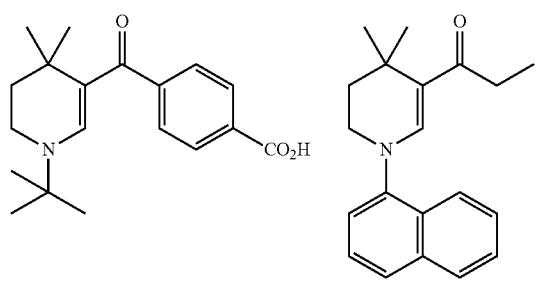
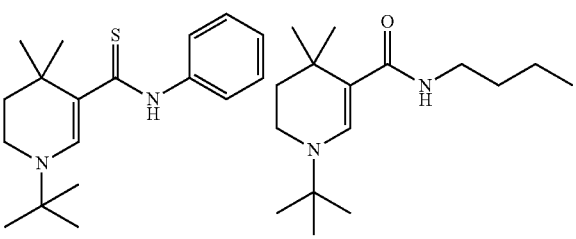
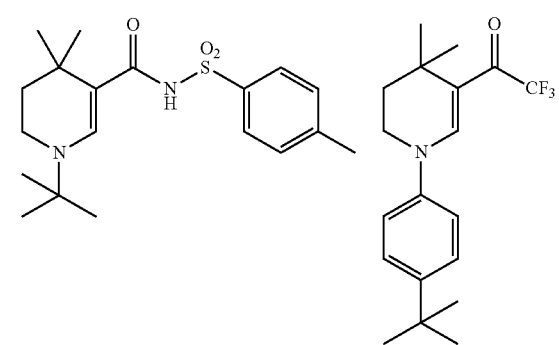
162
-continued
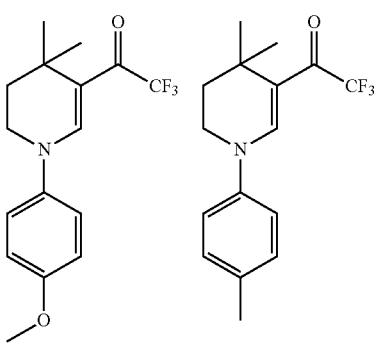
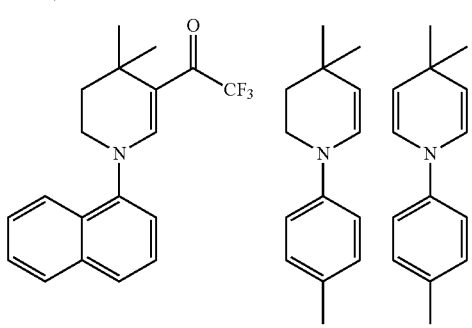
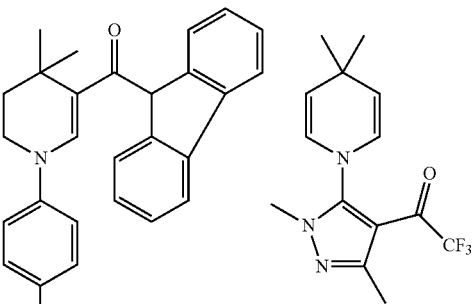
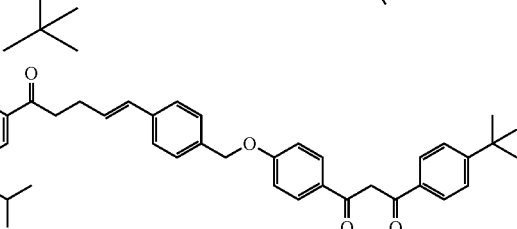
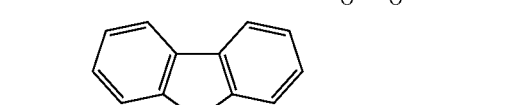
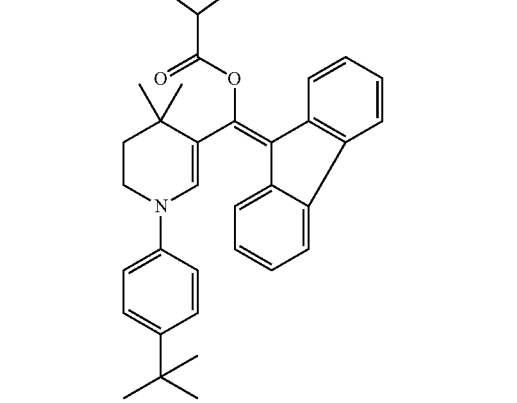

163
-continued
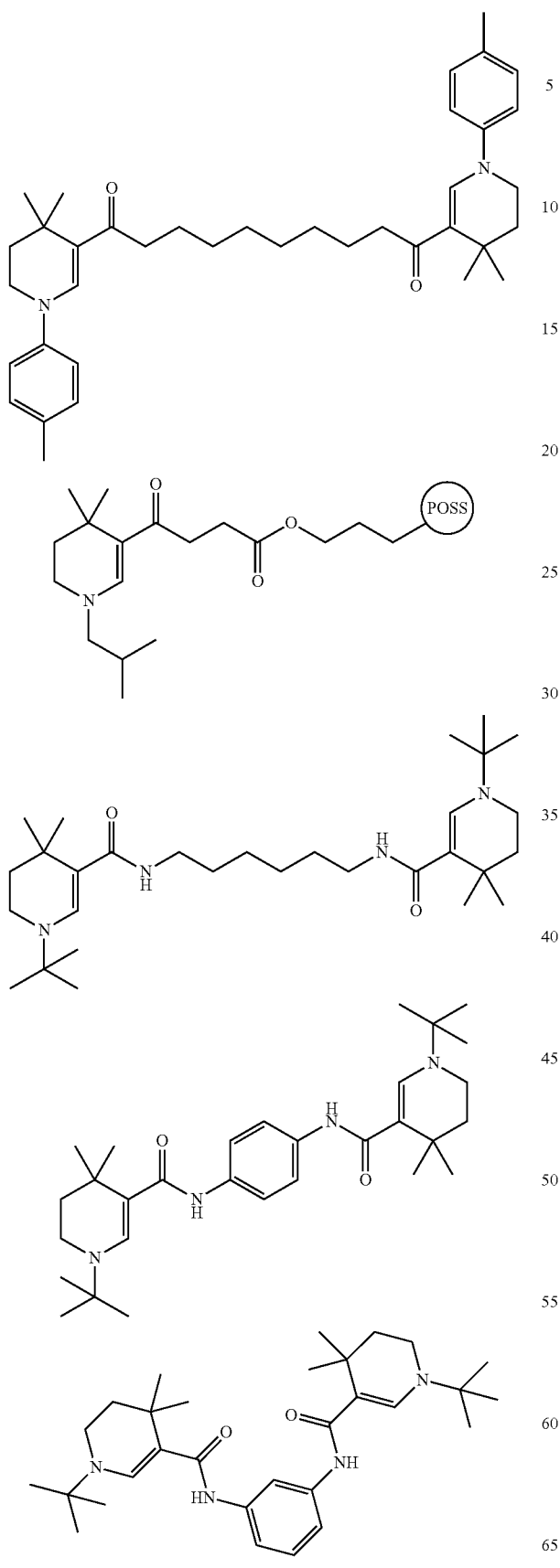
164
-continued
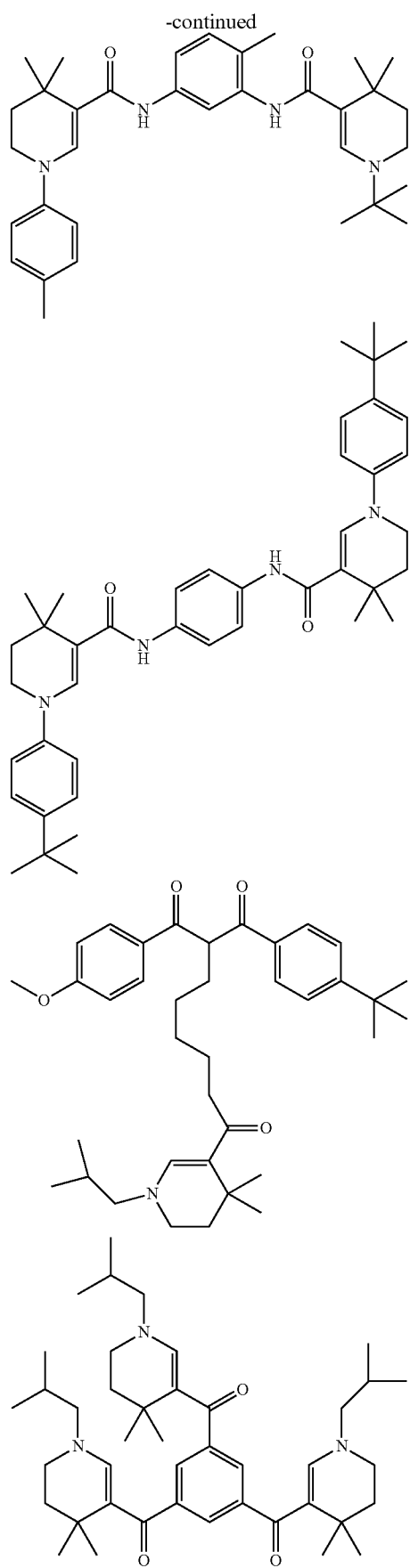

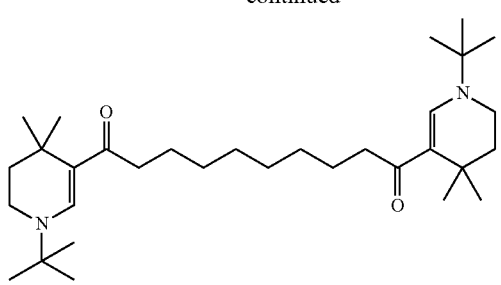
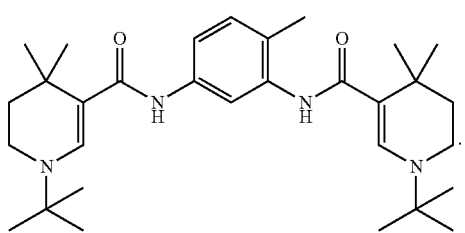
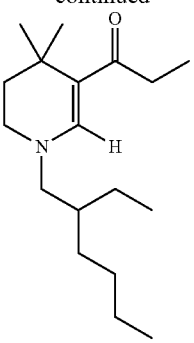
and
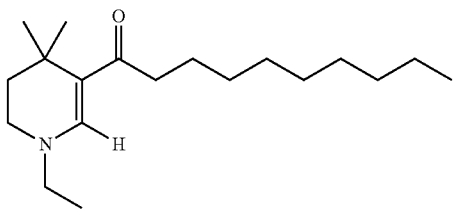
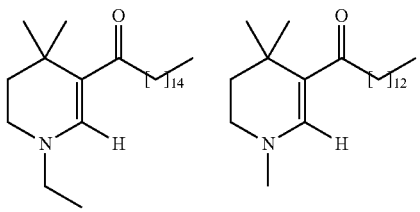
29. The compound of any one of the preceding items wherein the compound is not a compound selected from the group consisting of:
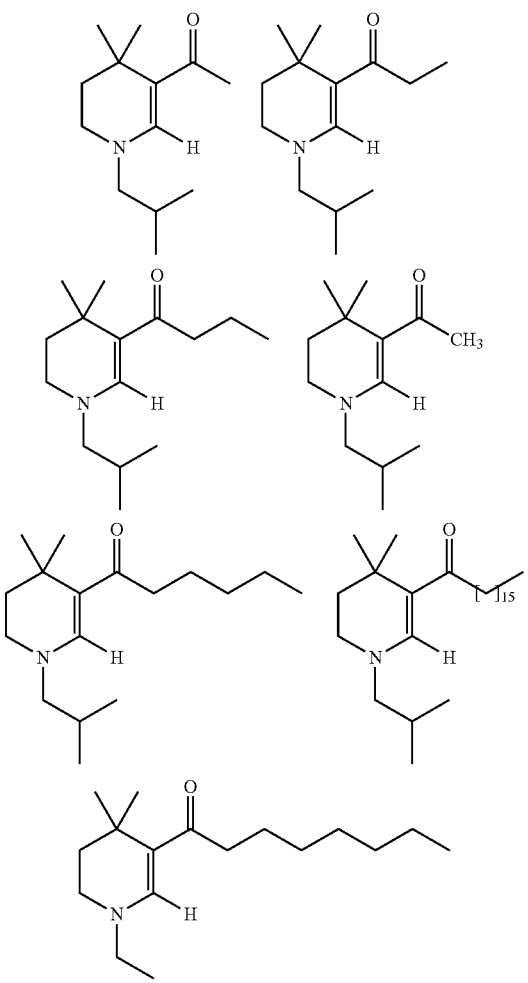
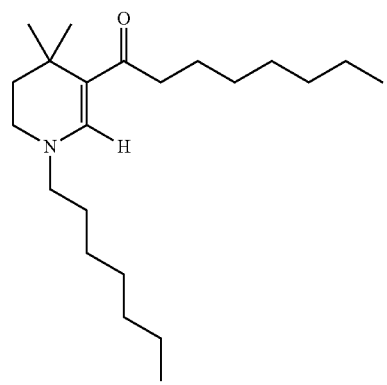
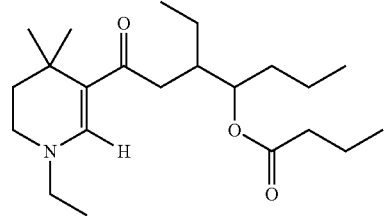
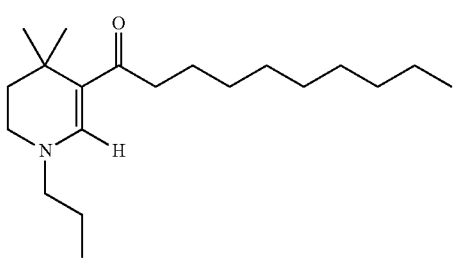

167
-continued
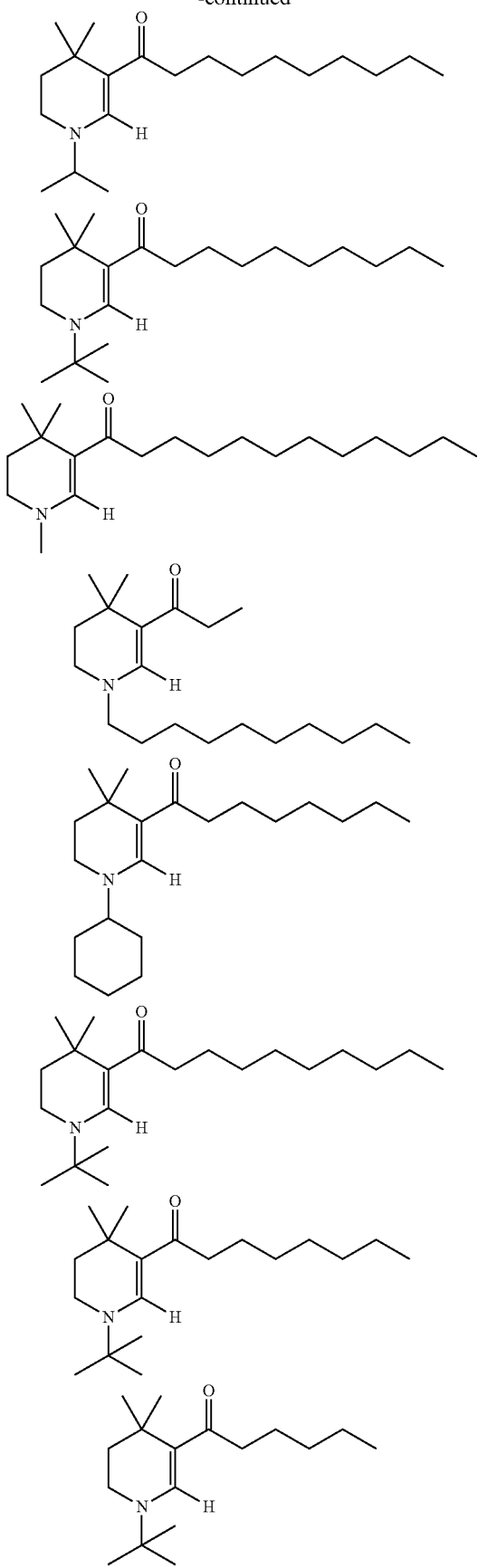
168
-continued
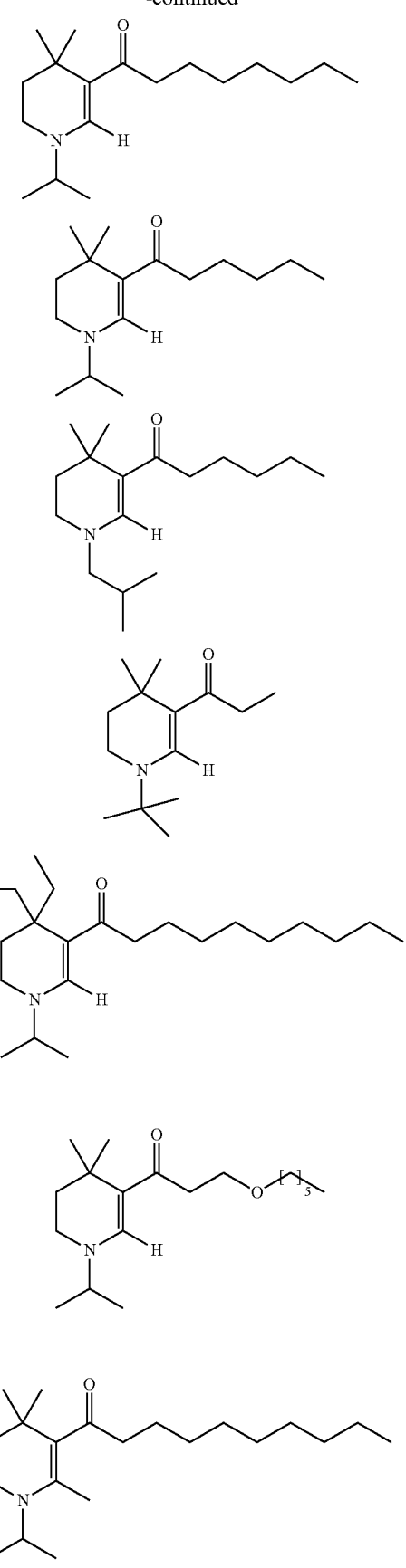

-continued

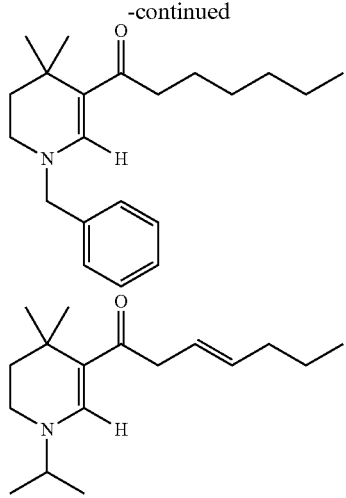

30. A composition comprising a compound of any one of item 1 to item 29, or a salt thereof, and a suitable carrier.
31. The composition of item 30 wherein composition is selected from the group consisting of a sunscreen composition, a coating composition and a glass or polymeric film-forming composition.
32. Use of a compound of any one of item 1 to item 29, or a salt thereof, as a UV absorbing compound.
33. The use of item 32 wherein the use is as a component of a sunscreen composition, a coating composition, a glass composition or a polymeric film-forming composition.
34. The use of item 32 in the formation of a UV protective ophthalmic lens.
35. A method of protecting a surface or tissue from UV rays including the step of applying a compound of any one of item 1 to item 29, or a salt thereof, to the surface or tissue.
36. The method of item 35 wherein the surface is a surface of a fabric, clothing material, plastic, timber, masonry and glass.
37. The method of item 35 wherein the tissue is the skin of a mammal.

The invention claimed is:
1. A compound of formula I, or a salt thereof:

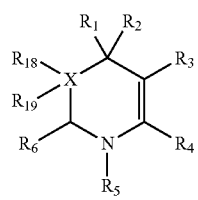

formula I wherein X is one carbon,
$R_1$ and $R_2$ are methyl, ethyl or propyl;
$R_3$ is

wherein W is oxygen and $R_7$ is selected from the group consisting of

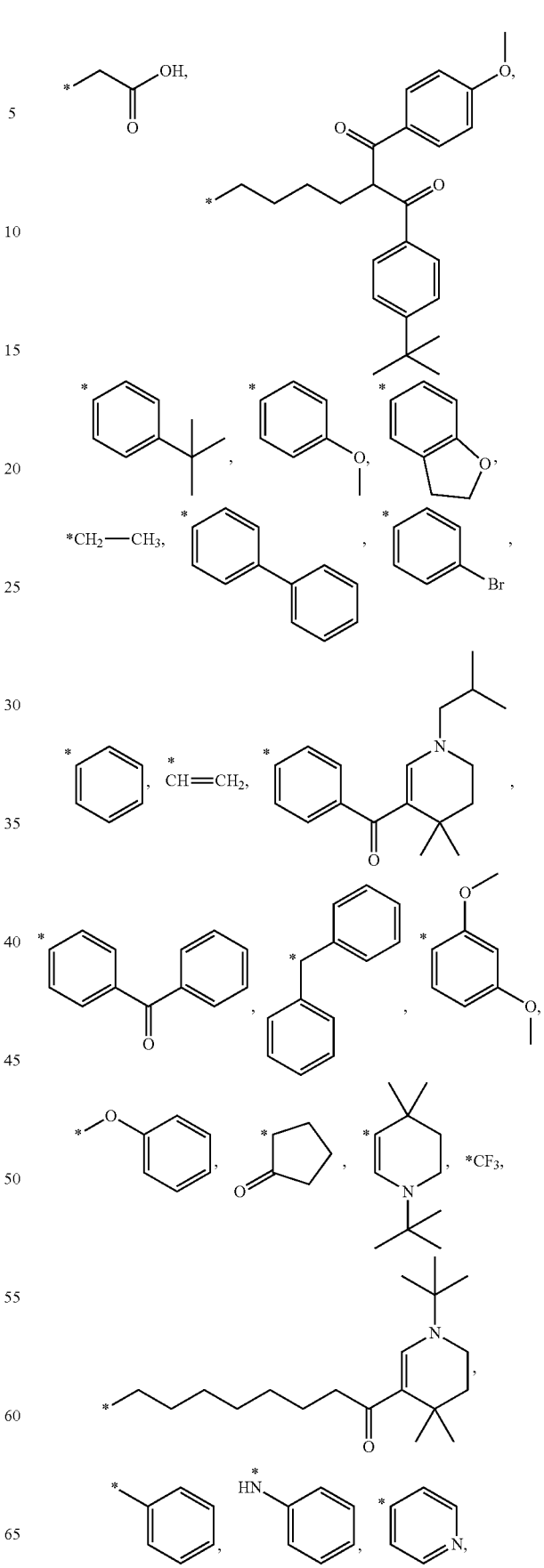

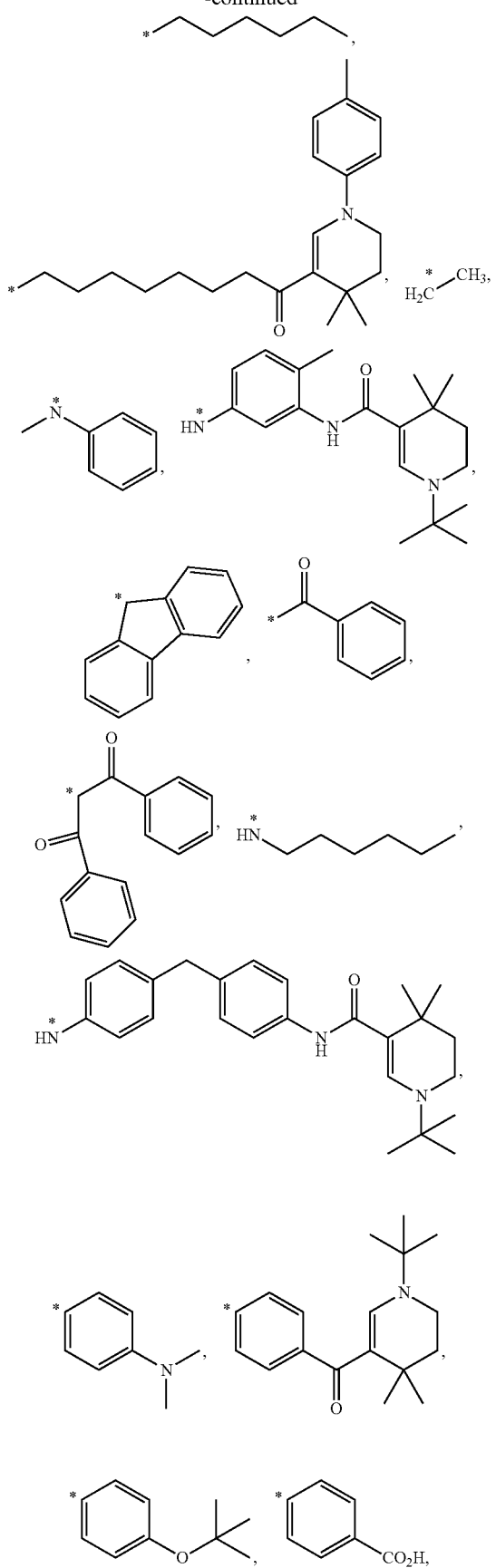
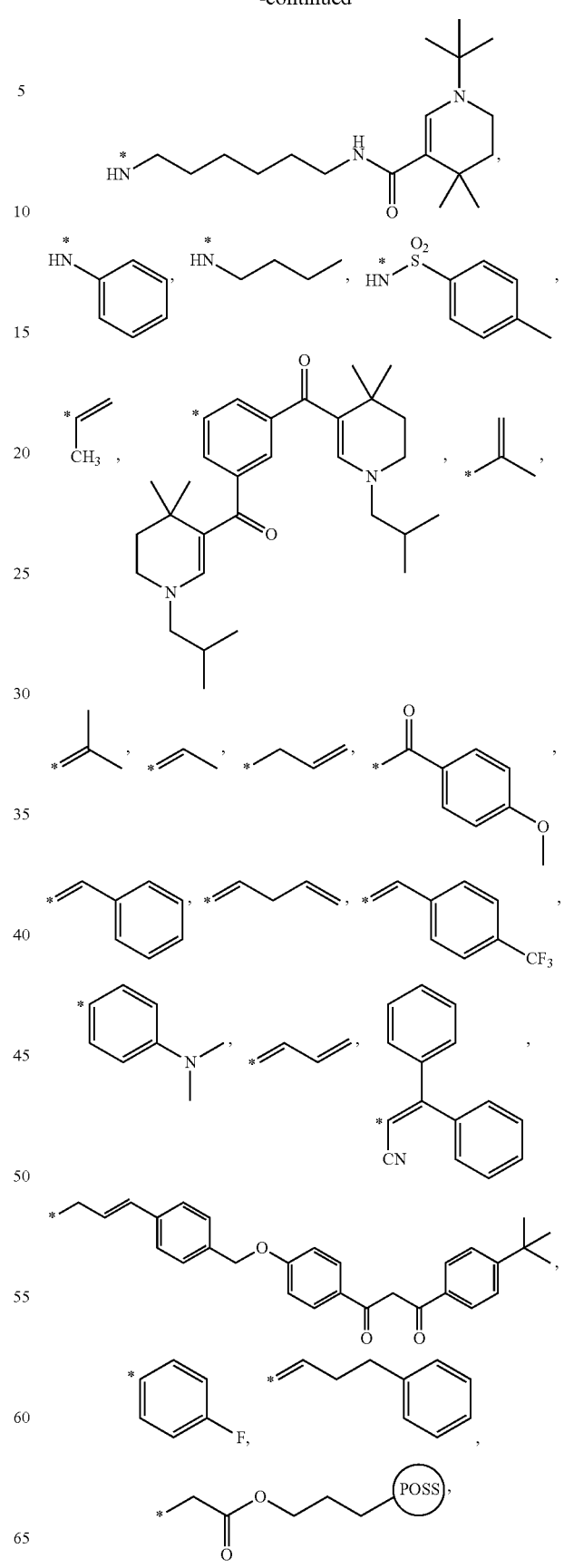

-continued

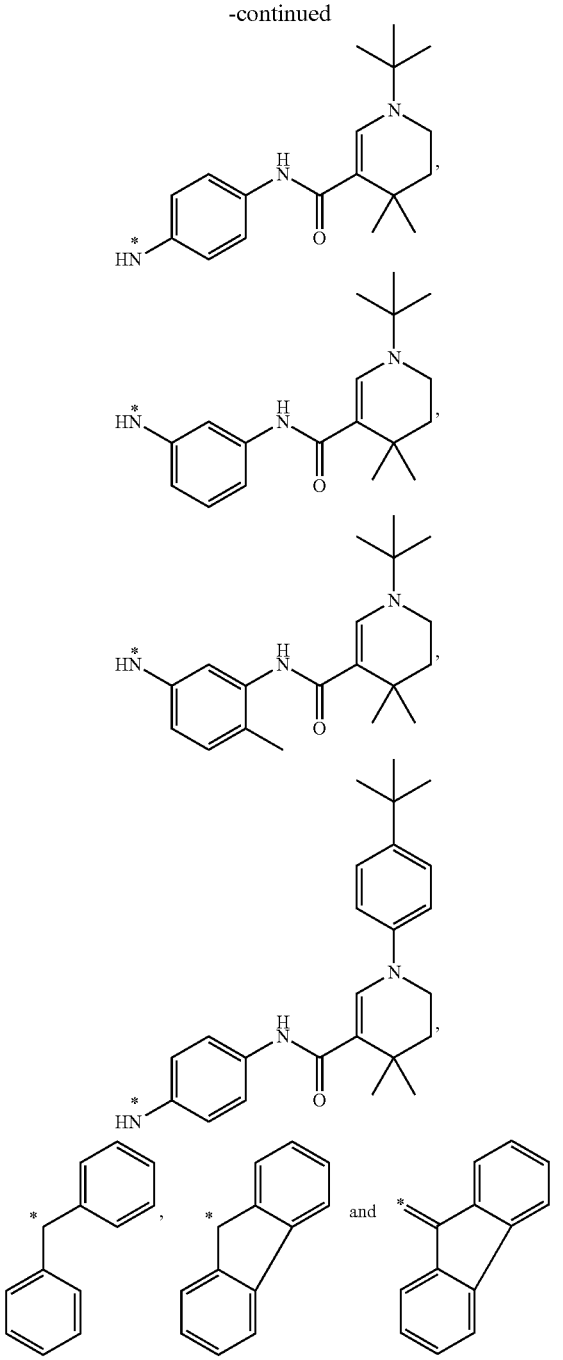

wherein * represents the carbon atom which is attached to the carbonyl carbon and with the proviso that R₃ comprises a carbon atom directly attached to the ring structure in formula I and that carbon is double bonded to another atom;
R₄ is selected from the group consisting of hydrogen, phenyl, butan-2-one and but-1-ene-2-yl propionate;
R₅ is selected from the group consisting of ethyl, propyl, isopropyl, n-butyl, sec-butyl, isobutyl, tert-butyl, phenyl and phenyl substituted with $C_1$ to $C_3$ alkoxy;
R₆ is hydrogen or oxo; and
R₁₈ and R₁₉ are hydrogen.

2. A composition comprising a compound of claim 1, or a salt thereof, and a suitable carrier.

3. The composition of claim 2, wherein the composition is selected from the group consisting of a sunscreen composition, a coating composition and a glass or polymeric film-forming composition.

4. A method of protecting a surface or tissue from UV rays including the step of applying a compound of claim 1, or a salt thereof, to the surface or tissue.

5. The method of claim 4 wherein the surface is a surface of a fabric, clothing material, plastic, timber, masonry and glass.

6. The method of claim 4 wherein the tissue is the skin of a mammal.

7. A compound of formula I, or a salt thereof:

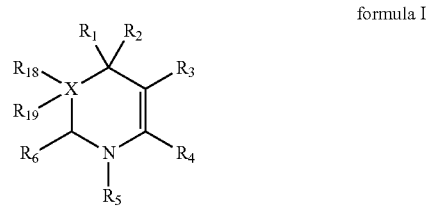

formula I wherein X is one carbon;
R₁ and R₂ are independently selected from the group consisting of methyl, ethyl, propyl and butyl;
R₄, R₆, R₁₈ and R₁₉ are hydrogen;
R₃ is

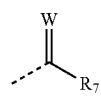

wherein W is oxygen and R₇ is selected from the group consisting of

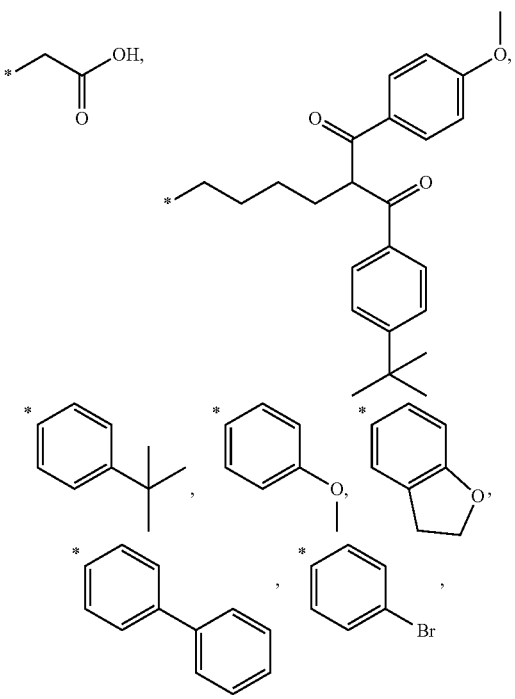

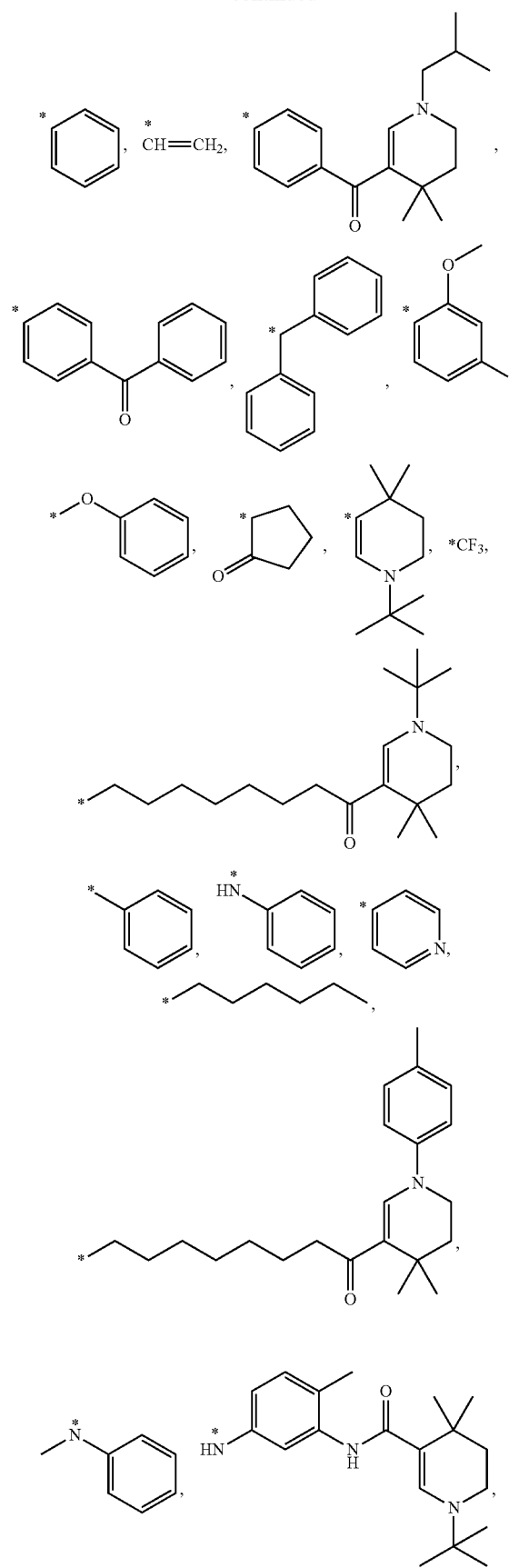
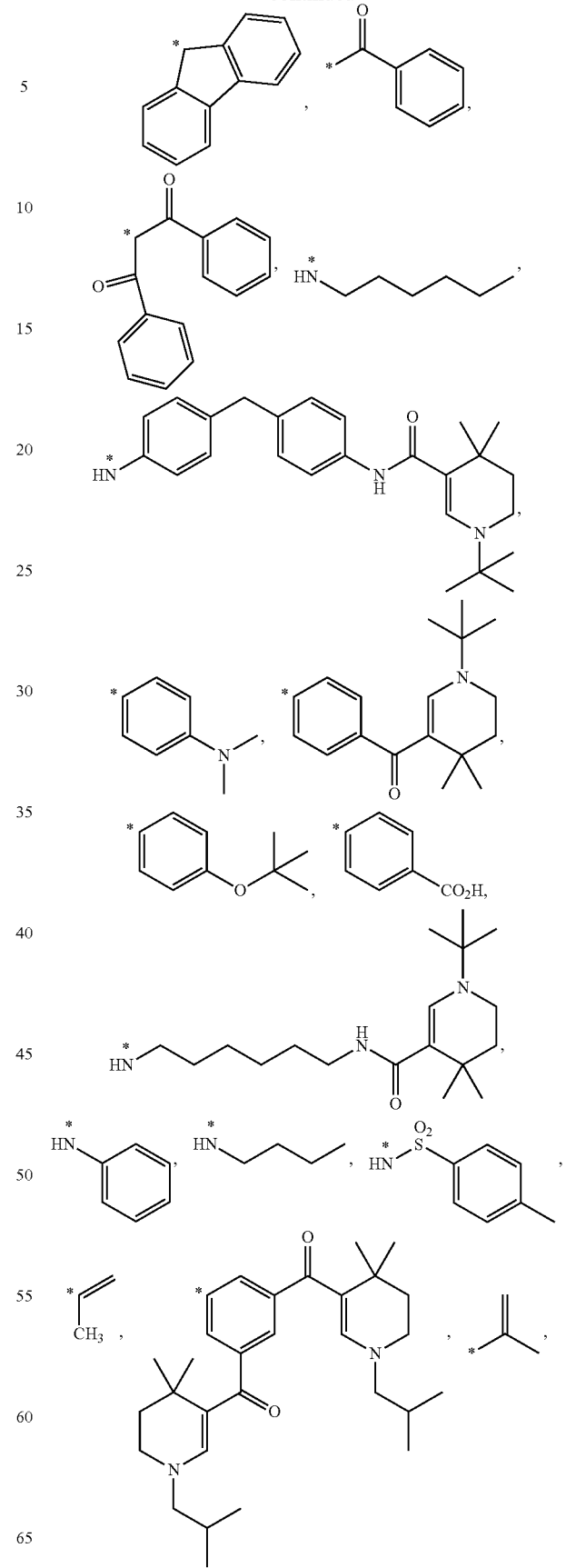

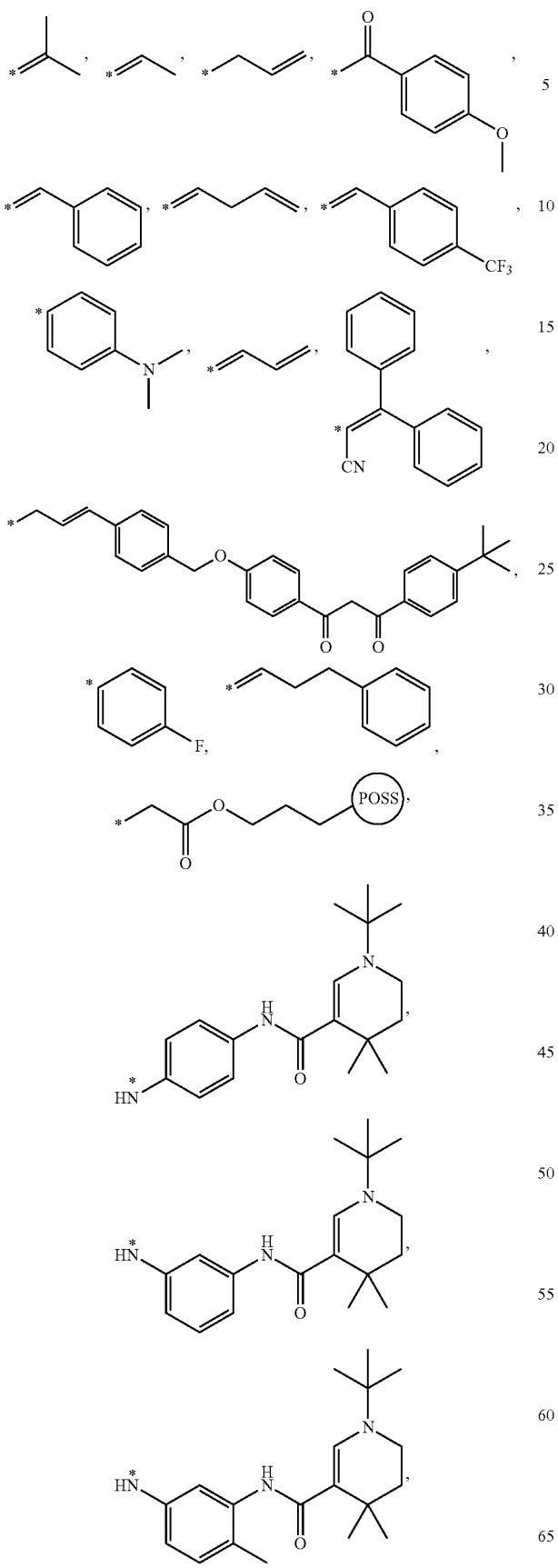
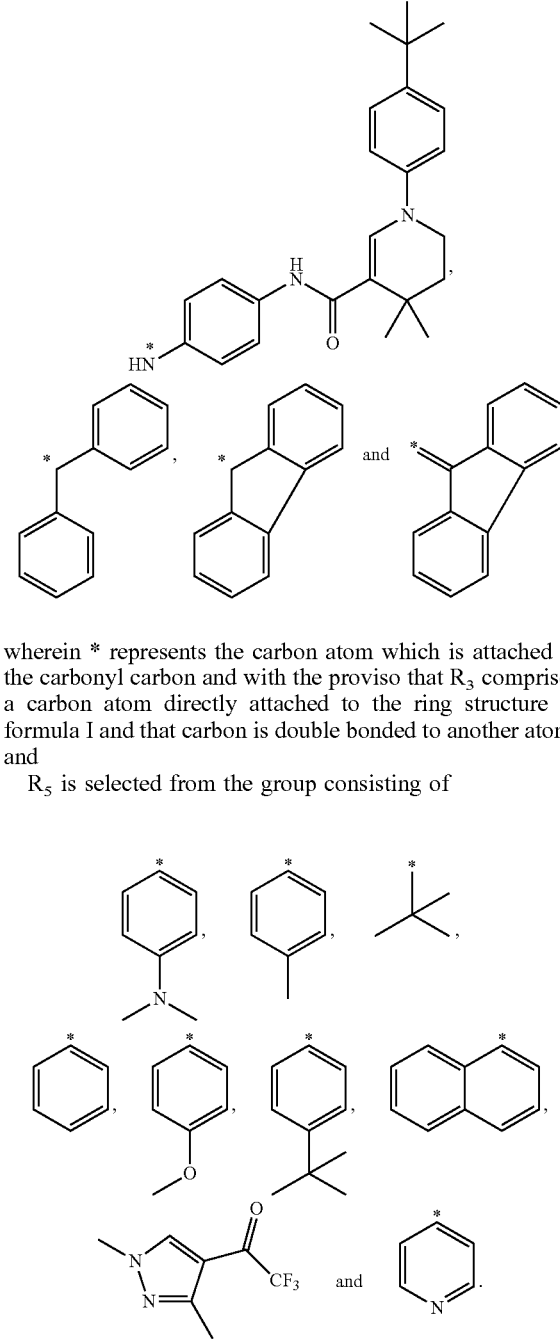

wherein * represents the carbon atom which is attached to the carbonyl carbon and with the proviso that $R_3$ comprises a carbon atom directly attached to the ring structure in formula I and that carbon is double bonded to another atom; and $R_5$ is selected from the group consisting of

8. A composition comprising a compound of claim 7, or a salt thereof, and a suitable carrier.

9. The composition of claim 8, wherein the composition is selected from the group consisting of a sunscreen composition, a coating composition and a glass or polymeric film-forming composition.

10. A method of protecting a surface or tissue from UV rays including the step of applying a compound of claim 7, or a salt thereof, to the surface or tissue.

11. The method of claim 10 wherein the surface is a surface of a fabric, clothing material, plastic, timber, masonry and glass.

12. The method of claim 10 wherein the tissue is the skin of a mammal.

13. A compound of formula IIa or IIb:

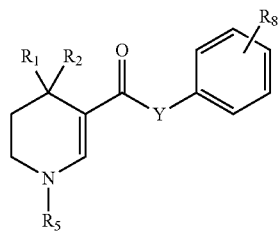

formula IIa

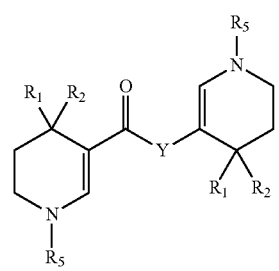

formula IIb wherein $R_1$ and $R_2$ are independently selected from the group consisting of $C_1$ to $C_{10}$ alkyl, $C_2$ to $C_{10}$ alkenyl and $C_1$ to $C_{10}$ alkoxy, each of which groups may be substituted or unsubstituted;

$R_5$ is selected from the group consisting of $C_1$ to $C_{12}$ alkyl, $C_2$ to $C_{12}$ alkenyl, $C_2$ to $C_{12}$ alkynyl, aryl, heteroaryl, $C_5$ to $C_9$ cycloalkyl, $C_5$ to $C_7$ cycloalkenyl, $C_2$ to $C_9$ alkanoyl, $C_2$ to $C_9$ alkanoyloxy and carbamoyl all of which groups may be substituted or unsubstituted;

Y, when present, is selected from nitrogen, N-alkyl, $C_6$, $C_7$, $C_8$, $C_9$, $C_{10}$, $C_{11}$ or $C_{12}$ alkyl optionally substituted with oxo, hydroxyl, alkoxy and halo and may be oxygen linked to the ring; and $R_8$, when present, may be selected from the group consisting of $C_1$ to $C_6$ alkyl, substituted or unsubstituted, aryl, alkoxy, halo and amino.

14. The compound of claim 13 wherein the compound is a compound of formula IIb and Y is selected from $C_8$, $C_9$, $C_{10}$, $C_{11}$ or $C_{12}$ alkyl optionally substituted with oxo, hydroxyl, alkoxy and halo.

15. The compound of claim 14 wherein Y is $C_9$ alkyl substituted with oxo.

16. The compound of claim 15 wherein $R_5$ is t-butyl.

17. A composition comprising a compound of claim 13, or a salt thereof, and a suitable carrier.

18. The composition of claim 17, wherein the composition is selected from the group consisting of a sunscreen composition, a coating composition and a glass or polymeric film-forming composition.

19. A method of protecting a surface or tissue from UV rays including the step of applying a compound of claim 13, or a salt thereof, to the surface or tissue.

20. The method of claim 19 wherein the surface is a surface of a fabric, clothing material, plastic, timber, masonry and glass.

21. The method of claim 19 wherein the tissue is the skin of a mammal.

22. A compound selected from the group consisting of:

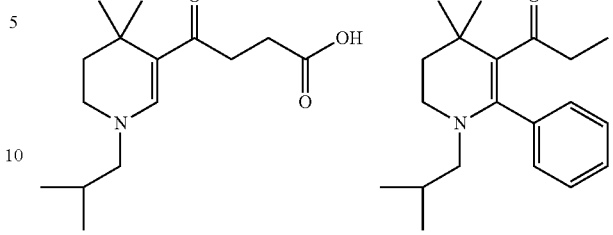

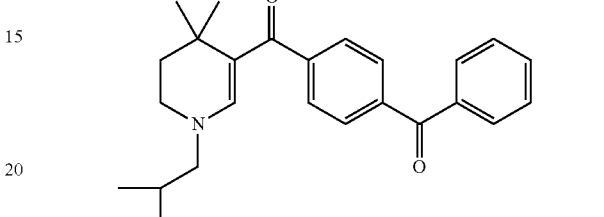

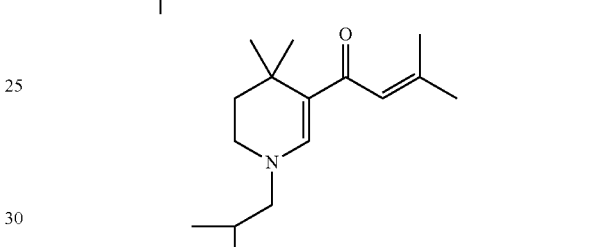

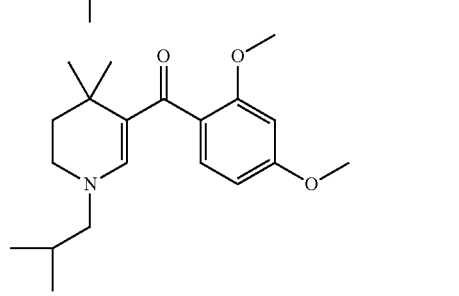

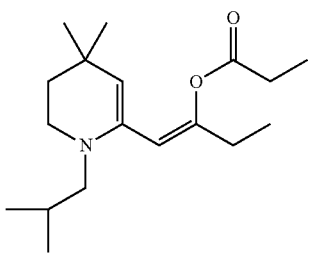

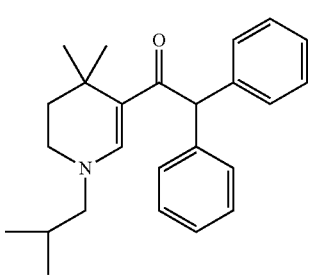

181
-continued
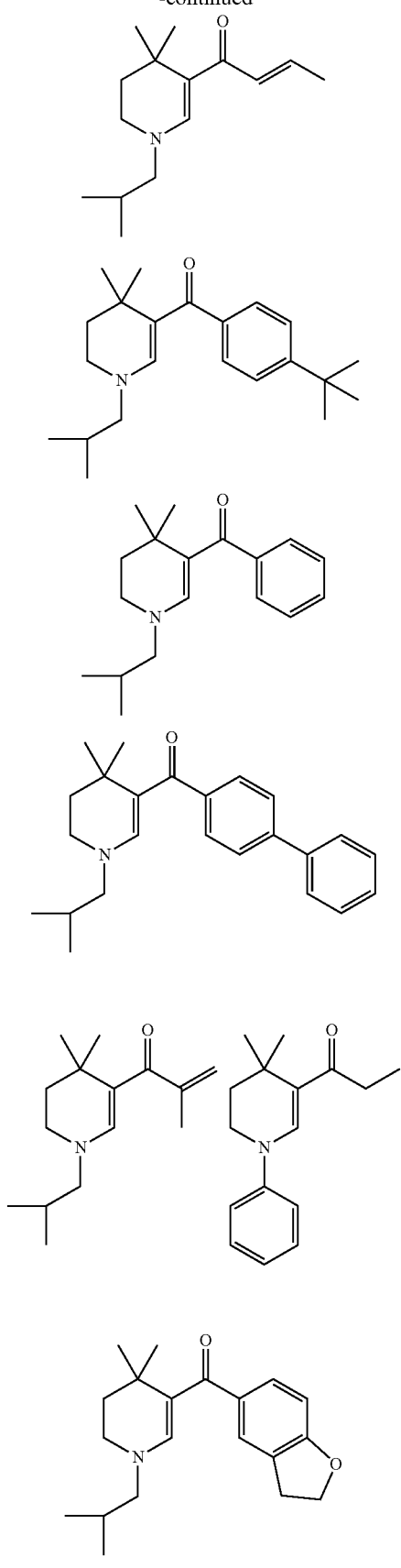
182
-continued
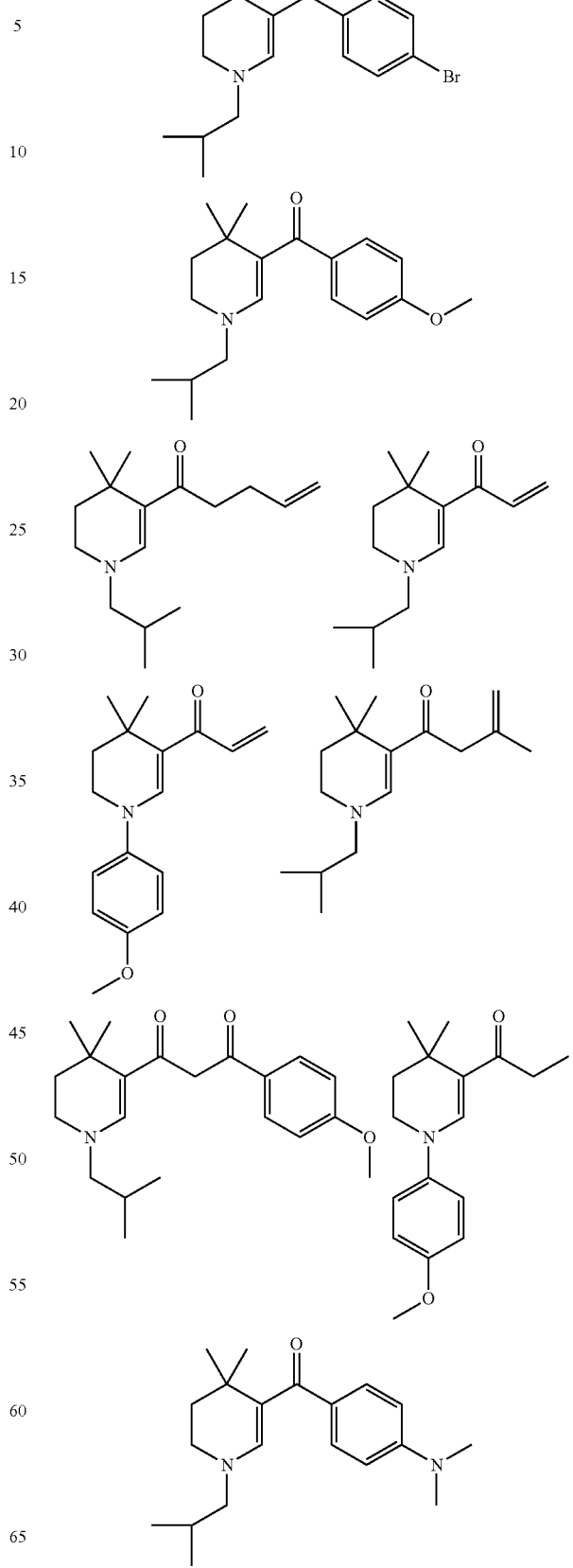

-continued
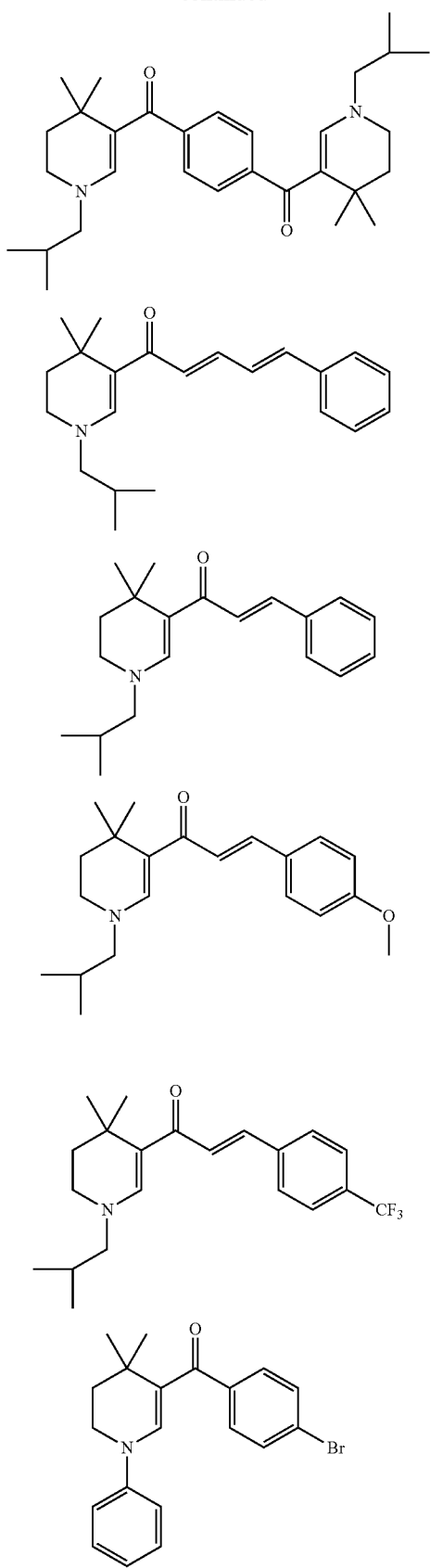
-continued
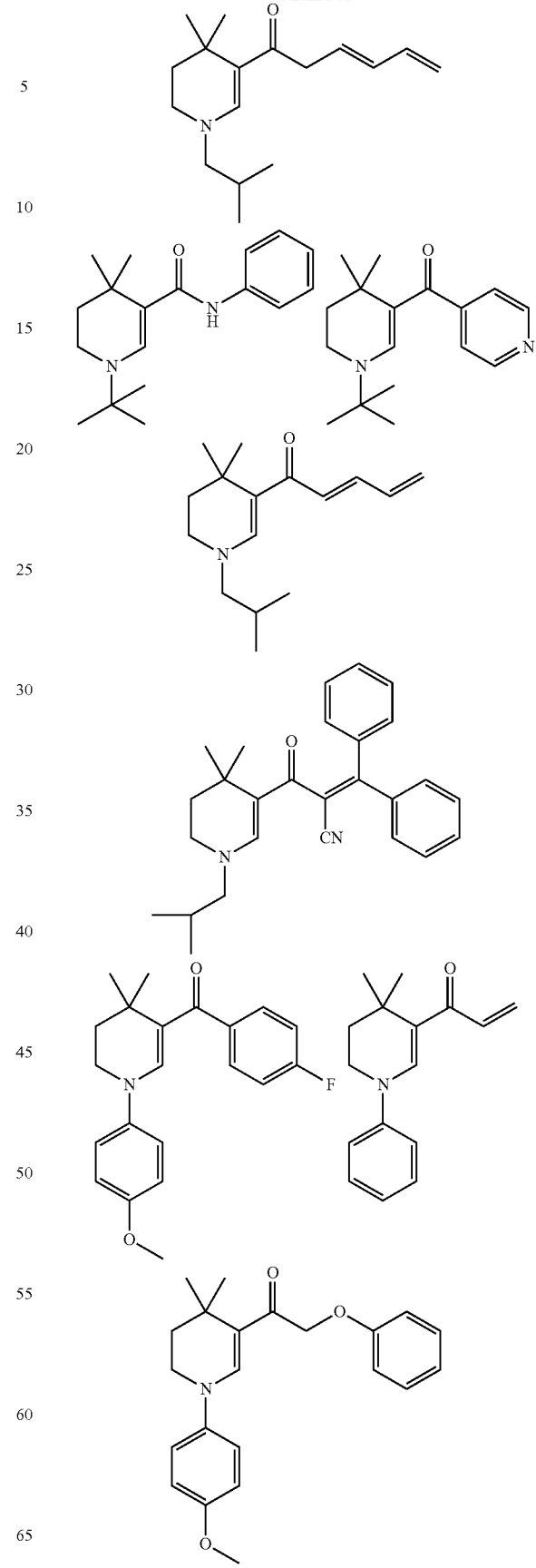

-continued
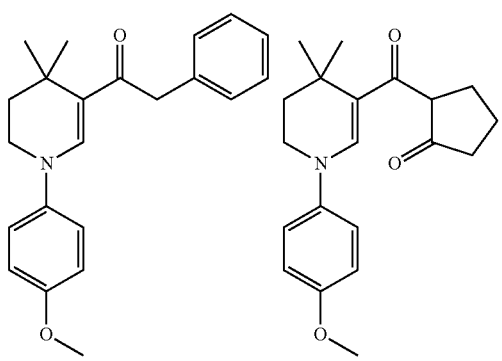
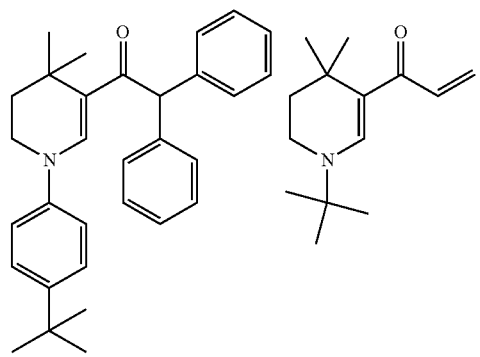
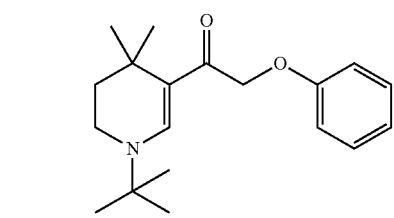
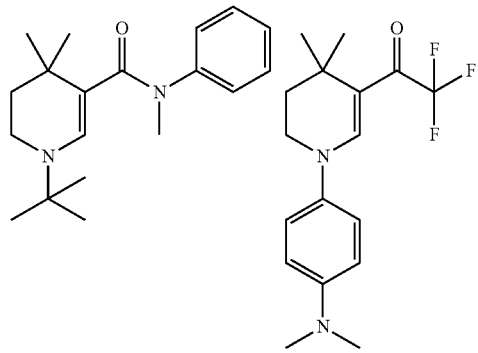
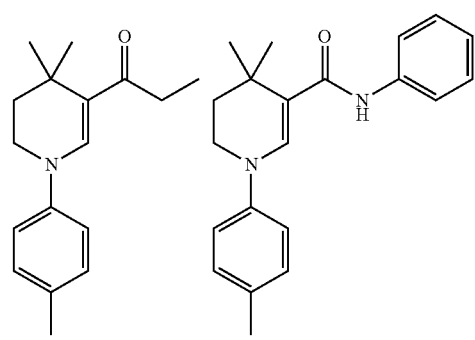
-continued
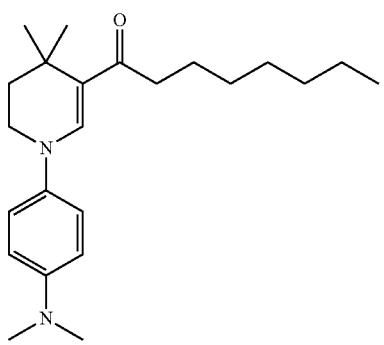
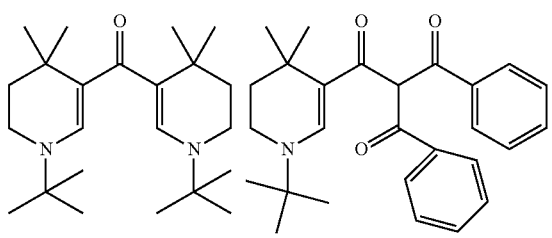
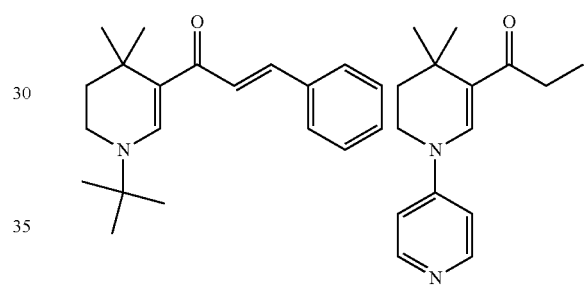
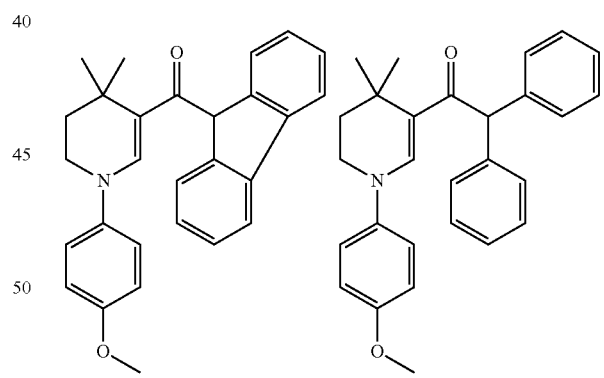
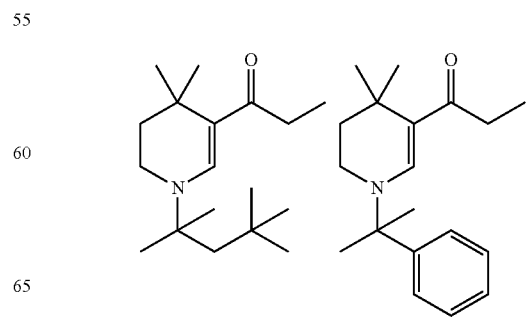

187
-continued
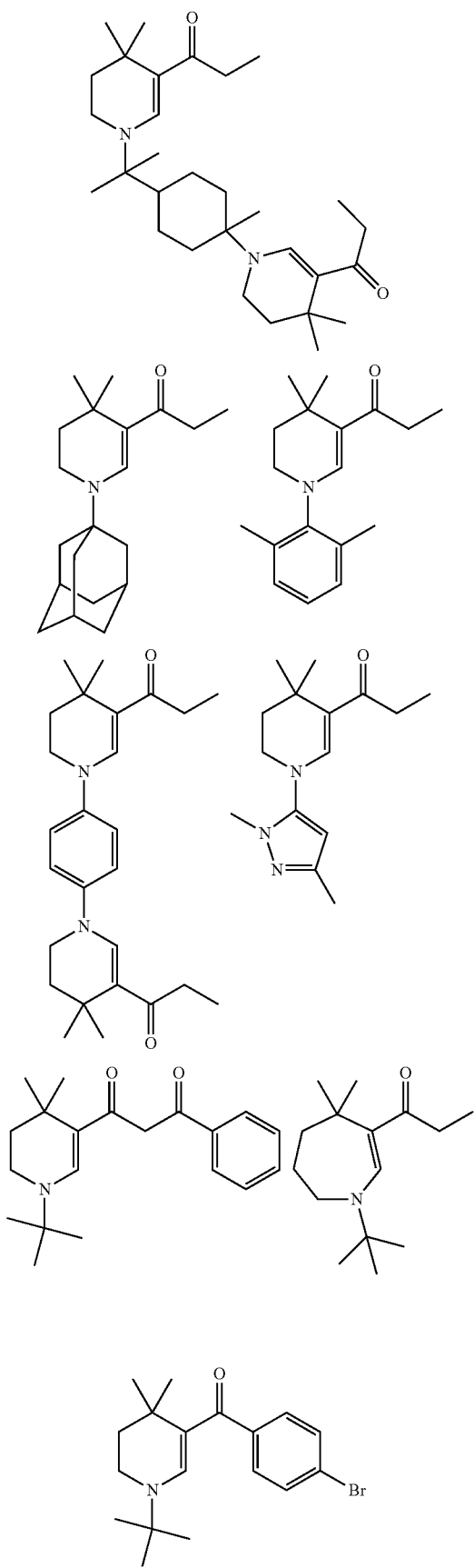
188
-continued
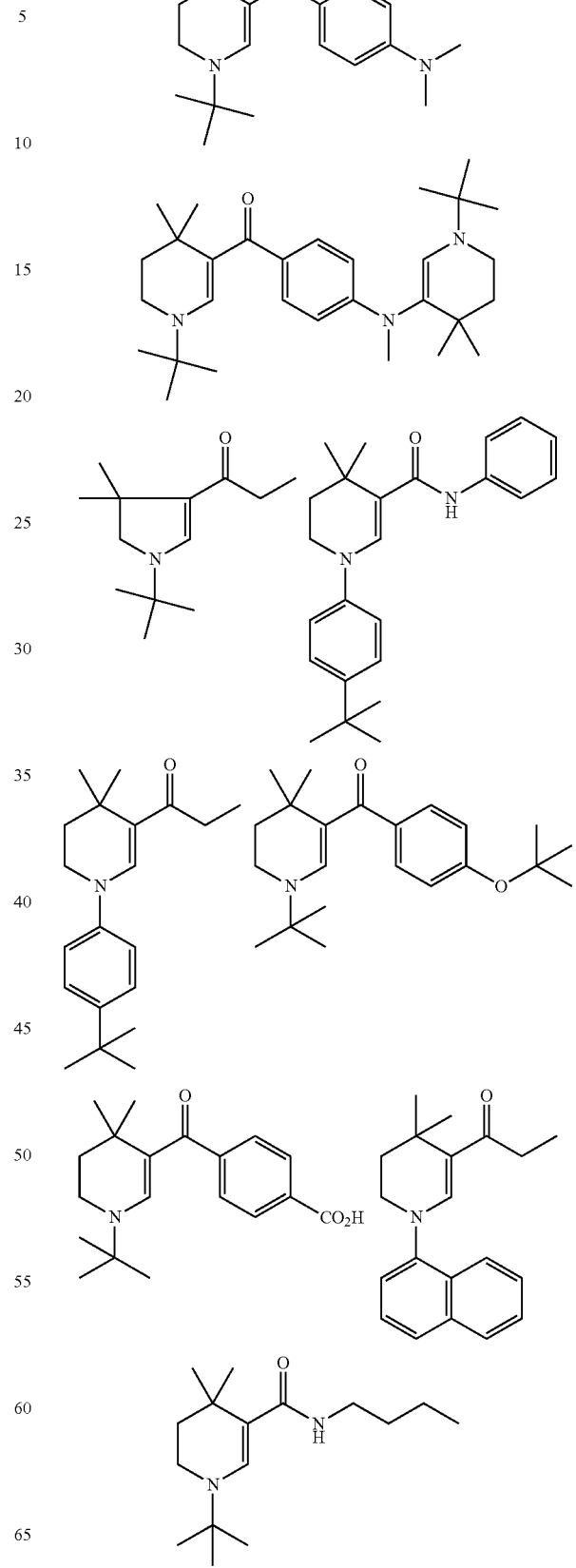

189
-continued
190
-continued
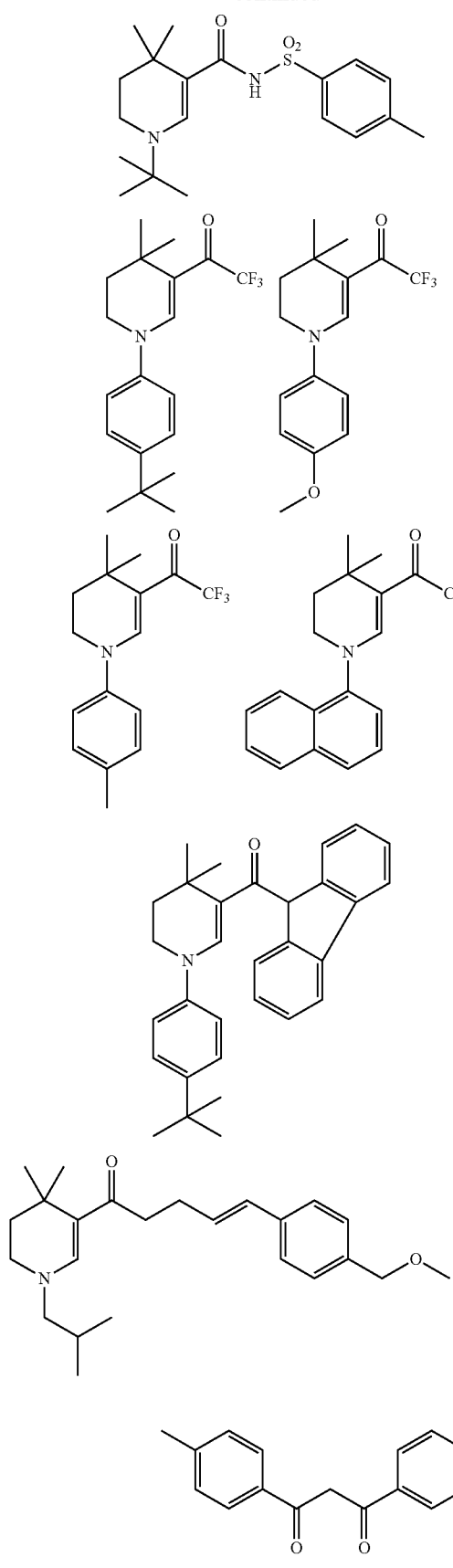
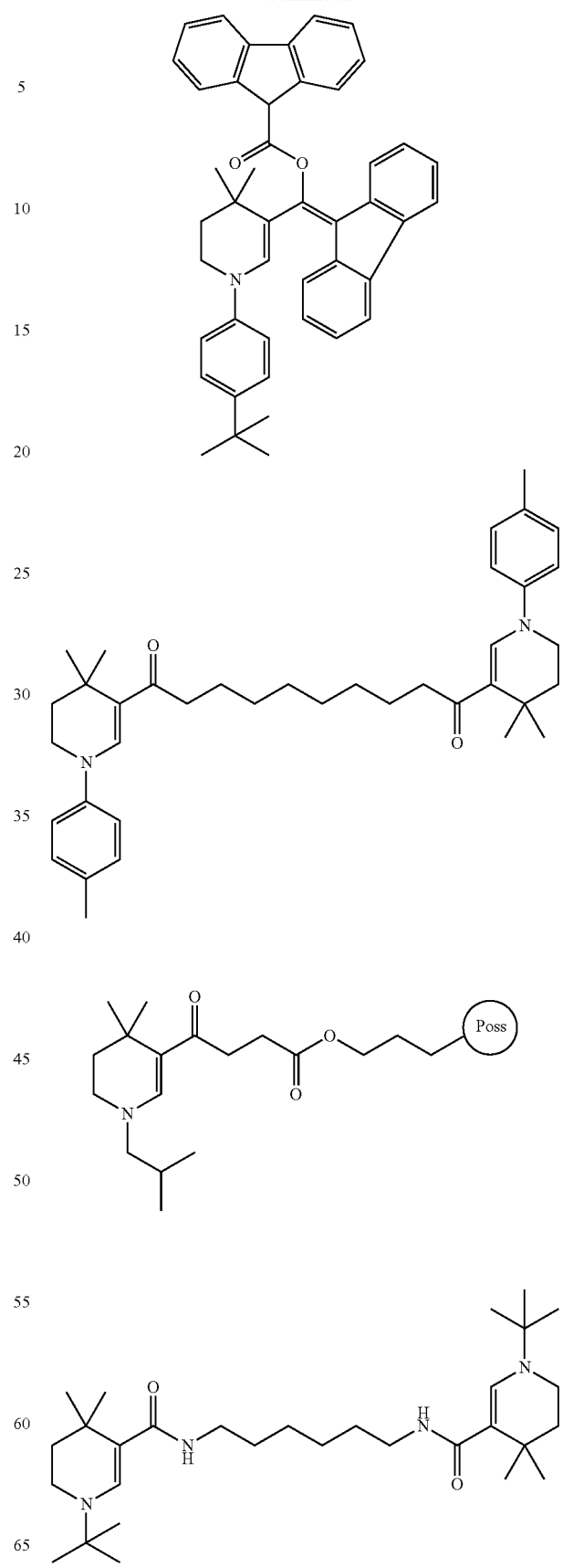

-continued

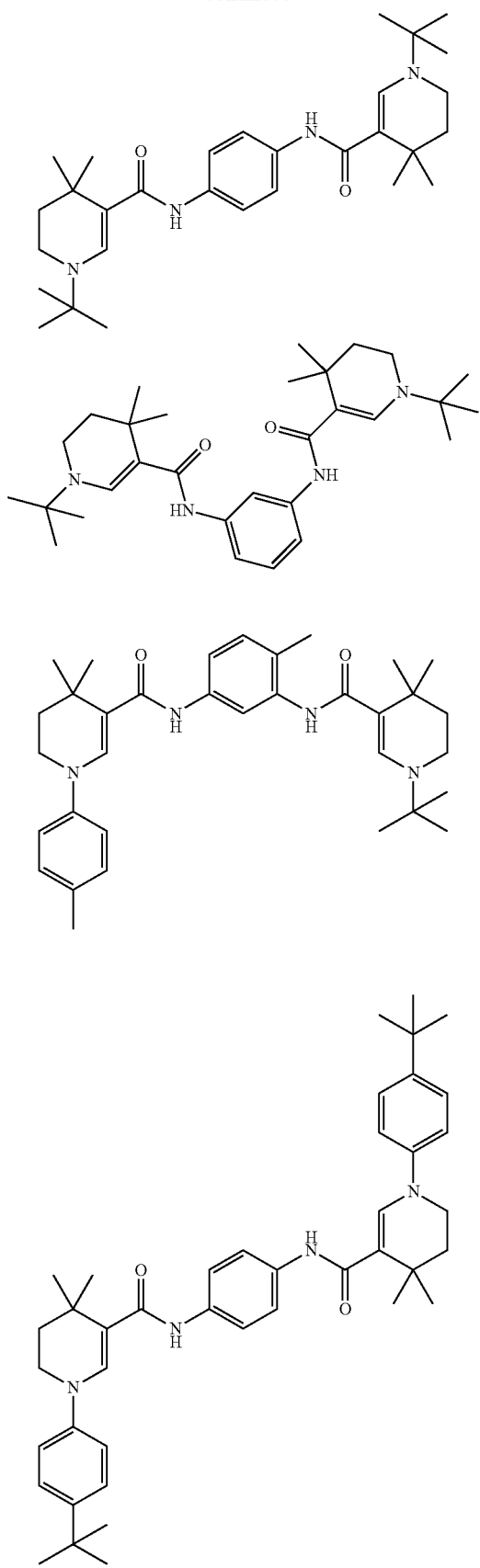

-continued

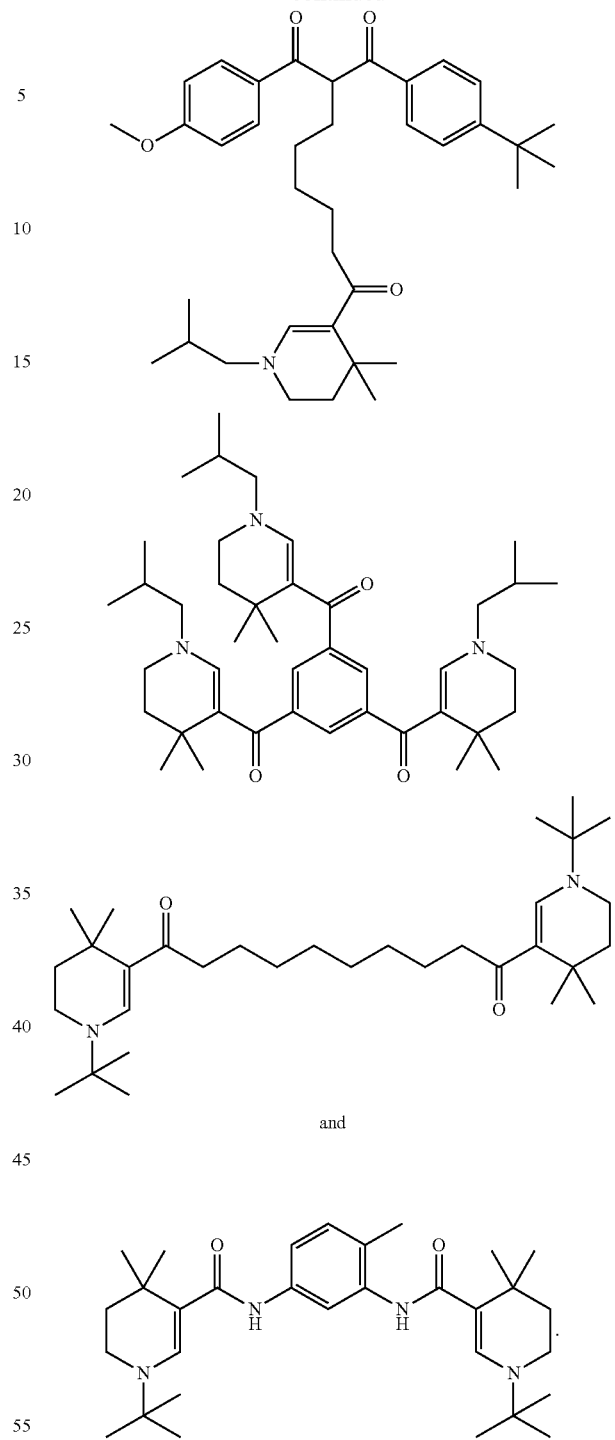

and

23. A composition comprising a compound of claim 22, or a salt thereof, and a suitable carrier.

24. The composition of claim 23, wherein the composition is selected from the group consisting of a sunscreen composition, a coating composition and a glass or polymeric film-forming composition.

25. A method of protecting a surface or tissue from UV rays including the step of applying a compound of claim 22, or a salt thereof, to the surface or tissue.

26. The method of claim 25 wherein the surface is a surface of a fabric, clothing material, plastic, timber, masonry and glass.

27. The method of claim 25 wherein the tissue is the skin of a mammal.

* * * * *